US009597411B2

(12) United States Patent
Chen et al.

(10) Patent No.: US 9,597,411 B2
(45) Date of Patent: *Mar. 21, 2017

(54) ANTI-PMEL17 ANTIBODIES AND IMMUNOCONJUGATES

(71) Applicant: GENENTECH, INC., South San Francisco, CA (US)

(72) Inventors: Youjun Chen, Redwood City, CA (US); William Mallet, Redwood City, CA (US); Paul Polakis, Mill Valley, CA (US); Christine Tan, San Mateo, CA (US); Jyoti Asundi, Foster City, CA (US); Suzanna Clark, Pacifica, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/705,525

(22) Filed: May 6, 2015

(65) Prior Publication Data

US 2015/0374847 A1    Dec. 31, 2015

Related U.S. Application Data

(63) Continuation of application No. 13/873,462, filed on Apr. 30, 2013, now Pat. No. 9,056,910.

(60) Provisional application No. 61/641,074, filed on May 1, 2012, provisional application No. 61/678,911, filed on Aug. 2, 2012.

(51) Int. Cl.

| | |
|---|---|
| *A61K 39/395* | (2006.01) |
| *A61K 47/48* | (2006.01) |
| *A61K 45/06* | (2006.01) |
| *A61K 51/10* | (2006.01) |
| *C07K 16/30* | (2006.01) |
| *G01N 33/60* | (2006.01) |
| *C07K 16/28* | (2006.01) |

(52) U.S. Cl.
CPC .. *A61K 47/48561* (2013.01); *A61K 39/39558* (2013.01); *A61K 45/06* (2013.01); *A61K 47/48* (2013.01); *A61K 47/48407* (2013.01); *A61K 47/48715* (2013.01); *A61K 47/48723* (2013.01); *A61K 51/1093* (2013.01); *C07K 16/2854* (2013.01); *C07K 16/30* (2013.01); *C07K 16/3053* (2013.01); *G01N 33/60* (2013.01); *C07K 2317/34* (2013.01); *C07K 2317/77* (2013.01)

(58) Field of Classification Search
None
See application file for complete search history.

(56) References Cited

U.S. PATENT DOCUMENTS

| | | | |
|---|---|---|---|
| 3,896,111 | A | 7/1975 | Kupchan et al. |
| 4,137,230 | A | 1/1979 | Hashimoto et al. |
| 4,248,870 | A | 2/1981 | Miyashita et al. |
| 4,256,746 | A | 3/1981 | Miyashita et al. |
| 4,260,608 | A | 4/1981 | Miyashita et al. |
| 4,265,814 | A | 5/1981 | Hashimoto et al. |
| 4,294,757 | A | 10/1981 | Asai |
| 4,307,016 | A | 12/1981 | Asai et al. |
| 4,308,268 | A | 12/1981 | Miyashita et al. |
| 4,308,269 | A | 12/1981 | Miyashita et al. |
| 4,309,428 | A | 1/1982 | Miyashita et al. |
| 4,313,946 | A | 2/1982 | Powell et al. |
| 4,315,929 | A | 2/1982 | Freedman et al. |
| 4,317,821 | A | 3/1982 | Miyashita et al. |
| 4,322,348 | A | 3/1982 | Asai et al. |
| 4,331,598 | A | 5/1982 | Hasegawa et al. |
| 4,361,650 | A | 11/1982 | Asai et al. |
| 4,362,663 | A | 12/1982 | Kida et al. |
| 4,364,866 | A | 12/1982 | Asai et al. |
| 4,371,533 | A | 2/1983 | Akimoto et al. |
| 4,424,219 | A | 1/1984 | Hashimoto et al. |
| 4,450,254 | A | 5/1984 | Isley et al. |
| 4,676,980 | A | 6/1987 | Segal et al. |
| 4,737,456 | A | 4/1988 | Weng et al. |
| 4,816,567 | A | 3/1989 | Cabilly et al. |
| 5,208,020 | A | 5/1993 | Chari et al. |
| 5,362,852 | A | 11/1994 | Geoghegan |
| 5,416,064 | A | 5/1995 | Chari et al. |
| 5,500,362 | A | 3/1996 | Robinson et al. |
| 5,571,894 | A | 11/1996 | Wels et al. |
| 5,587,458 | A | 12/1996 | King et al. |
| 5,591,828 | A | 1/1997 | Bosslet et al. |
| 5,624,821 | A | 4/1997 | Winter et al. |
| 5,635,483 | A | 6/1997 | Pettit et al. |
| 5,648,237 | A | 7/1997 | Carter et al. |

(Continued)

FOREIGN PATENT DOCUMENTS

| | | |
|---|---|---|
| EP | 328147 | 2/1989 |
| EP | 0 404 097 B1 | 6/1990 |

(Continued)

OTHER PUBLICATIONS

Ajani et al., "A Multi-Institutional Phase II Study of BMS-182248-01 (BR96-Doxorubicin Conjugate) Administered Every 21 Days in Patients with Advanced Gastric Adenocarcinoma" Cancer Journal 6:78-81 (2000).
Alley et al., "Antibody-drug conjugates: targeted drug delivery for cancer" Current Opinion in Chemical Biology 14:529-537 (2010).
Alley, S.C. et al., "Controlling the location of drug attachment in antibody-drug conjugates, Abstract No. 627, American Association for Cancer Research, 2004 Annual Meeting, Mar. 27-31, 2004 Proceedings of the AACR" 45:52 (2004).
Almagro et al., "Humanization of antibodies" Frontiers in Bioscience 13:1619-1633 (Jan. 2008).

(Continued)

*Primary Examiner* — Sheela J Huff
(74) *Attorney, Agent, or Firm* — McNeill Baur PLLC

(57) ABSTRACT

The invention provides anti-PMEL17 antibodies and immunoconjugates and methods of using the same.

49 Claims, 17 Drawing Sheets

(56) References Cited

U.S. PATENT DOCUMENTS

| | | | |
|---|---|---|---|
| 5,648,260 A | 7/1997 | Winter et al. |
| 5,663,149 A | 9/1997 | Pettit et al. |
| 5,712,374 A | 1/1998 | Kuntsmann et al. |
| 5,714,586 A | 2/1998 | Kunstmann et al. |
| 5,731,168 A | 3/1998 | Carter et al. |
| 5,739,116 A | 4/1998 | Hamann et al. |
| 5,750,373 A | 5/1998 | Garrard et al. |
| 5,767,237 A | 6/1998 | Sakakibara et al. |
| 5,767,285 A | 6/1998 | Hamann et al. |
| 5,770,429 A | 6/1998 | Lonberg et al. |
| 5,780,588 A | 7/1998 | Pettit et al. |
| 5,789,199 A | 8/1998 | Joly et al. |
| 5,821,337 A | 10/1998 | Carter et al. |
| 5,840,523 A | 11/1998 | Simmons et al. |
| 5,869,046 A | 2/1999 | Presta et al. |
| 5,959,177 A | 9/1999 | Hein et al. |
| 6,040,498 A | 3/2000 | Stomp et al. |
| 6,075,181 A | 6/2000 | Kucherlaopati et al. |
| 6,124,431 A | 9/2000 | Sakakibara et al. |
| 6,150,584 A | 11/2000 | Kucherlapati et al. |
| 6,171,586 B1 | 1/2001 | Lam et al. |
| 6,194,551 B1 | 2/2001 | Idusogie et al. |
| 6,214,345 B1 | 4/2001 | Firestone et al. |
| 6,248,516 B1 | 6/2001 | Winter et al. |
| 6,267,958 B1 | 7/2001 | Andya et al. |
| 6,333,410 B1 | 12/2001 | Chari et al. |
| 6,417,429 B1 | 7/2002 | Hein et al. |
| 6,420,548 B1 | 7/2002 | Vezina et al. |
| 6,441,163 B1 | 8/2002 | Chari et al. |
| 6,602,677 B1 | 8/2003 | Wood et al. |
| 6,602,684 B1 | 8/2003 | Umana et al. |
| 6,630,579 B2 | 10/2003 | Chari et al. |
| 6,737,056 B1 | 5/2004 | Presta |
| 6,824,780 B1 | 11/2004 | Devaux et al. |
| 6,884,799 B2 | 4/2005 | Kamal et al. |
| 6,913,748 B2 | 7/2005 | Widdison |
| 6,982,321 B2 | 1/2006 | Winter |
| 7,041,870 B2 | 5/2006 | Tomizuka et al. |
| 7,049,311 B1 | 5/2006 | Thurston et al. |
| RE39,151 E | 6/2006 | Chari et al. |
| 7,067,511 B2 | 6/2006 | Thurston et al. |
| 7,087,409 B2 | 8/2006 | Barbas et al. |
| 7,125,978 B1 | 10/2006 | Vezina et al. |
| 7,189,826 B2 | 3/2007 | Rodman |
| 7,265,105 B2 | 9/2007 | Thurston et al. |
| 7,276,497 B2 | 10/2007 | Chari et al. |
| 7,303,749 B1 | 12/2007 | Chari |
| 7,332,581 B2 | 2/2008 | Presta |
| 7,371,826 B2 | 5/2008 | Presta |
| 7,375,078 B2 | 5/2008 | Feng |
| 7,473,423 B2* | 1/2009 | Rodriguez ............ C07K 16/18 |
| | | | 424/142.1 |
| 7,498,298 B2 | 3/2009 | Doronina et al. |
| 7,511,032 B2 | 3/2009 | Liu et al. |
| 7,521,541 B2 | 4/2009 | Eigenbrot et al. |
| 7,527,791 B2 | 5/2009 | Adams et al. |
| 7,528,126 B2 | 5/2009 | Howard et al. |
| 7,557,099 B2 | 7/2009 | Howard et al. |
| 7,601,354 B2 | 10/2009 | Chari |
| 7,659,241 B2 | 2/2010 | Senter et al. |
| 7,662,936 B2 | 2/2010 | Kadkhodayan et al. |
| 7,691,568 B2 | 4/2010 | Niwa et al. |
| 7,745,394 B2 | 6/2010 | Doronina et al. |
| 7,749,753 B2 | 7/2010 | Kanda et al. |
| 7,754,681 B2 | 7/2010 | Feng |
| 7,785,903 B2 | 8/2010 | Bond et al. |
| 7,829,531 B2 | 11/2010 | Senter et al. |
| 7,851,437 B2 | 12/2010 | Senter et al. |
| 7,855,275 B2 | 12/2010 | Eigenbrot et al. |
| 7,947,839 B2 | 5/2011 | Gazzard et al. |
| 7,964,566 B2 | 6/2011 | Doronina et al. |
| 7,964,567 B2 | 6/2011 | Doronina et al. |
| 7,985,840 B2 | 7/2011 | Fuh et al. |
| 7,994,135 B2 | 8/2011 | Doronina et al. |
| 8,054,268 B2 | 11/2011 | Chen et al. |
| 8,088,387 B2 | 1/2012 | Steeves et al. |
| 8,142,784 B2 | 3/2012 | Ebens, Jr. et al. |
| 8,163,279 B2* | 4/2012 | Bergstein ............ C07K 16/2866 |
| | | | 424/130.1 |
| 8,198,417 B2 | 6/2012 | Steeves et al. |
| 8,309,300 B2 | 11/2012 | Junutula et al. |
| 8,389,697 B2 | 3/2013 | Beria et al. |
| 8,435,488 B2 | 5/2013 | Gill et al. |
| 8,557,780 B2 | 10/2013 | Doronina et al. |
| 8,580,257 B2 | 11/2013 | Tremblay et al. |
| 9,056,910 B2* | 6/2015 | Chen ................ A61K 39/39558 |
| 2002/0164328 A1 | 11/2002 | Shinkawa et al. |
| 2003/0096743 A1 | 5/2003 | Senter et al. |
| 2003/0115614 A1 | 6/2003 | Kanda et al. |
| 2003/0130189 A1 | 7/2003 | Senter et al. |
| 2003/0157108 A1 | 8/2003 | Presta |
| 2004/0093621 A1 | 5/2004 | Shitara et al. |
| 2004/0110704 A1 | 6/2004 | Yamane et al. |
| 2004/0110707 A1 | 6/2004 | Maden et al. |
| 2004/0132140 A1 | 7/2004 | Satoh et al. |
| 2005/0014934 A1 | 1/2005 | Hinton et al. |
| 2005/0031613 A1 | 2/2005 | Nakamura et al. |
| 2005/0079574 A1 | 4/2005 | Bond |
| 2005/0123536 A1 | 6/2005 | Law et al. |
| 2005/0123546 A1 | 6/2005 | Umana et al. |
| 2005/0238649 A1 | 10/2005 | Doronina et al. |
| 2005/0260186 A1 | 11/2005 | Bookbinder et al. |
| 2005/0276812 A1 | 12/2005 | Ebens et al. |
| 2006/0009622 A1* | 1/2006 | Fuselier ............ A61K 47/48338 |
| | | | 530/402 |
| 2006/0025576 A1 | 2/2006 | Miller et al. |
| 2006/0104968 A1 | 5/2006 | Bookbinder et al. |
| 2007/0061900 A1 | 3/2007 | Murphy et al. |
| 2007/0117126 A1 | 5/2007 | Sidhu et al. |
| 2007/0134243 A1 | 6/2007 | Gazzard et al. |
| 2007/0134759 A1 | 6/2007 | Nishiya et al. |
| 2007/0160598 A1 | 7/2007 | Dennis et al. |
| 2007/0237764 A1 | 10/2007 | Birtalan et al. |
| 2007/0292936 A1 | 12/2007 | Barthelemy et al. |
| 2008/0050311 A1 | 2/2008 | Goldenberg et al. |
| 2008/0069820 A1 | 3/2008 | Fuh et al. |
| 2008/0171040 A1 | 7/2008 | Ebens, et al. |
| 2008/0213289 A1 | 9/2008 | Francisco et al. |
| 2008/0241884 A1 | 10/2008 | Shitara et al. |
| 2009/0036431 A1 | 2/2009 | Gauzy et al. |
| 2009/0203078 A1 | 8/2009 | Ogawa et al. |
| 2009/0226465 A1 | 9/2009 | Jackson |
| 2009/0304710 A1 | 12/2009 | Park et al. |
| 2010/0034837 A1 | 2/2010 | Beria et al. |
| 2010/0047257 A1 | 2/2010 | Blanc et al. |
| 2010/0111856 A1 | 5/2010 | Gill et al. |
| 2010/0273843 A1 | 10/2010 | Feng |
| 2011/0064753 A1 | 3/2011 | Senter et al. |
| 2011/0076287 A1 | 3/2011 | Cohen et al. |
| 2011/0137017 A1 | 6/2011 | Eigenbrot et al. |
| 2011/0256157 A1 | 10/2011 | Howard et al. |
| 2011/0301334 A1 | 12/2011 | Bhakta et al. |
| 2012/0003247 A1 | 1/2012 | Doronina et al. |
| 2012/0027783 A1 | 2/2012 | Doronina et al. |
| 2012/0027784 A1 | 2/2012 | Doronina et al. |
| 2012/0034246 A1 | 2/2012 | Doronina et al. |
| 2012/0121615 A1 | 5/2012 | Flygare et al. |
| 2012/0141508 A1 | 6/2012 | Doronina et al. |
| 2012/0141509 A1 | 6/2012 | Doronina et al. |
| 2012/0141510 A1 | 6/2012 | Doronina et al. |
| 2012/0148608 A1 | 6/2012 | Doronina et al. |
| 2012/0148610 A1 | 6/2012 | Doronina et al. |
| 2012/0315645 A1 | 12/2012 | Kaur et al. |
| 2013/0028917 A1 | 1/2013 | Howard et al. |
| 2013/0216475 A1 | 8/2013 | Gill et al. |
| 2013/0266595 A1 | 10/2013 | Flygare et al. |
| 2014/0220047 A1 | 8/2014 | Doronina et al. |

FOREIGN PATENT DOCUMENTS

| | | |
|---|---|---|
| EP | 0425235 A2 | 5/1991 |
| WO | 81/01145 A1 | 4/1981 |
| WO | 93/01161 A1 | 1/1993 |
| WO | 93/08829 A1 | 5/1993 |

(56) References Cited

FOREIGN PATENT DOCUMENTS

| WO | 93/16185 | A2 | 8/1993 |
|---|---|---|---|
| WO | 93/21232 | A1 | 10/1993 |
| WO | 94/11026 | A2 | 5/1994 |
| WO | 94/29351 | A2 | 12/1994 |
| WO | 97/30087 | A1 | 8/1997 |
| WO | 98/58964 | A1 | 12/1998 |
| WO | 99/22764 | A1 | 5/1999 |
| WO | 99/51642 | A1 | 10/1999 |
| WO | 00/61739 | A1 | 10/2000 |
| WO | 01/29246 | A1 | 4/2001 |
| WO | 02/31140 | A1 | 4/2002 |
| WO | 02/088172 | A2 | 11/2002 |
| WO | 02/088172 | A3 | 11/2002 |
| WO | 02/088172 | R1 | 11/2002 |
| WO | 03/011878 | A2 | 2/2003 |
| WO | 03/026577 | A2 | 4/2003 |
| WO | 03/026577 | A3 | 4/2003 |
| WO | 03/043583 | | 5/2003 |
| WO | 03/084570 | A1 | 10/2003 |
| WO | 03/085107 | A1 | 10/2003 |
| WO | 03/085119 | | 10/2003 |
| WO | 2004/010957 | | 2/2004 |
| WO | 2004/032828 | A2 | 4/2004 |
| WO | 2004/032828 | A3 | 4/2004 |
| WO | 2004/056312 | A2 | 7/2004 |
| WO | 2005/035586 | A1 | 4/2005 |
| WO | 2005/035778 | A1 | 4/2005 |
| WO | 2005/053742 | A1 | 6/2005 |
| WO | 2005/081711 | A2 | 9/2005 |
| WO | 2005/082023 | | 9/2005 |
| WO | 2005/100402 | A1 | 10/2005 |
| WO | 2005/101017 | | 10/2005 |
| WO | 2005/117986 | A2 | 12/2005 |
| WO | 2006/029879 | A2 | 3/2006 |
| WO | 2006/034488 | A2 | 3/2006 |
| WO | 2006/034488 | A3 | 3/2006 |
| WO | 2006/044908 | A2 | 4/2006 |
| WO | 2006/060533 | | 6/2006 |
| WO | 2007/008603 | A1 | 1/2007 |
| WO | 2007/008848 | A2 | 1/2007 |
| WO | 2007/064345 | | 6/2007 |
| WO | 2007/100385 | | 9/2007 |
| WO | 2008/077546 | A1 | 7/2008 |
| WO | 2009/016516 | | 2/2009 |
| WO | 2009/089004 | A1 | 7/2009 |
| WO | 2009/099741 | A1 | 8/2009 |
| WO | 2010/009124 | | 1/2010 |
| WO | 2010/099273 | | 9/2010 |
| WO | 2010/135547 | | 11/2010 |
| WO | 2011/056983 | | 5/2011 |
| WO | 2011/130598 | | 10/2011 |
| WO | 2011/156328 | | 12/2011 |
| WO | 2010/074757 | | 6/2012 |
| WO | 2012/106587 | | 8/2012 |
| WO | 2012/155019 | | 11/2012 |
| WO | 2013/055987 | | 4/2013 |
| WO | 2013/149159 | | 10/2013 |
| WO | 2013/165940 | | 11/2013 |

OTHER PUBLICATIONS

Amsberry et al., "The lactonization of 2'-hydroxyhydrocinnamic acid amides: a potential prodrug for amines" J Org Chem 55:5867-5877 (1990).
Antonow et al., "Structure-Activity Relationships of Monomeric C2-Aryl Pyrrolo[2,1-c][1,4]benzodiazepine (PBD) Antitumor Agents" J Med Chem(53):2927-2941 (2010).
Baca et al., "Antibody humanization using monovalent phage display" J Biol Chem 272(16):10678-10684 (1997).
Bachur Anthracycline Antibiotics in Cancer Therapy "Free Radical Damage" Muggia et al., The Hague:Martinus.Nijhoff,:97-102 (1981).
Berson et al., "Proprotein convertase cleavage liberates a fibrillogenic fragment of a resident glycoprotein to initiate melanosome biogenesis," J Cell Biol, 2003, 161:521-533.
Boerner et al., "Production of Antigen-Specific Human Monoclonal Antibodies From in Vitro-Primed Human Splenocytes" J Immunol 147(1):86-95 (Jul. 1991).
Brennan et al., "Preparation of Biospecific Antibodies by Chemical Recombination of Monoclonal Immunoglobulin G1 Fragments" Science 229(4708):81-83 (Jul. 5, 1985).
Brodeur et al., "Mouse-human myeloma partners for the production of heterohybridomas" Monoclonal Antibody Production Techniques and Applications, pp. 51-63 (New York: Marcel Dekker, Inc.), (1987).
Brueggemann et al., "Comparison of the effector functions of human immunoglobulins using a matched set of chimeric antibodies" J. Exp. Med. 166:1351-1361 (1987).
Burris et al., "Phase II study of the antibody drug conjugate trastuzumab-DM1 for the treatment of human epidermal growth factor receptor 2 (HER2)-positive breast cancer after prior HER2-directed therapy," J Clin Oncol, 2011, 29:398-405.
Carter and Senter, "Antibody-drug conjugates for cancer therapy" Cancer J 14(3):154-169 (2008).
Carter et al., "Humanization of an anti-p185 HER2 antibody for human cancer therapy" P Natl Acad Sci USA 89:4285-4289 (May 1992).
Chandra et al., "A common role for various human truncated adenomatous polyposis coli isoforms in the control of beta-catenin activity and cell proliferation" PLoS One 7(4):e34479 (Apr. 3, 2012).
Chari et al., "Immunoconjugates containing novel maytansinoids: Promising anticancer drugs" Cancer Res 52:127-131 (1992).
Chari, "Targeted Cancer Therapy: Conferring Specificity to Cytotoxic Drugs" Accounts of Chemical Research 41(1):98-107 ( 2008).
Charlton, K.A., "Expression and isolation of recombinant antibody fragments in E. coli" Method Molec Biol 248:245-254 (2003).
Chen et al., "The melanosomal protein PMEL17 as a target for antibody drug conjugate therapy in melanoma," J Biol Chem, 2012, 287:24082-24091.
Chen et al., "Selection and analysis of an optimized anti-VEGF antibody: crystal structure of an affinity-matured Fab in complex with antigen" J Mol Biol. 293(4):865-81 (1999).
Chothia and Lesk, "Canonical structures for the hypervariable regions of immunoglobulins" J Mol Biol 196(4):901-917 (1987).
Chowdhury, "Engineering hot spots for affinity enhancement of antibodies" Methods Molec Biol 207:179-196 (2008).
Clackson et al., "Making antibody fragments using phage display libraries" Nature 352:624-628 (Aug. 1991).
Clynes et al., "Fc receptors are required in passive and active immunity to melanoma" Proc. Natl. Acad. Sci. USA 95:652-656 (Jan. 1998).
Cragg et al., "Complement-mediated lysis by anti-CD20 mAb correlates with segregation into lipid rafts" Blood 101(3):1045-1052 (2003).
Cree et al., "Methotrexate chemosensitivity by ATP luminescence in human leukemia cell lines and in breast cancer primary cultures: comparison of the TCA-100 assay with a clonogenic assay" Anticancer Drugs 6:398-404 (1995).
Crouch et al., "The use of ATP bioluminescence as a measure of cell proliferation and cytotoxicity" J Immunol Methods 160:81-88 (1993).
Cunningham and Wells, "High-resolution epitope mapping of hGH-receptor interactions by alanine-scanning mutagenesis" Science 24:1081-1085 (Jun. 2, 1989).
Dall'Acqua et al., "Antibody humanization by framework shuffling" Methods 36:43-60 ( 2005).
Doronina et al., "Development of potent monoclonal antibody auristatin conjugates for cancer therapy" Nat Biotechnol 21(7):778-784 (Jul. 2003).
Doronina et al., "Enhanced activity of monomethylauristatin F through monoclonal antibody delivery: effects of linker technology on efficacy and toxicity" Bioconjug Chem 17(1):114-124 (Jan. 2006).
Dubowchik and Radia, "Monomethoxytrityl (MMT) as a versatile amino protecting group for complex prodrugs of anticancer com-

(56) References Cited

OTHER PUBLICATIONS pounds sensitive to strong acids, bases and nucleophiles" Tetrahedron Lett 38(30):5257-5260 (1997).
Dubowchik et al., "Doxorubicin immunoconjugates containing bivalent, lysosomally-cleavable dipeptide linkages" Bioorg Med Chem Lett 12:1529-32 (2002).
Duncan et al., "The binding site for C1q on IgG" Nature 322:738-740 (1988).
Fellouse et al., "Synthetic antibodies from a four-amino-acid code: A dominant role for tyrosine in antigen recognition" P Natl Acad Sci USA 101(34):12467-12472 (Aug. 24, 2004).
Flatman et al., "Process analytics for purification of monoclonal antibodies" J Chromatogr 848:79-87 (2007).
Foote et al., "Antibody Framework Residues Affecting the Conformation of the Hypervariable Loops" J Mol Biol 224:487-499 (1992).
Fraker and Speck, "Protein and cell membrane iodinations with a sparingly soluble chloroamide, 1,3,4,6-tetrachloro-3a,6a-diphenylglycoluril" Biochem Bioph Res Co 80(4):849-857 (1978).
Francisco et al., "cAC10-vcMMAE, an anti-CD30 monomethyl auristatin E conjugate with potent and selective antitumor activity" Blood 102(4):1458-1465 (Aug. 15, 2003).
Frisch et al., "Synthesis of short polyoxyethylene-based heterobifunctional cross-linking reagents. Application to the coupling of peptides to liposomes" Bioconj Chem 7:180-186 (1996).
Garrett and Eng, "Cetuximab in the treatment of patients with colorectal cancer," Expert Opin Biol Ther., 2001, 11:937-949.
Gazzano-Santoro et al., "A non-radioactive complement-dependent cytotoxicity assay for anti-CD20 monoclonal antibody" J Immunol Methods 202(2):163-171 (Mar. 28, 1997).
Geoghegan and Stroh, "Site-directed conjugation of nonpeptide groups to peptides and proteins via periodate oxidation of a 2-amino alcohol. Application to modification at N-terminal serine" Bioconjugate Chem. 3:138-146 (1992).
Gerngross, T. U, "Advances in the production of human therapeutic proteins in yeasts and filamentous fungi" Nat Biotech 22(11):1409-1414 (Nov. 2004).
Goldenberg et al., "Antibody pretargeting advances cancer radioimmunodetection and radioimmunotherapy," J Clin Oncol, 2006,24:823-834.
Graham et al., "Characteristics of a human cell line transformed by DNA from human adenovirus type 5" J Gen Virol 36(1):59-72 (Jul. 1977).
Grandi et al., "Novel anthracycline analogs" Cancer Treatment Reviews 17:133-138 (1990).
Griffiths et al., "Human anti-self antibodies with high specificity from phage display libraries" EMBO J 12(2):725-735 (1993).
Gruber et al., "Efficient tumor cell lysis mediated by a bispecific single chain antibody expressed in *Escherichia coli*" J Immunol 152:5368-5374 (1994).
Guyer et al., "Immunoglobulin binding by mouse intestinal epithelial cell receptors" J Immunol 117(2):587-593 (Aug. 1976).
Hamann, "Monoclonal antibody-drug conjugates" Expert Opin Ther Patents 15(9):1087-1103 (2005).
Hamblett et al., "Effect of drug loading on the pharmacology, pharmacokinetics and toxicity of an anti-CD30 antibody-drug conjugate," Abstract No. 624, American Association for Cancer Research; 2004 Annual Meeting, Mar. 27-31, 2004, Proceedings of the AACR' 45:52 (2004).
Hamblett et al., "Effects of drug loading on the antitumor activity of a monoclonal antibody drug conjugate" Clin Cancer Res 10:7063-7070 (2004).
Harper et al., "Premelanosome amyloid-like fibrils are composed of only golgi-processed forms of Pme117 that have been proteolytically processed in endosomes," J Biol Chem, 2008, 283:2307-2322.
Hartley et al., "SG2285, a novel C2-aryl-substituted pyrrolobenzodiazepine dimer prodrug that cross-links DNA and exerts highly potent antitumor activity" Cancer Res. 70(17):6849-6858 (2010).

Hay et al., "A 2-nitroimidazole carbamate prodrug of 5-amino-1-(chloromethyl)-3-[(5,6,7-trimethoxyindol-2-YL)carbonyl]-1,2-dihydro-3H-benz[E]indole (amino-seco-DB1-TMI) for use with ADEPT and GDEPT" Bioorg Med Chem Lett 9:2237-2242 (1999).
Herweijer and Wolff, "Progress and prospects: naked DNA gene transfer and therapy," Gene Ther., 2003, 10:453-458.
Hellstrom et al., "Antitumor effects of L6, an IgG2a antibody that reacts with most human carcinomas" P Natl Acad Sci USA 83:7059-7063 (Sep. 1986).
Hellstrom et al., "Strong antitumor activities of IgG3 antibodies to a human melanoma-associated ganglioside" P Natl Acad Sci USA 82:1499-1502 (Mar. 1985).
Hinman et al., "Preparation and characterization of monoclonal antibody conjugates of the calicheamicins: A novel and potent family of antitumor antibiotics" Cancer Res 53:3336-3342 (1993).
Hoashi et al., "The secreted form of a melanocyte membrane-bound glycoprotein (Pme117/gp100) is released by ectodomain shedding," FASEB J, 2010, 24:916-930.
Hollinger et al., "'Diabodies': Small Bivalent and Bispecific Antibody Fragments" Proc. Natl. Acad. Sci. USA 90:6444-6448 (Jul. 1993).
Holmes et al., "Identification of Heregulin, a Specific Activator of p185$^{erbB2}$" Science 256:1205-1210 (May 22, 1992).
Hoogenboom et al., "By-passing Immunisation; Human Antibodies from Synthetic Repertoires of Germline $V_H$ Gene Segments Rearranged in Vitro" J Mol Biol 227:381-388 (1992).
Hoogenboom et al., "Overview of antibody phage-display technology and its applications" Methods Mol Biol 178:1-37 ( 2002).
Hongo et al., "Characterization of novel neutralizing monoclonal antibodies specific to human neurturin" Hybridoma, 2000, 19:303-315.
Howard et al., "Synthesis of a novel C2/C2'-aryl-substituted pyrrolo[2,1-c][1,4]benzodiazepine dimer prodrug with improved water solubility and reduced DNA reaction rate" Bioorg Med Chem Lett 19(22):6463-6466 (2009).
Hudson et al., "Engineered antibodies" Nature Medicine 9(1):129-134 (Jan. 2003).
Hurley et al., "Covalent Binding of Antitumor Antibiotics in the Minor Groove of DNA. Mechanism of Action of CC-1065 and the Pyrrolo(1,4)benzodiazepines" Acc Chem Res 19:230-237 ( 1986).
Idusogie et al., "Mapping of the C1q Binding Site on Rituxan, A Chimeric Antibody with a Human IgG1 Fc" J Immunol 164(8):4178-4184 (2000).
Iyer & Kadambi, "Antibody drug conjugates—Trojan horses in the war on cancer" Journal of Pharmacological and Toxicological Methods 64:207-212 (2011).
Jeffrey et al., "Dipeptide-based highly potent doxorubicin antibody conjugates" Bioorganic Med Chem Letters 16:358-362 (2006).
Kam et al., "Carbon nanotubes as multifunctional biological transporters and near-infrared agents for selective cancer cell destruction" P Natl Acad Sci USA 102(33):11600-11605 (Aug. 2005).
Kanda et al., "Comparison of cell lines for stable production of fucose-negative antibodies with enhanced ADCC" Biotechnol Bioeng 94(4):680-688 (Jul. 5, 2006).
Kashmiri et al., "SDR grafting—a new approach to antibody humanization" Methods 36:25-34 (2005).
Kim et al., "Localization of the site of the murine IgG1 molecule that is involved in binding to the murine intestinal Fc receptor" Eur. J. Immunol. 24:2429-2434 (1994).
Kindt et al. Kuby Immunology "Antigens and Antibodies Chapter 4" 6th ed edition, N.Y.:W.H. Freeman and Co,:p. 91 (2007).
King et al., "Monoclonal antibody conjugates of doxorubicin prepared with branched peptide linkers: Inhibition of aggregation by methoxytriethyleneglycol chains" Journal of Medical Chemistry 45:4336-4343 (2002).
Kingsbury et al., "A novel peptide delivery system involving peptidase activated prodrugs as antimicrobial agents. Synthesis and biological activity of peptidyl derivatives of 5-fluorouracil" J Med Chem 27:1447-1451 (1984).
Klimka et al., "Human anti-CD30 recombinant antibodies by guided phage antibody selection using cell panning" BR J Cancer 83(2):252-260 (2000).

(56) References Cited

OTHER PUBLICATIONS

Klussman et al., "Secondary mAb-vcMMAE conjugates are highly sensitive reporters of antibody internalization via the lysosome pathway" Bioconjugate Chem 15:765-773 (2004).
Kohler et al., "Functional definition of the mutation cluster region of adenomatous polyposis coli in colorectal tumours" Hum Mol Genet 17(13):1978-1987 (2008).
Kohn Antibiotics "Anthramycin" Corcoran et al., New York, NY:Springer-Verlag, vol. 3:3-11 (1975).
Kostelny et al., "Formation of a bispecific antibody by the use of leucine zippers" J Immunol. 148:1547-1553 (Mar. 1, 1992).
Kozbor et al., "A human hybrid myeloma for production of human monoclonal antibodies" J Immunol 133(6):3001-3005 (Dec. 1984).
Kratz et al., "Prodrugs of anthracyclines in cancer chemotherapy" Curr Med Chem 13:477-523 (2006).
Kummer et al., "Formation of Pme117 amyloid is regulated by juxtamembrane metalloproteinase cleavage, and the resulting C-terminal fragment is a substrate for gamma-secretase," J Biol Chem., 2009, 284:2296-2306.
Lee et al., "Bivalent antibody phage display mimics natural immunoglobulin" J Immunol Methods 284(1-2):119-132 (2004).
Lee et al., "High-affinity human antibodies from phage-displayed synthetic Fab libraries with a single framework scaffold" J Mol Biol 340(5):1073-1093 (2004).
Leimgruber et al., "Isolation and characterization of anthramycin, a new antitumor antibiotic" J Am Chem Soc 87(24):5791-5793 (1965).
Leimgruber et al., "The structure of anthramycin" J Am Chem Soc 87(24):5793-5795 (1965).
Leonhardt et al., "Proprotein convertases process Pme117 during secretion," J Biol Chem., 2011, 286:9321-9337.
Leonhardt et al., "Endoplasmic reticulum export, subcellular distribution, and fibril formation by Pme117 require an intact N-terminal domain junction" J Biol Chem, 2010, 285:16166-1683.
Li et al., "Human antibodies for immunotherapy development generated via a human B cell hybridoma technology" Proc Natl Acad Sci USA 103:3557-3562 (2006).
Li et al., "Optimization of humanized IgGs in glycoengineered Pichia pastoris" Nat Biotechnol 24(2):210-215 (Feb. 2006).
Liang et al., "Function blocking antibodies to neuropilin-1 generated from a designed human synthetic antibody phage library" J. Mol. Biol. 366:815-829 (2007).
Liu et al., "Eradication of Large Colon Tumor Xenografts by Targeted Delivery of Maytansinoids." P Natl Acad Sci USA 93:8618-8623 (1996).
Liu et al., "Hydrodynamics-based transfection in animals by systemic administration of plasmid DNA," Gene Ther, 1999, 6:1258-1266.
Lode et al., "Targeted therapy with a novel enediyene antibiotic calicheamicin V11 effectively suppresses growth and dissemination of liver metastases in a syngeneic model of murine neuroblastoma" Cancer Res 58:2925-2928 (1998).
Lonberg, "Fully human antibodies from transgenic mouse and phage display platforms" Current Opin Immunol 20:450-459 (2008).
Lonberg, N., "Human antibodies from transgenic animals" Nat Biotechnol 23(9):1117-11125 (2005).
Lyon et al., "Conjugation of anticancer drugs through endogenous monoclonal antibody cysteine residues" Methods Enzymol 502:123-138 (2012).
MacCallum et al. et al., "Antibody-antigen Interactions: Contact Analysis and Binding Site Topography" J Mol Biol 262:732-745 (1996).
Mandler et al., "Immunoconjugates of geldanamycin and Anti-HER2 monoclonal antibodies: antiproliferative activity on human breast carcinoma cell lines" J National Cancer Institute 92(19):1573-1581 (Oct. 4, 2000).
Mandler et al., "Modifications in synthesis strategy improve the yield and efficacy of geldanamycin—herceptin immunoconjugates" Bioconjugate Chem 13:786-791 (2002).
Mandler et al., "Synthesis and Evaluation of Antiproliferative Activity of a Geldanamycin-Herceptin(tm) Immunoconjugate" Bioorg Med Chem Lett 10:1025-1028 (2000).
Marks et al., "By-passing immunization, Human antibodies from V-gene libraries displayed on phage" J. Mol. Biol.222:581-597 (1991).
Marks et al., "Selection of human antibodies from phage display libraries" Methods Mol Biol. 248:161-76 (2004).
Mather et al., "Culture of testicular cells in hormone-supplemented serum-free medium" Ann NY Acad Sci 383:44-68 (1982).
Mather, "Establishment and characterization of two distinct mouse testicular epithelial cell lines" Biol Reprod 23:243-252 (1980).
McCafferty et al., "Phage Antibodies: Filamentous Phage Displaying Antibody Variable Domains" Nature 348:552-554 (Dec. 1990).
McDonagh et al., "Engineered antibody-drug conjugates with defined sites and stoichiometries of drug attachment" Protein Eng Des Sel. 19(7):299-307 (2006).
Milstein et al., "Hybrid hybridomas and their use in immunohistochemistry" Nature 305:537-540 (Oct. 6, 1983).
Morrison et al., "Chimeric human antibody molecules: Mouse antigen-binding domains with human constant region domains" P Natl Acad Sci USA 81:6851-6855 (Nov. 1984).
Nagy et al., "Stability of cytotoxic luteinizing hormone-releasing hormone conjugate (AN-152) containing doxorubicin 14-O-hemiglutarate in mouse and human serum in vitro: implications for the design of preclinical studies" P Natl Acad Sci USA 97(2):829-34 (Jan. 18, 2000).
Neuberger et al., "Recombinant Antibodies Possessing Novel Effector Functions" Nature 312:604-608 (Dec. 13, 1984).
Ni, "Research progress and future perspectives in antibodomics and antibodomic drugs" Xiandai Mianyixue ((Abstract only)), 26(4):265-168 (2006).
Nichols et al., "A Novel Splice Variant of Pme117 Expressed by Human Melanocytes and Melanoma Cells Lacking Some of the Internal Repeats," J Invest Dermatol, 2003, 121:821-830.
Okazaki et al., "Fucose depletion from human IgG1 oligosaccharide enhances binding enthalpy and association rate between IgG1 and FcγRIIIa" J Molec Biol 336:1239-1249 (2004).
Osbourn et al., "From rodent reagents to human therapeutics using antibody guided selection" Methods 36:61-68 (2005).
Pacciarini et al., "Phase I/II trial of nemorubicin hydrochloride in combination with cisplatin is supported by new preclinical evidences of its mechanism of action" J Clin Oncol (Abstract from 2006 ASCO Annual Meeting Proceedings (Post-Meeting Edition)), 24( Suppl 185):14116 (Jun. 20, 2006).
Padlan, "A possible procedure for reducing the immunogenicity of antibody variable domains while preserving their ligand-binding properties" Mol Immunol 28(4/4):489-498 (1991).
Peterson et al. Anthracycline Antibiotics in Cancer Therapy "Transport and Storage of Anthracyclines in Experimental Systems and Human Leukemia" Muggia et al., The Hague:Martinus Nijhoff,:132-146 (1981).
Petkova et al., "Enhanced half-life of genetically engineered human IgG1 antibodies in a humanized FcRn mouse model:potential application in humorally mediated autoimmune disease" Int Immunol 18(12):1759-69 (Dec. 2006).
Pettit et al., "Dolastatins 24: synthesis of (-)-dolastatin $10^1$ X-ray molecular structure of N,N-dimethylvalyl-valyl-dolaisoleuine tert-butyl ester" J Chem Soc Perkins Trans 1:859-863 (1996).
Pettit et al., "Specific activities of dolastatin 10 and peptide derivatives against cryptococcus neoformans" Antimicrob Agents and Chemotherapy 42(11):2961-2965 (Nov. 1998).
Pettit et al., "The absolute configuration and synthesis of natural (-)-Dolastatin $101^1$" J Am Chem Soc 111:5463-5465 (1989).
Pettit et al., "The dolastatins; 18: stereospecific synthesis of dolaproine" Synthesis:719-725 (Jun. 1996).
Pluckthun, A. The Pharmacology of Monoclonal Antibodies: Handbook of Pharmacology "Antibodies from *Escherichia coli*" (Chapter 11), Rosenberg and Moore, eds., Berlin:Springer-Verlag, vol. 113:269-315 (1994).
Polakis, "Arming antibodies for cancer therapy" Curr Opin Pharm 5:382-387 (2005).

(56) References Cited

OTHER PUBLICATIONS

Portolano et al., "Lack of promiscuity in autoantigen-specific H and L chain combinations as revealed by human H and L chain 'Roulette'" J Immunol 150(3):880-887 (Feb. 1993).
Presta et al., "Humanization of an Antibody Directed Against IgE" J Immunol 151(5):2623-2632 (Sep. 1, 1993).
Presta et al., "Humanization of an anti-vascular endothelial growth factor monoclonal antibody for the therapy of solid tumors and other disorders" Cancer Res 57:4593-4599 (Oct. 1997).
Queen et al., "A humanized antibody that binds to the interleukin 2 receptor" P Natl Acad Sci USA 86(24):10029-10033 (Dec. 1989).
Quintieri et al., "Formation and antitumor activity of PNU-159682, a major metabolite of nemorubicin in human liver microsomes" Clin Cancer Res 11:1608-17 (Feb. 15, 2005).
Quintieri et al., "In vitro cytotoxicity, cell cycle effects and DNA-binding properties of PNU-159682" Abstract (Abs #4649) Proceedings of the American Association of Cancer Research, pp. 925 (2003).
Raposo et al., "Distinct protein sorting and localization to premelanosomes, melanosomes, and lysosomes in pigmented melanocytic cells," J Biol Chem, 2001, 152:809-824.
Raposo and Marks, "Melanosomes—dark organelles enlighten endosomal membrane transport," Nat Rev Mol Cell Biol, 2007, 8:786-797.
Ravetch and Kinet, "Fc receptors" Ann Rev Immunol 9:457-492 (1991).
Remington's Pharmaceutical Sciences (Table of Contents), Osol, 16 edition, Easton, PA:Mack Publishing Company,:TOC (1980).
Ricart & Tolcher, "Technology Insight: cytotoxic drug immunoconjugates for cancer therapy" Nature Clinical Practice 4(4):245-255 (2007).
Riechmann et al., "Reshaping human antibodies for therapy" Nature 332:323-327 (Mar. 1988).
Ripamonti et al., "In vivo anti-tumour activity of FCE 23762, a methoxymorpholinyl derivative of doxorubicin active on doxorubicin-resistant tumour cells" Br J Cancer 65(5):703-707 (1992).
Ripka et al., "Two chinese hamster ovary glycosylation mutants affected in the conversion of GDP-mannose to GDP-fucose" Arch Biochem Biophys 249(2):533-545 (Sep. 1986).
Rodrigues et al., "Synthesis and β-lactamase-mediated activation of a cephalosporin-taxol prodrug" Chem Biol 2:223-227 (Apr. 1995).
Robila et al., "MHC class II presentation of gp100 epitopes in melanoma cells requires the function of conventional endosomes and is influenced by melanosomes," J Immunol, 2008, 181:7843-7852.
Rosok et al., "A combinatorial library strategy for the rapid humanization of anticarcinoma BR96 Fab" J Biol Chem 271(37):22611-22618 (Sep. 13, 1996).
Saleh et al., "Phase I trial of the anti-Lewis Y drug immunoconjugate BR96-doxorubicin in patients with lewis Y-expressing epithelial tumors" J Clin Oncol 18(11):2282-2292 (2000).
Schallreuter et al., "Regulation of melanogenesis—controversies and new concepts," Exper Dermatol, 2008, 17:395-404.
Shields et al. et al., "High resolution mapping of the binding site on human IgG1 for Fc gamma RI, Fc gamma RII, Fc gamma RIII, and FcRn and design of IgG1 variants with improved binding to the Fc gamma R" J Biol Chem 276(9):6591-6604 (Mar. 2, 2001).
Sidhu et al., "Phage-displayed antibody libraries of synthetic heavy chain complementarity determining regions" J Mol Biol 338(2):299-310 (2004).
Sims et al., "A Humanized CD18 Antibody Can Block Function without Cell Destruction" J. Immunol. 151(4):2296-2308 (Aug. 1993).
Somers et al., "The X-ray structure of a growth hormone-prolactin receptor complex" Nature 372:478-481 (1994).
Storm et al., "Effect of small changes in orientation on reaction rate" J Am Chem Soc 94:5815-5825 (1972).
Sun et al., "Enabling ScFvs as multi-drug carriers: a dendritic approach" Bioorg Med Chem 11:1761-1768 (2003).
Sun et al., "Phase I and pharmacokinetic study of nemorubicin hydrochloride (methoxymorpholino doxorubicin; PNU-152243) administered with iodinated oil via hepatic artery (IHA) to patients (pt) with unrestectable hepatocellular carcinoma (HCC)" Abstract (Abs #1448) 39th Annual Meeting of the American Society of Clinical Oncology, Chicago, IL, pp. 361 (May 31, 2003).
Sun et al., "Syntheses of dendritic linkers containing chlorambucil residues for the preparation of antibody-multidrug immunoconjugates" Bioorg Med Chem Lett 12:2213-2215 (2002).
Teicher, "Antibody-Drug Conjugate Targets" Current Cancer Drug Targets 9:982-1004 (2009).
Theos et al. "The Silver locus product Pme117/gp100/Silv/ME20: controversial in name and in function," Pigment Cell Res., 2005, 18:322-336.
Theos et al., "Dual loss of ER export and endocytic signals with altered melanosome morphology in the silver mutation of Pme117," Mol Biol Cell, 2006, 17:3598-3612.
Thurston and Bose, "Synthesis of DNA-Interactive Pyrrolo[2,1-c][1,4]benzodiazepines" Chem Rev 94:433-465 (1994).
Tijink et al., "A phase I dose escalation study with anti-CD44v6 bivatuzumab mertansine in patients with incurable squamous cell carcinoma of the head and neck or esophagus," Clin Cancer Res, 2006, 12:6064-6072.
Toki et al., "Protease-mediated fragmentation of p-amidobenzyl ethers: A new strategy for the activation of anticancer prodrugs" J Org Chem 67:1866-1872 (2002).
Tolcher et al., "Randomized phase II study of BR96-doxorubicin conjugate in patients with metastatic breast cancer" J Clin Oncol 17(2):478-484 (1999).
Torgov et al., "Generation of an intensely potent anthracycline by a monoclonal antibody—β-galactosidase conjugate" Bioconjugate Chem 16:717-21 (2005).
Traunecker et al., "Bispecific single chain molecules (Janusins) target cytotoxic lymphocytes on HIV infected cells" EMBO J 10(12):3655-3659 (1991).
Tutt et al., "Trispecific F(ab')$_3$ derivatives that use cooperative signaling via the TCR/CD3 complex and CD2 to activate and redirect resting cytotoxic T cells" J Immunol 147(1):60-69 (Jul. 1991).
Uong and Zon, "Melanocytes in development and cancer," J Cell Physiol, 2010, 222:38-41.
Urlaub et al., "Isolation of chinese hamster cell mutants deficient in dihydrofolate reductase activity" P Natl Acad Sci USA 77(7):4216 (Jul. 1980).
Vachtenheim and Borovansky, "'Transcription physiology' of pigment formation in melanocytes: central role of MITF," Exp Dermatol, 2010, 19:617-627.
Valencia et al., "Sorting of Pme117 to melanosomes through the plasma membrane by AP1 and AP2: evidence for the polarized nature of melanocytes," J Cell Sci, 2006, 119:1080-1091.
van Dijk and van de Winkel, "Human antibodies as next generation therapeutics" Curr Opin Chem Biol 5(4):368-74 (Aug. 2001).
Van Dongen et al., "Immuno-PET: A navigator in monoclonal antibody development and applications" Oncologist 12:1379-1389 (2007).
Verel et al., "$^{89}$Zr Immuno-PET: Comprehensive Procedures for the production of $^{89}$Zr-labeled monoclonal antibodies" J Nucl Med 44(8):1271-1281 (Aug. 2003).
Vollmers and Brandlein, "Death by stress: natural IgM-induced apoptosis" Methods Find Exp Clin Pharmacol 27(3):185-191 (2005).
Vollmers and Brandlein, "The 'early birds': Natural IgM antibodies and immune surveillance" Histol Histopathol 20:927-937 (2005).
Walker, M., "A high yielding synthesis of N-Alkyl maleimides using a novel modification of the Mitsunobu reaction" J Org Chem 60:5352-5355 (1995).
Watt et al., "N-terminal domains elicit formation of functional Pme117 amyloid fibrils," J Biol Chem, 2009, 284:35543-35555.
Wicki et al., "Kras in metastatic colorectal cancer" Swiss Med Wkly 140:w13112 (2010).
Widdison et al., "Semisynthetic Maytansine Analogues for the Targeted Treatment of Cancer" J Med Chem 49:4392-4408 (2006).

(56) References Cited

OTHER PUBLICATIONS

Wilhite and Barrett, "Strategies to explore functional genomics data sets in NCBI's GEO database," Methods Mol Biol., 2012, 802:41-53.
Winter et al., "Making antibodies by phage display technology" Annu Rev Immunol 12:433-455 (1994).
Woyke et al., "In vitro activities and postantifungal effects of the potent dolastatin 10 derivative auristatin PHE" Antimicrob Agents Chemother 45(12):3580-3584 (Dec. 2001).
Wright and Morrison, "Effect of glycosylation on antibody function: Implications for genetic engineering" Trends Biotechnol 15:26-32 (1997).
Wu and Kabat, "An analysis of the sequences of the variable regions of Bence Jones proteins and myeloma light chains and their implications for antibody complementarity" J Exp Med 132(2):211-250 (1970).
Yamaguchi and Hearing, "Physiological factors that regulate skin pigmentation," Biofactors, 2009, 35:193-199.
Yamane-Ohnuki et al., "Establishment of FUT8 knockout Chinese hamster ovary cells: an ideal host cell line for producing completely defucosylated antibodies with enhanced antibody-dependent cellular cytotoxicity" Biotechnol Bioeng 87(5):614-622 (Sep. 5, 2004).
Yasumoto et al., "Epitope mapping of the melanosomal matrix protein gp100 (PMEL17): rapid processing in the endoplasmic reticulum and glycosylation in the early Golgi compartment" J Biol Chem., 2004, 279:28330-28338.
Yazaki and Wu Methods in Molecular Biology Lo, B.K.C. (ed.), Totowa, NJ:Humana Press, vol. 248:255-268 (2004).
Younes et al., "Brentuximab vedotin (SGN-35) for relapsed CD30-positive lymphomas," N Engl J Med., 2010, 363:1812-1821.
Younes et al., "Brentuximab vedotin," Nat Rev Drug Discov, 2012, 11:19-20.
Yokota, "Are KRAS/BRAF mutations potent prognostic and/or predictive biomarkers in colorectal cancers?" Anticancer Agents Med Chem 12(2):163-171 (2012).
Yu et al., "The biosynthetic gene cluster of the maytansinoid antitumor agent ansamitocin from Actinosynnema pretiosum" P Natl Acad Sci USA 99(12):7968-7973 (Jun. 11, 2002).
Zhang et al., "High levels of foreign gene expression in hepatocytes after tail vein injections of naked plasmid DNA," Hum Gene Ther, 1999, 10:1735-1737.
Invitation to Pay Additional Fees and, Where Applicable, Protest Fee, for PCT/US2013/038742, mailed Jul. 15, 2013, 8 pages.
International Search Report and Written Opinion for PCT/US2013/038742, mailed Sep. 23, 2013, 19 pages.
Paul, Fundamental Immunology, $3^{rd}$ Edition, 1993, pp. 292-295.
Rudikoff et al., Proc. Natl. Acad. Sci. USA, 1982 vol. 79, p. 1979.
Pascalis et al., The Journal of Immunology, 2002, 169, 3076-3084.
Casset et al. (2003) BBRC 307, 198-205.
Brown et al., J. Immunol., May 1996; 156(9): 3285-3291.
Vajdos et al., J. Mol. Biol., Jul. 5, 2002; 320(2): 415-428.
Klein et al., "Epitope interactions of monoclonal antibodies targeting CD20 and their relationship to functional properties," mAbs, 5(1): 22-33 (2013).

* cited by examiner

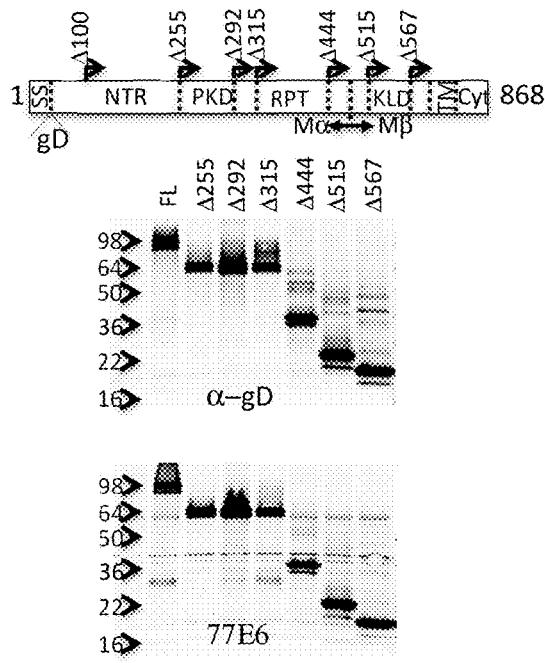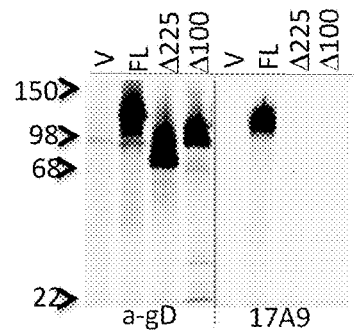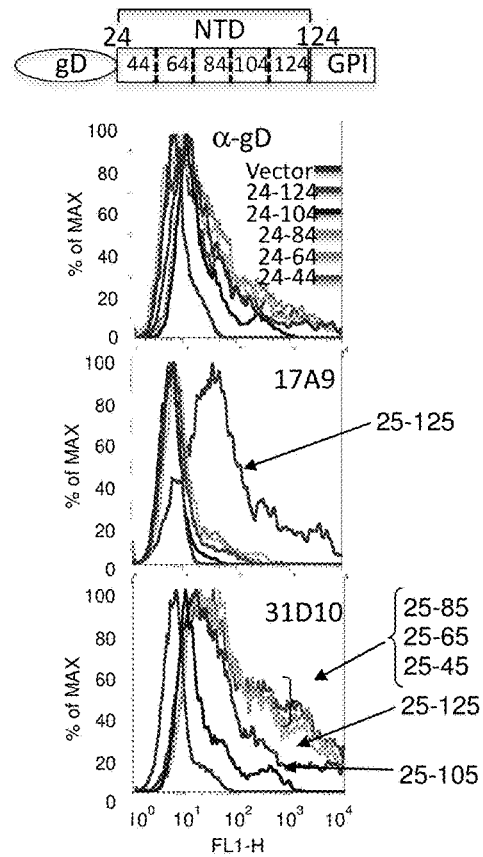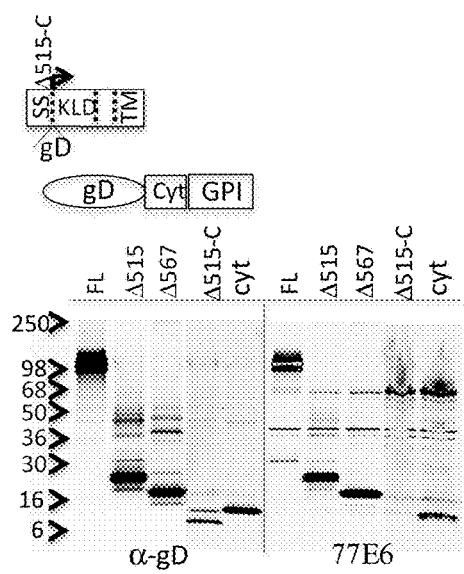

FIG. 7B IHC scores for human melanoma (n=58)

```
rat    -MGVQRRCFLPVLVLGALLALGSIEGSRNQNMWHGVSRQLVTKVNKQLYPEWTEVQGSNC    59
mouse  -MGVQRRSFLPVLVLSALLAVGALEGSRNQDWLGVPRQLVTKTWNRQLYPEWTEVQGSNC   59
human  MDLVLKRCLLHLAVIGALLAVGATKVPRNQDWLGVSRQLRTKAWNRQLYPEWTEAQRLDC   60
cyno   ------------------------KGPRNQDWLGVSRQLRTKAWNRQLYPEWTEAQRLDC   36
                                  .  .**. .*   ******:*:*** * .:* rat    WRGGQVSLKVRNDGPTLVGANTSFSIALHFPGSQKVLPDGQVIWVNNTIINGSQVWGGQP  119
mouse  WRGGQVSLRVINDGPTLVGANASFSIALHFPGSQKVLPDGQVIWANNTIINGSQVWGGQP  119
human  WRGGQVSLKVSNDGPTLIGANASFSIALNFPGSQKVLPDGQVIWVNNTIINGSQVWGGQP  120
cyno   WRGGQVSLKVSNDGPTLIGANASFSIALNFPGSQKVLPDGQVIWVNNT.IINGSQVWGGQP 96
       ********:*  ***::*:************.*********** rat    VYPREPDDACIFPDGGPCPSGPKPPRRSFVYVWKTWGQYWQVLGGPESKLSIPTGHARLG  179
mouse  VYPQEPDDACVFPDGGPCPSGPKPPKRSFVYVWKIWGKYWQVLGCPVSRLSIATGHAKLG  179
human  VYPQETDDACIFPDGGPCPSGSWSQKRSFVYVWKIWGQYWQVLGGPVSGLSIGTGRAMLG  180
cyno   VYPQETDDACIFPDGGPCPSGPWSQKRSFVYVWKTWGQYWQVLGGPVSGLSIGTGRAMLG  156
       ***:*:****:**********  *:*********:**:******** **** ** **:**

rat    THTMEVTVYHRRGSQSYVPLAHSSSSIFTIT-----------------------------  209
mouse  THTMEVTVYHRRGSQSYVPLAHASSIFTITTDQVPFSVSVSQLQALDGETKHFLRNHPLIF  239
human  THTMEVTVYHRRGSRSYVPLAHSSSAFTITDQVPFSVSVSQLRALDGGNKHFLRNQPLTF  240
cyno   THTMEVTVYHRRGSRSYVPLAHSSSAFTITDQVPFSVSVSQLRALDGGNKHFLRNQPLTF  216
       ************:***: **** +++++++ ++    +++++ ++ +++++ rat    ALQLHDPSGYLAEADLSYTWDFGDGTGTLLISRALDVTHTLESGSSVTAQVVLQAAIPLVS  299
mouse  ALQLHDPSGYLAEADLSYTWDFGDSSGTLISRALVVIHTLEPGPVTAQVVLQAVIPLTS  300
human  ALQLHDPSGYLAEADLSYTWDFGDSSGTLISRALVVIHTYLEPGPVTAQVVLQAAIPLTS  276
       ++ ++ +++++++++++++++++   +++++++   +  +    +++ ++++   ++ + rat    CGSSPVPGTTDGYMPTAEAPGTISRQGTITKVVGTIPGQMPTIQPSGTIVVQMPTIEVIA  359
mouse  CGSSPVPGTTDGHRPTAEAPNTTAGQVPTTEVVGTIPGQAPTAEPSGTESVQVPTTEVIS  360
human  CGSSPVPGTTDGHRPTAEAPDTTAGRGPTTEVVGTIPGVPTTQPSGTTSVQVPTTEVIS  336
       ++ +++ +++++   ++++  +  ++  ++ ++++++++    ++    ++  ++ ++

FIG. 9A rat   SEQ ID NO: 29
mouse SEQ ID NO: 31
human SEQ ID NO: 26
cyno  SEQ ID NO: 28
```

```
rat     TTSEQMLTSA--------------------VIDTTLAEVSTTEGTGTTPIRPSGTIVA----------  397
mouse   TAPVQMPTAESTGMTPEKVPVSEVMGTTLAEMSTPEATGMTPAEVSIVVLSGTTAAQVTT           420
human   TTPVQMPTAESTGITPEKVPVSEVMGTTLAEMSTPEAIGMTPAEVSIVVPSGTTAAQVTT           396
cyno                                                                          
          +   ++++++ ++ ++++++ ++ +++++ + + ++ +++++ +  +++ ++ rat     ------------QATTTEGPDASPLLPTQSSTGSIGSLGPLLDGTATLRLIVKRQVPLDCVLYRY      238
mouse   -------GSVSRLLDDTIMLVKRQVPLDCVLYRY                                     446
human   IEWVETTAREPLPIPEPEGPDASSIMSTESIIGSLGPLLDGTATLRLIVKRQVPLDCVLYRY         480
cyno    IEWVETTAGELPTPEPEGPDTSSIMSTESIIGSLGPLLDGTATLRLEKRQVPLDCVLYRY           456
             + +   *** *: . * :************* rat     GSFSLILDIVQGIESAEILQAVPSSEGDAFELTVSCRGGLPKEACMDISSPGCQPPAQRL           298
mouse   GSFSLALDIVQGIESAEILQAVPFSEGDAFELTVSCQGGLPKEACMDISSPGCQPPAQRL           506
human   GSFSVTLDIVQGIESAEILQAVPSGEGDAFELTVSCQGGLPKEACMEISSPGCQPPAQRL           540
cyno    GSFSVTLDIVQGIESAEILQVVPSSEGDAFELTVSCQGGLPTEACMEISSPGCQPPAQQL           516
        **:  :.:*: . * *  *****: * ***********  * rat     CQPVPPSPDCQLVLHQILKGGLGTYCLNVSLADANSLAVASTQLVVPGQEGSLGQAPLLV           358
mouse   CQSVPPSPDCQLVLHQVLKGGSGTYCLNVSLADANSLAVASTQLVVPGQDGGLGQAPLLV           566
human   CQPVLPSPACQLVLHQILKGGSGTYCLNVSLADINSLAVVSTQLIMPGQEAGLGQVPLIV           600
cyno    CQPVPPSPACQLVLYQILKGGLGTYCLNVSLADANSLAVVSTQLIVPGQEAGLGQAPLFV           576
        ** *  .*** *:** *******:*.:: .:.  **::* rat     GVLLVLVAVVLASLIYRHRLKKQD-SVSQTPHGSTHWLRLPPVFCARRLGESSPLLSGQQ           417
mouse   GILLVLVAVVLASLIHRHRLKKQG-SVSQMPHGSTHWLRLPPVFRARGLGENSPLLSGQQ           625
human   GILLVLMAVVLASLIYRRRLMKQDFSVPQLPHSSSHWLRLPRIFCSCPIGENSPLLSGQQ           660
cyno    GILLVLMAVVLASLIYRRRLMKQAFSIPQLPHGSSHWLRLPRIFRSCPIGRSCPIGQE            636
        *:****:*******:*::**:**  *::  **.*:*****   :*    :*.****  :

rat     V 418  SEQ ID NO: 29
mouse   V 626  SEQ ID NO: 31
human   V 661  SEQ ID NO: 26
cyno    V 637  SEQ ID NO: 28
        *
```

FIG. 9B

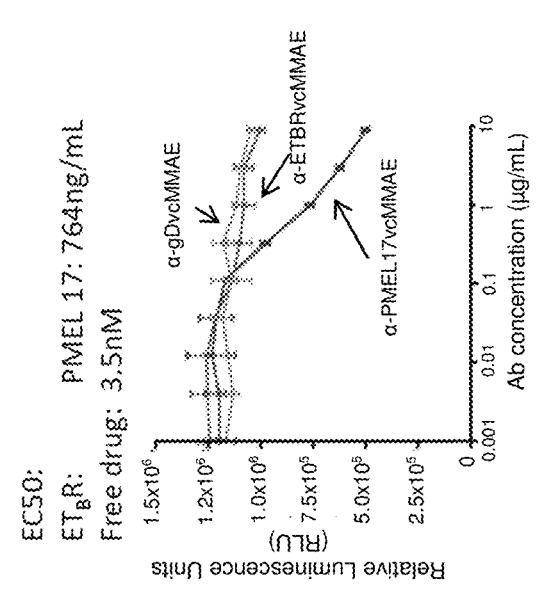
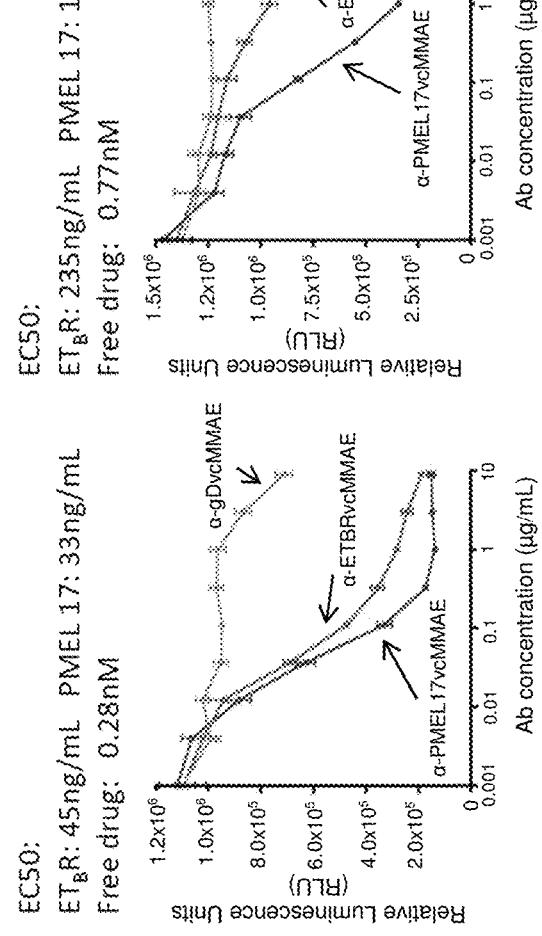
FIG. 12A Parental  FIG. 12B IN VIVO DERIVED  FIG. 12C IN VITRO DERIVED

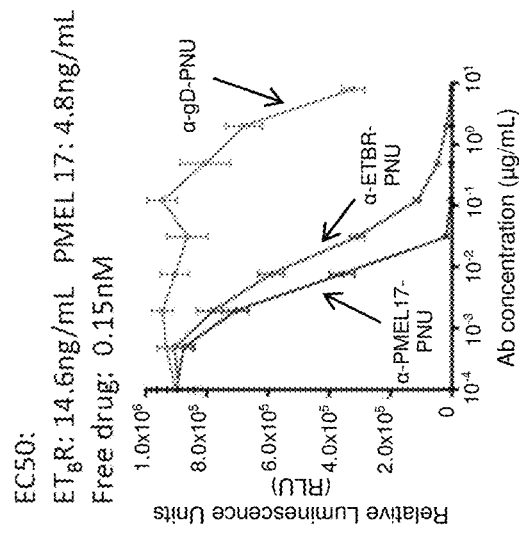
FIG. 13A  Parental
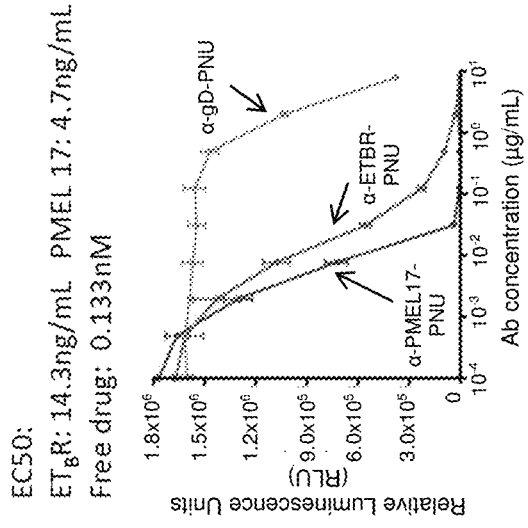
FIG. 13B  IN VIVO DERIVED
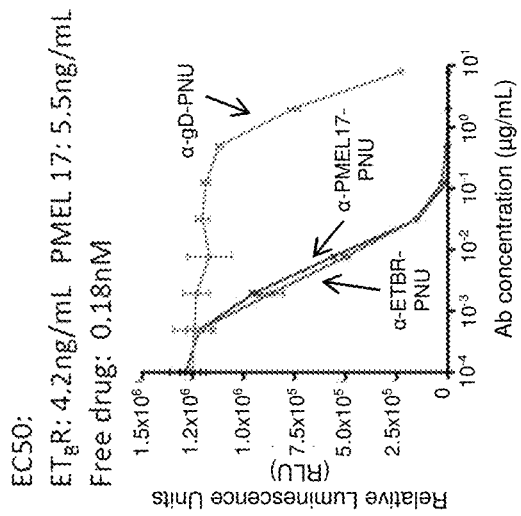
FIG. 13C  IN VITRO DERIVED

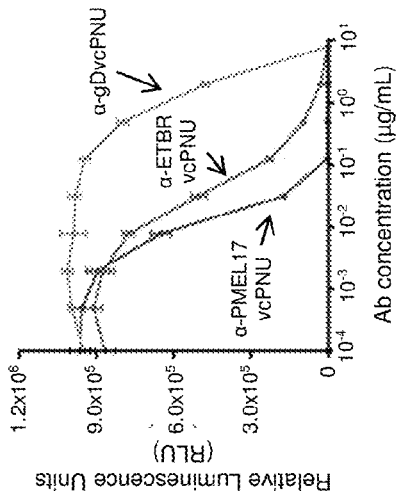
FIG. 14A  Parental
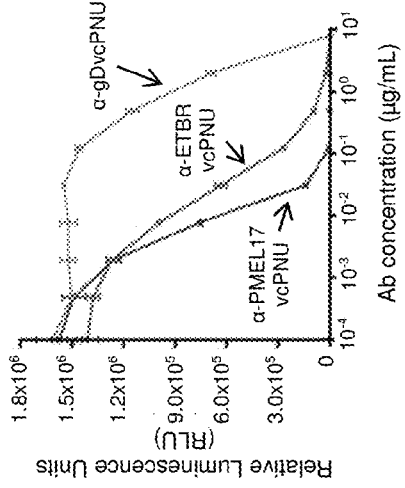
FIG. 14B  IN VIVO DERIVED
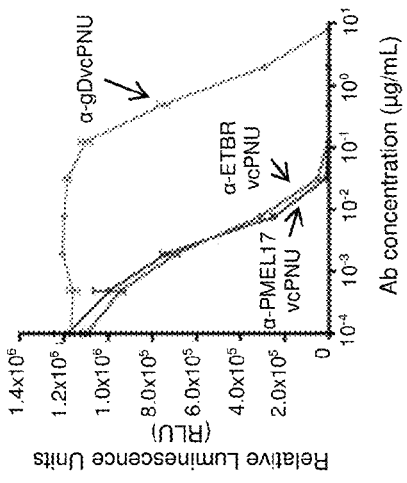
FIG. 14C  IN VITRO DERIVED

*FIG. 15A*  Ab-MC-val-cit-PAB-MMAE
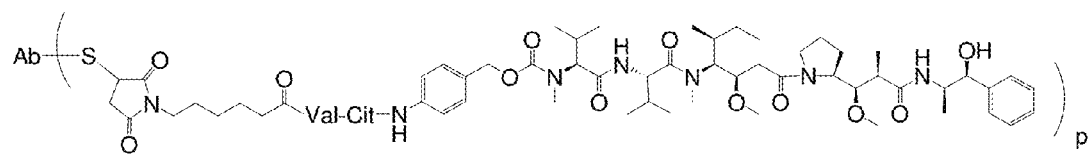
*FIG. 15B*  Ab-MC-acetal-PNU-159682
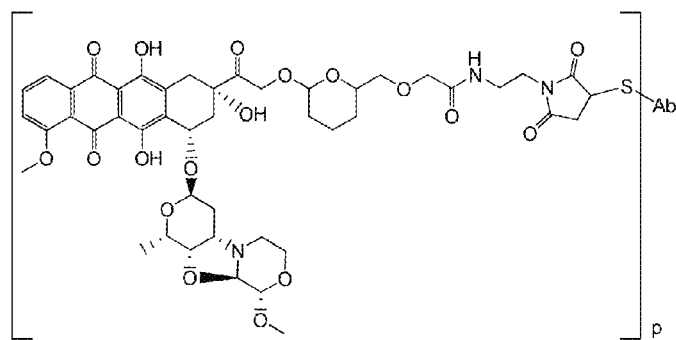
*FIG. 15C*  Ab-MC-val-cit-PAB-PNU-159682
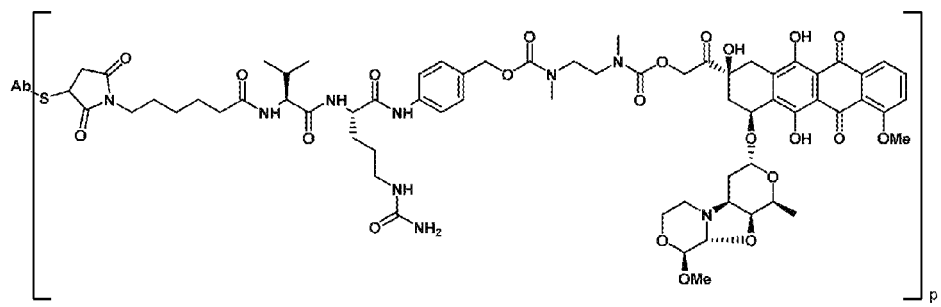

*FIG. 15D*  Ab-MC-val-cit-PAB-PBD
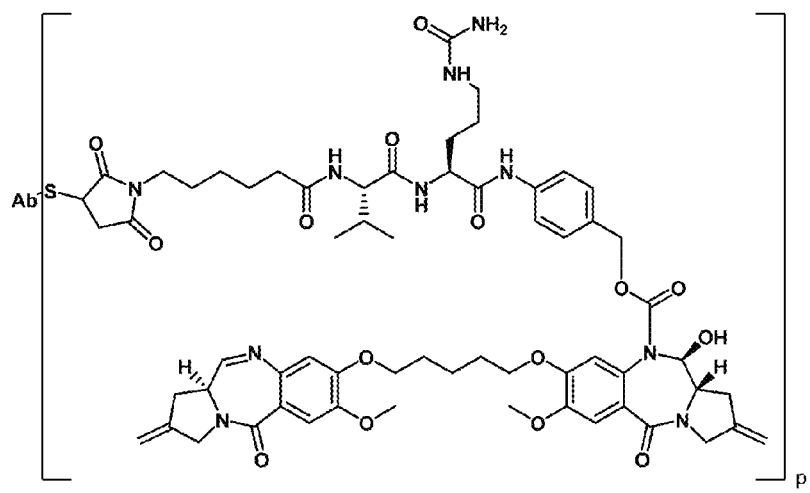
*FIG. 15E*  Ab-PNU-159682
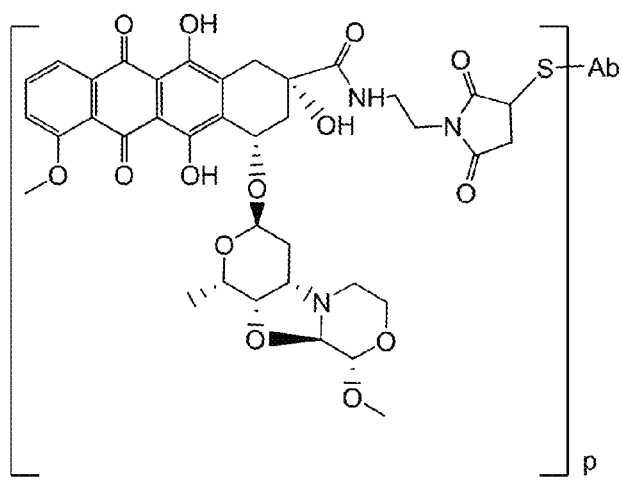

SEQUENCE LISTING

<160> NUMBER OF SEQ ID NOS: 51

<210> SEQ ID NO 1
<211> LENGTH: 122
<212> TYPE: PRT
<213> ORGANISM: Mus musculus

<400> SEQUENCE: 1

```
Glu Val Gln Leu Gln Gln Ser Gly Pro Glu Leu Val Lys Pro Gly Ala
1               5                   10                  15

Ser Met Lys Ile Ser Cys Lys Ser Ser Gly Tyr Ser Phe Thr Arg Tyr
            20                  25                  30

Thr Met Asn Trp Val Lys Gln Ser His Gly Lys Asn Leu Glu Trp Ile
        35                  40                  45

Gly Val Ile Asn Pro Tyr Asn Gly Gly Thr Val Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Thr Asp Tyr Asp Gly Tyr Ala Met Asp Tyr Trp Gly Gln Gly
            100                 105                 110

Thr Ser Val Thr Val Ser Ser Ala Lys Thr
        115                 120
```

<210> SEQ ID NO 2
<211> LENGTH: 107
<212> TYPE: PRT
<213> ORGANISM: Mus musculus

<400> SEQUENCE: 2

```
Asp Val Gln Ile Thr Gln Ser Pro Ser Tyr Leu Ala Ala Ser Pro Gly
1               5                   10                  15

Glu Thr Ile Thr Ile Asn Cys Arg Ala Thr Lys Ser Ile Ser Lys Tyr
            20                  25                  30

Leu Ala Trp Tyr Gln Glu Gln Pro Gly Lys Thr Asn Asn Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Tyr
                85                  90                  95
```

Thr Phe Gly Ser Gly Thr Lys Leu Glu Ile Lys
            100                 105

<210> SEQ ID NO 3
<211> LENGTH: 10
<212> TYPE: PRT
<213> ORGANISM: Mus musculus

<400> SEQUENCE: 3

Gly Tyr Ser Phe Thr Arg Tyr Thr Met Asn
1               5                   10

<210> SEQ ID NO 4
<211> LENGTH: 17
<212> TYPE: PRT
<213> ORGANISM: Mus musculus

<400> SEQUENCE: 4

Val Ile Asn Pro Tyr Asn Gly Gly Thr Val Tyr Asn Gln Lys Phe Lys
1               5                   10                  15

Gly

<210> SEQ ID NO 5
<211> LENGTH: 10
<212> TYPE: PRT
<213> ORGANISM: Mus musculus

<400> SEQUENCE: 5

Thr Asp Tyr Asp Gly Tyr Ala Met Asp Tyr
1               5                   10

<210> SEQ ID NO 6
<211> LENGTH: 11
<212> TYPE: PRT
<213> ORGANISM: Mus musculus

<400> SEQUENCE: 6

Arg Ala Thr Lys Ser Ile Ser Lys Tyr Leu Ala
1               5                   10

<210> SEQ ID NO 7
<211> LENGTH: 7
<212> TYPE: PRT
<213> ORGANISM: Mus musculus

<400> SEQUENCE: 7

Ser Gly Ser Thr Leu Gln Ser
1               5

<210> SEQ ID NO 8
<211> LENGTH: 9
<212> TYPE: PRT
<213> ORGANISM: Mus musculus

<400> SEQUENCE: 8

Gln Gln His Asn Glu Tyr Pro Tyr Thr
1               5

<210> SEQ ID NO 9
<211> LENGTH: 122
<212> TYPE: PRT
<213> ORGANISM: Mus musculus

<400> SEQUENCE: 9

-continued

Glu Val Gln Leu Gln Gln Ser Gly Pro Glu Leu Val Lys Pro Gly Ala
1               5                   10                  15

Ser Met Arg Ile Ser Cys Lys Ala Ser Gly Tyr Ser Phe Thr Gly Tyr
            20                  25                  30

Thr Met Asn Trp Val Lys Gln Ser His Gly Lys Asn Leu Glu Trp Ile
            35                  40                  45

Gly Val Tyr Asn Pro Tyr Asn Gly Gly Thr Val Tyr Asn Gln Lys Phe
        50                  55                  60

Lys Gly Lys Ala Thr Leu Thr Val Asp Lys Ser Ser Ser Thr Thr Tyr
65                  70                  75                  80

Met Glu Leu Leu Ser Leu Thr Ser Glu Asp Ser Ala Val Tyr Tyr Cys
                85                  90                  95

Ala Arg Thr Asp Ser Gly Gly Tyr Ala Met Asp Cys Trp Gly Gln Gly
            100                 105                 110

Thr Ser Val Thr Val Ser Ser Ala Lys Thr
            115                 120

<210> SEQ ID NO 10
<211> LENGTH: 107
<212> TYPE: PRT
<213> ORGANISM: Mus musculus

<400> SEQUENCE: 10

Asp Val Gln Ile Thr Gln Ser Pro Ser Tyr Leu Asp Ala Ser Pro Gly
1               5                   10                  15

Glu Thr Ile Thr Ile Asn Cys Arg Ala Ser Lys Thr Ile Ser Lys Tyr
            20                  25                  30

Leu Ala Trp Tyr Gln Glu Lys Pro Gly Lys Thr Asn Lys Leu Leu Ile
            35                  40                  45

Tyr Ser Gly Ser Thr Leu Gln Ser Gly Ile Pro Ser Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Tyr
                85                  90                  95

Thr Phe Gly Ser Gly Thr Lys Leu Glu Ile Lys
            100                 105

<210> SEQ ID NO 11
<211> LENGTH: 114
<212> TYPE: PRT
<213> ORGANISM: Mus musculus

<400> SEQUENCE: 11

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Lys Tyr
            20                  25                  30

Gly Val His Trp Val Arg Gln Pro Pro Gly Lys Gly Leu Glu Trp Leu
            35                  40                  45

Gly Val Ile Trp Ala Gly Gly Asn Thr Asn Tyr Asn Ser Ala Leu Met
        50                  55                  60

Ser Arg Leu Ser Ile Asn Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

```
Thr Phe Asp Val Trp Gly Ala Gly Thr Thr Val Thr Val Ser Ser Ala
            100                 105                 110
Lys Thr

<210> SEQ ID NO 12
<211> LENGTH: 112
<212> TYPE: PRT
<213> ORGANISM: Mus musculus

<400> SEQUENCE: 12

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Phe Leu Tyr Trp Phe Leu Gln Arg Pro Gly Gln Ser
        35                  40                  45

Pro Gln Leu Leu Ile Tyr Arg Met Ser Asn Leu Val Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Phe Tyr Tyr Cys Met Gln His
                85                  90                  95

Leu Glu Tyr Pro Tyr Thr Phe Gly Gly Gly Thr Lys Leu Glu Leu Lys
            100                 105                 110

<210> SEQ ID NO 13
<211> LENGTH: 10
<212> TYPE: PRT
<213> ORGANISM: Mus musculus

<400> SEQUENCE: 13

Gly Tyr Ser Phe Thr Gly Tyr Thr Met Asn
1               5                   10

<210> SEQ ID NO 14
<211> LENGTH: 17
<212> TYPE: PRT
<213> ORGANISM: Mus musculus

<400> SEQUENCE: 14

Val Tyr Asn Pro Tyr Asn Gly Gly Thr Val Tyr Asn Gln Lys Phe Lys
1               5                   10                  15

Gly

<210> SEQ ID NO 15
<211> LENGTH: 10
<212> TYPE: PRT
<213> ORGANISM: Mus musculus

<400> SEQUENCE: 15

Thr Asp Ser Gly Gly Tyr Ala Met Asp Cys
1               5                   10

<210> SEQ ID NO 16
<211> LENGTH: 11
<212> TYPE: PRT
<213> ORGANISM: Mus musculus

<400> SEQUENCE: 16

Arg Ala Ser Lys Thr Ile Ser Lys Tyr Leu Ala
```

<210> SEQ ID NO 17
<211> LENGTH: 10
<212> TYPE: PRT
<213> ORGANISM: Mus musculus
<220> FEATURE:
<221> NAME/KEY: MISC_FEATURE
<222> LOCATION: (6)..(6)
<223> OTHER INFORMATION: Xaa is selected from Arg, Lys, Gly, and Ala

<400> SEQUENCE: 17

Gly Tyr Ser Phe Thr Xaa Tyr Thr Met Asn
1               5                   10

<210> SEQ ID NO 18
<211> LENGTH: 17
<212> TYPE: PRT
<213> ORGANISM: Mus musculus
<220> FEATURE:
<221> NAME/KEY: MISC_FEATURE
<222> LOCATION: (2)..(2)
<223> OTHER INFORMATION: Xaa is selected from Tyr, Trp, Phe, Thr, Ser,
      Ile, Leu, Val, Met, Ala, and Norleucine

<400> SEQUENCE: 18

Val Xaa Asn Pro Tyr Asn Gly Gly Thr Val Tyr Asn Gln Lys Phe Lys
1               5                   10                  15

Gly

<210> SEQ ID NO 19
<211> LENGTH: 11
<212> TYPE: PRT
<213> ORGANISM: Mus musculus
<220> FEATURE:
<221> NAME/KEY: MISC_FEATURE
<222> LOCATION: (3)..(3)
<223> OTHER INFORMATION: Xaa is selected from Ser, Thr, and Val
<220> FEATURE:
<221> NAME/KEY: MISC_FEATURE
<222> LOCATION: (5)..(5)
<223> OTHER INFORMATION: Xaa is selected from Ser, Thr, and Val

<400> SEQUENCE: 19

Arg Ala Xaa Lys Xaa Ile Ser Lys Tyr Leu Ala
1               5                   10

<210> SEQ ID NO 20
<211> LENGTH: 10
<212> TYPE: PRT
<213> ORGANISM: Mus musculus

<400> SEQUENCE: 20

Gly Phe Ser Leu Thr Lys Tyr Gly Val His
1               5                   10

<210> SEQ ID NO 21
<211> LENGTH: 16
<212> TYPE: PRT
<213> ORGANISM: Mus musculus

<400> SEQUENCE: 21

Val Ile Trp Ala Gly Gly Asn Thr Asn Tyr Asn Ser Ala Leu Met Ser
1               5                   10                  15

<210> SEQ ID NO 22
<211> LENGTH: 4

```
<212> TYPE: PRT
<213> ORGANISM: Mus musculus

<400> SEQUENCE: 22

Thr Phe Asp Val
1

<210> SEQ ID NO 23
<211> LENGTH: 16
<212> TYPE: PRT
<213> ORGANISM: Mus musculus

<400> SEQUENCE: 23

Arg Ser Ser Lys Ser Leu Leu His Ser Asn Gly Asn Thr Phe Leu Tyr
1               5                   10                  15

<210> SEQ ID NO 24
<211> LENGTH: 7
<212> TYPE: PRT
<213> ORGANISM: Mus musculus

<400> SEQUENCE: 24

Arg Met Ser Asn Leu Val Ser
1               5

<210> SEQ ID NO 25
<211> LENGTH: 9
<212> TYPE: PRT
<213> ORGANISM: Mus musculus

<400> SEQUENCE: 25

Met Gln His Leu Glu Tyr Pro Tyr Thr
1               5

<210> SEQ ID NO 26
<211> LENGTH: 661
<212> TYPE: PRT
<213> ORGANISM: Homo sapiens

<400> SEQUENCE: 26

Met Asp Leu Val Leu Lys Arg Cys Leu Leu His Leu Ala Val Ile Gly
1               5                   10                  15

Ala Leu Leu Ala Val Gly Ala Thr Lys Val Pro Arg Asn Gln Asp Trp
                20                  25                  30

Leu Gly Val Ser Arg Gln Leu Arg Thr Lys Ala Trp Asn Arg Gln Leu
            35                  40                  45

Tyr Pro Glu Trp Thr Glu Ala Gln Arg Leu Asp Cys Trp Arg Gly Gly
        50                  55                  60

Gln Val Ser Leu Lys Val Ser Asn Asp Gly Pro Thr Leu Ile Gly Ala
65                  70                  75                  80

Asn Ala Ser Phe Ser Ile Ala Leu Asn Phe Pro Gly Ser Gln Lys Val
                85                  90                  95

Leu Pro Asp Gly Gln Val Ile Trp Val Asn Asn Thr Ile Ile Asn Gly
                100                 105                 110

Ser Gln Val Trp Gly Gly Gln Pro Val Tyr Pro Gln Glu Thr Asp Asp
            115                 120                 125

Ala Cys Ile Phe Pro Asp Gly Gly Pro Cys Pro Ser Gly Ser Trp Ser
        130                 135                 140

Gln Lys Arg Ser Phe Val Tyr Val Trp Lys Thr Trp Gly Gln Tyr Trp
145                 150                 155                 160
```

-continued

```
Gln Val Leu Gly Gly Pro Val Ser Gly Leu Ser Ile Gly Thr Gly Arg
                165                 170                 175
Ala Met Leu Gly Thr His Thr Met Glu Val Thr Val Tyr His Arg Arg
            180                 185                 190
Gly Ser Arg Ser Tyr Val Pro Leu Ala His Ser Ser Ala Phe Thr
        195                 200                 205
Ile Thr Asp Gln Val Pro Phe Ser Val Ser Val Ser Gln Leu Arg Ala
    210                 215                 220
Leu Asp Gly Gly Asn Lys His Phe Leu Arg Asn Gln Pro Leu Thr Phe
225                 230                 235                 240
Ala Leu Gln Leu His Asp Pro Ser Gly Tyr Leu Ala Glu Ala Asp Leu
                245                 250                 255
Ser Tyr Thr Trp Asp Phe Gly Asp Ser Ser Gly Thr Leu Ile Ser Arg
            260                 265                 270
Ala Leu Val Val Thr His Thr Tyr Leu Glu Pro Gly Pro Val Thr Ala
        275                 280                 285
Gln Val Val Leu Gln Ala Ala Ile Pro Leu Thr Ser Cys Gly Ser Ser
    290                 295                 300
Pro Val Pro Gly Thr Thr Asp Gly His Arg Pro Thr Ala Glu Ala Pro
305                 310                 315                 320
Asn Thr Thr Ala Gly Gln Val Pro Thr Thr Glu Val Val Gly Thr Thr
                325                 330                 335
Pro Gly Gln Ala Pro Thr Ala Glu Pro Ser Gly Thr Thr Ser Val Gln
            340                 345                 350
Val Pro Thr Thr Glu Val Ile Ser Thr Ala Pro Val Gln Met Pro Thr
        355                 360                 365
Ala Glu Ser Thr Gly Met Thr Pro Glu Lys Val Pro Val Ser Glu Val
    370                 375                 380
Met Gly Thr Thr Leu Ala Glu Met Ser Thr Pro Glu Ala Thr Gly Met
385                 390                 395                 400
Thr Pro Ala Glu Val Ser Ile Val Val Leu Ser Gly Thr Thr Ala Ala
                405                 410                 415
Gln Val Thr Thr Thr Glu Trp Val Glu Thr Thr Ala Arg Glu Leu Pro
            420                 425                 430
Ile Pro Glu Pro Glu Gly Pro Asp Ala Ser Ser Ile Met Ser Thr Glu
        435                 440                 445
Ser Ile Thr Gly Ser Leu Gly Pro Leu Leu Asp Gly Thr Ala Thr Leu
    450                 455                 460
Arg Leu Val Lys Arg Gln Val Pro Leu Asp Cys Val Leu Tyr Arg Tyr
465                 470                 475                 480
Gly Ser Phe Ser Val Thr Leu Asp Ile Val Gln Gly Ile Glu Ser Ala
                485                 490                 495
Glu Ile Leu Gln Ala Val Pro Ser Gly Glu Gly Asp Ala Phe Glu Leu
            500                 505                 510
Thr Val Ser Cys Gln Gly Gly Leu Pro Lys Glu Ala Cys Met Glu Ile
        515                 520                 525
Ser Ser Pro Gly Cys Gln Pro Pro Ala Gln Arg Leu Cys Gln Pro Val
    530                 535                 540
Leu Pro Ser Pro Ala Cys Gln Leu Val Leu His Gln Ile Leu Lys Gly
545                 550                 555                 560
Gly Ser Gly Thr Tyr Cys Leu Asn Val Ser Leu Ala Asp Thr Asn Ser
                565                 570                 575
Leu Ala Val Val Ser Thr Gln Leu Ile Met Pro Gly Gln Glu Ala Gly
```

```
                580             585              590
Leu Gly Gln Val Pro Leu Ile Val Gly Ile Leu Val Leu Met Ala
            595             600             605

Val Val Leu Ala Ser Leu Ile Tyr Arg Arg Leu Met Lys Gln Asp
610             615             620

Phe Ser Val Pro Gln Leu Pro His Ser Ser His Trp Leu Arg Leu
625             630             635             640

Pro Arg Ile Phe Cys Ser Cys Pro Ile Gly Glu Asn Ser Pro Leu Leu
            645             650             655

Ser Gly Gln Gln Val
            660

<210> SEQ ID NO 27
<211> LENGTH: 637
<212> TYPE: PRT
<213> ORGANISM: Homo sapiens

<400> SEQUENCE: 27

Lys Val Pro Arg Asn Gln Asp Trp Leu Gly Val Ser Arg Gln Leu Arg
1               5                   10                  15

Thr Lys Ala Trp Asn Arg Gln Leu Tyr Pro Glu Trp Thr Glu Ala Gln
            20                  25                  30

Arg Leu Asp Cys Trp Arg Gly Gly Gln Val Ser Leu Lys Val Ser Asn
        35                  40                  45

Asp Gly Pro Thr Leu Ile Gly Ala Asn Ala Ser Phe Ser Ile Ala Leu
    50                  55                  60

Asn Phe Pro Gly Ser Gln Lys Val Leu Pro Asp Gly Gln Val Ile Trp
65                  70                  75                  80

Val Asn Asn Thr Ile Ile Asn Gly Ser Gln Val Trp Gly Gly Gln Pro
                85                  90                  95

Val Tyr Pro Gln Glu Thr Asp Asp Ala Cys Ile Phe Pro Asp Gly Gly
            100                 105                 110

Pro Cys Pro Ser Gly Ser Trp Ser Gln Lys Arg Ser Phe Val Tyr Val
        115                 120                 125

Trp Lys Thr Trp Gly Gln Tyr Trp Gln Val Leu Gly Gly Pro Val Ser
    130                 135                 140

Gly Leu Ser Ile Gly Thr Gly Arg Ala Met Leu Gly Thr His Thr Met
145                 150                 155                 160

Glu Val Thr Val Tyr His Arg Arg Gly Ser Arg Ser Tyr Val Pro Leu
                165                 170                 175

Ala His Ser Ser Ser Ala Phe Thr Ile Thr Asp Gln Val Pro Phe Ser
            180                 185                 190

Val Ser Val Ser Gln Leu Arg Ala Leu Asp Gly Gly Asn Lys His Phe
        195                 200                 205

Leu Arg Asn Gln Pro Leu Thr Phe Ala Leu Gln Leu His Asp Pro Ser
    210                 215                 220

Gly Tyr Leu Ala Glu Ala Asp Leu Ser Tyr Thr Trp Asp Phe Gly Asp
225                 230                 235                 240

Ser Ser Gly Thr Leu Ile Ser Arg Ala Leu Val Val Thr His Thr Tyr
                245                 250                 255

Leu Glu Pro Gly Pro Val Thr Ala Gln Val Val Leu Gln Ala Ala Ile
            260                 265                 270

Pro Leu Thr Ser Cys Gly Ser Ser Pro Val Pro Gly Thr Thr Asp Gly
        275                 280                 285
```

```
His Arg Pro Thr Ala Glu Ala Pro Asn Thr Thr Ala Gly Gln Val Pro
290                 295                 300

Thr Thr Glu Val Val Gly Thr Thr Pro Gly Gln Ala Pro Thr Ala Glu
305                 310                 315                 320

Pro Ser Gly Thr Thr Ser Val Gln Val Pro Thr Thr Glu Val Ile Ser
                325                 330                 335

Thr Ala Pro Val Gln Met Pro Thr Ala Glu Ser Thr Gly Met Thr Pro
                340                 345                 350

Glu Lys Val Pro Val Ser Glu Val Met Gly Thr Thr Leu Ala Glu Met
                355                 360                 365

Ser Thr Pro Glu Ala Thr Gly Met Thr Pro Ala Glu Val Ser Ile Val
370                 375                 380

Val Leu Ser Gly Thr Thr Ala Ala Gln Val Thr Thr Glu Trp Val
385                 390                 395                 400

Glu Thr Thr Ala Arg Glu Leu Pro Ile Pro Glu Pro Glu Gly Pro Asp
                405                 410                 415

Ala Ser Ser Ile Met Ser Thr Glu Ser Ile Thr Gly Ser Leu Gly Pro
                420                 425                 430

Leu Leu Asp Gly Thr Ala Thr Leu Arg Leu Val Lys Arg Gln Val Pro
                435                 440                 445

Leu Asp Cys Val Leu Tyr Arg Tyr Gly Ser Phe Ser Val Thr Leu Asp
450                 455                 460

Ile Val Gln Gly Ile Glu Ser Ala Glu Ile Leu Gln Ala Val Pro Ser
465                 470                 475                 480

Gly Glu Gly Asp Ala Phe Glu Leu Thr Val Ser Cys Gln Gly Gly Leu
                485                 490                 495

Pro Lys Glu Ala Cys Met Glu Ile Ser Ser Pro Gly Cys Gln Pro Pro
                500                 505                 510

Ala Gln Arg Leu Cys Gln Pro Val Leu Pro Ser Pro Ala Cys Gln Leu
                515                 520                 525

Val Leu His Gln Ile Leu Lys Gly Gly Ser Gly Thr Tyr Cys Leu Asn
530                 535                 540

Val Ser Leu Ala Asp Thr Asn Ser Leu Ala Val Val Ser Thr Gln Leu
545                 550                 555                 560

Ile Met Pro Gly Gln Glu Ala Gly Leu Gly Gln Val Pro Leu Ile Val
                565                 570                 575

Gly Ile Leu Leu Val Leu Met Ala Val Val Leu Ala Ser Leu Ile Tyr
                580                 585                 590

Arg Arg Arg Leu Met Lys Gln Asp Phe Ser Val Pro Gln Leu Pro His
                595                 600                 605

Ser Ser Ser His Trp Leu Arg Leu Pro Arg Ile Phe Cys Ser Cys Pro
610                 615                 620

Ile Gly Glu Asn Ser Pro Leu Leu Ser Gly Gln Gln Val
625                 630                 635

<210> SEQ ID NO 28
<211> LENGTH: 637
<212> TYPE: PRT
<213> ORGANISM: Macaca fascicularis

<400> SEQUENCE: 28

Lys Gly Pro Arg Asn Gln Asp Trp Leu Gly Val Ser Arg Gln Leu Arg
1               5                   10                  15

Thr Lys Ala Trp Asn Arg Gln Leu Tyr Pro Glu Trp Thr Glu Ala Gln
                20                  25                  30
```

```
Arg Leu Asp Cys Trp Arg Gly Gly Gln Val Ser Leu Lys Val Ser Asn
            35                  40                  45

Asp Gly Pro Thr Leu Ile Gly Ala Asn Ala Ser Phe Ser Ile Ala Leu
    50                  55                  60

Asn Phe Pro Gly Ser Gln Lys Val Leu Pro Asp Gly Gln Val Ile Trp
65                  70                  75                  80

Val Asn Asn Thr Ile Ile Asn Gly Ser Gln Val Trp Gly Gly Gln Pro
                85                  90                  95

Val Tyr Pro Gln Glu Thr Asp Asp Ala Cys Ile Phe Pro Asp Gly Gly
                100                 105                 110

Pro Cys Pro Ser Gly Pro Trp Ser Gln Lys Arg Ser Phe Val Tyr Val
            115                 120                 125

Trp Lys Thr Trp Gly Gln Tyr Trp Gln Val Leu Gly Gly Pro Val Ser
            130                 135                 140

Gly Leu Ser Ile Gly Thr Gly Arg Ala Met Leu Gly Thr His Thr Met
145                 150                 155                 160

Glu Val Thr Val Tyr His Arg Arg Gly Ser Arg Ser Tyr Val Pro Leu
                165                 170                 175

Ala His Ser Ser Ser Ala Phe Thr Ile Thr Asp Gln Val Pro Phe Ser
            180                 185                 190

Val Ser Val Ser Gln Leu Arg Ala Leu Asp Gly Gly Asn Lys His Phe
            195                 200                 205

Leu Arg Asn Gln Pro Leu Thr Phe Ala Leu Gln Leu His Asp Pro Ser
    210                 215                 220

Gly Tyr Leu Ala Glu Ala Asp Leu Ser Tyr Thr Trp Asp Phe Gly Asp
225                 230                 235                 240

Ser Ser Gly Thr Leu Ile Ser Arg Ala Leu Val Val Thr His Thr Tyr
                245                 250                 255

Leu Glu Pro Gly Pro Val Thr Ala Gln Val Val Leu Gln Ala Ala Ile
            260                 265                 270

Pro Leu Thr Ser Cys Gly Ser Ser Pro Val Pro Gly Thr Thr Asp Gly
    275                 280                 285

His Arg Pro Thr Ala Glu Ala Pro Asp Thr Thr Ala Gly Arg Gly Pro
    290                 295                 300

Thr Thr Glu Val Val Gly Thr Thr Pro Gly Gln Val Pro Thr Thr Gln
305                 310                 315                 320

Pro Ser Gly Thr Thr Ser Val Gln Val Pro Thr Thr Glu Val Ile Ser
            325                 330                 335

Thr Thr Pro Val Gln Met Pro Thr Ala Glu Ser Thr Gly Thr Thr Pro
            340                 345                 350

Glu Lys Val Pro Val Ser Glu Val Met Gly Thr Thr Leu Ala Glu Met
            355                 360                 365

Ser Thr Pro Glu Ala Ile Gly Met Thr Pro Ala Glu Val Ser Ile Val
    370                 375                 380

Val Pro Ser Gly Thr Thr Ala Ala Gln Val Thr Thr Thr Glu Trp Val
385                 390                 395                 400

Glu Thr Thr Ala Gly Glu Leu Pro Thr Pro Glu Pro Glu Gly Pro Asp
                405                 410                 415

Thr Ser Ser Ile Met Ser Thr Glu Ser Ile Thr Gly Ser Leu Gly Pro
            420                 425                 430

Leu Leu Asp Gly Thr Ala Thr Leu Arg Leu Glu Lys Arg Gln Val Pro
            435                 440                 445
```

```
Leu Asp Cys Val Leu Tyr Arg Tyr Gly Ser Phe Ser Val Thr Leu Asp
    450                 455                 460

Ile Val Gln Gly Ile Glu Ser Ala Glu Ile Leu Gln Val Val Pro Ser
465                 470                 475                 480

Ser Glu Gly Asp Ala Phe Glu Leu Thr Val Ser Cys Gln Gly Gly Leu
                485                 490                 495

Pro Thr Glu Ala Cys Met Glu Ile Ser Ser Pro Gly Cys Gln Pro Pro
            500                 505                 510

Ala Gln Gln Leu Cys Gln Pro Val Pro Pro Ser Pro Ala Cys Gln Leu
        515                 520                 525

Val Leu Tyr Gln Ile Leu Lys Gly Gly Leu Gly Thr Tyr Cys Leu Asn
530                 535                 540

Val Ser Leu Ala Asp Ala Asn Ser Leu Ala Val Val Ser Thr Gln Leu
545                 550                 555                 560

Ile Val Pro Gly Gln Glu Ala Gly Leu Gly Gln Ala Pro Leu Phe Val
                565                 570                 575

Gly Ile Leu Leu Val Leu Met Ala Val Val Leu Ala Ser Leu Ile Tyr
            580                 585                 590

Arg Arg Arg Leu Met Lys Gln Ala Phe Ser Ile Pro Gln Leu Pro His
        595                 600                 605

Gly Ser Ser His Trp Leu Arg Leu Pro Arg Ile Phe Arg Ser Cys Pro
    610                 615                 620

Ile Gly Glu Asn Ser Pro Leu Leu Ser Gly Gln Glu Val
625                 630                 635

<210> SEQ ID NO 29
<211> LENGTH: 418
<212> TYPE: PRT
<213> ORGANISM: Rattus rattus

<400> SEQUENCE: 29

Met Gly Val Gln Arg Arg Cys Phe Leu Pro Val Leu Val Leu Gly Ala
1               5                   10                  15

Leu Leu Ala Leu Gly Ser Ile Glu Gly Ser Arg Asn Gln Asn Trp His
            20                  25                  30

Gly Val Ser Arg Gln Leu Val Thr Lys Val Trp Asn Lys Gln Leu Tyr
        35                  40                  45

Pro Glu Trp Thr Glu Val Gln Gly Ser Asn Cys Trp Arg Gly Gly Gln
    50                  55                  60

Val Ser Leu Lys Val Arg Asn Asp Gly Pro Thr Leu Val Gly Ala Asn
65                  70                  75                  80

Thr Ser Phe Ser Ile Ala Leu His Phe Pro Gly Ser Gln Lys Val Leu
                85                  90                  95

Pro Asp Gly Gln Val Ile Trp Val Asn Asn Thr Ile Ile Asn Gly Ser
            100                 105                 110

Gln Val Trp Gly Gly Gln Pro Val Tyr Pro Arg Glu Pro Asp Asp Ala
        115                 120                 125

Cys Ile Phe Pro Asp Gly Gly Pro Cys Pro Ser Gly Pro Lys Pro Pro
    130                 135                 140

Arg Arg Ser Phe Val Tyr Val Trp Lys Thr Trp Gly Gln Tyr Trp Gln
145                 150                 155                 160

Val Leu Gly Gly Pro Glu Ser Lys Leu Ser Ile Pro Thr Gly His Ala
                165                 170                 175

Arg Leu Gly Thr His Thr Met Glu Val Thr Val Tyr His Arg Arg Gly
            180                 185                 190
```

```
Ser Gln Ser Tyr Val Pro Leu Ala His Ser Ser Thr Phe Thr Ile
        195                 200                 205

Thr Gly Ser Val Ser Arg Leu Leu Asp Asp Thr Asp Thr Ile Met Leu
210                 215                 220

Val Lys Arg Gln Val Pro Leu Asp Cys Val Leu Tyr Arg Tyr Gly Ser
225                 230                 235                 240

Phe Ser Leu Thr Leu Asp Ile Val Gln Gly Ile Glu Ser Ala Glu Ile
                245                 250                 255

Leu Gln Ala Val Pro Ser Ser Glu Gly Asp Ala Phe Glu Leu Thr Val
                260                 265                 270

Ser Cys Arg Gly Gly Leu Pro Lys Glu Ala Cys Met Asp Ile Ser Ser
                275                 280                 285

Pro Gly Cys Gln Pro Pro Ala Gln Arg Leu Cys Gln Pro Val Pro Pro
                290                 295                 300

Ser Pro Asp Cys Gln Leu Val Leu His Gln Ile Leu Lys Gly Gly Leu
305                 310                 315                 320

Gly Thr Tyr Cys Leu Asn Val Ser Leu Ala Asp Ala Asn Ser Leu Ala
                325                 330                 335

Val Ala Ser Thr Gln Leu Val Val Pro Gly Gln Glu Gly Ser Leu Gly
                340                 345                 350

Gln Ala Pro Leu Leu Val Gly Val Leu Leu Val Leu Ala Val Val
                355                 360                 365

Leu Ala Ser Leu Ile Tyr Arg His Arg Leu Lys Lys Gln Asp Ser Val
                370                 375                 380

Ser Gln Thr Pro His Gly Ser Thr His Trp Leu Arg Leu Pro Pro Val
385                 390                 395                 400

Phe Cys Ala Arg Arg Leu Gly Glu Ser Ser Pro Leu Leu Ser Gly Gln
                405                 410                 415

Gln Val

<210> SEQ ID NO 30
<211> LENGTH: 393
<212> TYPE: PRT
<213> ORGANISM: Rattus rattus

<400> SEQUENCE: 30

Ser Arg Asn Gln Asn Trp His Gly Val Ser Arg Gln Leu Val Thr Lys
1               5                   10                  15

Val Trp Asn Lys Gln Leu Tyr Pro Glu Trp Thr Glu Val Gln Gly Ser
                20                  25                  30

Asn Cys Trp Arg Gly Gly Gln Val Ser Leu Lys Val Arg Asn Asp Gly
                35                  40                  45

Pro Thr Leu Val Gly Ala Asn Thr Ser Phe Ser Ile Ala Leu His Phe
            50                  55                  60

Pro Gly Ser Gln Lys Val Leu Pro Asp Gly Gln Val Ile Trp Val Asn
65                  70                  75                  80

Asn Thr Ile Ile Asn Gly Ser Gln Val Trp Gly Gly Gln Pro Val Tyr
                85                  90                  95

Pro Arg Glu Pro Asp Asp Ala Cys Ile Phe Pro Asp Gly Gly Pro Cys
                100                 105                 110

Pro Ser Gly Pro Lys Pro Arg Arg Ser Phe Val Tyr Val Trp Lys
                115                 120                 125

Thr Trp Gly Gln Tyr Trp Gln Val Leu Gly Gly Pro Glu Ser Lys Leu
                130                 135                 140
```

Ser Ile Pro Thr Gly His Ala Arg Leu Gly Thr His Thr Met Glu Val
145                 150                 155                 160

Thr Val Tyr His Arg Arg Gly Ser Gln Ser Tyr Val Pro Leu Ala His
            165                 170                 175

Ser Ser Ser Thr Phe Thr Ile Thr Gly Ser Val Ser Arg Leu Leu Asp
        180                 185                 190

Asp Thr Asp Thr Ile Met Leu Val Lys Arg Gln Val Pro Leu Asp Cys
    195                 200                 205

Val Leu Tyr Arg Tyr Gly Ser Phe Ser Leu Thr Leu Asp Ile Val Gln
210                 215                 220

Gly Ile Glu Ser Ala Glu Ile Leu Gln Ala Val Pro Ser Ser Glu Gly
225                 230                 235                 240

Asp Ala Phe Glu Leu Thr Val Ser Cys Arg Gly Gly Leu Pro Lys Glu
            245                 250                 255

Ala Cys Met Asp Ile Ser Ser Pro Gly Cys Gln Pro Ala Gln Arg
        260                 265                 270

Leu Cys Gln Pro Val Pro Ser Pro Asp Cys Gln Leu Val Leu His
    275                 280                 285

Gln Ile Leu Lys Gly Gly Leu Gly Thr Tyr Cys Leu Asn Val Ser Leu
290                 295                 300

Ala Asp Ala Asn Ser Leu Ala Val Ala Ser Thr Gln Leu Val Val Pro
305                 310                 315                 320

Gly Gln Glu Gly Ser Leu Gly Gln Ala Pro Leu Leu Val Gly Val Leu
            325                 330                 335

Leu Val Leu Val Ala Val Val Leu Ala Ser Leu Ile Tyr Arg His Arg
        340                 345                 350

Leu Lys Lys Gln Asp Ser Val Ser Gln Thr Pro His Gly Ser Thr His
    355                 360                 365

Trp Leu Arg Leu Pro Pro Val Phe Cys Ala Arg Arg Leu Gly Glu Ser
370                 375                 380

Ser Pro Leu Leu Ser Gly Gln Gln Val
385                 390

<210> SEQ ID NO 31
<211> LENGTH: 626
<212> TYPE: PRT
<213> ORGANISM: Mus musculus

<400> SEQUENCE: 31

Met Gly Val Gln Arg Arg Ser Phe Leu Pro Val Leu Val Leu Ser Ala
1               5                   10                  15

Leu Leu Ala Val Gly Ala Leu Glu Gly Ser Arg Asn Gln Asp Trp Leu
            20                  25                  30

Gly Val Pro Arg Gln Leu Val Thr Lys Thr Trp Asn Arg Gln Leu Tyr
        35                  40                  45

Pro Glu Trp Thr Glu Val Gln Gly Ser Asn Cys Trp Arg Gly Gly Gln
    50                  55                  60

Val Ser Leu Arg Val Ile Asn Asp Gly Pro Thr Leu Val Gly Ala Asn
65                  70                  75                  80

Ala Ser Phe Ser Ile Ala Leu His Phe Pro Gly Ser Gln Lys Val Leu
                85                  90                  95

Pro Asp Gly Gln Val Ile Trp Ala Asn Asn Thr Ile Ile Asn Gly Ser
            100                 105                 110

Gln Val Trp Gly Gly Gln Pro Val Tyr Pro Gln Glu Pro Asp Asp Ala

-continued

```
            115                 120                 125
Cys Val Phe Pro Asp Gly Gly Pro Cys Pro Ser Gly Pro Lys Pro Pro
130                 135                 140

Lys Arg Ser Phe Val Tyr Val Trp Lys Thr Trp Gly Lys Tyr Trp Gln
145                 150                 155                 160

Val Leu Gly Gly Pro Val Ser Arg Leu Ser Ile Ala Thr Gly His Ala
                165                 170                 175

Lys Leu Gly Thr His Thr Met Glu Val Thr Val Tyr His Arg Arg Gly
                180                 185                 190

Ser Gln Ser Tyr Val Pro Leu Ala His Ala Ser Ser Thr Phe Thr Ile
                195                 200                 205

Thr Asp Gln Val Pro Phe Ser Val Ser Val Ser Gln Leu Gln Ala Leu
210                 215                 220

Asp Gly Glu Thr Lys His Phe Leu Arg Asn His Pro Leu Ile Phe Ala
225                 230                 235                 240

Leu Gln Leu His Asp Pro Ser Gly Tyr Leu Ala Glu Ala Asp Leu Ser
                245                 250                 255

Tyr Thr Trp Asp Phe Gly Asp Gly Thr Gly Thr Leu Ile Ser Arg Ala
                260                 265                 270

Leu Asp Val Thr His Thr Tyr Leu Glu Ser Gly Ser Val Thr Ala Gln
                275                 280                 285

Val Val Leu Gln Ala Ala Ile Pro Leu Val Ser Cys Gly Ser Ser Pro
290                 295                 300

Val Pro Gly Thr Thr Asp Gly Tyr Met Pro Thr Ala Glu Ala Pro Gly
305                 310                 315                 320

Thr Thr Ser Arg Gln Gly Thr Thr Lys Val Val Gly Thr Thr Pro
                325                 330                 335

Gly Gln Met Pro Thr Thr Gln Pro Ser Gly Thr Thr Val Val Gln Met
                340                 345                 350

Pro Thr Thr Glu Val Thr Ala Thr Thr Ser Glu Gln Met Leu Thr Ser
                355                 360                 365

Ala Val Ile Asp Thr Thr Leu Ala Glu Val Ser Thr Thr Glu Gly Thr
                370                 375                 380

Gly Thr Thr Pro Thr Arg Pro Ser Gly Thr Thr Val Ala Gln Ala Thr
385                 390                 395                 400

Thr Thr Glu Gly Pro Asp Ala Ser Pro Leu Leu Pro Thr Gln Ser Ser
                405                 410                 415

Thr Gly Ser Ile Ser Pro Leu Leu Asp Asp Thr Asp Thr Ile Met Leu
                420                 425                 430

Val Lys Arg Gln Val Pro Leu Asp Cys Val Leu Tyr Arg Tyr Gly Ser
                435                 440                 445

Phe Ser Leu Ala Leu Asp Ile Val Gln Gly Ile Glu Ser Ala Glu Ile
                450                 455                 460

Leu Gln Ala Val Pro Phe Ser Glu Gly Asp Ala Phe Glu Leu Thr Val
465                 470                 475                 480

Ser Cys Gln Gly Gly Leu Pro Lys Glu Ala Cys Met Asp Ile Ser Ser
                485                 490                 495

Pro Gly Cys Gln Pro Pro Ala Gln Arg Leu Cys Gln Ser Val Pro Pro
                500                 505                 510

Ser Pro Asp Cys Gln Leu Val Leu His Gln Val Leu Lys Gly Gly Ser
                515                 520                 525

Gly Thr Tyr Cys Leu Asn Val Ser Leu Ala Asp Ala Asn Ser Leu Ala
530                 535                 540
```

```
Val Ala Ser Thr Gln Leu Val Pro Gly Gln Asp Gly Leu Gly
545                 550                 555                 560

Gln Ala Pro Leu Leu Val Gly Ile Leu Leu Val Leu Ala Val Val
                565                 570                 575

Leu Ala Ser Leu Ile His Arg His Arg Leu Lys Lys Gln Gly Ser Val
                580                 585                 590

Ser Gln Met Pro His Gly Ser Thr His Trp Leu Arg Leu Pro Pro Val
        595                 600                 605

Phe Arg Ala Arg Gly Leu Gly Glu Asn Ser Pro Leu Leu Ser Gly Gln
        610                 615                 620

Gln Val
625

<210> SEQ ID NO 32
<211> LENGTH: 601
<212> TYPE: PRT
<213> ORGANISM: Mus musculus

<400> SEQUENCE: 32

Ser Arg Asn Gln Asp Trp Leu Gly Val Pro Arg Gln Leu Val Thr Lys
1               5                   10                  15

Thr Trp Asn Arg Gln Leu Tyr Pro Glu Trp Thr Glu Val Gln Gly Ser
            20                  25                  30

Asn Cys Trp Arg Gly Gly Gln Val Ser Leu Arg Val Ile Asn Asp Gly
        35                  40                  45

Pro Thr Leu Val Gly Ala Asn Ala Ser Phe Ser Ile Ala Leu His Phe
50                  55                  60

Pro Gly Ser Gln Lys Val Leu Pro Asp Gly Gln Val Ile Trp Ala Asn
65                  70                  75                  80

Asn Thr Ile Ile Asn Gly Ser Gln Val Trp Gly Gly Gln Pro Val Tyr
                85                  90                  95

Pro Gln Glu Pro Asp Asp Ala Cys Val Phe Pro Asp Gly Gly Pro Cys
            100                 105                 110

Pro Ser Gly Pro Lys Pro Pro Lys Arg Ser Phe Val Tyr Val Trp Lys
        115                 120                 125

Thr Trp Gly Lys Tyr Trp Gln Val Leu Gly Gly Pro Val Ser Arg Leu
130                 135                 140

Ser Ile Ala Thr Gly His Ala Lys Leu Gly Thr His Thr Met Glu Val
145                 150                 155                 160

Thr Val Tyr His Arg Arg Gly Ser Gln Ser Tyr Val Pro Leu Ala His
                165                 170                 175

Ala Ser Ser Thr Phe Thr Ile Thr Asp Gln Val Pro Phe Ser Val Ser
            180                 185                 190

Val Ser Gln Leu Gln Ala Leu Asp Gly Glu Thr Lys His Phe Leu Arg
        195                 200                 205

Asn His Pro Leu Ile Phe Ala Leu Gln Leu His Asp Pro Ser Gly Tyr
        210                 215                 220

Leu Ala Glu Ala Asp Leu Ser Tyr Thr Trp Asp Phe Gly Asp Gly Thr
225                 230                 235                 240

Gly Thr Leu Ile Ser Arg Ala Leu Asp Val Thr His Thr Tyr Leu Glu
                245                 250                 255

Ser Gly Ser Val Thr Ala Gln Val Val Leu Gln Ala Ala Ile Pro Leu
            260                 265                 270

Val Ser Cys Gly Ser Ser Pro Val Pro Gly Thr Thr Asp Gly Tyr Met
```

```
            275                 280                 285
Pro Thr Ala Glu Ala Pro Gly Thr Thr Ser Arg Gln Gly Thr Thr Thr
290                 295                 300

Lys Val Val Gly Thr Thr Pro Gly Gln Met Pro Thr Thr Gln Pro Ser
305                 310                 315                 320

Gly Thr Thr Val Val Gln Met Pro Thr Thr Glu Val Thr Ala Thr Thr
                    325                 330                 335

Ser Glu Gln Met Leu Thr Ser Ala Val Ile Asp Thr Thr Leu Ala Glu
                340                 345                 350

Val Ser Thr Thr Glu Gly Thr Gly Thr Thr Pro Thr Arg Pro Ser Gly
                355                 360                 365

Thr Thr Val Ala Gln Ala Thr Thr Thr Glu Gly Pro Asp Ala Ser Pro
370                 375                 380

Leu Leu Pro Thr Gln Ser Ser Thr Gly Ser Ile Ser Pro Leu Leu Asp
385                 390                 395                 400

Asp Thr Asp Thr Ile Met Leu Val Lys Arg Gln Val Pro Leu Asp Cys
                405                 410                 415

Val Leu Tyr Arg Tyr Gly Ser Phe Ser Leu Ala Leu Asp Ile Val Gln
                420                 425                 430

Gly Ile Glu Ser Ala Glu Ile Leu Gln Ala Val Pro Phe Ser Glu Gly
                435                 440                 445

Asp Ala Phe Glu Leu Thr Val Ser Cys Gln Gly Gly Leu Pro Lys Glu
450                 455                 460

Ala Cys Met Asp Ile Ser Ser Pro Gly Cys Gln Pro Pro Ala Gln Arg
465                 470                 475                 480

Leu Cys Gln Ser Val Pro Pro Ser Pro Asp Cys Gln Leu Val Leu His
                485                 490                 495

Gln Val Leu Lys Gly Gly Ser Gly Thr Tyr Cys Leu Asn Val Ser Leu
                500                 505                 510

Ala Asp Ala Asn Ser Leu Ala Val Ala Ser Thr Gln Leu Val Val Pro
                515                 520                 525

Gly Gln Asp Gly Gly Leu Gly Gln Ala Pro Leu Leu Val Gly Ile Leu
                530                 535                 540

Leu Val Leu Val Ala Val Val Leu Ala Ser Leu Ile His Arg His Arg
545                 550                 555                 560

Leu Lys Lys Gln Gly Ser Val Ser Gln Met Pro His Gly Ser Thr His
                565                 570                 575

Trp Leu Arg Leu Pro Pro Val Phe Arg Ala Arg Gly Leu Gly Glu Asn
                580                 585                 590

Ser Pro Leu Leu Ser Gly Gln Gln Val
                595                 600

<210> SEQ ID NO 33
<211> LENGTH: 10
<212> TYPE: PRT
<213> ORGANISM: Mus musculus

<400> SEQUENCE: 33

Gly Tyr Thr Phe Thr Ser Tyr Trp Met Gln
1               5                   10

<210> SEQ ID NO 34
<211> LENGTH: 17
<212> TYPE: PRT
<213> ORGANISM: Mus musculus
```

-continued

```
<400> SEQUENCE: 34

Thr Ile Tyr Pro Gly Asp Gly Asp Thr Ser Tyr Ala Gln Lys Phe Lys
1               5                   10                  15

Gly

<210> SEQ ID NO 35
<211> LENGTH: 9
<212> TYPE: PRT
<213> ORGANISM: Mus musculus

<400> SEQUENCE: 35

Trp Gly Tyr Ala Tyr Asp Ile Asp Asn
1               5

<210> SEQ ID NO 36
<211> LENGTH: 16
<212> TYPE: PRT
<213> ORGANISM: Mus musculus

<400> SEQUENCE: 36

Lys Ser Ser Gln Ser Leu Leu Asp Ser Asp Gly Lys Thr Tyr Leu Asn
1               5                   10                  15

<210> SEQ ID NO 37
<211> LENGTH: 7
<212> TYPE: PRT
<213> ORGANISM: Mus musculus

<400> SEQUENCE: 37

Leu Val Ser Lys Leu Asp Ser
1               5

<210> SEQ ID NO 38
<211> LENGTH: 9
<212> TYPE: PRT
<213> ORGANISM: Mus musculus

<400> SEQUENCE: 38

Trp Gln Gly Thr His Phe Pro Tyr Thr
1               5

<210> SEQ ID NO 39
<211> LENGTH: 112
<212> TYPE: PRT
<213> ORGANISM: Artificial sequence
<220> FEATURE:
<223> OTHER INFORMATION: Synthetic

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asp Ser
            20                  25                  30

Asp Gly Lys Thr Tyr Leu Asn Trp Leu Gln Gln Lys Pro Gly Lys Ala
        35                  40                  45

Pro Lys Arg Leu Ile Tyr Leu Val Ser Lys Leu Asp Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Trp Gln Gly
                85                  90                  95
```

```
Thr His Phe Pro Tyr Thr Phe Gly Gln Gly Thr Lys Val Glu Ile Lys
            100                 105                 110
```

<210> SEQ ID NO 40
<211> LENGTH: 109
<212> TYPE: PRT
<213> ORGANISM: Artificial sequence
<220> FEATURE:
<223> OTHER INFORMATION: Synthetic

<400> SEQUENCE: 40

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Trp Met Gln Trp Val Arg Gln Ala Pro Gly Lys Gly Leu Glu Trp Ile
        35                  40                  45

Gly Thr Ile Tyr Pro Gly Asp Gly Asp Thr Ser Tyr Ala Gln Lys Phe
    50                  55                  60

Lys Gly Arg Ala Thr Leu Ser Thr Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Trp Gly Tyr Ala Tyr Asp Ile Asp Asn Trp Gly
            100                 105
```

<210> SEQ ID NO 41
<211> LENGTH: 112
<212> TYPE: PRT
<213> ORGANISM: Mus musculus

<400> SEQUENCE: 41

```
Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Thr Arg Val Glu Ala Glu Asp Leu Gly Val Tyr Tyr Cys Trp Gln Gly
                85                  90                  95

Thr His Phe Pro Tyr Thr Phe Gly Gly Gly Thr Lys Leu Glu Ile Lys
            100                 105                 110
```

<210> SEQ ID NO 42
<211> LENGTH: 109
<212> TYPE: PRT
<213> ORGANISM: Mus musculus

<400> SEQUENCE: 42

```
Gln Val Gln Leu Leu Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Trp Ile
        35                  40                  45
```

Gly Thr Ile Tyr Pro Gly Asp Gly Asp Thr Ser Tyr Ala Gln Lys Phe
            50                  55                  60

Lys Gly Lys Ala Thr Leu Thr Thr Asp Lys Tyr Ser Ser Thr Ala Tyr
 65                  70                  75                  80

Met Gln Leu Ser Ser Leu Ala Ser Glu Asp Ser Ala Val Tyr Tyr Cys
                 85                  90                  95

Ala Arg Trp Gly Tyr Ala Tyr Asp Ile Asp Asn Trp Gly
                100                 105

<210> SEQ ID NO 43
<211> LENGTH: 219
<212> TYPE: PRT
<213> ORGANISM: Artificial sequence
<220> FEATURE:
<223> OTHER INFORMATION: Synthetic

<400> SEQUENCE: 43

Asp Val Val Met Thr Gln Thr Pro Leu Thr Leu Ser Val Thr Ile Gly
 1               5                  10                  15

Gln Pro Ala Ser Ile Ser Cys Lys Ser Ser Gln Ser Leu Leu Asp Ser
                 20                  25                  30

Asp Gly Lys Thr Tyr Leu Asn Trp Leu Leu Gln Arg Pro Gly Gln Ser
             35                  40                  45

Pro Lys Arg Leu Ile Tyr Leu Val Ser Lys Leu Asp Ser Gly Val Pro
 50                  55                  60

Asp Arg Phe Thr Gly Ser Gly Ser Gly Thr Asp Phe Thr Leu Lys Ile
 65                  70                  75                  80

Thr Arg Val Glu Ala Glu Asp Leu Gly Val Tyr Tyr Cys Trp Gln Gly
                 85                  90                  95

Thr His Phe Pro Tyr Thr Phe Gly Gly Gly Thr Lys Leu Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
        210                 215

<210> SEQ ID NO 44
<211> LENGTH: 448
<212> TYPE: PRT
<213> ORGANISM: Artificial sequence
<220> FEATURE:
<223> OTHER INFORMATION: Synthetic

<400> SEQUENCE: 44

Gln Val Gln Leu Leu Gln Ser Gly Ala Glu Leu Ala Arg Pro Gly Ala
 1               5                  10                  15

Ser Val Lys Leu Ser Cys Lys Ala Ser Gly Tyr Thr Phe Thr Ser Tyr

```
              20                  25                  30
Trp Met Gln Trp Val Lys Gln Arg Pro Gly Gln Gly Leu Glu Trp Ile
             35                  40                  45
Gly Thr Ile Tyr Pro Gly Asp Gly Asp Thr Ser Tyr Ala Gln Lys Phe
         50                  55                  60
Lys Gly Lys Ala Thr Leu Thr Thr Asp Lys Tyr Ser Ser Thr Ala Tyr
 65                  70                  75                  80
Met Gln Leu Ser Ser Leu Ala Ser Glu Asp Ser Ala Val Tyr Tyr Cys
                 85                  90                  95
Ala Arg Trp Gly Tyr Ala Tyr Asp Ile Asp Asn Trp Gly Gln Gly Thr
            100                 105                 110
Leu Val Thr Val Ser Ser Ala Ser Thr Lys Gly Pro Ser Val Phe Pro
        115                 120                 125
Leu Ala Pro Ser Ser Lys Ser Thr Ser Gly Gly Thr Ala Ala Leu Gly
        130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
        195                 200                 205
Asn Thr Lys Val Asp Lys Lys Val Glu Pro Lys Ser Cys Asp Lys Thr
    210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
        275                 280                 285
Lys Thr Lys Pro Arg Glu Glu Gln Tyr Asn Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Glu Glu Met Thr Lys Asn Gln Val Ser Leu Thr Cys
        355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Lys
        435                 440                 445
```

<210> SEQ ID NO 45
<211> LENGTH: 219
<212> TYPE: PRT
<213> ORGANISM: Artificial sequence
<220> FEATURE:
<223> OTHER INFORMATION: Synthetic

<400> SEQUENCE: 45

```
Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asp Ser
            20                  25                  30

Asp Gly Lys Thr Tyr Leu Asn Trp Leu Gln Gln Lys Pro Gly Lys Ala
        35                  40                  45

Pro Lys Arg Leu Ile Tyr Leu Val Ser Lys Leu Asp Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Trp Gln Gly
                85                  90                  95

Thr His Phe Pro Tyr Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 46
<211> LENGTH: 448
<212> TYPE: PRT
<213> ORGANISM: Artificial sequence
<220> FEATURE:
<223> OTHER INFORMATION: Synthetic

<400> SEQUENCE: 46

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Trp Met Gln Trp Val Arg Gln Ala Pro Gly Lys Gly Leu Glu Trp Ile
        35                  40                  45

Gly Thr Ile Tyr Pro Gly Asp Gly Asp Thr Ser Tyr Ala Gln Lys Phe
    50                  55                  60

Lys Gly Arg Ala Thr Leu Ser Thr Asp Lys Ser Lys Asn Thr Ala Tyr
65                  70                  75                  80

Leu Gln Met Asn Ser Leu Arg Ala Glu Asp Thr Ala Val Tyr Tyr Cys
```

```
                    85                  90                  95
Ala Arg Trp Gly Tyr Ala Tyr Asp Ile Asp Asn Trp Gly Gln Gly Thr
                100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
    195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
    275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
    355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
    435                 440                 445

<210> SEQ ID NO 47
<211> LENGTH: 214
<212> TYPE: PRT
<213> ORGANISM: Artificial sequence
<220> FEATURE:
<223> OTHER INFORMATION: Synthetic

<400> SEQUENCE: 47

Asp Val Gln Ile Thr Gln Ser Pro Ser Tyr Leu Ala Ala Ser Pro Gly
```

```
            1               5                   10                  15
          Glu Thr Ile Thr Ile Asn Cys Arg Ala Thr Lys Ser Ile Ser Lys Tyr
                          20                  25                  30
          Leu Ala Trp Tyr Gln Glu Gln Pro Gly Lys Thr Asn Asn Leu Leu Ile
                          35                  40                  45
          Tyr Ser Gly Ser Thr Leu Gln Ser Gly Ile Pro Ser Arg Phe Ser Gly
                          50                  55                  60
          Ser Gly Ser Gly Thr Asp Phe Thr Leu Thr Ile Ser Ser Leu Glu Pro
           65                  70                  75                  80
          Glu Asp Phe Ala Met Tyr Tyr Cys Gln Gln His Asn Glu Tyr Pro Tyr
                          85                  90                  95
          Thr Phe Gly Ser Gly Thr Lys Leu Glu Ile Lys Arg Thr Val Ala Ala
                          100                 105                 110
          Pro Ser Val Phe Ile Phe Pro Pro Ser Asp Glu Gln Leu Lys Ser Gly
                          115                 120                 125
          Thr Ala Ser Val Val Cys Leu Leu Asn Asn Phe Tyr Pro Arg Glu Ala
                          130                 135                 140
          Lys Val Gln Trp Lys Val Asp Asn Ala Leu Gln Ser Gly Asn Ser Gln
          145                 150                 155                 160
          Glu Ser Val Thr Glu Gln Asp Ser Lys Asp Ser Thr Tyr Ser Leu Ser
                          165                 170                 175
          Ser Thr Leu Thr Leu Ser Lys Ala Asp Tyr Glu Lys His Lys Val Tyr
                          180                 185                 190
          Ala Cys Glu Val Thr His Gln Gly Leu Ser Ser Pro Val Thr Lys Ser
                          195                 200                 205
          Phe Asn Arg Gly Glu Cys
                          210

<210> SEQ ID NO 48
<211> LENGTH: 449
<212> TYPE: PRT
<213> ORGANISM: Artificial sequence
<220> FEATURE:
<223> OTHER INFORMATION: Synthetic

<400> SEQUENCE: 48

Glu Val Gln Leu Gln Gln Ser Gly Pro Glu Leu Val Lys Pro Gly Ala
 1               5                  10                  15
Ser Met Lys Ile Ser Cys Lys Ser Ser Gly Tyr Ser Phe Thr Arg Tyr
                20                  25                  30
Thr Met Asn Trp Val Lys Gln Ser His Gly Lys Asn Leu Glu Trp Ile
                35                  40                  45
Gly Val Ile Asn Pro Tyr Asn Gly Gly Thr Val Tyr Asn Gln Lys Phe
                50                  55                  60
Lys Gly Lys Ala Thr Leu Thr Val Asp Lys Ser Ser Ser Thr Ala Tyr
 65                  70                  75                  80
Met Glu Leu Leu Ser Leu Thr Ser Glu Asp Ser Ala Val Tyr Tyr Cys
                85                  90                  95
Ala Arg Thr Asp Tyr Asp Gly Tyr Ala Met Asp Tyr Trp Gly Gln Gly
                100                 105                 110
Thr Ser Val Thr Val Ser Ser Ala Lys Thr Lys Gly Pro Ser Val Phe
                115                 120                 125
Pro Leu Ala Pro Ser Ser Lys Ser Thr Ser Gly Gly Thr Ala Ala Leu
                130                 135                 140
Gly Cys Leu Val Lys Asp Tyr Phe Pro Glu Pro Val Thr Val Ser Trp
```

```
                145                 150                 155                 160
Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
                210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
                290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
                370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys

<210> SEQ ID NO 49
<211> LENGTH: 119
<212> TYPE: PRT
<213> ORGANISM: Mus musculus

<400> SEQUENCE: 49

Glu Val Gln Leu Gln Gln Ser Gly Pro Glu Leu Val Lys Pro Gly Ala
1               5                   10                  15

Ser Met Arg Ile Ser Cys Lys Ala Ser Gly Tyr Ser Phe Thr Gly Tyr
                20                  25                  30

Thr Met Asn Trp Val Lys Gln Ser His Gly Lys Asn Leu Glu Trp Ile
                35                  40                  45

Gly Val Tyr Asn Pro Tyr Asn Gly Gly Thr Val Tyr Asn Gln Lys Phe
                50                  55                  60

Lys Gly Lys Ala Thr Leu Thr Val Asp Lys Ser Ser Ser Thr Thr Tyr
```

```
                65                  70                  75                  80
Met Glu Leu Leu Ser Leu Thr Ser Glu Asp Ser Ala Val Tyr Tyr Cys
                        85                  90                  95

Ala Arg Thr Asp Ser Gly Gly Tyr Ala Met Asp Cys Trp Gly Gln Gly
                100                 105                 110

Thr Ser Val Thr Val Ser Ser
        115

<210> SEQ ID NO 50
<211> LENGTH: 119
<212> TYPE: PRT
<213> ORGANISM: Mus musculus

<400> SEQUENCE: 50

Glu Val Gln Leu Gln Gln Ser Gly Pro Glu Leu Val Lys Pro Gly Ala
1               5                   10                  15

Ser Met Lys Ile Ser Cys Lys Ser Ser Gly Tyr Ser Phe Thr Arg Tyr
                20                  25                  30

Thr Met Asn Trp Val Lys Gln Ser His Gly Lys Asn Leu Glu Trp Ile
            35                  40                  45

Gly Val Ile Asn Pro Tyr Asn Gly Gly Thr Val Tyr Asn Gln Lys Phe
        50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                        85                  90                  95

Ala Arg Thr Asp Tyr Asp Gly Tyr Ala Met Asp Tyr Trp Gly Gln Gly
                100                 105                 110

Thr Ser Val Thr Val Ser Ser
        115

<210> SEQ ID NO 51
<211> LENGTH: 111
<212> TYPE: PRT
<213> ORGANISM: Mus musculus

<400> SEQUENCE: 51

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Lys Tyr
                20                  25                  30

Gly Val His Trp Val Arg Gln Pro Pro Gly Lys Gly Leu Glu Trp Leu
            35                  40                  45

Gly Val Ile Trp Ala Gly Gly Asn Thr Asn Tyr Asn Ser Ala Leu Met
        50                  55                  60

Ser Arg Leu Ser Ile Asn Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                        85                  90                  95

Thr Phe Asp Val Trp Gly Ala Gly Thr Thr Val Thr Val Ser Ser
                100                 105                 110
```

ANTI-PMEL17 ANTIBODIES AND IMMUNOCONJUGATES

This application is a continuation of U.S. patent application Ser. No. 13/873,462, filed Apr. 30, 2013, now U.S. Pat. No. 9,056,910 B2, which claims the benefit of U.S. Provisional Application No. 61/641,074, filed May 1, 2012, and U.S. Provisional Application No. 61/678,911, filed Aug. 2, 2012; each of which is incorporated by reference herein in its entirety for any purpose.

FIELD OF THE INVENTION

The present invention relates to anti-PMEL17 antibodies and immunoconjugates and methods of using the same.

BACKGROUND

Melanocyte protein PMEL17 is an integral membrane protein that undergoes export from the endoplasmic reticulum to the Golgi apparatus where it is glycosylated and ultimately trafficked to the melanosome. The specific route by which mature PMEL17 makes it way to the melanosome has been a subject of debate, however, it is apparent that some fraction of the protein is presented transiently at the cell surface prior to its entry into stage I melanosomes. Melanosomes are a specialized lysosome-related organelle that produce melanin pigments, which are deposited on fibrils composed of proteolytic fragments derived from the PMEL17 protein. The synthesis of melanin pigments is largely restricted to melanocytes and the post-mitotic pigment epithelium of the eye. Melanocytes uniquely express specialized genes required for pigment formation, some of which are maintained following their transformation to melanoma.

Human PMEL17 is a 661 amino acid protein (including the amino-terminal signal sequence), with a transmembrane region located at amino acids 596 and 616. PMEL17 undergoes complex processing, but at least a portion of the protein's lifecycle is spent on the cell surface.

There is a need in the art for agents that target PMEL17 for the diagnosis and treatment of PMEL17-associated conditions, such as cancer. The invention fulfills that need and provides other benefits.

SUMMARY

The invention provides anti-PMEL17 antibodies and immunoconjugates and methods of using the same.

In some embodiments, an isolated antibody that binds PMEL17 is provided. In some such embodiments, the antibody binds an epitope within amino acids 105 to 125 of SEQ ID NO: 26. In some such embodiments, the antibody binds to an epitope within amino acids 25 to 45 of SEQ ID NO: 26. In some embodiments, the antibody is a monoclonal antibody. In some embodiments, the antibody is a human, humanized, or chimeric antibody. In some embodiments, the antibody is an antibody fragment that binds PMEL17. In some embodiments, PMEL17 is human PMEL17. In some embodiments, human PMEL17 has the sequence of SEQ ID NO: 26 or SEQ ID NO: 27. In some embodiments, the antibody is an IgG1, IgG2a or IgG2b antibody.

In some embodiments, the antibody comprises: a) (i) HVR-H3 comprising the amino acid sequence of SEQ ID NO: 5, (ii) HVR-L3 comprising the amino acid sequence of SEQ ID NO: 8, and (iii) HVR-H2 comprising the amino acid sequence of SEQ ID NO: 4; or b) (i) HVR-H3 comprising the amino acid sequence of SEQ ID NO: 15, (ii) HVR-L3 comprising the amino acid sequence of SEQ ID NO: 8, and (iii) HVR-H2 comprising the amino acid sequence of SEQ ID NO: 14; or c) HVR-H3, HVR-L3, and HVR-H2 of the antibody produced by hybridoma 7509(31D1.6.7) having ATCC Accession No. PTA-12862.

In some embodiments, the antibody comprises: a) (i) HVR-H1 comprising the amino acid sequence of SEQ ID NO: 3, (ii) HVR-H2 comprising the amino acid sequence of SEQ ID NO: 4, and (iii) HVR-H3 comprising the amino acid sequence of SEQ ID NO: 5; or b) (i) HVR-H1 comprising the amino acid sequence of SEQ ID NO: 13, (ii) HVR-H2 comprising the amino acid sequence of SEQ ID NO: 14, and (iii) HVR-H3 comprising the amino acid sequence of SEQ ID NO: 15; or c) HVR-H1, HVR-H2, and HVR-H3 of the antibody produced by hybridoma 7509(31D1.6.7) having ATCC Accession No. PTA-12862.

In some embodiments, the antibody comprises: a) (i) HVR-H1 comprising the amino acid sequence of SEQ ID NO: 3, (ii) HVR-H2 comprising the amino acid sequence of SEQ ID NO: 4, (iii) HVR-H3 comprising the amino acid sequence of SEQ ID NO: 5, (iv) HVR-L1 comprising the amino acid sequence of SEQ ID NO: 6, (v) HVR-L2 comprising the amino acid sequence of SEQ ID NO: 7, (vi) HVR-L3 comprising the amino acid sequence of SEQ ID NO: 8; or b) (i) HVR-H1 comprising the amino acid sequence of SEQ ID NO: 13, (ii) HVR-H2 comprising the amino acid sequence of SEQ ID NO: 14, and (iii) HVR-H3 comprising the amino acid sequence of SEQ ID NO: 15, (iv) HVR-L1 comprising the amino acid sequence of SEQ ID NO: 16, (v) HVR-L2 comprising the amino acid sequence of SEQ ID NO: 7, (vi) HVR-L3 comprising the amino acid sequence of SEQ ID NO: 8; or c) HVR-H1, HVR-H2, HVR-H3, HVR-L1, HVR-L2, and HVR-L3 of the antibody produced by hybridoma 7509(31D1.6.7) having ATCC Accession No. PTA-12862.

In some embodiments, the antibody comprises: a) (i) HVR-L1 comprising the amino acid sequence of SEQ ID NO: 6, (ii) HVR-L2 comprising the amino acid sequence of SEQ ID NO: 7, (iii) HVR-L3 comprising the amino acid sequence of SEQ ID NO: 8; or b) (i) HVR-L1 comprising the amino acid sequence of SEQ ID NO: 16, (ii) HVR-L2 comprising the amino acid sequence of SEQ ID NO: 7, (iii) HVR-L3 comprising the amino acid sequence of SEQ ID NO: 8; or c) HVR-L1, HVR-L2, and HVR-L3 of the antibody produced by hybridoma 7509(31D1.6.7) having ATCC Accession No. PTA-12862.

In some embodiments, the antibody comprises: a) a VH sequence having at least 95% sequence identity to the amino acid sequence of SEQ ID NO: 1 or 50; or b) a VL sequence having at least 95% sequence identity to the amino acid sequence of SEQ ID NO: 2; or c) a VH sequence as in (a) and a VL sequence as in (b); or d) a VH sequence having at least 95% sequence identity to the amino acid sequence of SEQ ID NO: 9 or 49; or e) a VL sequence having at least 95% sequence identity to the amino acid sequence of SEQ ID NO: 10; or f) a VH sequence as in (d) and a VL sequence as in (e); or g) a VH sequence having at least 95% sequence identity to the VH sequence of the antibody produced by hybridoma 7509(31D1.6.7) having ATCC Accession No. PTA-12862; or h) a VL sequence having at least 95% sequence identity to the VL sequence of the antibody produced by hybridoma 7509(31D1.6.7) having ATCC Accession No. PTA-12862; or i) a VH sequence as in (g) and a VL sequence as in (h).

In some embodiments, the antibody comprises a VH sequence having the amino acid sequence of SEQ ID NO: 1 or 50, a VH sequence having the amino acid sequence of SEQ ID NO: 9 or 49, or a VH sequence of the antibody produced by hybridoma 7509(31D1.6.7) having ATCC Accession No. PTA-12862. In some embodiments, the antibody comprises a VL sequence having the amino acid sequence of SEQ ID NO:2, a VL sequence having the amino acid sequence of SEQ ID NO: 10, or a VL sequence of the antibody produced by hybridoma 7509(31D1.6.7) having ATCC Accession No. PTA-12862. In some embodiments, the antibody comprises (a) a VH sequence having the amino acid sequence of SEQ ID NO: 1 or 50 and a VL sequence having the amino acid sequence of SEQ ID NO: 2; or (b) a VH sequence having the amino acid sequence of SEQ ID NO: 9 or 49 and a VL sequence having the amino acid sequence of SEQ ID NO: 10; or (c) a VH sequence of the antibody produced by hybridoma 7509(31D1.6.7) having ATCC Accession No. PTA-12862 and a VL sequence of the antibody produced by hybridoma 7509(31D1.6.7) having ATCC Accession No. PTA-12862.

In some embodiments, an isolated antibody that binds PMEL17 is provided, wherein the antibody comprises: a) (i) HVR-H3 comprising the amino acid sequence of SEQ ID NO: 22, (ii) HVR-L3 comprising the amino acid sequence of SEQ ID NO: 25, and (iii) HVR-H2 comprising the amino acid sequence of SEQ ID NO: 21; or b) (i) HVR-H1 comprising the amino acid sequence of SEQ ID NO: 20, (ii) HVR-H2 comprising the amino acid sequence of SEQ ID NO: 21, and (iii) HVR-H3 comprising the amino acid sequence of SEQ ID NO: 22; or c) (i) HVR-L1 comprising the amino acid sequence of SEQ ID NO: 23, (ii) HVR-L2 comprising the amino acid sequence of SEQ ID NO: 24, (iii) HVR-L3 comprising the amino acid sequence of SEQ ID NO: 25; or d) (i) HVR-H1 comprising the amino acid sequence of SEQ ID NO: 20, (ii) HVR-H2 comprising the amino acid sequence of SEQ ID NO: 21, and (iii) HVR-H3 comprising the amino acid sequence of SEQ ID NO: 22, (iv) HVR-L1 comprising the amino acid sequence of SEQ ID NO: 23, (v) HVR-L2 comprising the amino acid sequence of SEQ ID NO: 24, (vi) HVR-L3 comprising the amino acid sequence of SEQ ID NO: 25; or e) a VH sequence having at least 95% sequence identity to the amino acid sequence of SEQ ID NO: 11 or 51; or f) a VL sequence having at least 95% sequence identity to the amino acid sequence of SEQ ID NO: 12; or g) a VH sequence as in (e) and a VL sequence as in (f); or h) a VH sequence having the amino acid sequence of SEQ ID NO: 11 or 51; or i) a VL sequence having the amino acid sequence of SEQ ID NO: 12; or j) a VH sequence as in (h) and a VL sequence as in (i). In some embodiments, the antibody is an IgG1, IgG2a or IgG2b antibody.

In some embodiments, an isolated nucleic acid encoding any of the foregoing antibodies is provided. In some embodiments, a host cell comprising the nucleic acid is provided. In some embodiments, a method of producing an antibody is provided, comprising culturing the host cell so that the antibody is produced.

In some embodiments, an immunoconjugate is provided. In some such embodiments, the immunoconjugate comprises any of the foregoing antibodies and a cytotoxic agent. In some embodiments, the immunoconjugate has the formula Ab-(L-D)p, wherein: (a) Ab is the antibody of any one of claims 1 to 16; (b) L is a linker; (c) D is a drug selected from a maytansinoid, an auristatin, a calicheamicin, a pyrrolobenzodiazepine, and a nemorubicin derivative; and (d) p ranges from 1-8.

In some embodiments, D is an auristatin. In some such embodiments, D has formula $D_E$

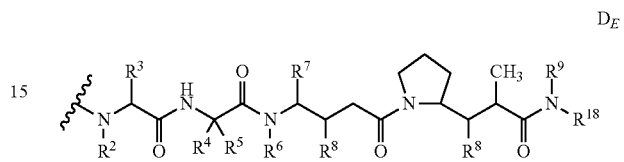

and wherein $R^2$ and $R^6$ are each methyl, $R^3$ and $R^4$ are each isopropyl, $R^5$ is H, $R^7$ is sec-butyl, each $R^8$ is independently selected from $CH_3$, $O$—$CH_3$, OH, and H; $R^9$ is H; and $R^{18}$ is —$C(R^8)_2$—$C(R^8)_2$-aryl.

In some embodiments, the drug (D) is MMAE.

In some embodiments, D is a pyrrolobenzodiazepine of Formula A:

wherein the dotted lines indicate the optional presence of a double bond between C1 and C2 or C2 and C3;

$R^2$ is independently selected from H, OH, =O, =$CH_2$, CN, R, OR, =CH—$R^D$, =$C(R^D)_2$, O—$SO_2$—R, $CO_2R$ and COR, and optionally further selected from halo or dihalo, wherein $R^D$ is independently selected from R, $CO_2R$, COR, CHO, $CO_2H$, and halo;

$R^6$ and $R^9$ are independently selected from H, R, OH, OR, SH, SR, $NH_2$, NHR, NRR', $NO_2$, $Me_3Sn$ and halo;

$R^7$ is independently selected from H, R, OH, OR, SH, SR, $NH_2$, NHR, NRR', $NO_2$, $Me_3Sn$ and halo;

Q is independently selected from O, S and NH;

$R^{11}$ is either H, or R or, where Q is O, $SO_3M$, where M is a metal cation;

R and R' are each independently selected from optionally substituted $C_{1-8}$ alkyl, $C_{3-8}$ heterocyclyl and $C_{5-20}$ aryl groups, and optionally in relation to the group NRR', R and R' together with the nitrogen atom to which they are attached form an optionally substituted 4-, 5-, 6- or 7-membered heterocyclic ring;

$R^{12}$, $R^{16}$, $R^{19}$ and $R^{17}$ are as defined for $R^2$, $R^6$, $R^9$ and $R^7$ respectively;

R" is a $C_{3-12}$ alkylene group, which chain may be interrupted by one or more heteroatoms and/or aromatic rings that are optionally substituted; and X and X' are independently selected from O, S and N(H).

In some such embodiments, D has the structure:

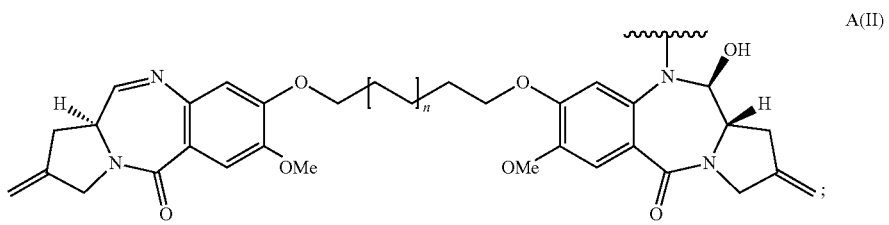
A(II)

wherein n is 0 or 1.
In some embodiments, D has a structure selected from:

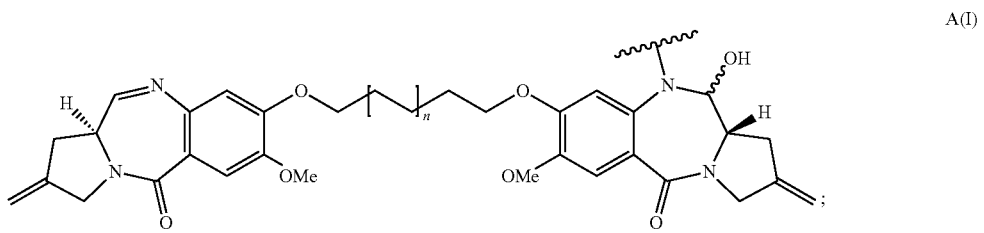
A(I)

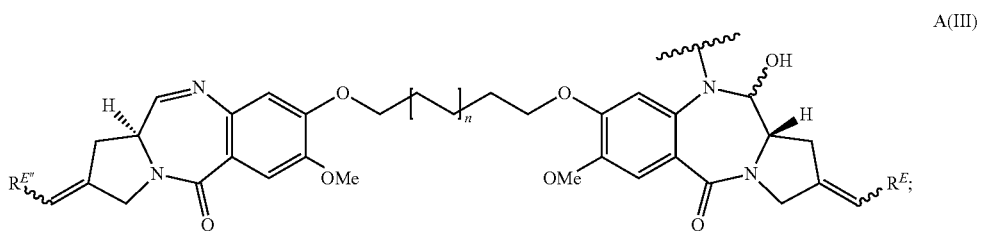
A(III)

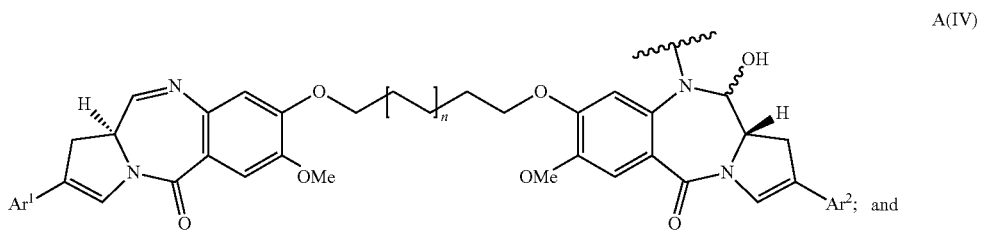
A(IV)

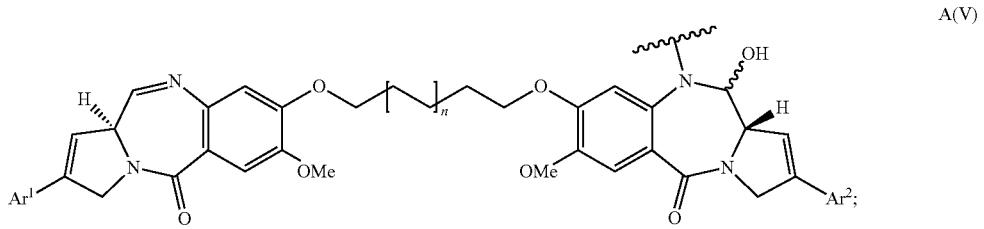
A(V)

wherein $R^E$ and $R^{E''}$ are each independently selected from H or $R^D$, wherein $R^D$ is independently selected from R, $CO_2R$, COR, CHO, $CO_2H$, and halo;

wherein $Ar^1$ and $Ar^2$ are each independently optionally substituted $C_{5-20}$ aryl; and wherein n is 0 or 1.

In some embodiments, D is a nemorubicin derivative. In some such embodiments, D has a structure selected from:

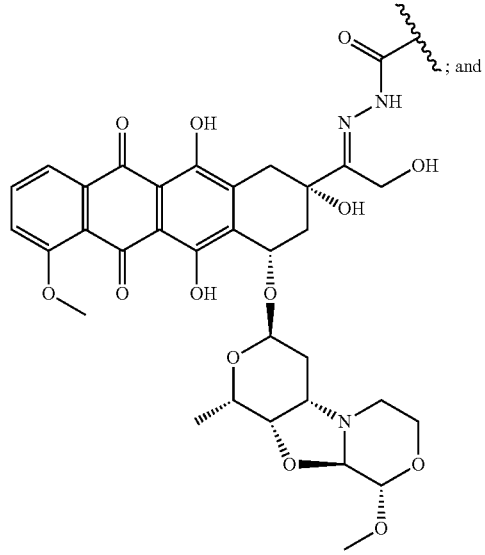

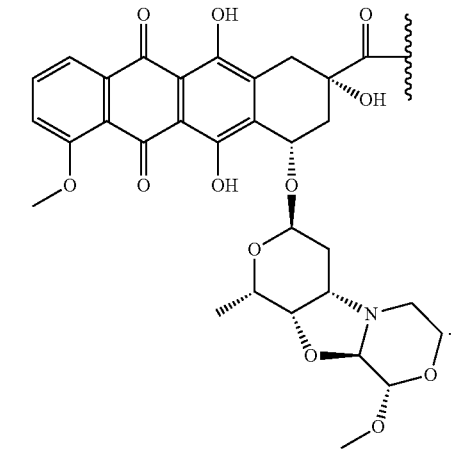

In some embodiments, the linker is cleavable by a protease. In some such embodiments, the linker comprises a val-cit dipeptide or a Phe-Lys dipeptide. In some embodiments, the linker is acid-labile. In some such embodiments, the linker comprises hydrazone.

In some embodiments, an immunoconjugate has the formula:

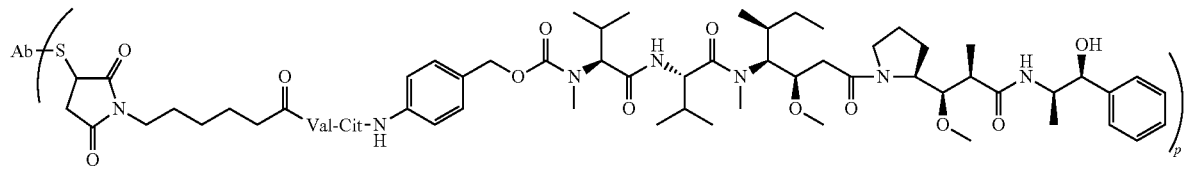

wherein S is a sulfur atom.

In some embodiments, an immunoconjugate has the formula:

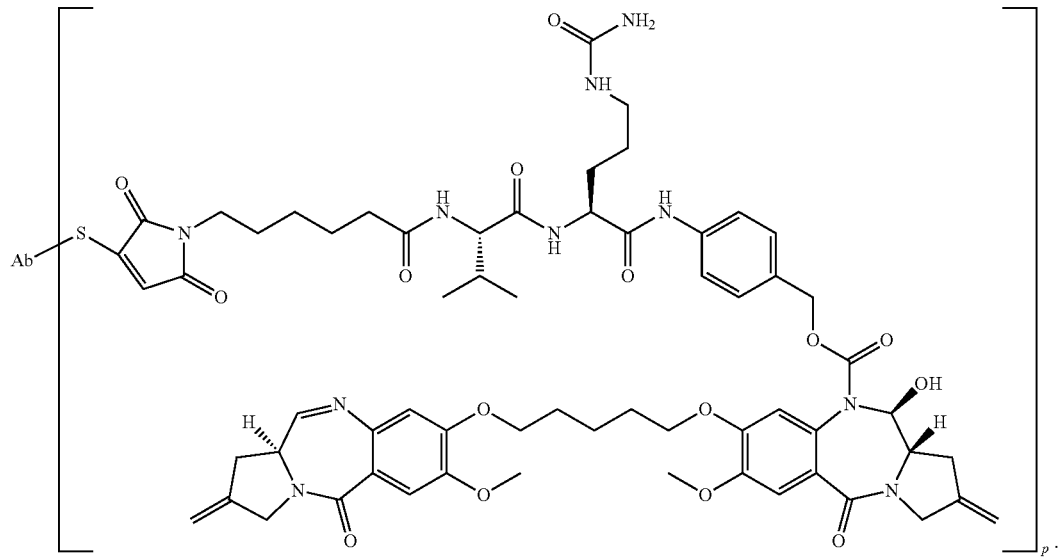

In some embodiments, an immunoconjugate has a formula selected from:
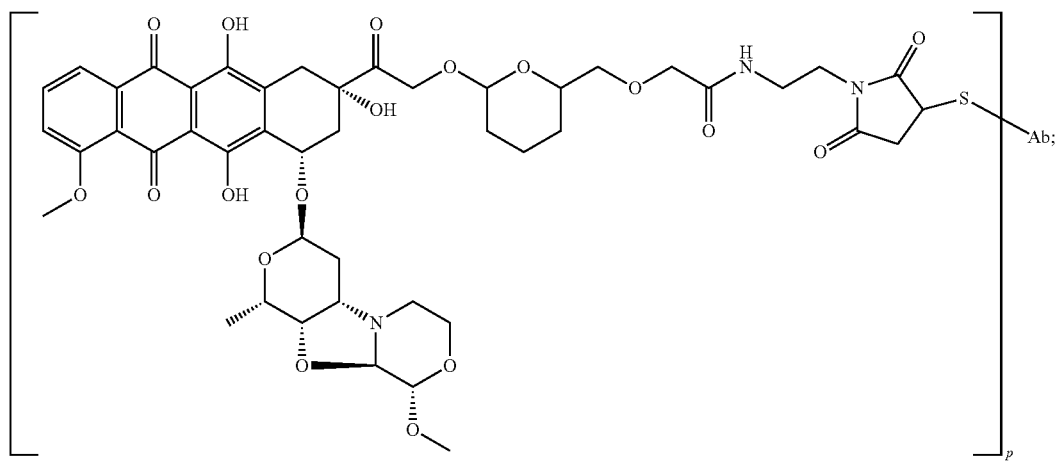
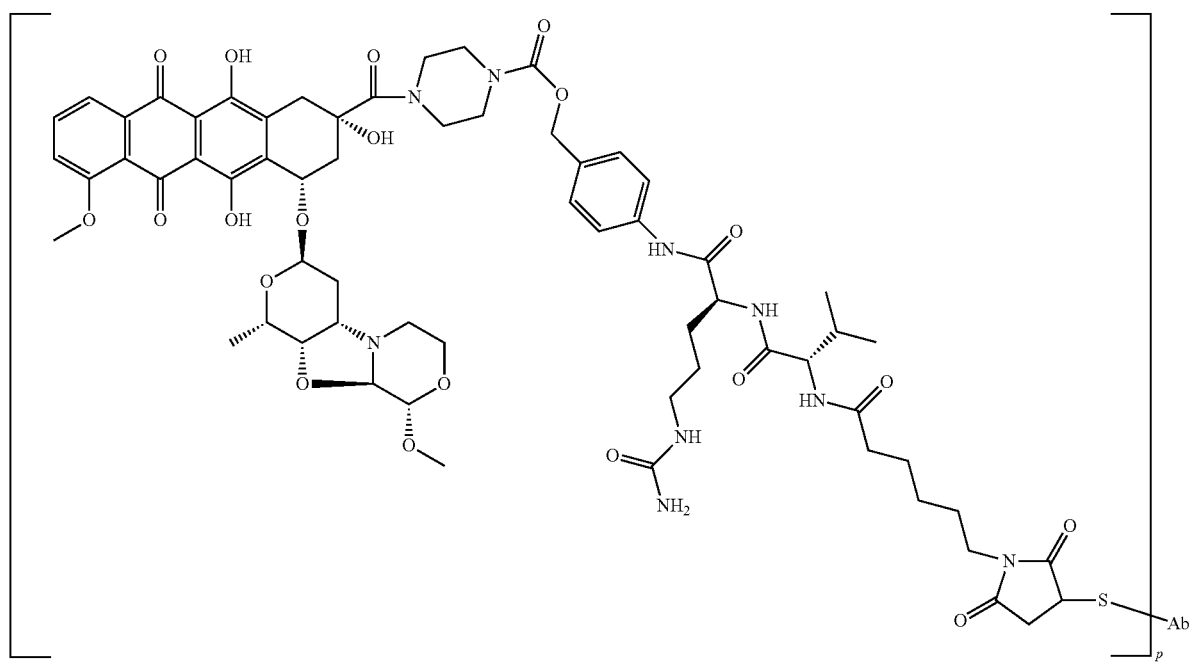
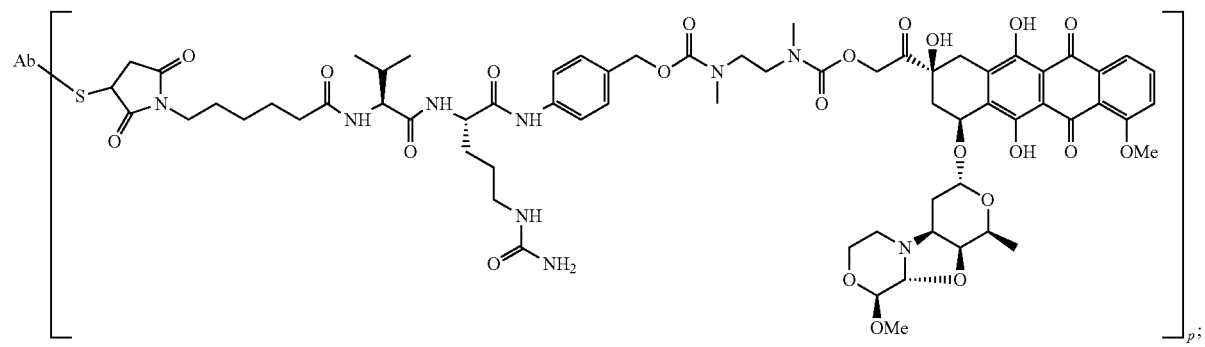

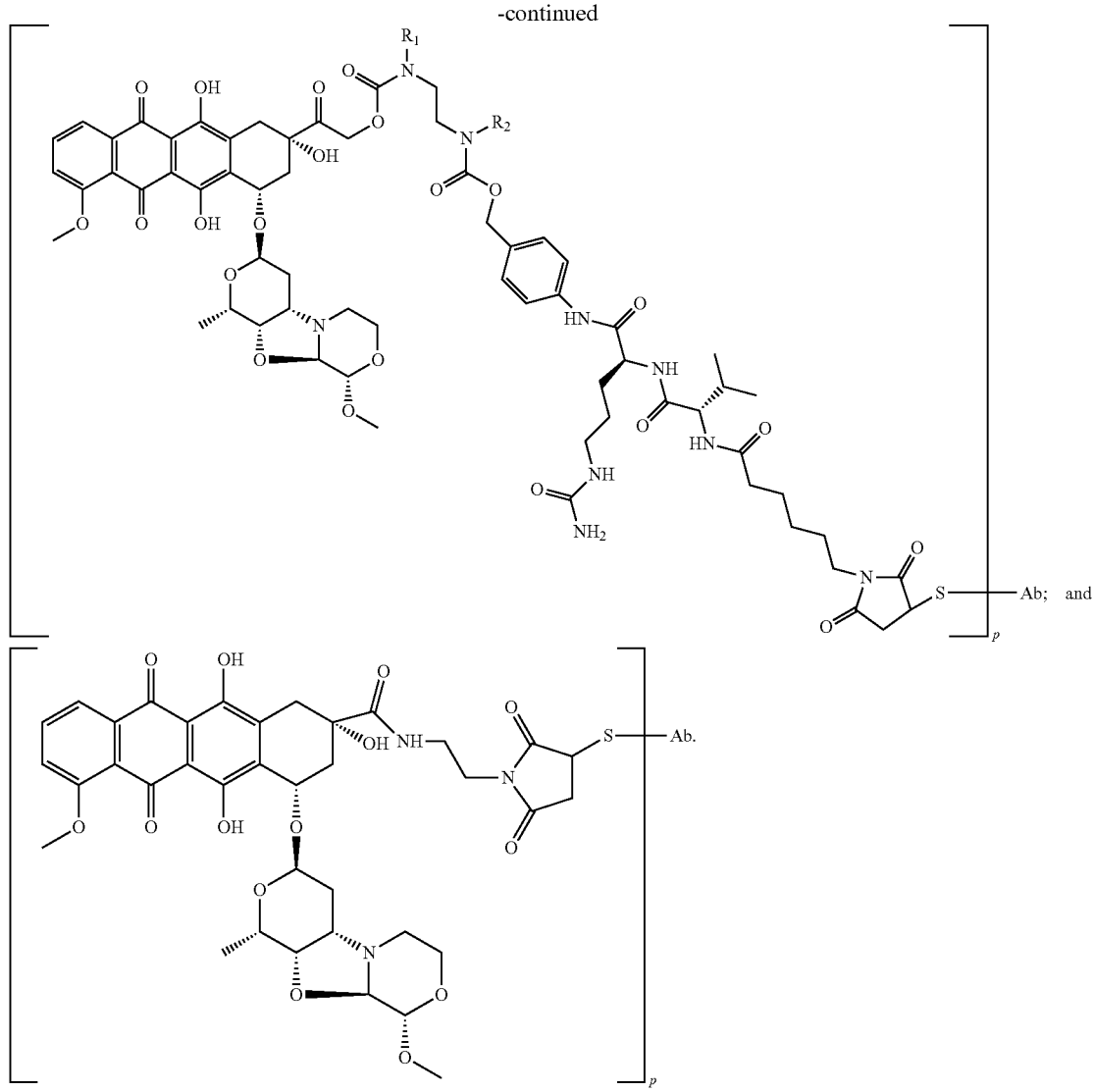

In some embodiments of the foregoing immunoconjugates, p ranges from 2-5.

In some embodiments, an immunoconjugate is provided, wherein the immunoconjugate comprises an antibody that comprises: a) (i) HVR-H1 comprising the amino acid sequence of SEQ ID NO: 3, (ii) HVR-H2 comprising the amino acid sequence of SEQ ID NO: 4, (iii) HVR-H3 comprising the amino acid sequence of SEQ ID NO: 5, (iv) HVR-L1 comprising the amino acid sequence of SEQ ID NO: 6, (v) HVR-L2 comprising the amino acid sequence of SEQ ID NO: 7, (vi) HVR-L3 comprising the amino acid sequence of SEQ ID NO: 8; or b) (i) HVR-H1 comprising the amino acid sequence of SEQ ID NO: 13, (ii) HVR-H2 comprising the amino acid sequence of SEQ ID NO: 14, and (iii) HVR-H3 comprising the amino acid sequence of SEQ ID NO: 15, (iv) HVR-L1 comprising the amino acid sequence of SEQ ID NO: 16, (v) HVR-L2 comprising the amino acid sequence of SEQ ID NO: 7, (vi) HVR-L3 comprising the amino acid sequence of SEQ ID NO: 8; or c) HVR-H1, HVR-H2, HVR-H3, HVR-L1, HVR-L2, and HVR-L3 of the antibody produced by hybridoma 7509 (31D1.6.7) having ATCC Accession No. PTA-12862.

In some embodiments, an immunoconjugate is provided, wherein the immunoconjugate comprises an antibody that comprises (a) a VH sequence having the amino acid sequence of SEQ ID NO: 1 or 50 and a VL sequence having the amino acid sequence of SEQ ID NO:2; or (b) a VH sequence having the amino acid sequence of SEQ ID NO: 9 or 49 and a VL sequence having the amino acid sequence of SEQ ID NO: 10; or (c) a VH sequence of the antibody produced by hybridoma 7509(31D1.6.7) having ATCC Accession No. PTA-12862 and a VL sequence of the antibody produced by hybridoma 7509(31D1.6.7) having ATCC Accession No. PTA-12862.

In some embodiments, pharmaceutical formulations are provided. In some such embodiments, the pharmaceutical formulation comprises an antibody described herein and a pharmaceutically acceptable carrier. In some embodiments, a pharmaceutical formulation further comprises an additional therapeutic agent.

In some embodiments, methods of treating an individual having a PMEL17-positive cancer are provided. In some such embodiments, the method comprises administering to the individual an effective amount of an immunoconjugate comprising an antibody that binds to PMEL17. In some such embodiments, the method comprises administering to the individual an effective amount of an immunoconjugate comprising an antibody that binds to the extracellular domain of PMEL17. In some such embodiments, the method comprises administering to the individual an effective amount of an immunoconjugate comprising an antibody described herein. In some embodiments, the PMEL17-positive cancer is melanoma. In some embodiments, a method of treating an individual having a PMEL17-positive cancer further comprises administering an additional therapeutic agent to the individual.

In some embodiments, methods of treating an individual having a PMEL17-positive cancer are provided, wherein the PMEL17-positive cancer is resistant to a first therapeutic. In some embodiments, the method comprises administering to the individual an effective amount of an immunoconjugate comprising an antibody that binds to PMEL17. In some embodiments, the PMEL17-positive cancer is melanoma. In some embodiments, the first therapeutic comprises a first antibody that binds an antigen other than PMEL17. In some embodiments, the first therapeutic is a first immunoconjugate comprising a first antibody that binds an antigen other than PMEL17 and a first cytotoxic agent. In some embodiments, the first antibody binds an antigen selected from endothelin B receptor (ETBR), tyrosinase-related protein 1 (TYRP1), cytotoxic T lymphocyte antigen 4 (CTLA-4), and glycoprotein NMB (GPNMB). In some embodiments, the first antibody binds ETBR. In some embodiments, the first antibody is hu5E9.v1. In some embodiments, the first immunoconjugate is hu5E9.v1-MC-val-cit-PAB-MMAE. In some embodiments, the first cytotoxic agent and the cytotoxic agent of the immunoconjugate comprising an antibody that binds to PMEL17 are different. In some such embodiments, the first cytotoxic agent is MMAE and the cytotoxic agent of the immunoconjugate comprising an antibody that binds to PMEL17 is selected from a calicheamicin, a pyrrolobenzodiazepine, and a nemorubicin derivative. In some embodiments, the cytotoxic agent of the immunoconjugate comprising an antibody that binds to PMEL17 is selected from a pyrrolobenzodiazepine and a nemorubicin derivative.

In some embodiments, a method of treating an individual with PMEL17-positive cancer is provided, wherein the method comprises administering to the individual an effective amount of a first immunoconjugate described herein in combination with a second immunoconjugate comprising an antibody that binds ETBR. In some embodiments, the antibody that binds ETBR comprises an HVR H1 comprising a sequence of SEQ ID NO: 33, an HVR H2 comprising a sequence of SEQ ID NO: 34, an HVR H3 comprising a sequence of SEQ ID NO: 35, an HVR L1 comprising a sequence of SEQ ID NO: 36, an HVR L2 comprising a sequence of SEQ ID NO: 37, and an HVR L3 comprising a sequence of SEQ ID NO: 38. In some embodiments, the antibody that binds ETBR comprises a heavy chain variable region comprising the sequence of SEQ ID NO: 40 and a light chain variable region comprising the sequence of SEQ ID NO: 39. In some embodiments, the first immunoconjugate comprises a cytotoxic agent selected from an auristatin, a pyrrolobenzodiazepine, and a nemorubicin derivative, and the second immunoconjugate comprises a cytotoxic agent selected from an auristatin, a pyrrolobenzodiazepine, and a nemorubicin derivative. In some embodiments, the first immunoconjugate comprises a cytotoxic agent selected from a pyrrolobenzodiazepine and a nemorubicin derivative, and the second immunoconjugate comprises an auristatin. In some embodiments, the second immunoconjugate comprises MMAE. In some such embodiments, the second immunoconjugate comprises a linker-drug portion comprising MC-val-cit-PAB-MMAE. In some embodiments, the second immunoconjugate is hu5E9.v1-MC-val-cit-PAB-MMAE. In any of the foregoing embodiments, the PMEL17-positive cancer may be melanoma. In some embodiments, the PMEL17-positive cancer is also ETBR-positive.

In some embodiments, a method of inhibiting proliferation of PMEL17-positive cell is provided. In some such embodiments, the method comprises exposing the cell to an immunoconjugate described herein under conditions permissive for binding of the immunoconjugate to PMEL17 on the surface of the cell, thereby inhibiting proliferation of the cell. In some embodiments, the cell is a melanoma cell.

In some embodiments, an antibody that binds to PMEL17 conjugated to a label is provided. In some embodiments, the label is a positron emitter. In some such embodiments, the positron emitter is $^{89}$Zr.

In some embodiments, a method of detecting human PMEL17 in a biological sample is provided. In some embodiments, the method comprises contacting the biological sample with an anti-PMEL17 antibody described herein under conditions permissive for binding of the anti-PMEL17 antibody to a naturally occurring human PMEL17. In some embodiments, the method further comprises detecting whether a complex is formed between the anti-PMEL17 antibody and a naturally occurring human PMEL17 in the biological sample. In some embodiments, the anti-PMEL17 antibody is the antibody produced by hybridoma 7509 (31D1.6.7) having ATCC Accession No. PTA-12862. In some embodiments, the antibody comprises a) (i) HVR-H1 comprising the amino acid sequence of SEQ ID NO: 3, (ii) HVR-H2 comprising the amino acid sequence of SEQ ID NO: 4, (iii) HVR-H3 comprising the amino acid sequence of SEQ ID NO: 5, (iv) HVR-L1 comprising the amino acid sequence of SEQ ID NO: 6, (v) HVR-L2 comprising the amino acid sequence of SEQ ID NO: 7, (vi) HVR-L3 comprising the amino acid sequence of SEQ ID NO: 8; or b) (i) HVR-H1 comprising the amino acid sequence of SEQ ID NO: 13, (ii) HVR-H2 comprising the amino acid sequence of SEQ ID NO: 14, and (iii) HVR-H3 comprising the amino acid sequence of SEQ ID NO: 15, (iv) HVR-L1 comprising the amino acid sequence of SEQ ID NO: 16, (v) HVR-L2 comprising the amino acid sequence of SEQ ID NO: 7, (vi) HVR-L3 comprising the amino acid sequence of SEQ ID NO: 8; or c) HVR-H1, HVR-H2, HVR-H3, HVR-L1, HVR-L2, and HVR-L3 of the antibody produced by hybridoma 7509(31D1.6.7) having ATCC Accession No. PTA-12862 In some embodiments, the biological sample is a melanoma sample.

In some embodiments, a method for detecting a PMEL17-positive cancer is provided. In some such embodiments, the method comprises (i) administering a labeled anti-PMEL17 antibody to a subject having or suspected of having a PMEL17-positive cancer, wherein the labeled anti-PMEL17 antibody comprises an anti-PMEL17 antibody described herein, and (ii) detecting the labeled anti-PMEL17 antibody in the subject, wherein detection of the labeled anti-PMEL17 antibody indicates a PMEL17-positive cancer in the subject. In some such embodiments, the labeled anti-PMEL17 antibody comprises an anti-PMEL17 antibody conjugated to a positron emitter. In some embodiments, the positron emitter is $^{89}$Zr.

BRIEF DESCRIPTION OF THE FIGURES

FIGS. 2A and 2B show alignments of the (A) light chain and (B) heavy chain variable regions sequences for antibodies 8G3, 17A9, and 15F2.

FIGS. 3A to 3D shows epitope mapping of 77E6 (A and B), 17A9 (C and D), and 31D1 (D), as described in Example D.

FIGS. 7A to 7B show (A) exemplary staining for each level of PMEL17 staining and (B) IHC scores for a panel of human melanoma samples, as described in Example K.

FIGS. 9A and 9B show an alignment of human, mouse, rat, and cynomolgus monkey PMEL17, as described in Example F.

FIGS. 12A to 12C show sensitivity of (A) parental UACC-257X2.2 cells, (B) in vivo derived resistant UACC-257X2.2 cells, and (C) in vitro derived resistant UACC-257X2.2 cells to increasing concentrations of anti-ETBR-vc-MMAE, anti-PMEL17-vc-MMAE, and anti-gD-vc-MMAE, as described in Example M.

FIGS. 13A to 13C show sensitivity of (A) parental UACC-257X2.2 cells, (B) in vivo derived resistant UACC-257X2.2 cells, and (C) in vitro derived resistant UACC-257X2.2 cells to increasing concentrations of anti-ETBR-PNU, anti-PMEL17-PNU, and anti-gD-PNU, as described in Example M.

FIGS. 14A to 14C show sensitivity of (A) parental UACC-257X2.2 cells, (B) in vivo derived resistant UACC-257X2.2 cells, and (C) in vitro derived resistant UACC-257X2.2 cells to increasing concentrations of anti-ETBR-vc-PNU, anti-PMEL17-vc-PNU, and anti-gD-vc-PNU, as described in Example M.

FIGS. 15A to 15E show the structures of various antibody-drug conjugates, including (A) Ab-MC-val-cit-PAB-MMAE; (B) Ab-MC-acetal-PNU-159682; (C) Ab-MC-val-cit-PAB-PNU-159682; (D) Ab-MC-val-cit-PAB-PBD; and (E) Ab-PNU-159682.

DETAILED DESCRIPTION OF CERTAIN EMBODIMENTS OF THE INVENTION

I. Definitions

Figure 1A:
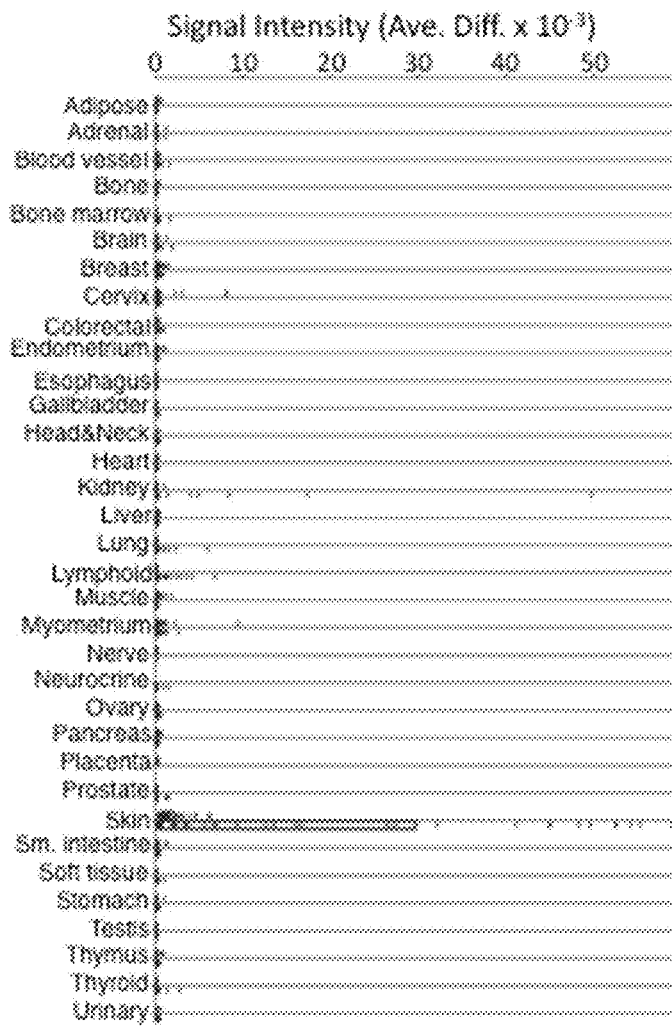
FIGS. 1A and 1B show (A) a graphic representation of the levels of human PMEL17 gene expression in various tissues, and (B) a graphic representation of the levels of human PMEL17 in various human cell lines, as described in Example A.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-PMEL17 antibody" and "an antibody that binds to PMEL17" refer to an antibody that is capable of binding PMEL17 with sufficient affinity such that the antibody is useful as a diagnostic and/or therapeutic agent in targeting PMEL17. In one embodiment, the extent of binding of an anti-PMEL17 antibody to an unrelated, non-PMEL17 protein is less than about 10% of the binding of the antibody to PMEL17 as measured, e.g., by a radioimmunoassay (RIA). In certain embodiments, an antibody that binds to PMEL17 has a dissociation constant (Kd) of $\leq 1$ μM, $\leq 100$ nM, $\leq 10$ nM, $\leq 5$ Nm, $\leq 4$ nM, $\leq 3$ nM, $\leq 2$ nM, $\leq 1$ nM, $\leq 0.1$ nM, $\leq 0.01$ nM, or $\leq 0.001$ nM (e.g., $10^{-8}$M or less, e.g. from $10^{-8}$ M to $10^{-13}$ M, e.g., from $10^{-9}$M to $10^{-13}$ M). In certain embodiments, an anti-PMEL17 antibody binds to an epitope of PMEL17 that is conserved among PMEL17 from different species.

The term "antibody" is used herein in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody and that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The terms "cancer" and "cancerous" refer to or describe the physiological condition in mammals that is typically characterized by unregulated cell growth/proliferation. Examples of cancer include, but are not limited to, melanoma, carcinoma, lymphoma (e.g., Hodgkin's and non-Hodgkin's lymphoma), blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called $\alpha$, $\delta$, $\epsilon$, $\gamma$, and $\mu$, respectively.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

A "chemotherapeutic agent" is a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylolomelamine; acetogenins (especially bullatacin and bullatacinone); delta-9-tetrahydrocannabinol (dronabinol, MARINOL'); beta-lapachone; lapachol; colchicines; betulinic acid; a camptothecin (including the synthetic analogue topotecan (HYCAMTN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e. g., calicheamicin, especially calicheamicin gammaII and calicheamicin omegaII (see, e.g., Agnew, Chem Intl. Ed. Engl., 33: 183-186 (1994)); dynemicin, including dynemicin A; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., paclitaxel (TAXOL®; Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and docetaxel (TAXOTERE®; Rhone-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone; CVP, an abbreviation for a combined therapy of cyclophosphamide, vincristine, and prednisolone; and FOLFOX, an abbreviation for a treatment regimen with oxaliplatin (ELOXATIN™) combined with 5-FU and leucovorin.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "epitope" refers to the particular site on an antigen molecule to which an antibody binds.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The term "glycosylated forms of PMEL17" refers to naturally occurring forms of PMEL17 that are post-translationally modified by the addition of carbohydrate residues.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences of Proteins of Immunological Interest*, 5th Ed. Public Health Service, National Institutes of Health, Bethesda, Md. (1991).) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, Front. Biosci. 13:1619-1633 (2008).) Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" is a mammal Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated antibody" is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated nucleic acid" refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-PMEL17 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "PMEL17," as used herein, refers to any native PMEL17. The term includes PMEL17 from any vertebrate source, including mammals such as primates (e.g. humans and cynomolgus monkeys) and rodents (e.g., mice and rats), unless otherwise indicated. The term encompasses "full-length," unprocessed PMEL17, as well as any form of PMEL17 that results from processing in the cell. The term also includes naturally occurring variants of PMEL17, e.g., splice variants or allelic variants. The amino acid sequence of an exemplary human PMEL17 preproprotein, with signal sequence (amino acids 1-24) is shown in SEQ ID NO: 26. The amino acid sequence of an exemplary human PMEL17 proprotein is shown in SEQ ID NO: 27. The predicted sequence of an exemplary cynomolgus monkey PMEL17 (without signal sequence) is shown in SEQ ID NO: 28. The amino acid sequences for exemplary rat PMEL17 with signal sequence (amino acids 1-25) and without signal sequence are shown in SEQ ID NOs: 29 and 30, respectively. The amino acid sequences for exemplary mouse PMEL17 with signal sequence (amino acids 1-25) and without signal sequence are shown in SEQ ID NOs: 31 and 32, respectively.

The term "PMEL17-positive cancer" refers to a cancer comprising cells that express (including transiently express) PMEL17 on their surface.

The term "PMEL17-positive cell" refers to a cell that expresses PMEL17 on its surface.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CHL CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. Kuby Immunology, 6th ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

"Alkyl" is $C_1$-$C_{18}$ hydrocarbon containing normal, secondary, tertiary or cyclic carbon atoms. Examples are methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$).

The term "$C_1$-$C_8$ alkyl," as used herein refers to a straight chain or branched, saturated or unsaturated hydrocarbon having from 1 to 8 carbon atoms. Representative "$C_1$-$C_8$ alkyl" groups include, but are not limited to, -methyl, -ethyl, -n-propyl, -n-butyl, -n-pentyl, -n-hexyl, -n-heptyl, -n-octyl, -n-nonyl and -n-decyl; while branched $C_1$-$C_8$ alkyls include, but are not limited to, -isopropyl, -sec-butyl, -isobutyl, -tert-butyl, -isopentyl, 2-methylbutyl, unsaturated $C_1$-$C_8$ alkyls include, but are not limited to, -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, 1-hexyl, 2-hexyl, 3-hexyl, -acetylenyl, -propynyl, -1-butynyl, -2-butynyl, -1-pentynyl, -2-pentynyl, -3-methyl-1 butynyl. A $C_1$-$C_8$ alkyl group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)$NH_2$, —C(O)NHR', —C(O)N(R')$_2$—NHC(O)R', —$SO_3$R', —S(O)$_2$R', —S(O)R', —OH, -halogen, —$N_3$, —$NH_2$, —NH(R'), —N(R')$_2$ and —CN; where each R' is independently selected from H, —$C_1$-$C_8$ alkyl and aryl.

The term "$C_1$-$C_{12}$ alkyl," as used herein refers to a straight chain or branched, saturated or unsaturated hydrocarbon having from 1 to 12 carbon atoms. A $C_1$-$C_{12}$ alkyl group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)$NH_2$, —C(O)NHR', —C(O)N(R')$_2$—NHC(O)R', —$SO_3$R', —S(O)$_2$R', —S(O)R', —OH, -halogen, —$N_3$, —$NH_2$, —NH(R'), —N(R')$_2$ and —CN; where each R' is independently selected from H, —$C_1$-$C_8$ alkyl and aryl.

The term "$C_1$-$C_6$ alkyl," as used herein refers to a straight chain or branched, saturated or unsaturated hydrocarbon having from 1 to 6 carbon atoms. Representative "$C_1$-$C_6$ alkyl" groups include, but are not limited to, -methyl, -ethyl, -n-propyl, -n-butyl, -n-pentyl, - and n-hexyl; while branched $C_1$-$C_6$ alkyls include, but are not limited to, -isopropyl, -sec-butyl, -isobutyl, -tert-butyl, -isopentyl, and 2-methylbutyl; unsaturated $C_1$-$C_6$ alkyls include, but are not limited to, -vinyl, -allyl, -1-butenyl, -2-butenyl, and -isobutylenyl, -1-pentenyl, -2-pentenyl, -3-methyl-1-butenyl, -2-methyl-2-butenyl, -2,3-dimethyl-2-butenyl, 1-hexyl, 2-hexyl, and 3-hexyl. A $C_1$-$C_6$ alkyl group can be unsubstituted or substituted with one or more groups, as described above for $C_1$-$C_8$ alkyl group.

The term "$C_1$-$C_4$ alkyl," as used herein refers to a straight chain or branched, saturated or unsaturated hydrocarbon having from 1 to 4 carbon atoms. Representative "$C_1$-$C_4$ alkyl" groups include, but are not limited to, -methyl, -ethyl, -n-propyl, -n-butyl; while branched $C_1$-$C_4$ alkyls include, but are not limited to, -isopropyl, -sec-butyl, -isobutyl, -tert-butyl; unsaturated $C_1$-$C_4$ alkyls include, but are not limited to, -vinyl, -allyl, -1-butenyl, -2-butenyl, and -isobutylenyl. A $C_1$-$C_4$ alkyl group can be unsubstituted or substituted with one or more groups, as described above for $C_1$-$C_8$ alkyl group.

"Alkoxy" is an alkyl group singly bonded to an oxygen. Exemplary alkoxy groups include, but are not limited to, methoxy (—$OCH_3$) and ethoxy (—$OCH_2CH_3$). A "$C_1$-$C_5$ alkoxy" is an alkoxy group with 1 to 5 carbon atoms. Alkoxy groups may can be unsubstituted or substituted with one or more groups, as described above for alkyl groups.

"Alkenyl" is $C_2$-$C_{18}$ hydrocarbon containing normal, secondary, tertiary or cyclic carbon atoms with at least one site of unsaturation, i.e. a carbon-carbon, $sp^2$ double bond. Examples include, but are not limited to: ethylene or vinyl (—CH=$CH_2$), allyl (—$CH_2$CH=$CH_2$), cyclopentenyl (—$C_5H_7$), and 5-hexenyl (—$CH_2CH_2CH_2CH_2$CH=$CH_2$). A "$C_2$-$C_8$ alkenyl" is a hydrocarbon containing 2 to 8 normal, secondary, tertiary or cyclic carbon atoms with at least one site of unsaturation, i.e. a carbon-carbon, $sp^2$ double bond.

"Alkynyl" is $C_2$-$C_{18}$ hydrocarbon containing normal, secondary, tertiary or cyclic carbon atoms with at least one site of unsaturation, i.e. a carbon-carbon, sp triple bond. Examples include, but are not limited to: acetylenic (—C≡CH) and propargyl (—$CH_2$C≡CH). A "$C_2$-$C_8$ alkynyl" is a hydrocarbon containing 2 to 8 normal, secondary, tertiary or cyclic carbon atoms with at least one site of unsaturation, i.e. a carbon-carbon, sp triple bond.

"Alkylene" refers to a saturated, branched or straight chain or cyclic hydrocarbon radical of 1-18 carbon atoms, and having two monovalent radical centers derived by the removal of two hydrogen atoms from the same or two different carbon atoms of a parent alkane. Typical alkylene radicals include, but are not limited to: methylene (—$CH_2$—) 1,2-ethyl (—$CH_2CH_2$—), 1,3-propyl (—$CH_2CH_2CH_2$—), 1,4-butyl (—$CH_2CH_2CH_2CH_2$—), and the like.

A "$C_1$-$C_{10}$ alkylene" is a straight chain, saturated hydrocarbon group of the formula —$(CH_2)_{1-10}$—. Examples of a $C_1$-$C_{10}$ alkylene include methylene, ethylene, propylene, butylene, pentylene, hexylene, heptylene, ocytylene, nonylene and decalene.

"Alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to: 1,2-ethylene (—CH=CH—).

"Alkynylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkyne. Typical alkynylene radicals include, but are not limited to: acetylene (—C≡C—), propargyl (—$CH_2$C≡C—), and 4-pentynyl (—$CH_2CH_2CH_2$C≡C—).

"Aryl" refers to a carbocyclic aromatic group. Examples of aryl groups include, but are not limited to, phenyl, naphthyl and anthracenyl. A carbocyclic aromatic group or a heterocyclic aromatic group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)$NH_2$, —C(O)NHR', —C(O)N(R')$_2$—NHC(O)R', —S(O)$_2$R', —S(O)R', —OH, -halogen, —$N_3$, —$NH_2$, —NH(R'), —N(R')$_2$ and —CN; wherein each R' is independently selected from H, —$C_1$-$C_8$ alkyl and aryl.

A "$C_5$-$C_{20}$ aryl" is an aryl group with 5 to 20 carbon atoms in the carbocyclic aromatic rings. Examples of $C_5$-$C_{20}$ aryl groups include, but are not limited to, phenyl, naphthyl and anthracenyl. A $C_5$-$C_{20}$ aryl group can be substituted or unsubstituted as described above for aryl groups. A "$C_5$-$C_{14}$ aryl" is an aryl group with 5 to 14 carbon atoms in the carbocyclic aromatic rings. Examples of $C_5$-$C_{14}$ aryl groups include, but are not limited to, phenyl, naphthyl and anthracenyl. A $C_5$-$C_{14}$ aryl group can be substituted or unsubstituted as described above for aryl groups.

An "arylene" is an aryl group which has two covalent bonds and can be in the ortho, meta, or para configurations as shown in the following structures:

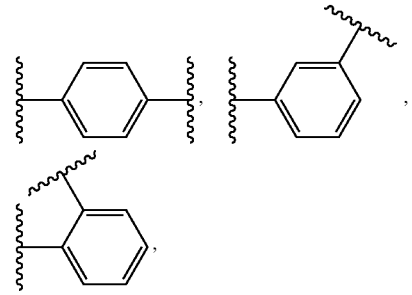

in which the phenyl group can be unsubstituted or substituted with up to four groups including, but not limited to, —$C_1$-$C_8$ alkyl, —O—($C_1$-$C_8$ alkyl), -aryl, —C(O)R', —OC(O)R', —C(O)OR', —C(O)$NH_2$, —C(O)NHR', —C(O)N(R')$_2$—NHC(O)R', —S(O)$_2$R', —S(O)R', —OH, -halogen, —$N_3$, —$NH_2$, —NH(R'), —N(R')$_2$ and —CN; wherein each R' is independently selected from H, —$C_1$-$C_8$ alkyl and aryl.

"Arylalkyl" refers to an acyclic alkyl radical in which one of the hydrogen atoms bonded to a carbon atom, typically a terminal or $sp^3$ carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. The arylalkyl group comprises 6 to 20 carbon atoms, e.g. the alkyl moiety, including alkanyl, alkenyl or alkynyl groups, of the arylalkyl group is 1 to 6 carbon atoms and the aryl moiety is 5 to 14 carbon atoms.

"Heteroarylalkyl" refers to an acyclic alkyl radical in which one of the hydrogen atoms bonded to a carbon atom, typically a terminal or spa carbon atom, is replaced with a heteroaryl radical. Typical heteroarylalkyl groups include, but are not limited to, 2-benzimidazolylmethyl, 2-furylethyl, and the like. The heteroarylalkyl group comprises 6 to 20 carbon atoms, e.g. the alkyl moiety, including alkanyl, alkenyl or alkynyl groups, of the heteroarylalkyl group is 1 to 6 carbon atoms and the heteroaryl moiety is 5 to 14 carbon atoms and 1 to 3 heteroatoms selected from N, O, P, and S.

The heteroaryl moiety of the heteroarylalkyl group may be a monocycle having 3 to 7 ring members (2 to 6 carbon atoms or a bicycle having 7 to 10 ring members (4 to 9 carbon atoms and 1 to 3 heteroatoms selected from N, O, P, and S), for example: a bicyclo [4,5], [5,5], [5,6], or [6,6] system.

"Substituted alkyl," "substituted aryl," and "substituted arylalkyl" mean alkyl, aryl, and arylalkyl respectively, in which one or more hydrogen atoms are each independently replaced with a substituent. Typical substituents include, but are not limited to, —X, —R, —O⁻, —OR, —SR, —S⁻, —NR$_2$, —NR$_3$, =NR, —CX$_3$, —CN, —OCN, —SCN, —N=C=O, —NCS, —NO, —NO$_2$, =N$_2$, —N$_3$, NC(=O)R, —C(=O)R, —C(=O)NR$_2$, —SO$_3^-$, —SO$_3$H, —S(=O)$_2$R, —OS(=O)$_2$OR, —S(=O)$_2$NR, —S(=O)R, —OP(=O)(OR)$_2$, —P(=O)(OR)$_2$, —PO$^-_3$, —PO$_3$H$_2$, —C(=O)R, —C(=O)X, —C(=S)R, —CO$_2$R, —CO$_2^-$, —C(=S)OR, —C(=O)SR, —C(=S)SR, —C(=O)NR$_2$, —C(=S)NR$_2$, —C(=NR)NR$_2$, where each X is independently a halogen: F, Cl, Br, or I; and each R is independently —H, C$_2$-C$_{18}$ alkyl, C$_6$-C$_{20}$ aryl, C$_3$-C$_{14}$ heterocycle, protecting group or prodrug moiety. Alkylene, alkenylene, and alkynylene groups as described above may also be similarly substituted.

"Heteroaryl" and "heterocycle" refer to a ring system in which one or more ring atoms is a heteroatom, e.g. nitrogen, oxygen, and sulfur. The heterocycle radical comprises 3 to 20 carbon atoms and 1 to 3 heteroatoms selected from N, O, P, and S. A heterocycle may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S), for example: a bicyclo [4,5], [5,5], [5,6], or [6,6] system.

Exemplary heterocycles are described, e.g., in Paquette, Leo A., "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and *J. Am. Chem. Soc.* (1960) 82:5566.

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or 3-carboline. Still more typically, nitrogen bonded heterocycles include 1-aziridyl, 1-azetedyl, 1-pyrrolyl, 1-imidazolyl, 1-pyrazolyl, and 1-piperidinyl.

A "C$_3$-C$_8$ heterocycle" refers to an aromatic or non-aromatic C$_3$-C$_8$ carbocycle in which one to four of the ring carbon atoms are independently replaced with a heteroatom from the group consisting of O, S and N. Representative examples of a C$_3$-C$_8$ heterocycle include, but are not limited to, benzofuranyl, benzothiophene, indolyl, benzopyrazolyl, coumarinyl, isoquinolinyl, pyrrolyl, thiophenyl, furanyl, thiazolyl, imidazolyl, pyrazolyl, triazolyl, quinolinyl, pyrimidinyl, pyridinyl, pyridonyl, pyrazinyl, pyridazinyl, isothiazolyl, isoxazolyl and tetrazolyl. A C$_3$-C$_8$ heterocycle can be unsubstituted or substituted with up to seven groups including, but not limited to, —C$_1$-C$_8$ alkyl, —O—(C$_1$-C$_8$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; wherein each R' is independently selected from H, —C$_1$-C$_8$ alkyl and aryl.

"C$_3$-C$_8$ heterocyclo" refers to a C$_3$-C$_8$ heterocycle group defined above wherein one of the heterocycle group's hydrogen atoms is replaced with a bond. A C$_3$-C$_8$ heterocyclo can be unsubstituted or substituted with up to six groups including, but not limited to, —O—C$_8$ alkyl, —O—(C$_1$-C$_8$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; wherein each R' is independently selected from H, —O—C$_8$ alkyl and aryl.

A "C$_3$-C$_{20}$ heterocycle" refers to an aromatic or non-aromatic C$_3$-C$_8$ carbocycle in which one to four of the ring carbon atoms are independently replaced with a heteroatom from the group consisting of O, S and N. A C$_3$-C$_{20}$ heterocycle can be unsubstituted or substituted with up to seven groups including, but not limited to, —C$_1$-C$_8$ alkyl, —O—(C$_1$-C$_8$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; wherein each R' is independently selected from H, —C$_1$-C$_8$ alkyl and aryl.

"C$_3$-C$_{20}$ heterocyclo" refers to a C$_3$-C$_{20}$ heterocycle group defined above wherein one of the heterocycle group's hydrogen atoms is replaced with a bond.

"Carbocycle" means a saturated or unsaturated ring having 3 to 7 carbon atoms as a monocycle or 7 to 12 carbon atoms as a bicycle. Monocyclic carbocycles have 3 to 6 ring atoms, still more typically 5 or 6 ring atoms. Bicyclic carbocycles have 7 to 12 ring atoms, e.g. arranged as a bicyclo [4,5], [5,5], [5,6] or [6,6] system, or 9 or 10 ring atoms arranged as a bicyclo [5,6] or [6,6] system. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cycloheptyl, and cyclooctyl.

A "$C_3$-$C_8$ carbocycle" is a 3-, 4-, 5-, 6-, 7- or 8-membered saturated or unsaturated non-aromatic carbocyclic ring. Representative $C_3$-$C_8$ carbocycles include, but are not limited to, -cyclopropyl, -cyclobutyl, -cyclopentyl, -cyclopentadienyl, -cyclohexyl, -cyclohexenyl, -1,3-cyclohexadienyl, -1,4-cyclohexadienyl, -cycloheptyl, -1,3-cycloheptadienyl, -1,3,5-cycloheptatrienyl, -cyclooctyl, and -cyclooctadienyl. A $C_3$-$C_8$ carbocycle group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; where each R' is independently selected from H, —$C_1$-$C_8$ alkyl and aryl.

A "$C_3$-$C_8$ carbocyclo" refers to a $C_3$-$C_8$ carbocycle group defined above wherein one of the carbocycle groups' hydrogen atoms is replaced with a bond.

"Linker" refers to a chemical moiety comprising a covalent bond or a chain of atoms that covalently attaches an antibody to a drug moiety. In various embodiments, linkers include a divalent radical such as an alkyldiyl, an aryldiyl, a heteroaryldiyl, moieties such as: (CR$_2$)$_n$O(CR$_2$)$_n$—, repeating units of alkyloxy (e.g. polyethylenoxy, PEG, polymethyleneoxy) and alkylamino (e.g. polyethyleneamino, Jeffamine™); and diacid ester and amides including succinate, succinamide, diglycolate, malonate, and caproamide. In various embodiments, linkers can comprise one or more amino acid residues, such as valine, phenylalanine, lysine, and homolysine.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

"Leaving group" refers to a functional group that can be substituted by another functional group. Certain leaving groups are well known in the art, and examples include, but are not limited to, a halide (e.g., chloride, bromide, iodide), methanesulfonyl (mesyl), p-toluenesulfonyl (tosyl), trifluoromethylsulfonyl (triflate), and trifluoromethylsulfonate.

The term "protecting group" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include, but are not limited to, acetyl, trifluoroacetyl, t-butoxycarbonyl (BOC), benzyloxycarbonyl (CBZ) and 9-fluorenylmethylenoxycarbonyl (Fmoc). For a general description of protecting groups and their use, see T. W. Greene, Protective Groups in Organic Synthesis, John Wiley & Sons, New York, 1991, or a later edition.

II. Compositions and Methods

In one aspect, the invention is based, in part, on antibodies that bind to PMEL17 and immunoconjugates comprising such antibodies. Antibodies and immunoconjugates of the invention are useful, e.g., for the diagnosis or treatment of PMEL17-positive cancers.

A. Exemplary Anti-PMEL17 Antibodies

In some embodiments, the invention provides isolated antibodies that bind to PMEL17. PMEL17 is an integral membrane protein the is presented transiently at the cell surface of melanocytes. As demonstrated herein, PMEL17 is expressed in the majority of human melanoma specimens examined.

An exemplary naturally occurring human PMEL17 pre-proprotein sequence, with signal sequence (amino acids 1-24) is provided in SEQ ID NO: 26, and the corresponding PMEL17 proprotein sequence is shown in SEQ ID NO: 27 (corresponding to amino acids 25-661 of SEQ ID NO: 26).

In certain embodiments, an anti-PMEL17 antibody binds an epitope within amino acids 105 to 125 of SEQ ID NO: 26, or binds to an epitope within amino acids 25 to 45 of SEQ ID NO: 26. Nonlimiting exemplary such antibodies include 17A9, 8G3, and 31D1. In some embodiments, an anti-PMEL17 antibody binds human PMEL17. In some embodiments, an anti-PMEL17 antibody binds PMEL selected from human, cynomolgus monkey, mouse, and rat PMEL17.

In some embodiments, an anti-PMEL17 antibody binds to an epitope within amino acids 105 to 125 of SEQ ID NO: 26. In some such embodiments, the anti-PMEL17 antibody binds PMEL17 with an affinity of ≤5 nM, or ≤4 nM, or ≤3 nM, or ≤2 nM, or ≤1 nM, and optionally ≥0.0001 nM, or ≥0.001 nM, or ≥0.01 nM. Nonlimiting exemplary such antibodies include 17A9 and 8G3, described herein. In some embodiments, an anti-PMEL17 antibody that binds to an epitope within amino acids 105 to 125 of SEQ ID NO: 26 binds to human PMEL17. In some embodiments, an anti-PMEL17 antibody that binds to an epitope within amino acids 105 to 125 of SEQ ID NO: 26 binds to human PMEL17 and/or cynomolgus monkey PMEL17.

In some embodiments, an anti-PMEL17 antibody binds to an epitope within amino acids 25 to 45 of SEQ ID NO: 26. In some such embodiments, the anti-PMEL17 antibody binds PMEL17 with an affinity of ≤5 nM, or ≤4 nM, or ≤3 nM, or ≤2 nM, or ≤1 nM, and optionally ≥0.0001 nM, or ≥0.001 nM, or ≥0.01 nM. A nonlimiting exemplary such antibody is 31D1, described herein. In some embodiments, an anti-PMEL17 antibody that binds to an epitope within amino acids 25 to 45 of SEQ ID NO: 26 binds to human PMEL17. In some embodiments, an anti-PMEL17 antibody that binds to an epitope within amino acids 105 to 125 of SEQ ID NO: 26 binds to human PMEL17 and/or cynomolgus monkey PMEL17.

Further antibodies that bind PMEL17 are provided. A nonlimiting exemplary anti-PMEL17 antibody is 15F2, described herein. In some embodiments, the anti-PMEL17 antibody binds PMEL17 with an affinity of ≤5 nM, or ≤4 nM, or ≤3 nM, or ≤2 nM, or ≤1 nM, and optionally ≥0.0001 nM, or ≥0.001 nM, or ≥0.01 nM. In some embodiments, an anti-PMEL17 antibody binds to human PMEL17. In some embodiments, an anti-PMEL17 antibody binds to human PMEL17 and/or cynomolgus monkey PMEL17.

Assays

To determine whether an anti-PMEL17 antibody "binds to an epitope within amino acids 105 to 125 of SEQ ID NO: 26" or "binds to an epitope within amino acids 25 to 45 of SEQ ID NO: 26," PMEL17 polypeptides with N- and C-terminal deletions are expressed in 293 cells and binding of the antibody to the truncated polypeptides is tested by FACS as described in Example D, wherein a substantial reduction (≥70% reduction) or elimination of binding of the antibody to a truncated polypeptide relative to binding to full-length PMEL17 expressed in 293 cells indicates that the antibody does not bind to that truncated polypeptide.

Whether an anti-PMEL17 antibody "binds with an affinity of ≤5 nM, or ≤4 nM, or ≤3 nM, or ≤2 nM, or ≤1 nM," is determined according to a BIAcore® assay. For example, Kd is measured using surface plasmon resonance assays using a BIACORE®-3000 (BIAcore, Inc., Piscataway, N.J.). BIAcore™ research grade CM5 chips are activated with 1-ethyl-3-(3-dimethylaminopropyl) carbodiimide (EDC) and N-hydroxysuccinimide (NHS) reagents according to the supplier's instructions. Goat anti-human Fc IgGs are coupled to the chips to achieve approximately 10,000 response units (RU) in each flow cell. Unreacted coupling groups are blocked with 1M ethanolamine. For kinetics measurements, anti-PMEL17 antibodies are captured to achieve approximately 300 RU. Two-fold serial dilutions of human PMEL17 ECD (for example, amino acids 25 to 291 fused to a C-terminal Fc expressed in a baculovirus system, or amino acids 22-558 fused to Fc; 125 nM to 0.49 nM) are injected in HBS-P buffer (0.01M HEPES pH7.4, 0.15M NaCl, 0.005% surfactant P20) at 25° C. with a flow rate of 30 μl/min. Association rates ($k_{on}$) and dissociation rates ($k_{off}$) are calculated using a 1:1 Langmuir binding model (BIAcore™ Evaluation Software version 3.2). The equilibrium dissociation constant (Kd) is calculated as the ratio $k_{off}/k_{on}$. If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-Aminco® spectrophotometer (ThermoSpectronic) with a stirred cuvette.

Antibody 17A9 and Other Embodiments

In some embodiments, the invention provides an anti-PMEL17 antibody comprising at least one, two, three, four, five, or six HVRs selected from (a) HVR-H1 comprising the amino acid sequence of SEQ ID NO: 3; (b) HVR-H2 comprising the amino acid sequence of SEQ ID NO: 4; (c) HVR-H3 comprising the amino acid sequence of SEQ ID NO: 5; (d) HVR-L1 comprising the amino acid sequence of SEQ ID NO: 6; (e) HVR-L2 comprising the amino acid sequence of SEQ ID NO: 7; and (f) HVR-L3 comprising the amino acid sequence of SEQ ID NO: 8.

In one aspect, the invention provides an antibody comprising at least one, at least two, or all three VH HVR sequences selected from (a) HVR-H1 comprising the amino acid sequence of SEQ ID NO: 3; (b) HVR-H2 comprising the amino acid sequence of SEQ ID NO: 4; and (c) HVR-H3 comprising the amino acid sequence of SEQ ID NO: 5. In one embodiment, the antibody comprises HVR-H3 comprising the amino acid sequence of SEQ ID NO: 5. In another embodiment, the antibody comprises HVR-H3 comprising the amino acid sequence of SEQ ID NO: 5 and HVR-L3 comprising the amino acid sequence of SEQ ID NO: 8. In a further embodiment, the antibody comprises HVR-H3 comprising the amino acid sequence of SEQ ID NO: 5, HVR-L3 comprising the amino acid sequence of SEQ ID NO: 8, and HVR-H2 comprising the amino acid sequence of SEQ ID NO: 4. In a further embodiment, the antibody comprises (a) HVR-H1 comprising the amino acid sequence of SEQ ID NO: 3; (b) HVR-H2 comprising the amino acid sequence of SEQ ID NO: 4; and (c) HVR-H3 comprising the amino acid sequence of SEQ ID NO: 5.

In another aspect, the invention provides an antibody comprising at least one, at least two, or all three VL HVR sequences selected from (a) HVR-L1 comprising the amino acid sequence of SEQ ID NO: 6; (b) HVR-L2 comprising the amino acid sequence of SEQ ID NO: 7; and (c) HVR-L3 comprising the amino acid sequence of SEQ ID NO: 8. In one embodiment, the antibody comprises (a) HVR-L1 comprising the amino acid sequence of SEQ ID NO: 6; (b) HVR-L2 comprising the amino acid sequence of SEQ ID NO: 7; and (c) HVR-L3 comprising the amino acid sequence of SEQ ID NO: 8.

In another aspect, an antibody of the invention comprises (a) a VH domain comprising at least one, at least two, or all three VH HVR sequences selected from (i) HVR-H1 comprising the amino acid sequence of SEQ ID NO: 3, (ii) HVR-H2 comprising the amino acid sequence of SEQ ID NO: 4, and (iii) HVR-H3 comprising an amino acid sequence selected from SEQ ID NO: 5; and (b) a VL domain comprising at least one, at least two, or all three VL HVR sequences selected from (i) HVR-L1 comprising the amino acid sequence of SEQ ID NO: 6, (ii) HVR-L2 comprising the amino acid sequence of SEQ ID NO: 7, and (c) HVR-L3 comprising the amino acid sequence of SEQ ID NO: 8.

In another aspect, the invention provides an antibody comprising (a) HVR-H1 comprising the amino acid sequence of SEQ ID NO: 3; (b) HVR-H2 comprising the amino acid sequence of SEQ ID NO: 4; (c) HVR-H3 comprising the amino acid sequence of SEQ ID NO: 5; (d) HVR-L1 comprising the amino acid sequence of SEQ ID NO: 6; (e) HVR-L2 comprising the amino acid sequence of SEQ ID NO: 7; and (f) HVR-L3 comprising the amino acid sequence of SEQ ID NO: 8.

In some embodiments, the invention provides an anti-PMEL17 antibody comprising at least one, two, three, four, five, or six HVRs selected from (a) HVR-H1 comprising the amino acid sequence of SEQ ID NO: 17; (b) HVR-H2 comprising the amino acid sequence of SEQ ID NO: 18; (c) HVR-H3 comprising the amino acid sequence of SEQ ID NO: 5; (d) HVR-L1 comprising the amino acid sequence of SEQ ID NO: 19; (e) HVR-L2 comprising the amino acid sequence of SEQ ID NO: 7; and (f) HVR-L3 comprising the amino acid sequence of SEQ ID NO: 8.

In one aspect, the invention provides an antibody comprising at least one, at least two, or all three VH HVR sequences selected from (a) HVR-H1 comprising the amino acid sequence of SEQ ID NO: 17; (b) HVR-H2 comprising the amino acid sequence of SEQ ID NO: 18; and (c) HVR-H3 comprising the amino acid sequence of SEQ ID NO: 5. In a further embodiment, the antibody comprises HVR-H3 comprising the amino acid sequence of SEQ ID NO: 5, HVR-L3 comprising the amino acid sequence of SEQ ID NO: 8, and HVR-H2 comprising the amino acid sequence of SEQ ID NO: 18. In a further embodiment, the antibody comprises (a) HVR-H1 comprising the amino acid sequence of SEQ ID NO: 17; (b) HVR-H2 comprising the amino acid sequence of SEQ ID NO: 18; and (c) HVR-H3 comprising the amino acid sequence of SEQ ID NO: 5.

In another aspect, the invention provides an antibody comprising at least one, at least two, or all three VL HVR sequences selected from (a) HVR-L1 comprising the amino acid sequence of SEQ ID NO: 19; (b) HVR-L2 comprising the amino acid sequence of SEQ ID NO: 7; and (c) HVR-L3 comprising the amino acid sequence of SEQ ID NO: 8. In one embodiment, the antibody comprises (a) HVR-L1 comprising the amino acid sequence of SEQ ID NO: 19; (b) HVR-L2 comprising the amino acid sequence of SEQ ID NO: 7; and (c) HVR-L3 comprising the amino acid sequence of SEQ ID NO: 8.

In another aspect, an antibody of the invention comprises (a) a VH domain comprising at least one, at least two, or all three VH HVR sequences selected from (i) HVR-H1 comprising the amino acid sequence of SEQ ID NO: 17, (ii) HVR-H2 comprising the amino acid sequence of SEQ ID NO: 18, and (iii) HVR-H3 comprising an amino acid sequence selected from SEQ ID NO: 5; and (b) a VL domain comprising at least one, at least two, or all three VL HVR sequences selected from (i) HVR-L1 comprising the amino acid sequence of SEQ ID NO: 19, (ii) HVR-L2 comprising the amino acid sequence of SEQ ID NO: 7, and (c) HVR-L3 comprising the amino acid sequence of SEQ ID NO: 8.

In another aspect, the invention provides an antibody comprising (a) HVR-H1 comprising the amino acid sequence of SEQ ID NO: 17; (b) HVR-H2 comprising the amino acid sequence of SEQ ID NO: 18; (c) HVR-H3 comprising the amino acid sequence of SEQ ID NO: 5; (d) HVR-L1 comprising the amino acid sequence of SEQ ID NO: 19; (e) HVR-L2 comprising the amino acid sequence of SEQ ID NO: 7; and (f) HVR-L3 comprising the amino acid sequence of SEQ ID NO: 8.

In some embodiments, $X_1$ in SEQ ID NO: 17 is selected from Arg, Lys, Gln, Asn, Gly, and Ala. In some embodiments, $X_1$ in SEQ ID NO: 17 is selected from Arg, Lys, Gly, and Ala. In some embodiments, $X_1$ in SEQ ID NO: 17 is selected from Arg and Gly. In some embodiments, $X_2$ in SEQ ID NO: 18 is selected from Tyr, Trp, Phe, Thr, Ser, Ile, Leu, Val, Met, Ala, and Norleucine. In some embodiments, $X_2$ in SEQ ID NO: 18 is selected from Tyr, Phe, Ile, Leu, and Val. In some embodiments, $X_2$ in SEQ ID NO: 18 is selected from Tyr and Ile. In some embodiments, $X_3$ in SEQ ID NO: 19 is selected from Ser, Thr, and Val. In some embodiments, $X_3$ in SEQ ID NO: 19 is selected from Ser and Thr. In some embodiments, $X_4$ in SEQ ID NO: 19 is selected from Ser, Thr, and Val. In some embodiments, $X_4$ in SEQ ID NO: 19 is selected from Ser and Thr.

In any of the above embodiments, an anti-PMEL17 antibody is humanized. In one embodiment, an anti-PMEL17 antibody comprises HVRs as in any of the above embodiments, and further comprises a human acceptor framework, e.g. a human immunoglobulin framework or a human consensus framework. In certain embodiments, the human acceptor framework is the human VL kappa 1 ($VL_{KI}$) framework and/or the VH framework $VH_1$. In some embodiments, a humanized anti-PMEL17 antibody comprises (a) HVR-H1 comprising the amino acid sequence of SEQ ID NO: 3; (b) HVR-H2 comprising the amino acid sequence of SEQ ID NO: 4; (c) HVR-H3 comprising the amino acid sequence of SEQ ID NO: 5; (d) HVR-L1 comprising the amino acid sequence of SEQ ID NO: 6; (e) HVR-L2 comprising the amino acid sequence of SEQ ID NO: 7; and (f) HVR-L3 comprising the amino acid sequence of SEQ ID NO: 8. In some embodiments, a humanized anti-PMEL17 antibody comprises (a) HVR-H1 comprising the amino acid sequence of SEQ ID NO: 17; (b) HVR-H2 comprising the amino acid sequence of SEQ ID NO: 18; (c) HVR-H3 comprising the amino acid sequence of SEQ ID NO: 5; (d) HVR-L1 comprising the amino acid sequence of SEQ ID NO: 19; (e) HVR-L2 comprising the amino acid sequence of SEQ ID NO: 7; and (f) HVR-L3 comprising the amino acid sequence of SEQ ID NO: 8.

In another aspect, an anti-PMEL17 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 1 or 50. In certain embodiments, a VH sequence having at least 90%, 91%, 92%, 93%, 94%, 95%, 96%, 97%, 98%, or 99% identity to the amino acid sequence of SEQ ID NO: 1 or 50 contains substitutions (e.g., conservative substitutions), insertions, or deletions relative to the reference sequence, but an anti-PMEL17 antibody comprising that sequence retains the ability to bind to PMEL17. In certain embodiments, a total of 1 to 10 amino acids have been substituted, inserted and/or deleted in SEQ ID NO: 1 or 50. In certain embodiments, a total of 1 to 5 amino acids have been substituted, inserted and/or deleted in SEQ ID NO: 1 or 50. In certain embodiments, substitutions, insertions, or deletions occur in regions outside the HVRs (i.e., in the FRs). Optionally, the anti-PMEL17 antibody comprises the VH sequence of SEQ ID NO: 1 or 50, including post-translational modifications of that sequence. In a particular embodiment, the VH comprises one, two or three HVRs selected from: (a) HVR-H1 comprising the amino acid sequence of SEQ ID NO: 3, (b) HVR-H2 comprising the amino acid sequence of SEQ ID NO: 4, and (c) HVR-H3 comprising the amino acid sequence of SEQ ID NO: 5. In some embodiments, the VH comprises one, two or three HVRs selected from: (a) HVR-H1 comprising the amino acid sequence of SEQ ID NO: 17, (b) HVR-H2 comprising the amino acid sequence of SEQ ID NO: 18, and (c) HVR-H3 comprising the amino acid sequence of SEQ ID NO: 5.

In some embodiments, an anti-PMEL17 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 2. In certain embodiments, a VL sequence having at least 90%, 91%, 92%, 93%, 94%, 95%, 96%, 97%, 98%, or 99% identity to the amino acid sequence of SEQ ID NO: 2 contains substitutions (e.g., conservative substitutions), insertions, or deletions relative to the reference sequence, but an anti-PMEL17 antibody comprising that sequence retains the ability to bind to PMEL17. In certain embodiments, a total of 1 to 10 amino acids have been substituted, inserted and/or deleted in SEQ ID NO: 2. In certain embodiments, a total of 1 to 5 amino acids have been substituted, inserted and/or deleted in SEQ ID NO: 2. In certain embodiments, the substitutions, insertions, or deletions occur in regions outside the HVRs (i.e., in the FRs). Optionally, the anti-PMEL17 antibody comprises the VL sequence of SEQ ID NO: 2, including post-translational modifications of that sequence. In a particular embodiment, the VL comprises one, two or three HVRs selected from (a) HVR-L1 comprising the amino acid sequence of SEQ ID NO: 6; (b) HVR-L2 comprising the amino acid sequence of SEQ ID NO: 7; and (c) HVR-L3 comprising the amino acid sequence of SEQ ID NO: 8. In some embodiments, the VL comprises one, two or three HVRs selected from (a) HVR-L1 comprising the amino acid sequence of SEQ ID NO: 19; (b) HVR-L2 comprising the amino acid sequence of SEQ ID NO: 7; and (c) HVR-L3 comprising the amino acid sequence of SEQ ID NO: 8.

In another aspect, an anti-PMEL17 antibody is provided, wherein the antibody comprises a VH as in any of the embodiments provided above, and a VL as in any of the embodiments provided above. In one embodiment, the antibody comprises the VH and VL sequences in SEQ ID NO: 1 and SEQ ID NO: 2, respectively, including post-translational modifications of those sequences. In some embodiments, the antibody comprises the VH and VL sequences in SEQ ID NO: 50 and SEQ ID NO: 2, respectively, including post-translational modifications of those sequences.

In a further aspect, the invention provides an antibody that binds to the same epitope as an anti-PMEL17 antibody provided herein. For example, in certain embodiments, an antibody is provided that binds to the same epitope as an anti-PMEL17 antibody comprising a VH sequence of SEQ ID NO: 1 or 50 and a VL sequence of SEQ ID NO: 2. In certain embodiments, an antibody is provided that binds to an epitope of SEQ ID NO: 26 from, within, or overlapping amino acids 105 to 125.

In a further aspect of the invention, an anti-PMEL17 antibody according to any of the above embodiments is a monoclonal antibody, including a chimeric, humanized or human antibody. In one embodiment, an anti-PMEL17 antibody is an antibody fragment, e.g., a Fv, Fab, Fab', scFv, diabody, or F(ab')2 fragment. In another embodiment, the antibody is a substantially full length antibody, e.g., an IgG1 antibody or other antibody class or isotype as defined herein.

In a further aspect, an anti-PMEL17 antibody according to any of the above embodiments may incorporate any of the features, singly or in combination, as described in Sections 1-7 below.

Antibody 8G3 and Other Embodiments

In some embodiments, the invention provides an anti-PMEL17 antibody comprising at least one, two, three, four, five, or six HVRs selected from (a) HVR-H1 comprising the amino acid sequence of SEQ ID NO: 13; (b) HVR-H2 comprising the amino acid sequence of SEQ ID NO: 14; (c) HVR-H3 comprising the amino acid sequence of SEQ ID NO: 15; (d) HVR-L1 comprising the amino acid sequence of SEQ ID NO: 16; (e) HVR-L2 comprising the amino acid sequence of SEQ ID NO: 7; and (f) HVR-L3 comprising the amino acid sequence of SEQ ID NO: 8.

In one aspect, the invention provides an antibody comprising at least one, at least two, or all three VH HVR sequences selected from (a) HVR-H1 comprising the amino acid sequence of SEQ ID NO: 13; (b) HVR-H2 comprising the amino acid sequence of SEQ ID NO: 14; and (c) HVR-H3 comprising the amino acid sequence of SEQ ID NO: 15. In one embodiment, the antibody comprises HVR-H3 comprising the amino acid sequence of SEQ ID NO: 15. In another embodiment, the antibody comprises HVR-H3 comprising the amino acid sequence of SEQ ID NO: 15 and HVR-L3 comprising the amino acid sequence of SEQ ID NO: 8. In a further embodiment, the antibody comprises HVR-H3 comprising the amino acid sequence of SEQ ID NO: 15, HVR-L3 comprising the amino acid sequence of SEQ ID NO: 8, and HVR-H2 comprising the amino acid sequence of SEQ ID NO: 14. In a further embodiment, the antibody comprises (a) HVR-H1 comprising the amino acid sequence of SEQ ID NO: 13; (b) HVR-H2 comprising the amino acid sequence of SEQ ID NO: 14; and (c) HVR-H3 comprising the amino acid sequence of SEQ ID NO: 15.

In another aspect, the invention provides an antibody comprising at least one, at least two, or all three VL HVR sequences selected from (a) HVR-L1 comprising the amino acid sequence of SEQ ID NO: 16; (b) HVR-L2 comprising the amino acid sequence of SEQ ID NO: 7; and (c) HVR-L3 comprising the amino acid sequence of SEQ ID NO: 8. In one embodiment, the antibody comprises (a) HVR-L1 comprising the amino acid sequence of SEQ ID NO: 16; (b) HVR-L2 comprising the amino acid sequence of SEQ ID NO: 7; and (c) HVR-L3 comprising the amino acid sequence of SEQ ID NO: 8.

In another aspect, an antibody of the invention comprises (a) a VH domain comprising at least one, at least two, or all three VH HVR sequences selected from (i) HVR-H1 comprising the amino acid sequence of SEQ ID NO: 13, (ii) HVR-H2 comprising the amino acid sequence of SEQ ID NO: 14, and (iii) HVR-H3 comprising an amino acid sequence selected from SEQ ID NO: 15; and (b) a VL domain comprising at least one, at least two, or all three VL HVR sequences selected from (i) HVR-L1 comprising the amino acid sequence of SEQ ID NO: 16, (ii) HVR-L2 comprising the amino acid sequence of SEQ ID NO: 7, and (c) HVR-L3 comprising the amino acid sequence of SEQ ID NO: 8.

In another aspect, the invention provides an antibody comprising (a) HVR-H1 comprising the amino acid sequence of SEQ ID NO: 13; (b) HVR-H2 comprising the amino acid sequence of SEQ ID NO: 14; (c) HVR-H3 comprising the amino acid sequence of SEQ ID NO: 15; (d) HVR-L1 comprising the amino acid sequence of SEQ ID NO: 16; (e) HVR-L2 comprising the amino acid sequence of SEQ ID NO: 7; and (f) HVR-L3 comprising the amino acid sequence of SEQ ID NO: 8.

In some embodiments, the invention provides an anti-PMEL17 antibody comprising at least one, two, three, four, five, or six HVRs selected from (a) HVR-H1 comprising the amino acid sequence of SEQ ID NO: 17; (b) HVR-H2 comprising the amino acid sequence of SEQ ID NO: 18; (c) HVR-H3 comprising the amino acid sequence of SEQ ID NO: 15; (d) HVR-L1 comprising the amino acid sequence of SEQ ID NO: 19; (e) HVR-L2 comprising the amino acid sequence of SEQ ID NO: 7; and (f) HVR-L3 comprising the amino acid sequence of SEQ ID NO: 8.

In one aspect, the invention provides an antibody comprising at least one, at least two, or all three VH HVR sequences selected from (a) HVR-H1 comprising the amino acid sequence of SEQ ID NO: 17; (b) HVR-H2 comprising the amino acid sequence of SEQ ID NO: 18; and (c) HVR-H3 comprising the amino acid sequence of SEQ ID NO: 15. In a further embodiment, the antibody comprises HVR-H3 comprising the amino acid sequence of SEQ ID NO: 15, HVR-L3 comprising the amino acid sequence of SEQ ID NO: 8, and HVR-H2 comprising the amino acid sequence of SEQ ID NO: 18. In a further embodiment, the antibody comprises (a) HVR-H1 comprising the amino acid sequence of SEQ ID NO: 17; (b) HVR-H2 comprising the amino acid sequence of SEQ ID NO: 18; and (c) HVR-H3 comprising the amino acid sequence of SEQ ID NO: 15.

In another aspect, the invention provides an antibody comprising at least one, at least two, or all three VL HVR sequences selected from (a) HVR-L1 comprising the amino acid sequence of SEQ ID NO: 19; (b) HVR-L2 comprising the amino acid sequence of SEQ ID NO: 7; and (c) HVR-L3 comprising the amino acid sequence of SEQ ID NO: 8. In one embodiment, the antibody comprises (a) HVR-L1 comprising the amino acid sequence of SEQ ID NO: 19; (b) HVR-L2 comprising the amino acid sequence of SEQ ID NO: 7; and (c) HVR-L3 comprising the amino acid sequence of SEQ ID NO: 8.

In another aspect, an antibody of the invention comprises (a) a VH domain comprising at least one, at least two, or all three VH HVR sequences selected from (i) HVR-H1 comprising the amino acid sequence of SEQ ID NO: 17, (ii) HVR-H2 comprising the amino acid sequence of SEQ ID NO: 18, and (iii) HVR-H3 comprising an amino acid sequence selected from SEQ ID NO: 15; and (b) a VL domain comprising at least one, at least two, or all three VL HVR sequences selected from (i) HVR-L1 comprising the amino acid sequence of SEQ ID NO: 19, (ii) HVR-L2 comprising the amino acid sequence of SEQ ID NO: 7, and (c) HVR-L3 comprising the amino acid sequence of SEQ ID NO: 8.

In another aspect, the invention provides an antibody comprising (a) HVR-H1 comprising the amino acid sequence of SEQ ID NO: 17; (b) HVR-H2 comprising the amino acid sequence of SEQ ID NO: 18; (c) HVR-H3 comprising the amino acid sequence of SEQ ID NO: 15; (d) HVR-L1 comprising the amino acid sequence of SEQ ID NO: 19; (e) HVR-L2 comprising the amino acid sequence of SEQ ID NO: 7; and (f) HVR-L3 comprising the amino acid sequence of SEQ ID NO: 8.

In some embodiments, $X_1$ in SEQ ID NO: 17 is selected from Arg, Lys, Gln, Asn, Gly, and Ala. In some embodiments, $X_1$ in SEQ ID NO: 17 is selected from Arg, Lys, Gly, and Ala. In some embodiments, $X_1$ in SEQ ID NO: 17 is selected from Arg and Gly. In some embodiments, $X_2$ in SEQ ID NO: 18 is selected from Tyr, Trp, Phe, Thr, Ser, Ile, Leu, Val, Met, Ala, and Norleucine. In some embodiments, $X_2$ in SEQ ID NO: 18 is selected from Tyr, Phe, Ile, Leu, and Val. In some embodiments, $X_2$ in SEQ ID NO: 18 is selected from Tyr and Ile. In some embodiments, $X_3$ in SEQ ID NO: 19 is selected from Ser, Thr, and Val. In some embodiments, $X_3$ in SEQ ID NO: 19 is selected from Ser and Thr. In some embodiments, $X_4$ in SEQ ID NO: 19 is selected from Ser, Thr, and Val. In some embodiments, $X_4$ in SEQ ID NO: 19 is selected from Ser and Thr.

In any of the above embodiments, an anti-PMEL17 antibody is humanized. In one embodiment, an anti-PMEL17 antibody comprises HVRs as in any of the above embodiments, and further comprises a human acceptor framework, e.g. a human immunoglobulin framework or a human consensus framework. In some embodiments, a humanized anti-PMEL17 antibody comprises (a) HVR-H1 comprising the amino acid sequence of SEQ ID NO: 13; (b) HVR-H2 comprising the amino acid sequence of SEQ ID NO: 14; (c) HVR-H3 comprising the amino acid sequence of SEQ ID NO: 15; (d) HVR-L1 comprising the amino acid sequence of SEQ ID NO: 16; (e) HVR-L2 comprising the amino acid sequence of SEQ ID NO: 7; and (f) HVR-L3 comprising the amino acid sequence of SEQ ID NO: 8. In some embodiments, a humanized anti-PMEL17 antibody comprises (a) HVR-H1 comprising the amino acid sequence of SEQ ID NO: 17; (b) HVR-H2 comprising the amino acid sequence of SEQ ID NO: 18; (c) HVR-H3 comprising the amino acid sequence of SEQ ID NO: 15; (d) HVR-L1 comprising the amino acid sequence of SEQ ID NO: 19; (e) HVR-L2 comprising the amino acid sequence of SEQ ID NO: 7; and (f) HVR-L3 comprising the amino acid sequence of SEQ ID NO: 8.

In another aspect, an anti-PMEL17 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 9 or 49. In certain embodiments, a VH sequence having at least 90%, 91%, 92%, 93%, 94%, 95%, 96%, 97%, 98%, or 99% identity to the amino acid sequence of SEQ ID NO: 9 or 49 contains substitutions (e.g., conservative substitutions), insertions, or deletions relative to the reference sequence, but an anti-PMEL17 antibody comprising that sequence retains the ability to bind to PMEL17. In certain embodiments, a total of 1 to 10 amino acids have been substituted, inserted and/or deleted in SEQ ID NO: 9 or 49. In certain embodiments, a total of 1 to 5 amino acids have been substituted, inserted and/or deleted in SEQ ID NO: 9 or 49. In certain embodiments, substitutions, insertions, or deletions occur in regions outside the HVRs (i.e., in the FRs). Optionally, the anti-PMEL17 antibody comprises the VH sequence of SEQ ID NO: 9 or 49, including post-translational modifications of that sequence. In a particular embodiment, the VH comprises one, two or three HVRs selected from: (a) HVR-H1 comprising the amino acid sequence of SEQ ID NO: 13, (b) HVR-H2 comprising the amino acid sequence of SEQ ID NO: 14, and (c) HVR-H3 comprising the amino acid sequence of SEQ ID NO: 15. In some embodiments, the VH comprises one, two or three HVRs selected from: (a) HVR-H1 comprising the amino acid sequence of SEQ ID NO: 17, (b) HVR-H2 comprising the amino acid sequence of SEQ ID NO: 18, and (c) HVR-H3 comprising the amino acid sequence of SEQ ID NO: 15.

In some embodiments, an anti-PMEL17 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 10. In certain embodiments, a VL sequence having at least 90%, 91%, 92%, 93%, 94%, 95%, 96%, 97%, 98%, or 99° A identity to the amino acid sequence of SEQ ID NO: 10 contains substitutions (e.g., conservative substitutions), insertions, or deletions relative to the reference sequence, but an anti-PMEL17 antibody comprising that sequence retains the ability to bind to PMEL17. In certain embodiments, a total of 1 to 10 amino acids have been substituted, inserted and/or deleted in SEQ ID NO: 10. In certain embodiments, a total of 1 to 5 amino acids have been substituted, inserted and/or deleted in SEQ ID NO: 10. In certain embodiments, the substitutions, insertions, or deletions occur in regions outside the HVRs (i.e., in the FRs). Optionally, the anti-PMEL17 antibody comprises the VL sequence of SEQ ID NO: 10, including post-translational modifications of that sequence. In a particular embodiment, the VL comprises one, two or three HVRs selected from (a) HVR-L1 comprising the amino acid sequence of SEQ ID NO: 16; (b) HVR-L2 comprising the amino acid sequence of SEQ ID NO: 7; and (c) HVR-L3 comprising the amino acid sequence of SEQ ID NO: 8. In some embodiments, the VL comprises one, two or three HVRs selected from (a) HVR-L1 comprising the amino acid sequence of SEQ ID NO: 19; (b) HVR-L2 comprising the amino acid sequence of SEQ ID NO: 7; and (c) HVR-L3 comprising the amino acid sequence of SEQ ID NO: 8.

In another aspect, an anti-PMEL17 antibody is provided, wherein the antibody comprises a VH as in any of the embodiments provided above, and a VL as in any of the embodiments provided above. In one embodiment, the antibody comprises the VH and VL sequences in SEQ ID NO: 9 and SEQ ID NO: 10, respectively, including post-translational modifications of those sequences. In some embodiments, the antibody comprises the VH and VL sequences in SEQ ID NO: 49 and SEQ ID NO: 10, respectively, including post-translational modifications of those sequences.

In a further aspect, the invention provides an antibody that binds to the same epitope as an anti-PMEL17 antibody provided herein. For example, in certain embodiments, an antibody is provided that binds to the same epitope as an anti-PMEL17 antibody comprising a VH sequence of SEQ ID NO: 9 or 49 and a VL sequence of SEQ ID NO: 10. In certain embodiments, an antibody is provided that binds to an epitope of SEQ ID NO: 26 from, within, or overlapping amino acids 105 to 125.

In a further aspect of the invention, an anti-PMEL17 antibody according to any of the above embodiments is a monoclonal antibody, including a chimeric, humanized or human antibody. In one embodiment, an anti-PMEL17 antibody is an antibody fragment, e.g., a Fv, Fab, Fab', scFv, diabody, or F(ab')2 fragment. In another embodiment, the antibody is a substantially full length antibody, e.g., an IgG1 antibody or other antibody class or isotype as defined herein.

In a further aspect, an anti-PMEL17 antibody according to any of the above embodiments may incorporate any of the features, singly or in combination, as described in Sections 1-7 below.

Antibody 15F2 and Other Embodiments

In some embodiments, the invention provides an anti-PMEL17 antibody comprising at least one, two, three, four, five, or six HVRs selected from (a) HVR-H1 comprising the amino acid sequence of SEQ ID NO: 20; (b) HVR-H2 comprising the amino acid sequence of SEQ ID NO: 21; (c) HVR-H3 comprising the amino acid sequence of SEQ ID NO: 22; (d) HVR-L1 comprising the amino acid sequence of SEQ ID NO: 23; (e) HVR-L2 comprising the amino acid sequence of SEQ ID NO: 24; and (f) HVR-L3 comprising the amino acid sequence of SEQ ID NO: 25.

In one aspect, the invention provides an antibody comprising at least one, at least two, or all three VH HVR sequences selected from (a) HVR-H1 comprising the amino acid sequence of SEQ ID NO: 20; (b) HVR-H2 comprising the amino acid sequence of SEQ ID NO: 21; and (c) HVR-H3 comprising the amino acid sequence of SEQ ID NO: 22. In one embodiment, the antibody comprises HVR-H3 comprising the amino acid sequence of SEQ ID NO: 22. In another embodiment, the antibody comprises HVR-H3 comprising the amino acid sequence of SEQ ID NO: 22 and HVR-L3 comprising the amino acid sequence of SEQ ID NO: 25. In a further embodiment, the antibody comprises HVR-H3 comprising the amino acid sequence of SEQ ID NO: 22, HVR-L3 comprising the amino acid sequence of SEQ ID NO: 25, and HVR-H2 comprising the amino acid sequence of SEQ ID NO: 21. In a further embodiment, the antibody comprises (a) HVR-H1 comprising the amino acid sequence of SEQ ID NO: 20; (b) HVR-H2 comprising the amino acid sequence of SEQ ID NO: 21; and (c) HVR-H3 comprising the amino acid sequence of SEQ ID NO: 22.

In another aspect, the invention provides an antibody comprising at least one, at least two, or all three VL HVR sequences selected from (a) HVR-L1 comprising the amino acid sequence of SEQ ID NO: 23; (b) HVR-L2 comprising the amino acid sequence of SEQ ID NO: 24; and (c) HVR-L3 comprising the amino acid sequence of SEQ ID NO: 25. In one embodiment, the antibody comprises (a) HVR-L1 comprising the amino acid sequence of SEQ ID NO: 23; (b) HVR-L2 comprising the amino acid sequence of SEQ ID NO: 24; and (c) HVR-L3 comprising the amino acid sequence of SEQ ID NO: 25.

In another aspect, an antibody of the invention comprises (a) a VH domain comprising at least one, at least two, or all three VH HVR sequences selected from (i) HVR-H1 comprising the amino acid sequence of SEQ ID NO: 20, (ii) HVR-H2 comprising the amino acid sequence of SEQ ID NO: 21, and (iii) HVR-H3 comprising an amino acid sequence selected from SEQ ID NO: 22; and (b) a VL domain comprising at least one, at least two, or all three VL HVR sequences selected from (i) HVR-L1 comprising the amino acid sequence of SEQ ID NO: 23, (ii) HVR-L2 comprising the amino acid sequence of SEQ ID NO: 24, and (c) HVR-L3 comprising the amino acid sequence of SEQ ID NO: 25.

In another aspect, the invention provides an antibody comprising (a) HVR-H1 comprising the amino acid sequence of SEQ ID NO: 20; (b) HVR-H2 comprising the amino acid sequence of SEQ ID NO: 21; (c) HVR-H3 comprising the amino acid sequence of SEQ ID NO: 22; (d) HVR-L1 comprising the amino acid sequence of SEQ ID NO: 23; (e) HVR-L2 comprising the amino acid sequence of SEQ ID NO: 24; and (f) HVR-L3 comprising the amino acid sequence of SEQ ID NO: 25.

In any of the above embodiments, an anti-PMEL17 antibody is humanized. In one embodiment, an anti-PMEL17 antibody comprises HVRs as in any of the above embodiments, and further comprises a human acceptor framework, e.g. a human immunoglobulin framework or a human consensus framework. In some embodiments, a humanized anti-PMEL17 antibody comprises (a) HVR-H1 comprising the amino acid sequence of SEQ ID NO: 20; (b) HVR-H2 comprising the amino acid sequence of SEQ ID NO: 21; (c) HVR-H3 comprising the amino acid sequence of SEQ ID NO: 22; (d) HVR-L1 comprising the amino acid sequence of SEQ ID NO: 23; (e) HVR-L2 comprising the amino acid sequence of SEQ ID NO: 24; and (f) HVR-L3 comprising the amino acid sequence of SEQ ID NO: 25.

In another aspect, an anti-PMEL17 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 11 or 51. In certain embodiments, a VH sequence having at least 90%, 91%, 92%, 93%, 94%, 95%, 96%, 97%, 98%, or 99% identity to the amino acid sequence of SEQ ID NO: 11 or 51 contains substitutions (e.g., conservative substitutions), insertions, or deletions relative to the reference sequence, but an anti-PMEL17 antibody comprising that sequence retains the ability to bind to PMEL17. In certain embodiments, a total of 1 to 10 amino acids have been substituted, inserted and/or deleted in SEQ ID NO: 11 or 51. In certain embodiments, a total of 1 to 5 amino acids have been substituted, inserted and/or deleted in SEQ ID NO: 11 or 51. In certain embodiments, substitutions, insertions, or deletions occur in regions outside the HVRs (i.e., in the FRs). Optionally, the anti-PMEL17 antibody comprises the VH sequence of SEQ ID NO: 11 or 51, including post-translational modifications of that sequence. In a particular embodiment, the VH comprises one, two or three HVRs selected from: (a) HVR-H1 comprising the amino acid sequence of SEQ ID NO: 20, (b) HVR-H2 comprising the amino acid sequence of SEQ ID NO: 21, and (c) HVR-H3 comprising the amino acid sequence of SEQ ID NO: 22.

In some embodiments, an anti-PMEL17 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 12. In certain embodiments, a VL sequence having at least 90%, 91%, 92%, 93%, 94%, 95%, 96%, 97%, 98%, or 99% identity to the amino acid sequence of SEQ ID NO: 12 contains substitutions (e.g., conservative substitutions), insertions, or deletions relative to the reference sequence, but an anti-PMEL17 antibody comprising that sequence retains the ability to bind to PMEL17. In certain embodiments, a total of 1 to 10 amino acids have been substituted, inserted and/or deleted in SEQ ID NO: 12. In certain embodiments, a total of 1 to 5 amino acids have been substituted, inserted and/or deleted in SEQ ID NO: 12. In certain embodiments, the substitutions, insertions, or deletions occur in regions outside the HVRs (i.e., in the FRs). Optionally, the anti-PMEL17 antibody comprises the VL sequence of SEQ ID NO: 12, including post-translational modifications of that sequence. In a particular embodiment, the VL comprises one, two or three HVRs selected from (a) HVR-L1 comprising the amino acid sequence of SEQ ID NO: 23; (b) HVR-L2 comprising the amino acid sequence of SEQ ID NO: 24; and (c) HVR-L3 comprising the amino acid sequence of SEQ ID NO: 25.

In another aspect, an anti-PMEL17 antibody is provided, wherein the antibody comprises a VH as in any of the embodiments provided above, and a VL as in any of the embodiments provided above. In one embodiment, the antibody comprises the VH and VL sequences in SEQ ID NO: 11 and SEQ ID NO: 12, respectively, including post-translational modifications of those sequences. In some embodiments, the antibody comprises the VH and VL sequences in SEQ ID NO: 51 and SEQ ID NO: 12, respectively, including post-translational modifications of those sequences.

In a further aspect, the invention provides an antibody that binds to the same epitope as an anti-PMEL17 antibody provided herein. For example, in certain embodiments, an antibody is provided that binds to the same epitope as an anti-PMEL17 antibody comprising a VH sequence of SEQ ID NO: 11 or 51 and a VL sequence of SEQ ID NO: 12.

In a further aspect of the invention, an anti-PMEL17 antibody according to any of the above embodiments is a monoclonal antibody, including a chimeric, humanized or human antibody. In one embodiment, an anti-PMEL17 antibody is an antibody fragment, e.g., a Fv, Fab, Fab', scFv, diabody, or F(ab')2 fragment. In another embodiment, the antibody is a substantially full length antibody, e.g., an IgG1 antibody or other antibody class or isotype as defined herein.

In a further aspect, an anti-PMEL17 antibody according to any of the above embodiments may incorporate any of the features, singly or in combination, as described in Sections 1-7 below.

Antibody 31D1 and Other Embodiments

In one aspect, the invention provides an anti-PMEL17 antibody comprising at least one, two, three, four, five, or six HVRs of the antibody produced by the hybridoma designated "7509(31D1.6.7)" and deposited with the ATCC on Apr. 24, 2012 and having ATCC Accession No. PTA-12862. For purposes of this section, HVRs are delineated by the amino acid ranges corresponding to CDRs, i.e., CDRs that occur at amino acid residues 24-34, 50-56, and 89-97 of the light chain variable region, and amino acid residues 31-35B, 50-65, and 95-102 of the heavy chain variable region (CDR-L1, CDR-L2, CDR-L3, CDR-H1, CDR-H2, and CDR-H3, respectively). See Kabat et al., *Sequences of Proteins of Immunological Interest*, 5th Ed. Public Health Service, National Institutes of Health, Bethesda, Md. (1991).

In one aspect, the invention provides an antibody comprising at least one, at least two, or all three VH HVR sequences of the antibody produced by hybridoma 7509 (31D1.6.7) having ATCC Accession No. PTA-12862. In one embodiment, the antibody comprises HVR-H3 of the antibody produced by hybridoma 7509(31D1.6.7) having ATCC Accession No. PTA-12862. In another embodiment, the antibody comprises HVR-H3 and HVR-L3 of the antibody produced by hybridoma 7509(31D1.6.7) having ATCC Accession No. PTA-12862. In a further embodiment, the antibody comprises HVR-H3, HVR-L3, and HVR-H2 of the antibody produced by hybridoma 7509(31D1.6.7) having ATCC Accession No. PTA-12862. In a further embodiment, the antibody comprises HVR-H1, HVR-H2, and HVR-H3 of the antibody produced by hybridoma 7509(31D1.6.7) having ATCC Accession No. PTA-12862.

In another aspect, the invention provides an antibody comprising at least one, at least two, or all three VL HVR sequences of the antibody produced by hybridoma 7509 (31D1.6.7) having ATCC Accession No. PTA-12862. In one embodiment, the antibody comprises HVR-L1, HVR-L2, and HVR-L3 of the antibody produced by hybridoma 7509 (31D1.6.7) having ATCC Accession No. PTA-12862.

In another aspect, an antibody of the invention comprises (a) a VH domain comprising at least one, at least two, or all three VH HVR sequences of the antibody produced by hybridoma 7509(31D1.6.7) having ATCC Accession No. PTA-12862; and (b) a VL domain comprising at least one, at least two, or all three VL HVR sequences of the antibody produced by hybridoma 7509(31D1.6.7) having ATCC Accession No. PTA-12862.

In another aspect, the invention provides an antibody comprising HVR-H1, HVR-H2, HVR-H3, HVR-L1, HVR-L2, and HVR-L3 of the antibody produced by hybridoma 7509(31D1.6.7) having ATCC Accession No. PTA-12862.

In any of the above embodiments, an anti-PMEL17 antibody is humanized. In one such embodiment, the antibody is a humanized form of the antibody produced by hybridoma 7509(31D1.6.7) having ATCC Accession No. PTA-12862. In a further embodiment, an anti-PMEL17 antibody comprises HVRs as in any of the above embodiments, and further comprises an acceptor human framework, e.g. a human immunoglobulin framework or a human consensus framework.

In another aspect, an anti-PMEL17 antibody comprises a heavy chain variable domain (VH) sequence having at least 90%, 91%, 92%, 93%, 94%, 95%, 96%, 97%, 98%, 99%, or 100% sequence identity to the VH of the antibody produced by hybridoma 7509(31D1.6.7) having ATCC Accession No. PTA-12862. In certain embodiments, a VH sequence contains substitutions (e.g., conservative substitutions), insertions, or deletions relative to the reference sequence, but an anti-PMEL17 antibody comprising that sequence retains the ability to bind to PMEL17. In certain embodiments, a total of 1 to 10 amino acids have been substituted, inserted and/or deleted in the VH of the antibody produced by hybridoma 7509(31D1.6.7) having ATCC Accession No. PTA-12862. In certain embodiments, substitutions, insertions, or deletions occur in regions outside the HVRs (i.e., in the FRs). Optionally, the anti-PMEL17 antibody comprises the VH sequence of the antibody produced by hybridoma 7509 (31D1.6.7) having ATCC Accession No. PTA-12862, including post-translational modifications of that sequence. In a particular embodiment, the VH comprises one, two, or three HVRs selected from HVR-H1, HVR-H2, and HVR-H3 of the antibody produced by hybridoma 7509(31D1.6.7) having ATCC Accession No. PTA-12862.

In another aspect, an anti-PMEL17 antibody is provided, wherein the antibody comprises a light chain variable domain (VL) having at least 90%, 91%, 92%, 93%, 94%, 95%, 96%, 97%, 98%, 99%, or 100% sequence identity to the VL of the antibody produced by hybridoma 7509 (31D1.6.7) having ATCC Accession No. PTA-12862. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-PMEL17 antibody comprising that sequence retains the ability to bind to PMEL17. In certain embodiments, a total of 1 to 10 amino acids have been substituted, inserted and/or deleted in the VL of the antibody produced by hybridoma 7509(31D1.6.7) having ATCC Accession No. PTA-12862. In certain embodiments, the substitutions, insertions, or deletions occur in regions outside the HVRs (i.e., in the FRs). Optionally, the anti-PMEL17 antibody comprises the VL sequence of the antibody produced by hybridoma 7509(31D1.6.7) having ATCC Accession No. PTA-12862, including post-translational modifications of that sequence. In a particular embodiment, the VL comprises one, two or three HVRs selected from HVR-L1, HVR-L2, and HVR-L3 of the antibody produced by hybridoma 7509(31D1.6.7) having ATCC Accession No. PTA-12862.

In another aspect, an anti-PMEL17 antibody is provided, wherein the antibody comprises a VH as in any of the embodiments provided above, and a VL as in any of the embodiments provided above. In one embodiment, the antibody comprises the VH and VL sequences of the antibody produced by hybridoma 7509(31D1.6.7) having ATCC Accession No. PTA-12862, respectively, including post-translational modifications of those sequences.

In a further aspect, the invention provides an antibody that binds to the same epitope as an anti-PMEL17 antibody provided herein. For example, in certain embodiments, an antibody is provided that binds to the same epitope as the antibody produced by hybridoma 7509(31D1.6.7) having ATCC Accession No. PTA-12862.

In a further aspect of the invention, an anti-PMEL17 antibody according to any of the above embodiments is a monoclonal antibody, including a chimeric, humanized or human antibody. In one embodiment, an anti-PMEL17 antibody is an antibody fragment, e.g., a Fv, Fab, Fab', scFv, diabody, or F(ab')2 fragment. In another embodiment, the antibody is a substantially full length antibody, e.g., an IgG2b antibody or other antibody class or isotype as defined herein.

In a further aspect, an anti-PMEL17 antibody according to any of the above embodiments may incorporate any of the features, singly or in combination, as described in Sections 1-7 below.

1. Antibody Affinity

In certain embodiments, an antibody provided herein has a dissociation constant (Kd) of ≤1 µM, ≤100 nM, ≤10 nM, ≤1 nM, ≤0.1 nM, ≤0.01 nM, or ≤0.001 nM, and optionally is ≥$10^{-13}$ M. (e.g. $10^{-8}$ M or less, e.g. from $10^{-8}$ M to $10^{-13}$ M, e.g., from $10^{-9}$ M to $10^{-13}$ M).

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 mM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')2, Fv, and scFv fragments, and other fragments described below. For a review of certain antibody fragments, see Hudson et al. Nat. Med. 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA*, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA*, 89:4285 (1992); and Presta et al. *J. Immunol.*, 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HuMab® technology; U.S. Pat. No. 7,041,870 describing K-M MOUSE® technology, and U.S. Patent Application Publication No. US 2007/0061900, describing VelociMouse® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.*, 133: 3001 (1984); Brodeur et al., *Monoclonal Antibody Production Techniques and Applications*, pp. 51-63 (Marcel Dekker, Inc., New York, 1987); and Boerner et al., *J. Immunol.*, 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for PMEL17 and the other is for any other antigen. In certain embodiments, one of the binding specificities is for PMEL17 and the other is for CD3. See, e.g., U.S. Pat. No. 5,821,337. In certain embodiments, bispecific antibodies may bind to two different epitopes of PMEL17. Bispecific antibodies may also be used to localize cytotoxic agents to cells which express PMEL17. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.,* 148(5):1547-1553 (1992)); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see,e.g. Gruber et al., *J. Immunol.,* 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to PMEL17 as well as another, different antigen (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, Methods Mol. Biol. 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in Methods in Molecular Biology 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) Science, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex is used to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the $CH_2$ domain of the Fc region. See, e.g., Wright et al. TIBTECH 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. No. 5,648,260; U.S. Pat. No. 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816,567. In one embodiment, isolated nucleic acid encoding an anti-PMEL17 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-PMEL17 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-PMEL17 antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251

(1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR⁻ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J.), pp. 255-268 (2003).

C. Assays

Anti-PMEL17 antibodies provided herein may be identified, screened for, or characterized for their physical/chemical properties and/or biological activities by various assays known in the art.

In one aspect, an antibody of the invention is tested for its antigen binding activity, e.g., by known methods such as ELISA, BIACore®, FACS, or Western blot.

In another aspect, competition assays may be used to identify an antibody that competes with any of the antibodies described herein for binding to PMEL17. In certain embodiments, such a competing antibody binds to the same epitope (e.g., a linear or a conformational epitope) that is bound by an antibody described herein. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In an exemplary competition assay, immobilized PMEL17 is incubated in a solution comprising a first labeled antibody that binds to PMEL17 (e.g., any of the antibodies described herein) and a second unlabeled antibody that is being tested for its ability to compete with the first antibody for binding to PMEL17. The second antibody may be present in a hybridoma supernatant. As a control, immobilized PMEL17 is incubated in a solution comprising the first labeled antibody but not the second unlabeled antibody. After incubation under conditions permissive for binding of the first antibody to PMEL17, excess unbound antibody is removed, and the amount of label associated with immobilized PMEL17 is measured. If the amount of label associated with immobilized PMEL17 is substantially reduced in the test sample relative to the control sample, then that indicates that the second antibody is competing with the first antibody for binding to PMEL17. See Harlow and Lane (1988) *Antibodies: A Laboratory Manual* ch. 14 (Cold Spring Harbor Laboratory, Cold Spring Harbor, N.Y.).

D. Immunoconjugates

The invention also provides immunoconjugates comprising an anti-PMEL17 antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes (i.e., a radioconjugate).

Immunoconjugates allow for the targeted delivery of a drug moiety to a tumor, and, in some embodiments intracellular accumulation therein, where systemic administration of unconjugated drugs may result in unacceptable levels of toxicity to normal cells (Polakis P. (2005) *Current Opinion in Pharmacology* 5:382-387).

Antibody-drug conjugates (ADC) are targeted chemotherapeutic molecules which combine properties of both antibodies and cytotoxic drugs by targeting potent cytotoxic drugs to antigen-expressing tumor cells (Teicher, B. A. (2009) *Current Cancer Drug Targets* 9:982-1004), thereby enhancing the therapeutic index by maximizing efficacy and minimizing off-target toxicity (Carter, P. J. and Senter P. D. (2008) *The Cancer Jour.* 14(3):154-169; Chari, R. V. (2008) *Acc. Chem. Res.* 41:98-107.

The ADC compounds of the invention include those with anticancer activity. In some embodiments, the ADC compounds include an antibody conjugated, i.e. covalently attached, to the drug moiety. In some embodiments, the antibody is covalently attached to the drug moiety through a linker. The antibody-drug conjugates (ADC) of the invention selectively deliver an effective dose of a drug to tumor tissue whereby greater selectivity, i.e. a lower efficacious dose, may be achieved while increasing the therapeutic index ("therapeutic window").

The drug moiety (D) of the antibody-drug conjugates (ADC) may include any compound, moiety or group that has a cytotoxic or cytostatic effect. Drug moieties may impart their cytotoxic and cytostatic effects by mechanisms including but not limited to tubulin binding, DNA binding or intercalation, and inhibition of RNA polymerase, protein synthesis, and/or topoisomerase. Exemplary drug moieties include, but are not limited to, a maytansinoid, dolastatin, auristatin, calicheamicin, pyrrolobenzodiazepine (PBD), nemorubicin and its derivatives, PNU-159682, anthracycline, duocarmycin, vinca alkaloid, taxane, trichothecene, CC1065, camptothecin, elinafide, and stereoisomers, isosteres, analogs, and derivatives thereof that have cytotoxic activity. Nonlimiting examples of such immunoconjugates are discussed in further detail below.

1. Exemplary Antibody-Drug Conjugates

An exemplary embodiment of an antibody-drug conjugate (ADC) compound comprises an antibody (Ab) which targets a tumor cell, a drug moiety (D), and a linker moiety (L) that attaches Ab to D. In some embodiments, the antibody is attached to the linker moiety (L) through one or more amino acid residues, such as lysine and/or cysteine.

An exemplary ADC has Formula I:

Ab-(L-D)$_p$           I where p is 1 to about 20. In some embodiments, the number of drug moieties that can be conjugated to an antibody is limited by the number of free cysteine residues. In some embodiments, free cysteine residues are introduced into the antibody amino acid sequence by the methods described herein. Exemplary ADC of Formula I include, but are not limited to, antibodies that have 1, 2, 3, or 4 engineered cysteine amino acids (Lyon, R. et al (2012) *Methods in Enzym.* 502:123-138). In some embodiments, one or more free cysteine residues are already present in an antibody, without the use of engineering, in which case the existing free cysteine residues may be used to conjugate the antibody to a drug. In some embodiments, an antibody is exposed to reducing conditions prior to conjugation of the antibody in order to generate one or more free cysteine residues.

a) Exemplary Linkers

A "Linker" (L) is a bifunctional or multifunctional moiety that can be used to link one or more drug moieties (D) to an antibody (Ab) to form an antibody-drug conjugate (ADC) of Formula I. In some embodiments, antibody-drug conjugates (ADC) can be prepared using a Linker having reactive functionalities for covalently attaching to the drug and to the antibody. For example, in some embodiments, a cysteine thiol of an antibody (Ab) can form a bond with a reactive functional group of a linker or a drug-linker intermediate to make an ADC.

In one aspect, a linker has a functionality that is capable of reacting with a free cysteine present on an antibody to form a covalent bond. Nonlimiting exemplary such reactive functionalities include maleimide, haloacetamides, a-haloacetyl, activated esters such as succinimide esters, 4-nitrophenyl esters, pentafluorophenyl esters, tetrafluorophenyl esters, anhydrides, acid chlorides, sulfonyl chlorides, isocyanates, and isothiocyanates. See, e.g., the conjugation method at page 766 of Klussman, et al (2004), *Bioconjugate Chemistry* 15(4):765-773, and the Examples herein.

In some embodiments, a linker has a functionality that is capable of reacting with an electrophilic group present on an antibody. Exemplary such electrophilic groups include, but are not limited to, aldehyde and ketone carbonyl groups. In some embodiments, a heteroatom of the reactive functionality of the linker can react with an electrophilic group on an antibody and form a covalent bond to an antibody unit. Nonlimiting exemplary such reactive functionalities include, but are not limited to, hydrazide, oxime, amino, hydrazine, thiosemicarbazone, hydrazine carboxylate, and arylhydrazide.

A linker may comprise one or more linker components. Exemplary linker components include 6-maleimidocaproyl ("MC"), maleimidopropanoyl ("MP"), valine-citrulline ("val-cit" or "vc"), alanine-phenylalanine ("ala-phe"), p-aminobenzyloxycarbonyl (a "PAB"), N-Succinimidyl 4-(2-pyridylthio) pentanoate ("SPP"), and 4-(N-maleimidomethyl) cyclohexane-1 carboxylate ("MCC"). Various linker components are known in the art, some of which are described below.

A linker may be a "cleavable linker," facilitating release of a drug. Nonlimiting exemplary cleavable linkers include acid-labile linkers (e.g., comprising hydrazone), protease-sensitive (e.g., peptidase-sensitive) linkers, photolabile linkers, or disulfide-containing linkers (Chari et al., *Cancer Research* 52:127-131 (1992); U.S. Pat. No. 5,208,020).

In certain embodiments, a linker has the following Formula II:

-A$_a$-W$_w$-Y$_y$-  II wherein A is a "stretcher unit", and a is an integer from 0 to 1; W is an "amino acid unit", and w is an integer from 0 to 12; Y is a "spacer unit", and y is 0, 1, or 2; and Ab, D, and p are defined as above for Formula I. Exemplary embodiments of such linkers are described in U.S. Pat. No. 7,498,298, which is expressly incorporated herein by reference.

In some embodiments, a linker component comprises a "stretcher unit" that links an antibody to another linker component or to a drug moiety. Nonlimiting exemplary stretcher units are shown below (wherein the wavy line indicates sites of covalent attachment to an antibody, drug, or additional linker components):

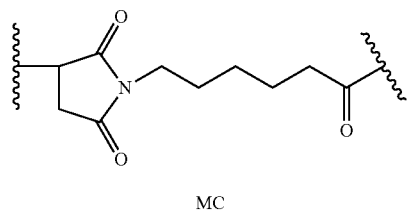

MC

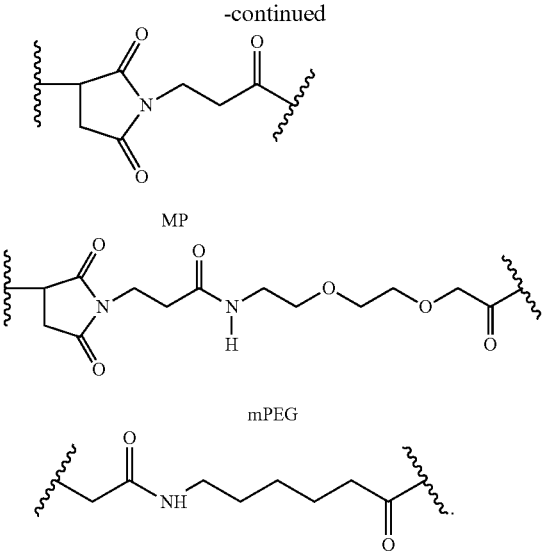

-continued

MP mPEG

In some embodiments, a linker component comprises an "amino acid unit". In some such embodiments, the amino acid unit allows for cleavage of the linker by a protease, thereby facilitating release of the drug from the immunoconjugate upon exposure to intracellular proteases, such as lysosomal enzymes (Doronina et al. (2003) *Nat. Biotechnol.* 21:778-784). Exemplary amino acid units include, but are not limited to, dipeptides, tripeptides, tetrapeptides, and pentapeptides. Exemplary dipeptides include, but are not limited to, valine-citrulline (vc or val-cit), alanine-phenylalanine (af or ala-phe); phenylalanine-lysine (fk or phe-lys); phenylalanine-homolysine (phe-homolys); and N-methyl-valine-citrulline (Me-val-cit). Exemplary tripeptides include, but are not limited to, glycine-valine-citrulline (gly-val-cit) and glycine-glycine-glycine (gly-gly-gly). An amino acid unit may comprise amino acid residues that occur naturally and/or minor amino acids and/or non-naturally occurring amino acid analogs, such as citrulline Amino acid units can be designed and optimized for enzymatic cleavage by a particular enzyme, for example, a tumor-associated protease, cathepsin B, C and D, or a plasmin protease.

In some embodiments, a linker component comprises a "spacer" unit that links the antibody to a drug moiety, either directly or through a stretcher unit and/or an amino acid unit. A spacer unit may be "self-immolative" or a "non-self-immolative." A "non-self-immolative" spacer unit is one in which part or all of the spacer unit remains bound to the drug moiety upon cleavage of the ADC. Examples of non-self-immolative spacer units include, but are not limited to, a glycine spacer unit and a glycine-glycine spacer unit. In some embodiments, enzymatic cleavage of an ADC containing a glycine-glycine spacer unit by a tumor-cell associated protease results in release of a glycine-glycine-drug moiety from the remainder of the ADC. In some such embodiments, the glycine-glycine-drug moiety is subjected to a hydrolysis step in the tumor cell, thus cleaving the glycine-glycine spacer unit from the drug moiety.

A "self-immolative" spacer unit allows for release of the drug moiety. In certain embodiments, a spacer unit of a linker comprises a p-aminobenzyl unit. In some such embodiments, a p-aminobenzyl alcohol is attached to an amino acid unit via an amide bond, and a carbamate, methylcarbamate, or carbonate is made between the benzyl alcohol and the drug (Hamann et al. (2005) *Expert Opin. Ther. Patents* (2005) 15:1087-1103). In some embodiments, the spacer unit is p-aminobenzyloxycarbonyl (PAB). In some embodiments, an ADC comprising a self-immolative linker has the structure:

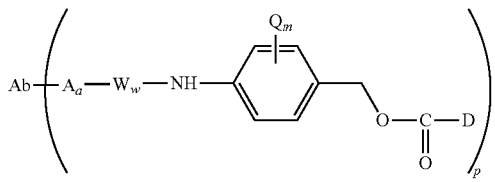

wherein Q is —$C_1$-$C_8$ alkyl, —O—($C_1$-$C_8$ alkyl), -halogen, -nitro, or -cyano; m is an integer ranging from 0 to 4; and p ranges from 1 to about 20. In some embodiments, p ranges from 1 to 10, 1 to 7, 1 to 5, or 1 to 4.

Other examples of self-immolative spacers include, but are not limited to, aromatic compounds that are electronically similar to the PAB group, such as 2-aminoimidazol-5-methanol derivatives (U.S. Pat. No. 7,375,078; Hay et al. (1999) *Bioorg. Med. Chem. Lett.* 9:2237) and ortho- or para-aminobenzylacetals. In some embodiments, spacers can be used that undergo cyclization upon amide bond hydrolysis, such as substituted and unsubstituted 4-aminobutyric acid amides (Rodrigues et al (1995) *Chemistry Biology* 2:223), appropriately substituted bicyclo[2.2.1] and bicyclo[2.2.2] ring systems (Storm et al (1972) *J. Amer. Chem. Soc.* 94:5815) and 2-aminophenylpropionic acid amides (Amsberry, et al (1990) *J. Org. Chem.* 55:5867). Linkage of a drug to the α-carbon of a glycine residue is another example of a self-immolative spacer that may be useful in ADC (Kingsbury et al (1984)*J. Med. Chem.* 27:1447).

In some embodiments, linker L may be a dendritic type linker for covalent attachment of more than one drug moiety to an antibody through a branching, multifunctional linker moiety (Sun et al (2002) *Bioorganic & Medicinal Chemistry Letters* 12:2213-2215; Sun et al (2003) *Bioorganic & Medicinal Chemistry* 11:1761-1768). Dendritic linkers can increase the molar ratio of drug to antibody, i.e. loading, which is related to the potency of the ADC. Thus, where an antibody bears only one reactive cysteine thiol group, a multitude of drug moieties may be attached through a dendritic linker.

Nonlimiting exemplary linkers are shown below in the context of an ADC of Formula I:

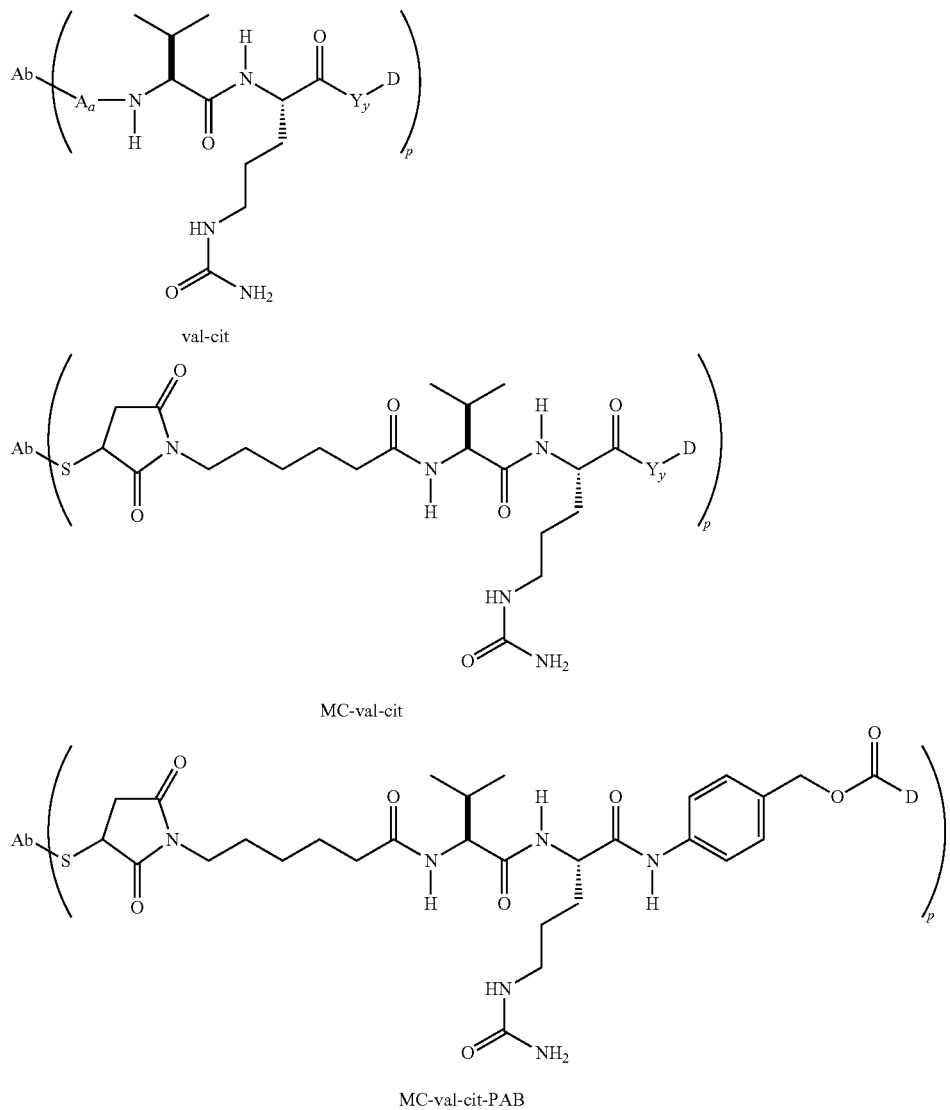

Further nonlimiting exemplary ADCs include the structures:

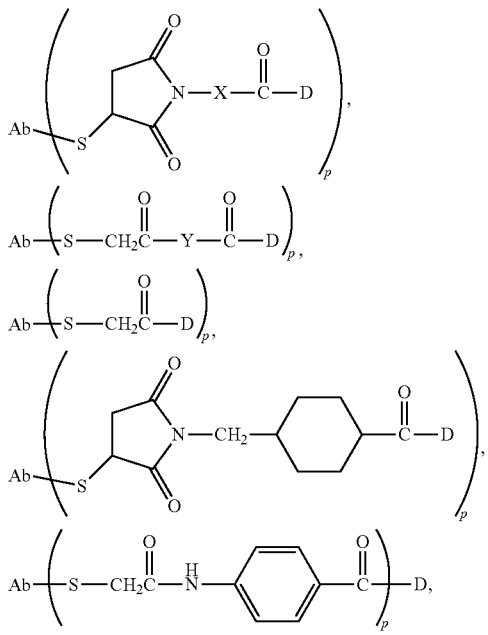

where X is:

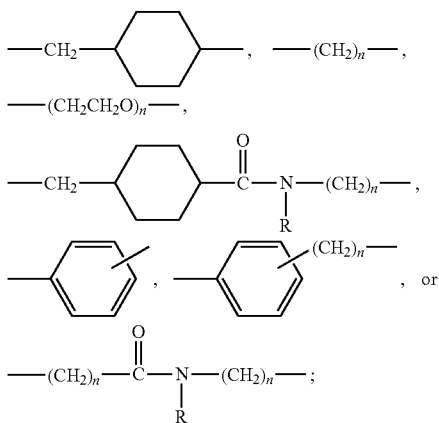

Y is:

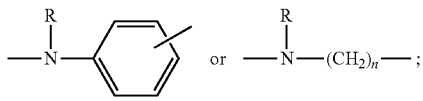

each R is independently H or $C_1$-$C_6$ alkyl; and n is 1 to 12.

Typically, peptide-type linkers can be prepared by forming a peptide bond between two or more amino acids and/or peptide fragments. Such peptide bonds can be prepared, for example, according to a liquid phase synthesis method (e.g., E. Schröder and K. Lübke (1965) "The Peptides", volume 1, pp 76-136, Academic Press).

In some embodiments, a linker is substituted with groups that modulate solubility and/or reactivity. As a nonlimiting example, a charged substituent such as sulfonate ($-SO_3^-$) or ammonium may increase water solubility of the linker reagent and facilitate the coupling reaction of the linker reagent with the antibody and/or the drug moiety, or facilitate the coupling reaction of Ab-L (antibody-linker intermediate) with D, or D-L (drug-linker intermediate) with Ab, depending on the synthetic route employed to prepare the ADC. In some embodiments, a portion of the linker is coupled to the antibody and a portion of the linker is coupled to the drug, and then the Ab-(linker portion)$^a$ is coupled to drug-(linker portion)$^b$ to form the ADC of Formula I. In some such embodiments, the antibody comprises more than one (linker portion)$^a$ substituents, such that more than one drug is coupled to the antibody in the ADC of Formula I.

The compounds of the invention expressly contemplate, but are not limited to, ADC prepared with the following linker reagents: bis-maleimido-trioxyethylene glycol (BMPEO), N-(β-maleimidopropyloxy)-N-hydroxy succinimide ester (BMPS), N-(ε-maleimidocaproyloxy) succinimide ester (EMCS), N-[γ-maleimidobutyryloxy]succinimide ester (GMBS), 1,6-hexane-bis-vinylsulfone (HBVS), succinimidyl 4-(N-maleimidomethyl)cyclohexane-1-carboxy-(6-amidocaproate) (LC-SMCC), m-maleimidobenzoyl-N-hydroxysuccinimide ester (MBS), 4-(4-N-Maleimidophenyl)butyric acid hydrazide (MPBH), succinimidyl 3-(bromoacetamido)propionate (SBAP), succinimidyl iodoacetate (SIA), succinimidyl (4-iodoacetyl) aminobenzoate (STAB), N-succinimidyl-3-(2-pyridyldithio) propionate (SPDP), N-succinimidyl-4-(2-pyridylthio)pentanoate (SPP), succinimidyl 4-(N-maleimidomethyl)cyclohexane-1-carboxylate (SMCC), succinimidyl 4-(p-maleimidophenyl)butyrate (SMPB), succinimidyl 6-[(beta-maleimidopropionamido)hexanoate] (SMPH), iminothiolane (IT), sulfo-EMCS, sulfo-GMBS, sulfo-KMUS, sulfo-MBS, sulfo-SIAB, sulfo-SMCC, and sulfo-SMPB, and succinimidyl-(4-vinylsulfone)benzoate (SVSB), and including bis-maleimide reagents: dithiobismaleimidoethane (DTME), 1,4-Bismaleimidobutane (BMB), 1,4 Bismaleimidyl-2,3-dihydroxybutane (BMDB), bismaleimidohexane (BMH), bismaleimidoethane (BMOE), BM(PEG)$_2$ (shown below), and BM(PEG)$_3$ (shown below); bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). In some embodiments, bis-maleimide reagents allow the attachment of the thiol group of a cysteine in the antibody to a thiol-containing drug moiety, linker, or linker-drug intermediate. Other functional groups that are reactive with thiol groups include, but are not limited to, iodoacetamide, bromoacetamide, vinyl pyridine, disulfide, pyridyl disulfide, isocyanate, and isothiocyanate.

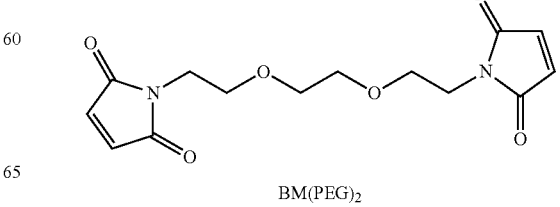

BM(PEG)$_2$

-continued

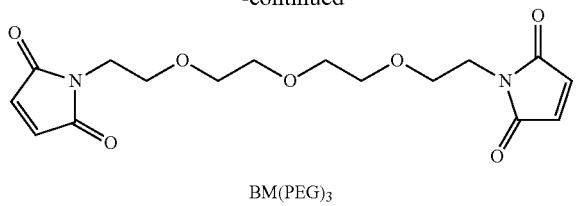

BM(PEG)₃

Certain useful linker reagents can be obtained from various commercial sources, such as Pierce Biotechnology, Inc. (Rockford, Ill.), Molecular Biosciences Inc. (Boulder, Colo.), or synthesized in accordance with procedures described in the art; for example, in Toki et al (2002) *J. Org. Chem.* 67:1866-1872; Dubowchik, et al. (1997) *Tetrahedron Letters*, 38:5257-60; Walker, M. A. (1995)*J. Org. Chem.* 60:5352-5355; Frisch et al (1996) *Bioconjugate Chem.* 7:180-186; U.S. Pat. No. 6,214,345; WO 02/088172; US2003130189; US2003096743; WO 03/026577; WO 03/043583; and WO 04/032828.

Carbon-14-labeled 1-isothiocyanatobenzyl-3-methyldiethylene triaminepentaacetic acid (MX-DTPA) is an exemplary chelating agent for conjugation of radionucleotide to the antibody. See, e.g., WO94/11026.

b) Exemplary Drug Moieties (1) Maytansine and Maytansinoids

In some embodiments, an immunoconjugate comprises an antibody conjugated to one or more maytansinoid molecules. Maytansinoids are derivatives of maytansine, and are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinoids are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

Maytansinoid drug moieties are attractive drug moieties in antibody-drug conjugates because they are: (i) relatively accessible to prepare by fermentation or chemical modification or derivatization of fermentation products, (ii) amenable to derivatization with functional groups suitable for conjugation through non-disulfide linkers to antibodies, (iii) stable in plasma, and (iv) effective against a variety of tumor cell lines.

Certain maytansinoids suitable for use as maytansinoid drug moieties are known in the art and can be isolated from natural sources according to known methods or produced using genetic engineering techniques (see, e.g., Yu et al (2002) PNAS 99:7968-7973). Maytansinoids may also be prepared synthetically according to known methods.

Exemplary maytansinoid drug moieties include, but are not limited to, those having a modified aromatic ring, such as: C-19-dechloro (U.S. Pat. No. 4,256,746) (prepared, for example, by lithium aluminum hydride reduction of ansamytocin P2); C-20-hydroxy (or C-20-demethyl)+/−C-19-dechloro (U.S. Pat. Nos. 4,361,650 and 4,307,016) (prepared, for example, by demethylation using *Streptomyces* or *Actinomyces* or dechlorination using LAH); and C-20-demethoxy, C-20-acyloxy (—OCOR), +/−dechloro (U.S. Pat. No. 4,294,757) (prepared, for example, by acylation using acyl chlorides), and those having modifications at other positions of the aromatic ring.

Exemplary maytansinoid drug moieties also include those having modifications such as: C-9-SH (U.S. Pat. No. 4,424,219) (prepared, for example, by the reaction of maytansinol with $H_2S$ or $P_2S_5$); C-14-alkoxymethyl(demethoxy/$CH_2OR$) (U.S. Pat. No. 4,331,598); C-14-hydroxymethyl or acyloxymethyl ($CH_2OH$ or $CH_2OAc$) (U.S. Pat. No. 4,450,254) (prepared, for example, from *Nocardia*); C-15-hydroxy/acyloxy (U.S. Pat. No. 4,364,866) (prepared, for example, by the conversion of maytansinol by *Streptomyces*); C-15-methoxy (U.S. Pat. Nos. 4,313,946 and 4,315,929) (for example, isolated from *Trewia nudlflora*); C-18-N-demethyl (U.S. Pat. Nos. 4,362,663 and 4,322,348) (prepared, for example, by the demethylation of maytansinol by *Streptomyces*); and 4,5-deoxy (U.S. Pat. No. 4,371,533) (prepared, for example, by the titanium trichloride/LAH reduction of maytansinol).

Many positions on maytansinoid compounds are useful as the linkage position. For example, an ester linkage may be formed by reaction with a hydroxyl group using conventional coupling techniques. In some embodiments, the reaction may occur at the C-3 position having a hydroxyl group, the C-14 position modified with hydroxymethyl, the C-15 position modified with a hydroxyl group, and the C-20 position having a hydroxyl group. In some embodiments, the linkage is formed at the C-3 position of maytansinol or a maytansinol analogue.

Maytansinoid drug moieties include those having the structure:

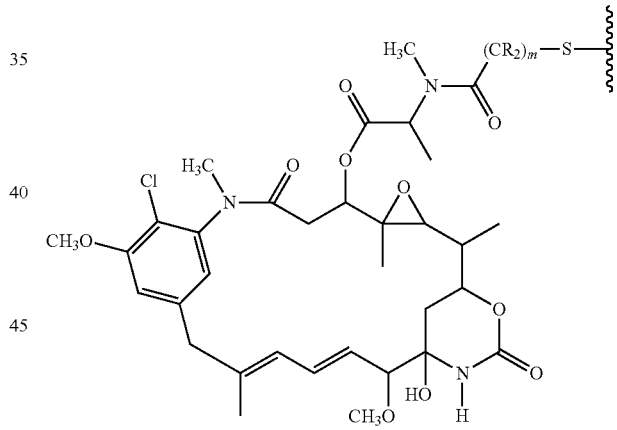

where the wavy line indicates the covalent attachment of the sulfur atom of the maytansinoid drug moiety to a linker of an ADC. Each R may independently be H or a $C_1$-$C_6$ alkyl. The alkylene chain attaching the amide group to the sulfur atom may be methanyl, ethanyl, or propyl, i.e., m is 1, 2, or 3 (U.S. Pat. No. 633,410; U.S. Pat. No. 5,208,020; Chari et al (1992) *Cancer Res.* 52:127-131; Liu et al (1996) *Proc. Natl. Acad. Sci USA* 93:8618-8623).

All stereoisomers of the maytansinoid drug moiety are contemplated for the ADC of the invention, i.e. any combination of R and S configurations at the chiral carbons (U.S. Pat. No. 7,276,497; U.S. Pat. No. 6,913,748; U.S. Pat. No. 6,441,163; U.S. Pat. No. 633,410 (RE39151); U.S. Pat. No. 5,208,020; Widdison et al (2006) *J. Med. Chem.* 49:4392-4408, which are incorporated by reference in their entirety). In some embodiments, the maytansinoid drug moiety has the following stereochemistry:

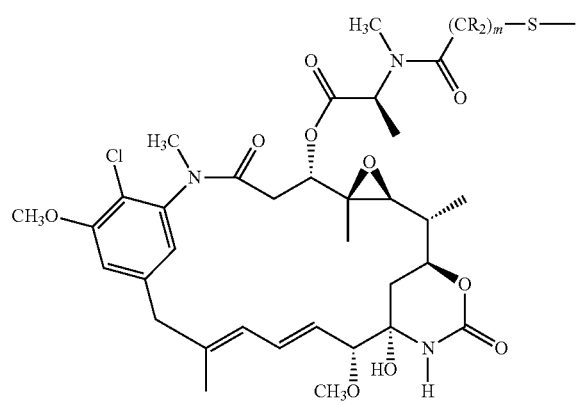

Exemplary embodiments of maytansinoid drug moieties include, but are not limited to, DM1; DM3; and DM4, having the structures:

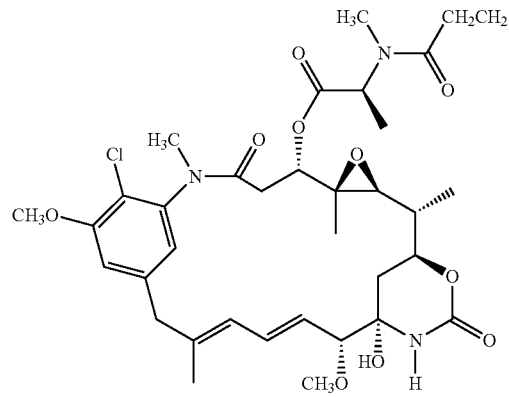

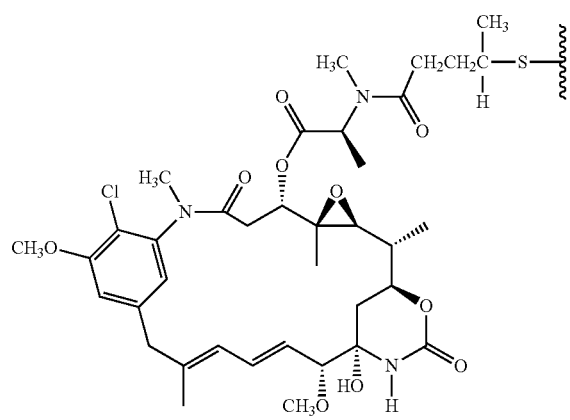

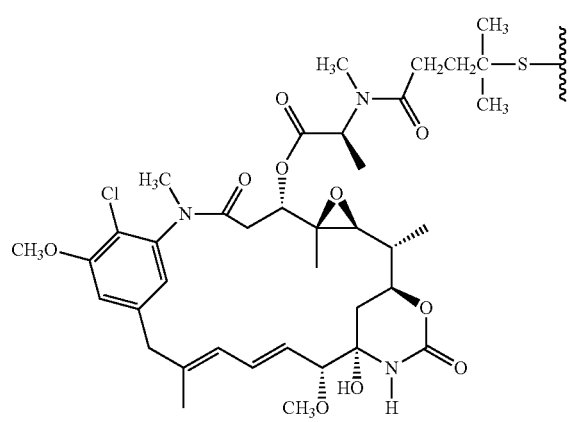

wherein the wavy line indicates the covalent attachment of the sulfur atom of the drug to a linker (L) of an antibody-drug conjugate.

Other exemplary maytansinoid antibody-drug conjugates have the following structures and abbreviations (wherein Ab is antibody and p is 1 to about 20. In some embodiments, p is 1 to 10, p is 1 to 7, p is 1 to 5, or p is 1 to 4):

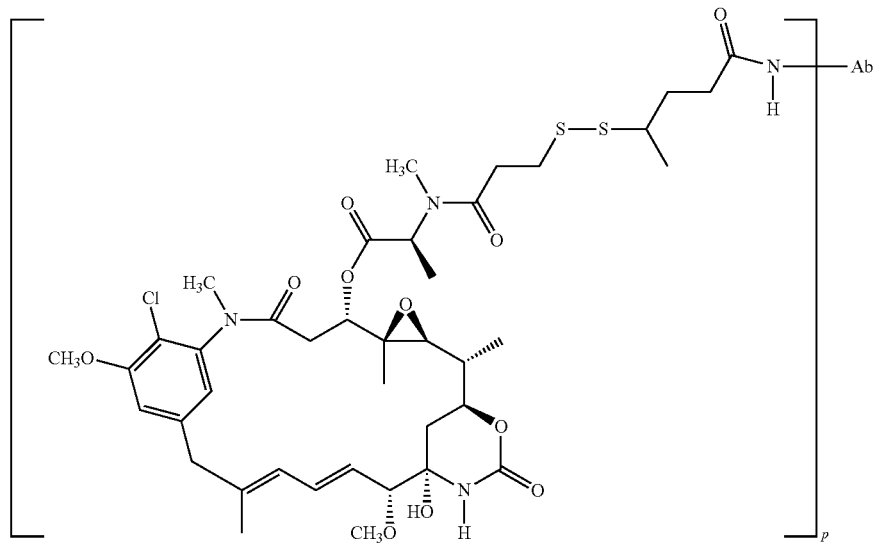

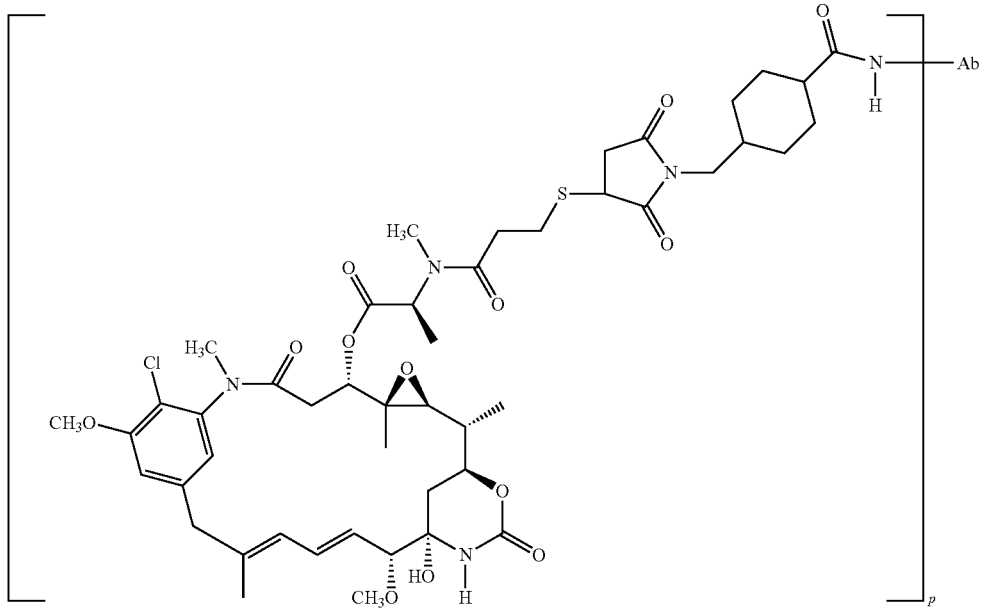

Ab-SMCC-DM1

Exemplary antibody-drug conjugates where DM1 is linked through a BMPEO linker to a thiol group of the antibody have the structure and abbreviation:

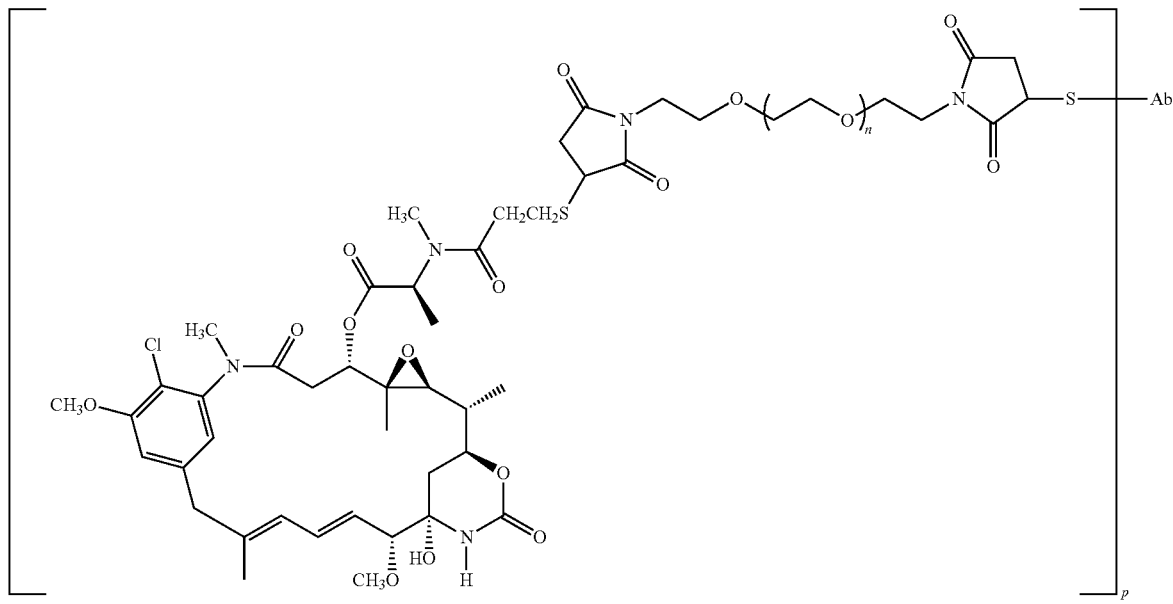

where Ab is antibody; n is 0, 1, or 2; and p is 1 to about 20. In some embodiments, p is 1 to 10, p is 1 to 7, p is 1 to 5, or p is 1 to 4.

Immunoconjugates containing maytansinoids, methods of making the same, and their therapeutic use are disclosed, for example, in U.S. Pat. Nos. 5,208,020 and 5,416,064; US 2005/0276812 A1; and European Patent EP 0 425 235 B1, the disclosures of which are hereby expressly incorporated by reference. See also Liu et al. *Proc. Natl. Acad. Sci. USA* 93:8618-8623 (1996); and Chari et al. *Cancer Research* 52:127-131 (1992).

In some embodiments, antibody-maytansinoid conjugates may be prepared by chemically linking an antibody to a maytansinoid molecule without significantly diminishing the biological activity of either the antibody or the maytansinoid molecule. See, e.g., U.S. Pat. No. 5,208,020 (the disclosure of which is hereby expressly incorporated by reference). In some embodiments, ADC with an average of 3-4 maytansinoid molecules conjugated per antibody molecule has shown efficacy in enhancing cytotoxicity of target cells without negatively affecting the function or solubility of the antibody. In some instances, even one molecule of toxin/antibody is expected to enhance cytotoxicity over the use of naked antibody.

Exemplary linking groups for making antibody-maytansinoid conjugates include, for example, those described herein and those disclosed in U.S. Pat. No. 5,208,020; EP Patent 0 425 235 B1; Chari et al. *Cancer Research* 52:127-131 (1992); US 2005/0276812 A1; and US 2005/016993 A1, the disclosures of which are hereby expressly incorporated by reference.

(2) Auristatins and Dolastatins

Drug moieties include dolastatins, auristatins, and analogs and derivatives thereof (U.S. Pat. No. 5,635,483; U.S. Pat. No. 5,780,588; U.S. Pat. No. 5,767,237; U.S. Pat. No. 6,124,431). Auristatins are derivatives of the marine mollusk compound dolastatin-10. While not intending to be bound by any particular theory, dolastatins and auristatins have been shown to interfere with microtubule dynamics, GTP hydrolysis, and nuclear and cellular division (Woyke et al (2001) *Antimicrob. Agents and Chemother.* 45(12):3580-3584) and have anticancer (U.S. Pat. No. 5,663,149) and antifungal activity (Pettit et al (1998) *Antimicrob. Agents Chemother.* 42:2961-2965). The dolastatin/auristatin drug moiety may be attached to the antibody through the N (amino) terminus or the C (carboxyl) terminus of the peptidic drug moiety (WO 02/088172; Doronina et al (2003) *Nature Biotechnology* 21(7):778-784; Francisco et al (2003) *Blood* 102(4): 1458-1465).

Exemplary auristatin embodiments include the N-terminus linked monomethylauristatin drug moieties $D_E$ and $D_F$, disclosed in U.S. Pat. No. 7,498,298 and U.S. Pat. No. 7,659,241, the disclosures of which are expressly incorporated by reference in their entirety:

$R^7$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

each $R^8$ is independently selected from H, OH, $C_1$-$C_8$ alkyl, $C_3$-$C_8$ carbocycle and O—($C_1$-$C_8$ alkyl);

$R^9$ is selected from H and $C_1$-$C_8$ alkyl;

$R^{10}$ is selected from aryl or $C_3$-$C_8$ heterocycle;

Z is O, S, NH, or $NR^{12}$, wherein $R^{12}$ is $C_1$-$C_8$ alkyl;

$R^{11}$ is selected from H, $C_1$-$C_{20}$ alkyl, aryl, $C_3$-$C_8$ heterocycle, —($R^{13}O$)$_m$—$R^{14}$, or —($R^{13}O$)$_m$—$CH(R^{15})_2$;

m is an integer ranging from 1-1000;

$R^{13}$ is $C_2$-$C_8$ alkyl;

$R^{14}$ is H or $C_1$-$C_8$ alkyl;

each occurrence of $R^{15}$ is independently H, COOH, —($CH_2$)$_n$—$N(R^{16})_2$, —($CH_2$)$_n$—$SO_3H$, or —($CH_2$)$_n$—$SO_3$—$C_1$-$C_8$ alkyl;

each occurrence of $R^{16}$ is independently H, $C_1$-$C_8$ alkyl, or —($CH_2$)$_n$—COOH;

$R^{18}$ is selected from —$C(R^8)_2$—$C(R^8)_2$-aryl, —$C(R^8)_2$—$C(R^8)_2$—($C_3$-$C_8$ heterocycle), and —$C(R^8)_2$—$C(R^8)_2$—($C_3$-$C_8$ carbocycle); and n is an integer ranging from 0 to 6.

In one embodiment, $R^3$, $R^4$ and $R^7$ are independently isopropyl or sec-butyl and $R^5$ is —H or methyl. In an exemplary embodiment, $R^3$ and $R^4$ are each isopropyl, $R^5$ is —H, and $R^7$ is sec-butyl.

In yet another embodiment, $R^2$ and $R^6$ are each methyl, and $R^9$ is —H.

In still another embodiment, each occurrence of $R^8$ is —$OCH_3$.

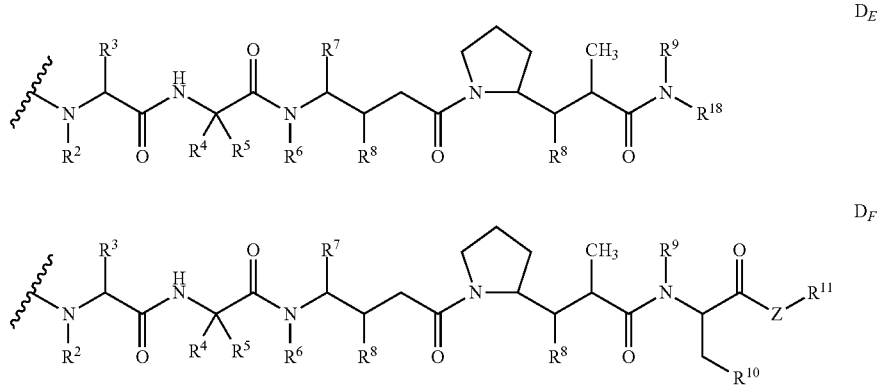

wherein the wavy line of $D_E$ and $D_F$ indicates the covalent attachment site to an antibody or antibody-linker component, and independently at each location:

$R^2$ is selected from H and $C_1$-$C_8$ alkyl;

$R^3$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^4$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^5$ is selected from H and methyl;

or $R^4$ and $R^5$ jointly form a carbocyclic ring and have the formula —($CR^aR^b$)$_n$— wherein $R^a$ and $R^b$ are independently selected from H, $C_1$-$C_8$ alkyl and $C_3$-$C_8$ carbocycle and n is selected from 2, 3, 4, 5 and 6;

$R^6$ is selected from H and $C_1$-$C_8$ alkyl;

In an exemplary embodiment, $R^3$ and $R^4$ are each isopropyl, $R^2$ and $R^6$ are each methyl, $R^5$ is —H, $R^7$ is sec-butyl, each occurrence of $R^8$ is —$OCH_3$, and $R^9$ is —H.

In one embodiment, Z is —O— or —NH—.

In one embodiment, $R^{10}$ is aryl.

In an exemplary embodiment, $R^{10}$ is -phenyl.

In an exemplary embodiment, when Z is —O—, $R^{11}$ is —H, methyl or t-butyl.

In one embodiment, when Z is —NH, $R^{11}$ is —$CH(R^{15})_2$, wherein $R^{15}$ is —($CH_2$)$_n$—$N(R^{16})_2$, and $R^{16}$ is —$C_1$-$C_8$ alkyl or —($CH_2$)$_n$—COOH.

In another embodiment, when Z is —NH, $R^{11}$ is —CH($R^{15}$)$_2$, wherein $R^{15}$ is —($CH_2$)$_n$$SO_3H$.

An exemplary auristatin embodiment of formula $D_E$ is MMAE, wherein the wavy line indicates the covalent attachment to a linker (L) of an antibody-drug conjugate:

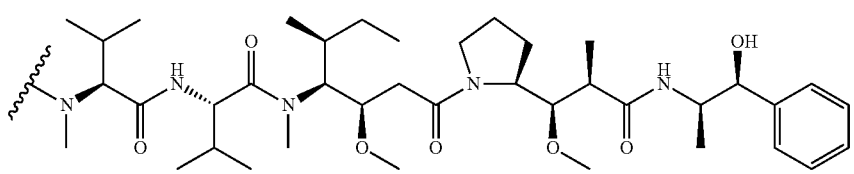

MMAE

An exemplary auristatin embodiment of formula $D_E$ is MMAF, wherein the wavy line indicates the covalent attachment to a linker (L) of an antibody-drug conjugate:

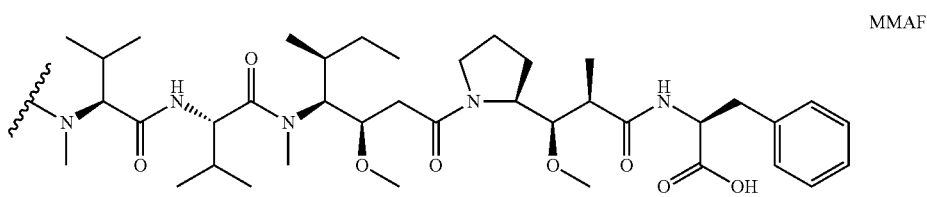 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@@H](Cc1ccccc1)C(=O)O)OC)C(C)C)C(C)C]

MMAF

Other exemplary embodiments include monomethylvaline compounds having phenylalanine carboxy modifications at the C-terminus of the pentapeptide auristatin drug moiety (WO 2007/008848) and monomethylvaline compounds having phenylalanine sidechain modifications at the C-terminus of the pentapeptide auristatin drug moiety (WO 2007/008603).

Nonlimiting exemplary embodiments of ADC of Formula I comprising MMAE or MMAF and various linker components have the following structures and abbreviations (wherein "Ab" is an antibody; p is 1 to about 8, "Val-Cit" is a valine-citrulline dipeptide; and "S" is a sulfur atom:

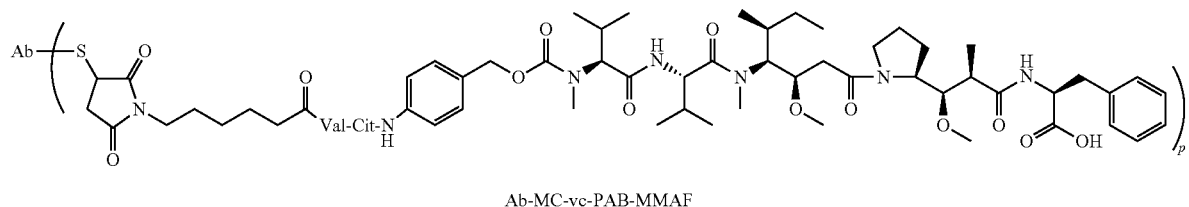

Ab-MC-vc-PAB-MMAF

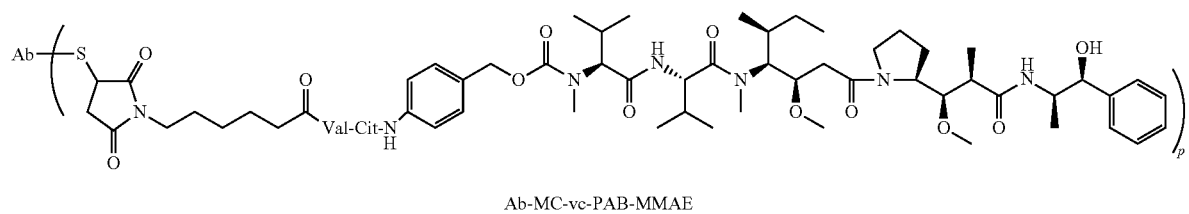

Ab-MC-vc-PAB-MMAE

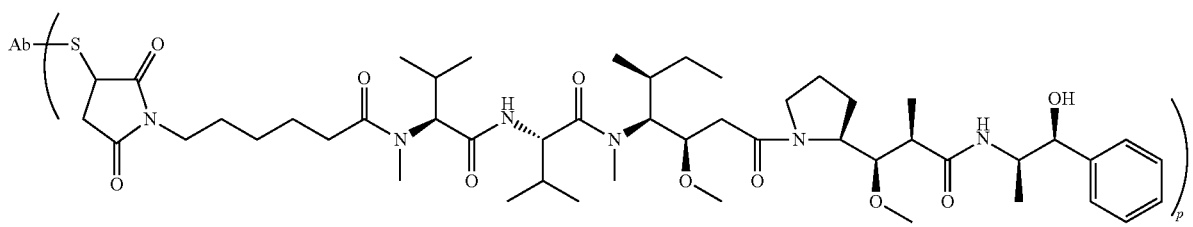

Ab-MC-MMAE

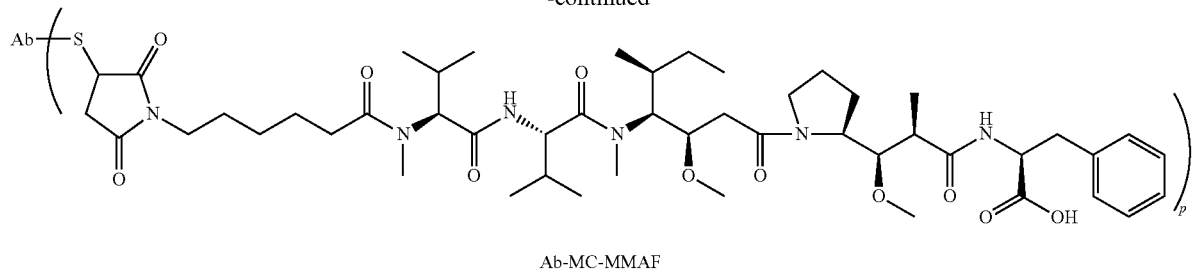

Ab-MC-MMAF

Nonlimiting exemplary embodiments of ADCs of Formula I comprising MMAF and various linker components further include Ab-MC-PAB-MMAF and Ab-PAB-MMAF. Immunoconjugates comprising MMAF attached to an antibody by a linker that is not proteolytically cleavable have been shown to possess activity comparable to immunoconjugates comprising MMAF attached to an antibody by a proteolytically cleavable linker (Doronina et al. (2006) Bioconjugate Chem. 17:114-124). In some such embodiments, drug release is believed to be effected by antibody degradation in the cell.

Typically, peptide-based drug moieties can be prepared by forming a peptide bond between two or more amino acids and/or peptide fragments. Such peptide bonds can be prepared, for example, according to a liquid phase synthesis method (see, e.g., E. Schröder and K. Lübke, "The Peptides", volume 1, pp 76-136, 1965, Academic Press). Auristatin/dolastatin drug moieties may, in some embodiments, be prepared according to the methods of: U.S. Pat. No. 7,498,298; U.S. Pat. No. 5,635,483; U.S. Pat. No. 5,780,588; Pettit et al (1989) J. Am. Chem. Soc. 111:5463-5465; Pettit et al (1998) Anti-Cancer Drug Design 13:243-277; Pettit, G. R., et al. Synthesis, 1996, 719-725; Pettit et al (1996)J. Chem. Soc. Perkin Trans. 1 5:859-863; and Doronina (2003) Nat. Biotechnol. 21(7):778-784.

In some embodiments, auristatin/dolastatin drug moieties of formulas $D_E$ such as MMAE, and $D_F$, such as MMAF, and drug-linker intermediates and derivatives thereof, such as MC-MMAF, MC-MMAE, MC-vc-PAB-MMAF, and MC-vc-PAB-MMAE, may be prepared using methods described in U.S. Pat. No. 7,498,298; Doronina et al. (2006) Bioconjugate Chem. 17:114-124; and Doronina et al. (2003) Nat. Biotech. 21:778-784 and then conjugated to an antibody of interest.

(3) Calicheamicin

In some embodiments, the immunoconjugate comprises an antibody conjugated to one or more calicheamicin molecules. The calicheamicin family of antibiotics, and analogues thereof, are capable of producing double-stranded DNA breaks at sub-picomolar concentrations (Hinman et al., (1993) Cancer Research 53:3336-3342; Lode et al., (1998) Cancer Research 58:2925-2928). Calicheamicin has intracellular sites of action but, in certain instances, does not readily cross the plasma membrane. Therefore, cellular uptake of these agents through antibody-mediated internalization may, in some embodiments, greatly enhances their cytotoxic effects. Nonlimiting exemplary methods of preparing antibody-drug conjugates with a calicheamicin drug moiety are described, for example, in U.S. Pat. No. 5,712,374; U.S. Pat. No. 5,714,586; U.S. Pat. No. 5,739,116; and U.S. Pat. No. 5,767,285.

(4) Pyrrolobenzodiazepines

In some embodiments, an ADC comprises a pyrrolobenzodiazepine (PBD). In some embodiments, PDB dimers recognize and bind to specific DNA sequences. The natural product anthramycin, a PBD, was first reported in 1965 (Leimgruber, et al., (1965) J. Am. Chem. Soc., 87:5793-5795; Leimgruber, et al., (1965) J. Am. Chem. Soc., 87:5791-5793). Since then, a number of PBDs, both naturally-occurring and analogues, have been reported (Thurston, et al., (1994) Chem. Rev. 1994, 433-465 including dimers of the tricyclic PBD scaffold (U.S. Pat. No. 6,884,799; U.S. Pat. No. 7,049,311; U.S. Pat. No. 7,067,511; U.S. Pat. No. 7,265,105; U.S. Pat. No. 7,511,032; U.S. Pat. No. 7,528,126; U.S. Pat. No. 7,557,099). Without intending to be bound by any particular theory, it is believed that the dimer structure imparts the appropriate three-dimensional shape for isohelicity with the minor groove of B-form DNA, leading to a snug fit at the binding site (Kohn, In Antibiotics III. Springer-Verlag, New York, pp. 3-11 (1975); Hurley and Needham-VanDevanter, (1986) Acc. Chem. Res., 19:230-237). Dimeric PBD compounds bearing C2 aryl substituents have been shown to be useful as cytotoxic agents (Hartley et al (2010) Cancer Res. 70(17):6849-6858; Antonow (2010)J. Med. Chem. 53(7):2927-2941; Howard et al (2009) Bioorganic and Med. Chem. Letters 19(22):6463-6466).

PBD dimers have been conjugated to antibodies and the resulting ADC shown to have anti-cancer properties. Nonlimiting exemplary linkage sites on the PBD dimer include the five-membered pyrrolo ring, the tether between the PBD units, and the N10-C11 imine group (WO 2009/016516; US 2009/304710; US 2010/047257; US 2009/036431; US 2011/0256157; WO 2011/130598).

Nonlimiting exemplary PBD dimer components of ADCs are of Formula A:

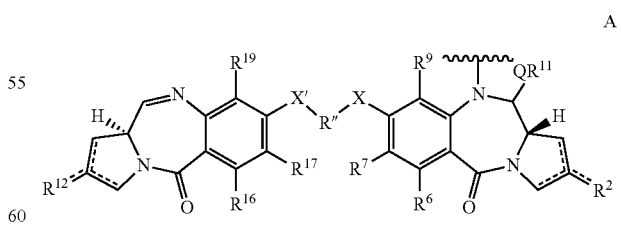

A and salts and solvates thereof, wherein:

the wavy line indicates the covalent attachment site to the linker;

the dotted lines indicate the optional presence of a double bond between C1 and C2 or C2 and C3;

$R^2$ is independently selected from H, OH, =O, =CH$_2$, CN, R, OR, =CH—R$^D$, =C(R$^D$)$_2$, O—SO$_2$—R, CO$_2$R and COR, and optionally further selected from halo or dihalo, wherein R$^D$ is independently selected from R, CO$_2$R, COR, CHO, CO$_2$H, and halo;

$R^6$ and $R^9$ are independently selected from H, R, OH, OR, SH, SR, NH$_2$, NHR, NRR', NO$_2$, Me$_3$Sn and halo;

$R^7$ is independently selected from H, R, OH, OR, SH, SR, NH$_2$, NHR, NRR', NO$_2$, Me$_3$Sn and halo;

Q is independently selected from O, S and NH;

$R^{11}$ is either H, or R or, where Q is O, SO$_3$M, where M is a metal cation;

R and R' are each independently selected from optionally substituted C$_{1-8}$ alkyl, C$_{1-2}$ alkyl, C$_{3-8}$ heterocyclyl, C$_{3-20}$ heterocycle, and C$_{5-20}$ aryl groups, and optionally in relation to the group NRR', R and R' together with the nitrogen atom to which they are attached form an optionally substituted 4-, 5-, 6- or 7-membered heterocyclic ring;

$R^{12}$, $R^{16}$, $R^{19}$ and $R^{17}$ are as defined for $R^2$, $R^6$, $R^9$ and $R^7$ respectively;

R" is a C$_{3-12}$ alkylene group, which chain may be interrupted by one or more heteroatoms, e.g. O, S, N(H), NMe and/or aromatic rings, e.g. benzene or pyridine, which rings are optionally substituted; and X and X' are independently selected from O, S and N(H).

In some embodiments, $R^9$ and $R^{19}$ are H.

In some embodiments, $R^6$ and $R^{16}$ are H.

In some embodiments, $R^7$ are $R^{17}$ are both OR$^{7A}$, where R$^{7A}$ is optionally substituted C$_{1-4}$ alkyl. In some embodiments, R$^{7A}$ is Me. In some embodiments, R$^{7A}$ is Ch$_2$Ph, where Ph is a phenyl group.

In some embodiments, X is O.

In some embodiments, $R^{11}$ is H.

In some embodiments, there is a double bond between C$_2$ and C$_3$ in each monomer unit.

In some embodiments, $R^2$ and $R^{12}$ are independently selected from H and R. In some embodiments, $R^2$ and $R^{12}$ are independently R. In some embodiments, $R^2$ and $R^{12}$ are independently optionally substituted C$_{5-20}$ aryl or C$_{5-7}$ aryl or C$_{5-10}$ aryl. In some embodiments, $R^2$ and $R^{12}$ are independently optionally substituted phenyl, thienyl, napthyl, pyridyl, quinolinyl, or isoquinolinyl. In some embodiments, $R^2$ and $R^{12}$ are independently selected from =O, =CH$_2$, =CH—R$^D$, and =C(R$^D$)$_2$. In some embodiments, $R^2$ and $R^{12}$ each =CH$_2$. In some embodiments, $R^2$ and $R^{12}$ are each H. In some embodiments, $R^2$ and $R^{12}$ are each =O. In some embodiments, $R^2$ and $R^{12}$ are each =CF$_2$. In some embodiments, $R^2$ and/or $R^{12}$ are independently =C(R$^D$)$_2$. In some embodiments, $R^2$ and/or $R^{12}$ are independently =CH—R$^D$.

In some embodiments, when $R^2$ and/or $R^{12}$ is =CH—R$^D$, each group may independently have either configuration shown below:

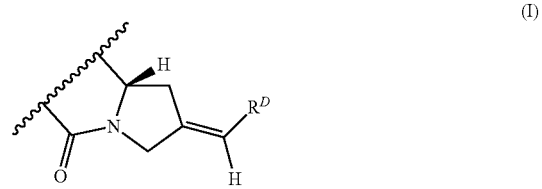

(I)

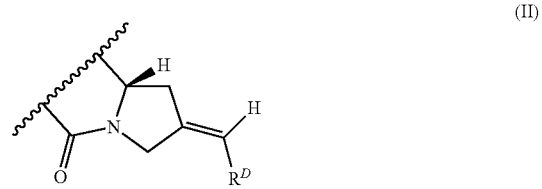

(II)

In some embodiments, a =CH—R$^D$ is in configuration (I).

In some embodiments, R" is a C$_3$ alkylene group or a C$_5$ alkylene group.

In some embodiments, an exemplary PBD dimer component of an ADC has the structure of Formula A(I):

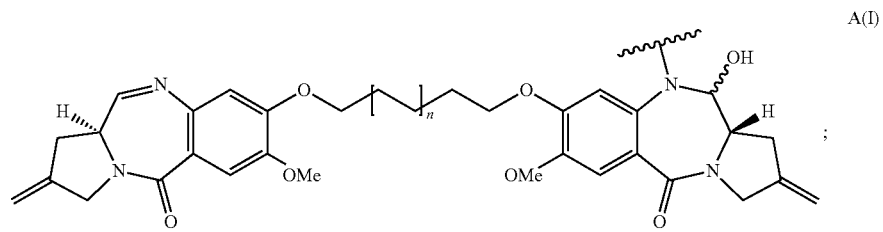

A(I)

wherein n is 0 or 1.

In some embodiments, an exemplary PBD dimer component of an ADC has the structure of Formula A(II):

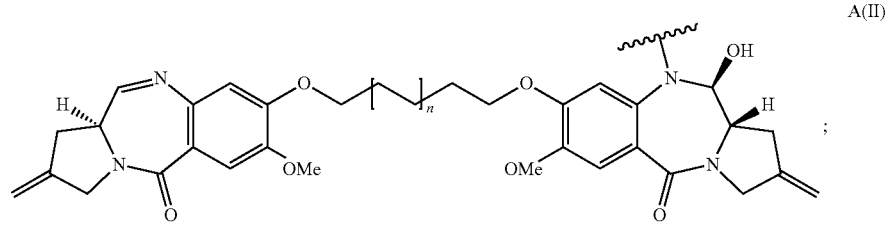

A(II)

wherein n is 0 or 1.

In some embodiments, an exemplary PBD dimer component of an ADC has the structure of Formula A(III):

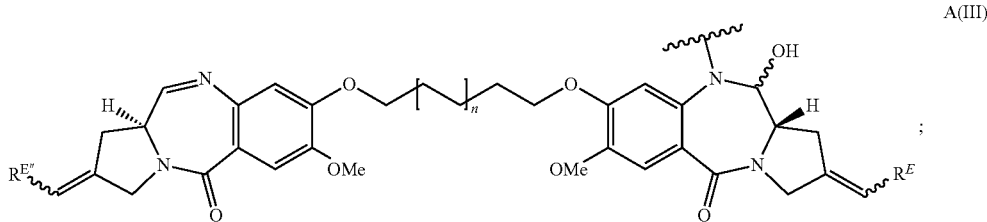

wherein $R^E$ and $R^{E''}$ are each independently selected from H or $R^D$, wherein $R^D$ is defined as above; and
wherein n is 0 or 1.

In some embodiments, n is 0. In some embodiments, n is 1. In some embodiments, $R^E$ and/or $R^{E''}$ is H. In some embodiments, $R^E$ and $R^{E''}$ are H. In some embodiments, $R^E$ and/or $R^{E''}$ is $R^D$, wherein $R^D$ is optionally substituted $C_{1-12}$ alkyl. In some embodiments, $R^E$ and/or $R^{E''}$ is $R^D$, wherein $R^D$ is methyl.

In some embodiments, an exemplary PBD dimer component of an ADC has the structure of Formula A(IV):

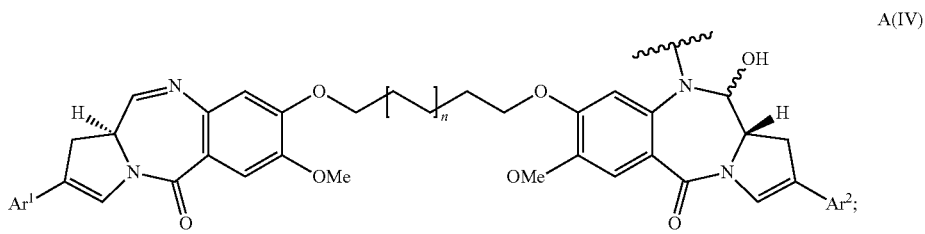

wherein $Ar^1$ and $Ar^2$ are each independently optionally substituted $C_{5-20}$ aryl; wherein $Ar^1$ and $Ar^2$ may be the same or different; and
wherein n is 0 or 1.

In some embodiments, an exemplary PBD dimer component of an ADC has the structure of Formula A(V):

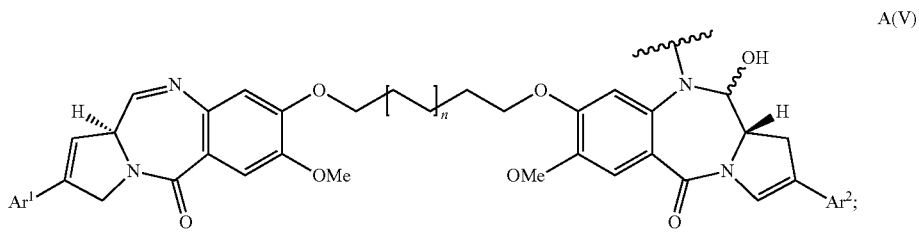

wherein $Ar^1$ and $Ar^2$ are each independently optionally substituted $C_{5-20}$ aryl; wherein $Ar^1$ and $Ar^2$ may be the same or different; and
wherein n is 0 or 1.

In some embodiments, $Ar^1$ and $Ar^2$ are each independently selected from optionally substituted phenyl, furanyl, thiophenyl and pyridyl. In some embodiments, $Ar_1$ and $Ar^2$ are each independently optionally substituted phenyl. In some embodiments, $Ar_1$ and $Ar^2$ are each independently optionally substituted thien-2-yl or thien-3-yl. In some embodiments, $Ar^1$ and $Ar^2$ are each independently optionally substituted quinolinyl or isoquinolinyl. The quinolinyl or isoquinolinyl group may be bound to the PBD core through any available ring position. For example, the quinolinyl may be quinolin-2-yl, quinolin-3-yl, quinolin-4yl, quinolin-5-yl, quinolin-6-yl, quinolin-7-yl and quinolin-8-yl. In some embodiments, the quinolinyl is selected from quinolin-3-yl and quinolin-6-yl. The isoquinolinyl may be isoquinolin-1-yl, isoquinolin-3-yl, isoquinolin-4yl, isoquinolin-5-yl, isoquinolin-6-yl, isoquinolin-7-yl and isoquinolin-8-yl. In some embodiments, the isoquinolinyl is selected from isoquinolin-3-yl and isoquinolin-6-yl.

Further nonlimiting exemplary PBD dimer components of ADCs are of Formula B:

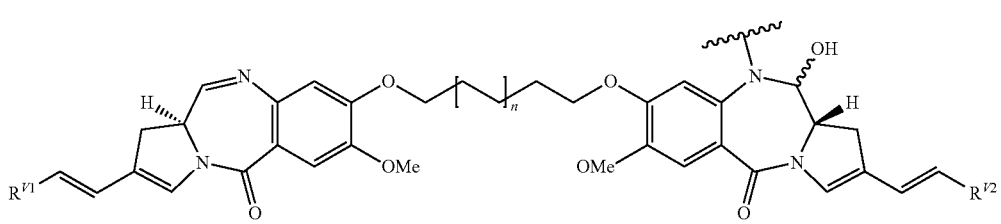

B and salts and solvates thereof, wherein:

the wavy line indicates the covalent attachment site to the linker;

the wavy line connected to the OH indicates the S or R configuration;

$R^{V1}$ and $R^{V2}$ are independently selected from H, methyl, ethyl and phenyl (which phenyl may be optionally substituted with fluoro, particularly in the 4 position) and $C_{5-6}$ heterocyclyl; wherein $R^{V1}$ and $R^{V2}$ may be the same or different; and n is 0 or 1.

In some embodiments, $R^{V1}$ and $R^{V2}$ are independently selected from H, phenyl, and 4-fluorophenyl.

In some embodiments, a linker may be attached at one of various sites of the PBD dimer drug moiety, including the N10 imine of the B ring, the C-2 endo/exo position of the C ring, or the tether unit linking the A rings (see structures C(I) and C(II) below).

Nonlimiting exemplary PBD dimer components of ADCs include Formulas C(I) and C(II):

Z and Z' are independently selected from OR and $NR_2$, where R is a primary, secondary or tertiary alkyl chain containing 1 to 5 carbon atoms;

$R_1$, $R'_1$, $R_2$ and $R'_2$ are each independently selected from H, $C_1$-$C_8$ alkyl, $C_2$-$C_8$ alkenyl, $C_2$-$C_8$ alkynyl, $C_{5-20}$ aryl (including substituted aryls), $C_{5-20}$ heteroaryl groups, —$NH_2$, —NHMe, —OH, and —SH, where, in some embodiments, alkyl, alkenyl and alkynyl chains comprise up to 5 carbon atoms;

$R_3$ and $R'_3$ are independently selected from H, OR, NHR, and $NR_2$, where R is a primary, secondary or tertiary alkyl chain containing 1 to 5 carbon atoms;

$R_4$ and $R'_4$ are independently selected from H, Me, and OMe;

$R_5$ is selected from $C_1$-$C_8$ alkyl, $C_2$-$C_8$ alkenyl, $C_2$-$C_8$ alkynyl, $C_{5-20}$ aryl (including aryls substituted by halo, nitro, cyano, alkoxy, alkyl, heterocyclyl) and $C_{5-20}$ heteroaryl groups, where, in some embodiments, alkyl, alkenyl and alkynyl chains comprise up to 5 carbon atoms;

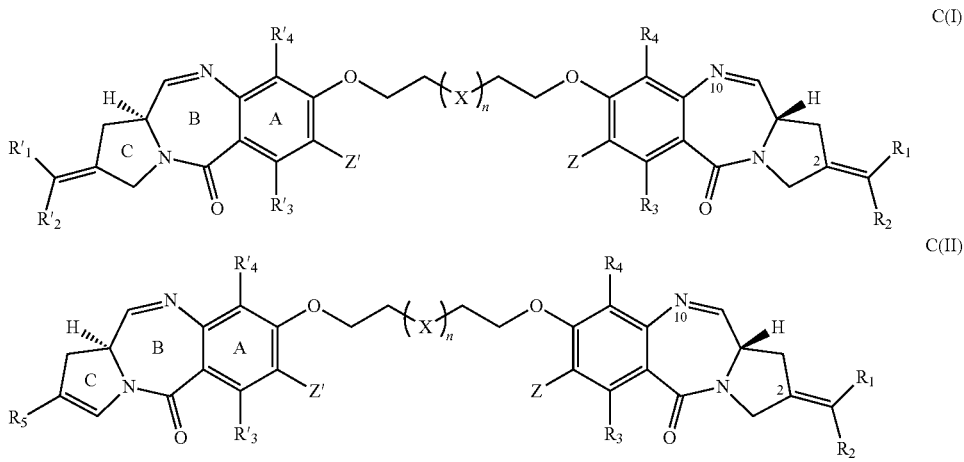

C(I)

C(II)

Formulas C(I) and C(II) are shown in their N10-C11 imine form. Exemplary PBD drug moieties also include the carbinolamine and protected carbinolamine forms as well, as shown in the table below:

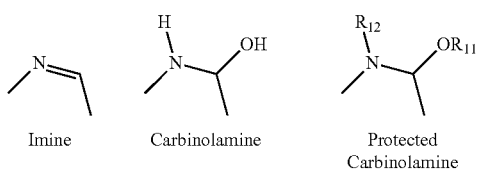

| Imine | Carbinolamine | Protected Carbinolamine | wherein:
X is $CH_2$ (n=1 to 5), N, or O;

$R_{11}$ is H, $C_1$-$C_8$ alkyl, or a protecting group (such as acetyl, trifluoroacetyl, t-butoxycarbonyl (BOC), benzyloxycarbonyl (CBZ), 9-fluorenylmethylenoxycarbonyl (Fmoc), or a moiety comprising a self-immolating unit such as valine-citrulline-PAB);

$R_{12}$ is H, $C_1$-$C_8$ alkyl, or a protecting group;

wherein a hydrogen of one of $R_1$, $R'_1$, $R_2$, $R'_2$, $R_5$, or $R_{12}$ or a hydrogen of the —$OCH_2CH_2(X)_nCH_2CH_2O$— spacer between the A rings is replaced with a bond connected to the linker of the ADC.

Exemplary PDB dimer portions of ADC include, but are not limited to (the wavy line indicates the site of covalent attachment to the linker):

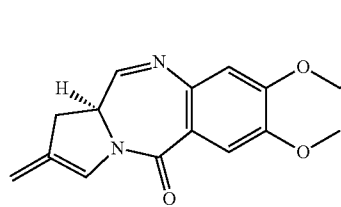
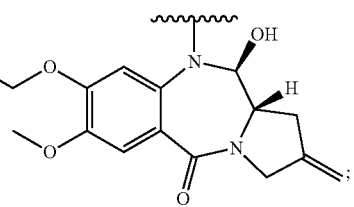
PBD dimer
Nonlimiting exemplary embodiments of ADCs comprising PBD dimers have the following structures:
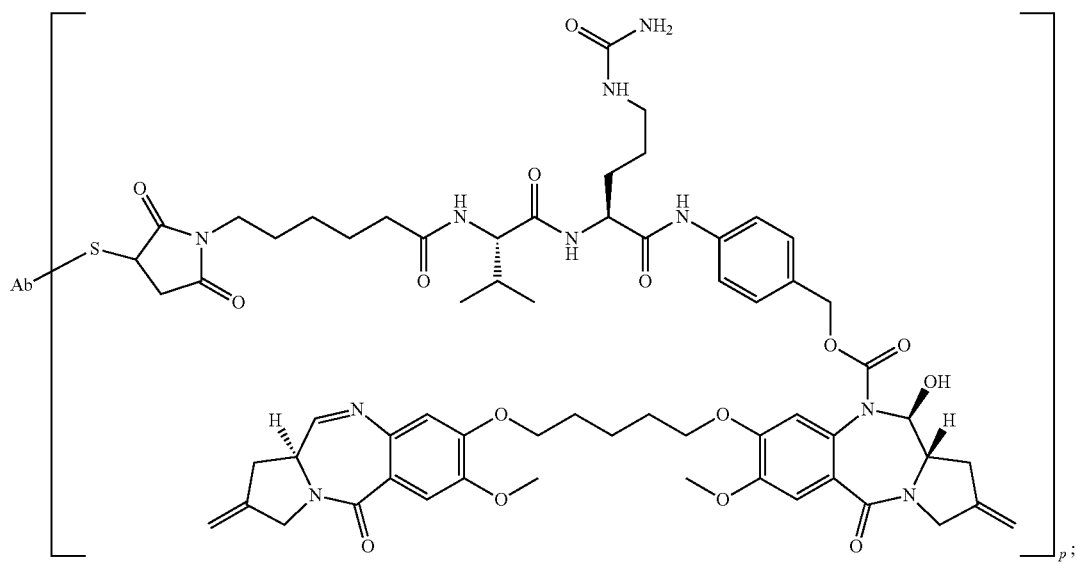
PBD dimer-val-cit-PAB-Ab
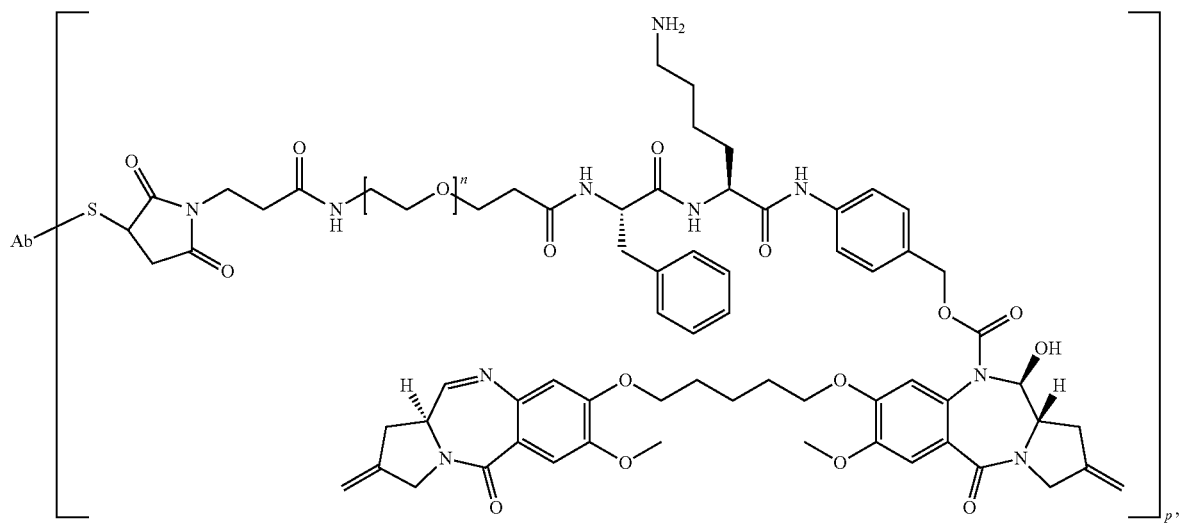
PBD dimer-Phe-Lys-PAB-Ab wherein:
n is 0 to 12. In some embodiments, n is 2 to 10. In some embodiments, n is 4 to 8. In some embodiments, n is selected from 4, 5, 6, 7, and 8.

The linkers of PBD dimer-val-cit-PAB-Ab and the PBD dimer-Phe-Lys-PAB-Ab are protease cleavable, while the linker of PBD dimer-maleimide-acetal is acid-labile.

PBD dimers and ADC comprising PBD dimers may be prepared according to methods known in the art. See, e.g., WO 2009/016516; US 2009/304710; US 2010/047257; US 2009/036431; US 2011/0256157; WO 2011/130598.

(5) Anthracyclines

In some embodiments, an ADC comprising anthracycline. Anthracyclines are antibiotic compounds that exhibit cytotoxic activity. While not intending to be bound by any particular theory, studies have indicated that anthracyclines may operate to kill cells by a number of different mechanisms, including: 1) intercalation of the drug molecules into the DNA of the cell thereby inhibiting DNA-dependent nucleic acid synthesis; 2) production by the drug of free radicals which then react with cellular macromolecules to cause damage to the cells, and/or 3) interactions of the drug molecules with the cell membrane (see, e.g., C. Peterson et al., "Transport And Storage Of Anthracycline In Experimental Systems And Human Leukemia" in *Anthracycline Antibiotics In Cancer Therapy*; N. R. Bachur, "Free Radical Damage" id. at pp. 97-102). Because of their cytotoxic potential anthracyclines have been used in the treatment of numerous cancers such as leukemia, breast carcinoma, lung carcinoma, ovarian adenocarcinoma and sarcomas (see e.g., P. H-Wiernik, in *Anthracycline: Current Status And New Developments* p 11).

Nonlimiting exemplary anthracyclines include doxorubicin, epirubicin, idarubicin, daunomycin, nemorubicin, and derivatives thereof. Immunoconjugates and prodrugs of daunorubicin and doxorubicin have been prepared and studied (Kratz et al (2006) *Current Med. Chem.* 13:477-523; Jeffrey et al (2006) *Bioorganic & Med. Chem. Letters* 16:358-362; Torgov et al (2005) *Bioconj. Chem.* 16:717-721; Nagy et al (2000) *Proc. Natl. Acad. Sci. USA* 97:829-834; Dubowchik et al (2002) *Bioorg. & Med. Chem. Letters* 12:1529-1532; King et al (2002) *J. Med. Chem.* 45:4336-4343; EP 0328147; U.S. Pat. No. 6,630,579). The antibody-drug conjugate BR96-doxorubicin reacts specifically with the tumor-associated antigen Lewis-Y and has been evaluated in phase I and II studies (Saleh et al (2000) *J. Clin. Oncology* 18:2282-2292; Ajani et al (2000) *Cancer Jour.* 6:78-81; Tolcher et al (1999) *J. Clin. Oncology* 17:478-484).

PNU-159682 is a potent metabolite (or derivative) of nemorubicin (Quintieri, et al. (2005) *Clinical Cancer Research* 11(4):1608-1617). Nemorubicin is a semisynthetic analog of doxorubicin with a 2-methoxymorpholino group on the glycoside amino of doxorubicin and has been under clinical evaluation (Grandi et al (1990) *Cancer Treat. Rev.* 17:133; Ripamonti et al (1992) *Brit. J. Cancer* 65:703;), including phase II/III trials for hepatocellular carcinoma (Sun et al (2003) *Proceedings of the American Society for Clinical Oncology* 22, Abs 1448; Quintieri (2003) *Proceedings of the American Association of Cancer Research*, 44:1st Ed, Abs 4649; Pacciarini et al (2006) *Jour. Clin. Oncology* 24:14116).

A nonlimiting exemplary ADC comprising nemorubicin or nemorubicin derivatives is shown in Formula Ia:

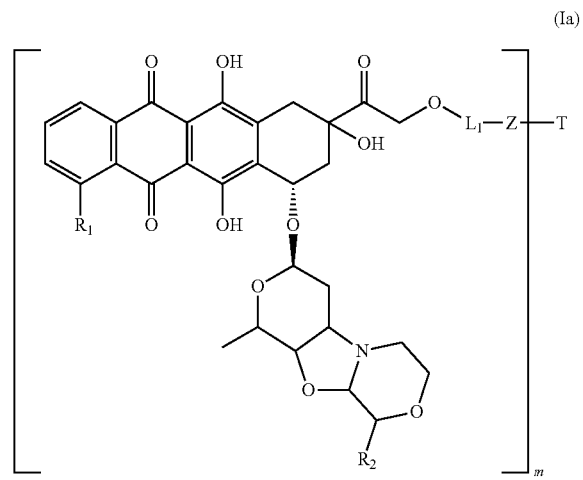

(Ia)

wherein $R_1$ is hydrogen atom, hydroxy or methoxy group and $R_2$ is a $C_1$-$C_5$ alkoxy group, or a pharmaceutically acceptable salt thereof;

$L_1$ and Z together are a linker (L) as described herein;

T is an antibody (Ab) as described herein; and m is 1 to about 20. In some embodiments, m is 1 to 10, 1 to 7, 1 to 5, or 1 to 4.

In some embodiments, $R_1$ and $R_2$ are both methoxy (—OMe).

A further nonlimiting exemplary ADC comprising nemorubicin or nemorubicin derivatives is shown in Formula Ib:

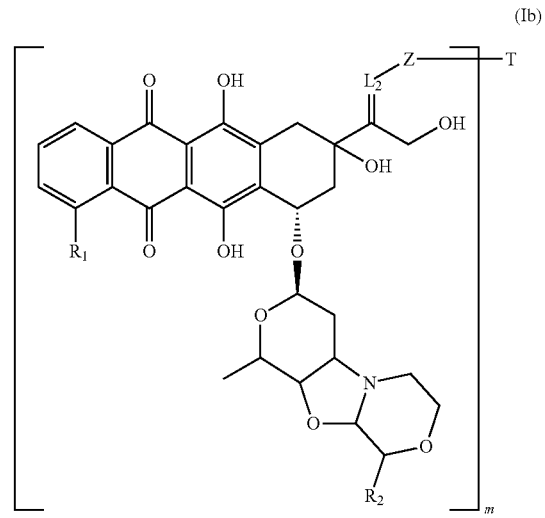

(Ib)

wherein $R_1$ is hydrogen atom, hydroxy or methoxy group and $R_2$ is a $C_1$-$C_5$ alkoxy group, or a pharmaceutically acceptable salt thereof;

$L_2$ and Z together are a linker (L) as described herein;

T is an antibody (Ab) as described herein; and m is 1 to about 20. In some embodiments, m is 1 to 10, 1 to 7, 1 to 5, or 1 to 4.

In some embodiments, $R_1$ and $R_2$ are both methoxy (—OMe).

In some embodiments, the nemorubicin component of a nemorubicin-containing ADC is PNU-159682. In some such embodiments, the drug portion of the ADC may have one of the following structures:

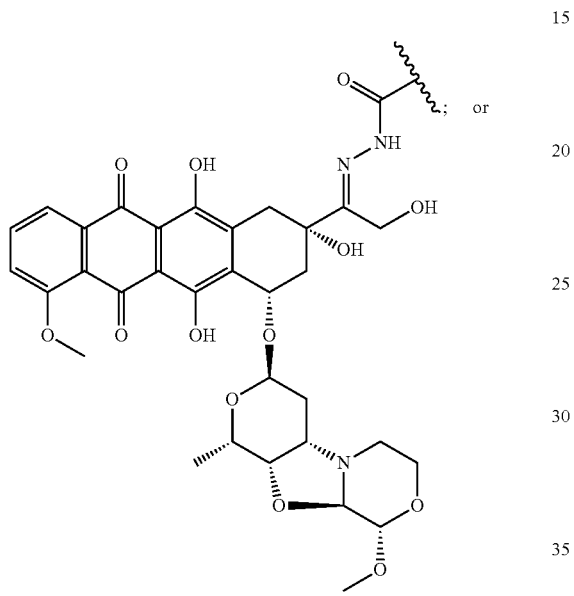

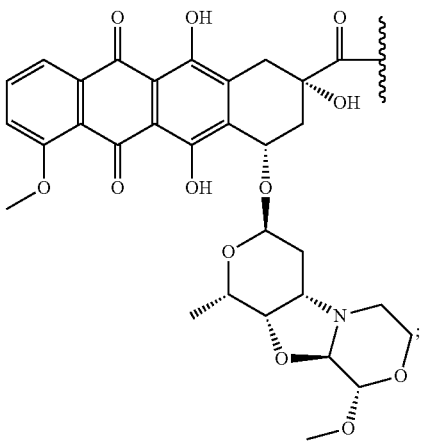

wherein the wavy line indicates the attachment to the linker (L).

Anthracyclines, including PNU-159682, may be conjugated to antibodies through several linkage sites and a variety of linkers (US 2011/0076287; WO2009/099741; US 2010/0034837; WO 2010/009124), including the linkers described herein.

Exemplary ADCs comprising a nemorubicin and linker include, but are not limited to:

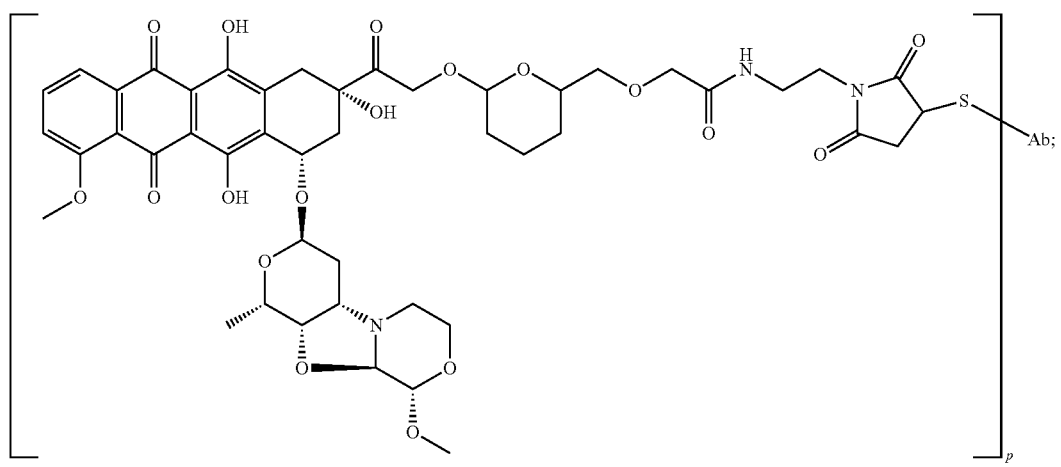

PNU-159682 maleimide acetal-Ab

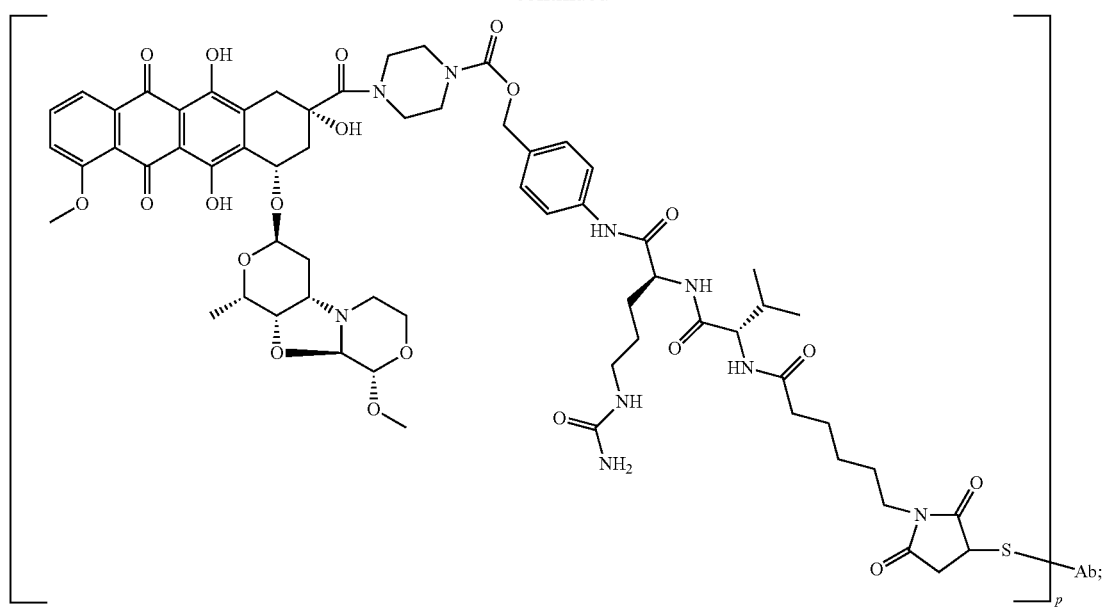
PNU-159682-val-cit-PAB-Ab
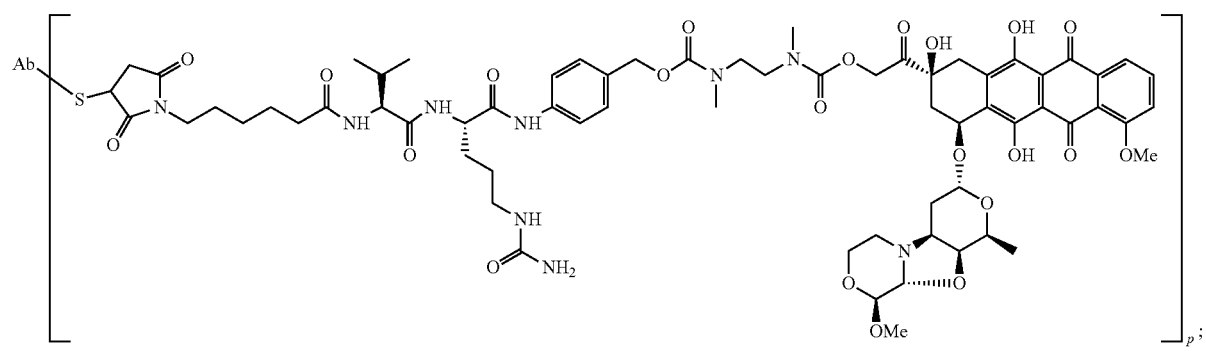
PNU-159682-val-cit-PAB-spacer-Ab
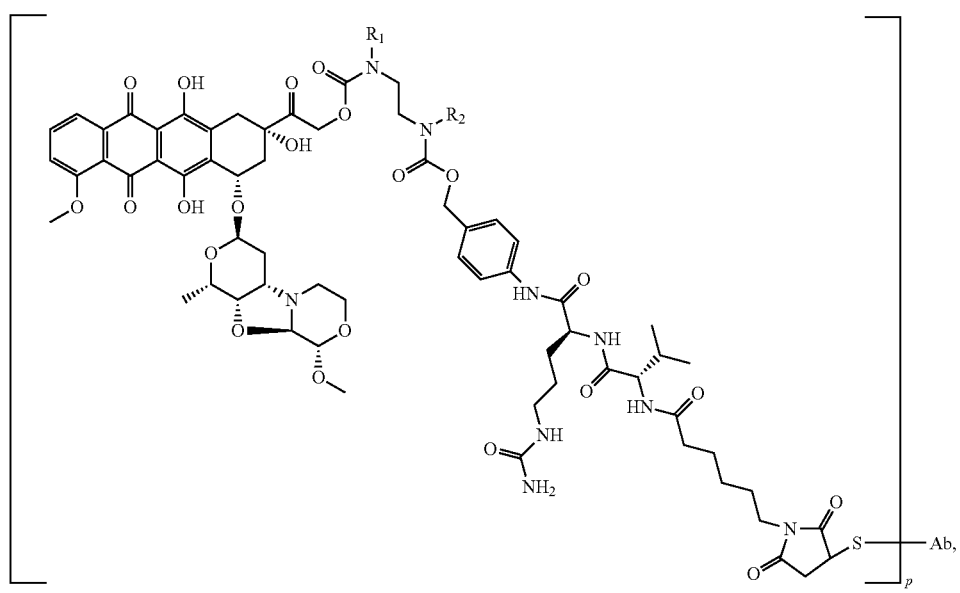
PNU-159682-val-cit-PAB-spacer(R$^1$R$^2$)-Ab wherein:

R₁ and R₂ are independently selected from H and $C_1$-$C_6$ alkyl; and

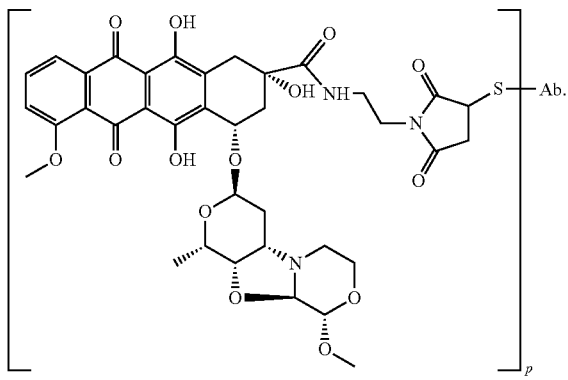

PNU-159682-maleimide-Ab

The linker of PNU-159682 maleimide acetal-Ab is acid-labile, while the linkers of PNU-159682-val-cit-PAB-Ab, PNU-159682-val-cit-PAB-spacer-Ab, and PNU-159682-val-cit-PAB-spacer($R^1R^2$)-Ab are protease cleavable.

(6) Other Drug Moieties

Drug moieties also include geldanamycin (Mandler et al (2000) *J. Nat. Cancer Inst.* 92(19):1573-1581; Mandler et al (2000) *Bioorganic & Med. Chem. Letters* 10:1025-1028; Mandler et al (2002) *Bioconjugate Chem.* 13:786-791); and enzymatically active toxins and fragments thereof, including, but not limited to, diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes. See, e.g., WO 93/21232.

Drug moieties also include compounds with nucleolytic activity (e.g., a ribonuclease or a DNA endonuclease).

In certain embodiments, an immunoconjugate may comprise a highly radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. In some embodiments, when an immunoconjugate is used for detection, it may comprise a radioactive atom for scintigraphic studies, for example $Tc^{99}$ or $I^{123}$, or a spin label for nuclear magnetic resonance (NMR) imaging (also known as magnetic resonance imaging, MRI), such as zirconium-89, iodine-123, iodine-131, indium-111, fluorine-19, carbon-13, nitrogen-15, oxygen-17, gadolinium, manganese or iron. Zirconium-89 may be complexed to various metal chelating agents and conjugated to antibodies, e.g., for PET imaging (WO 2011/056983).

The radio- or other labels may be incorporated in the immunoconjugate in known ways. For example, a peptide may be biosynthesized or chemically synthesized using suitable amino acid precursors comprising, for example, one or more fluorine-19 atoms in place of one or more hydrogens. In some embodiments, labels such as $Tc^{99}$, $I^{123}$, $Re^{186}$, $Re^{188}$ and $In^{111}$ can be attached via a cysteine residue in the antibody. In some embodiments, yttrium-90 can be attached via a lysine residue of the antibody. In some embodiments, the IODOGEN method (Fraker et al (1978) *Biochem. Biophys. Res. Commun.* 80: 49-57 can be used to incorporate iodine-123. "Monoclonal Antibodies in Immunoscintigraphy" (Chatal, CRC Press 1989) describes certain other methods.

In certain embodiments, an immunoconjugate may comprise an antibody conjugated to a prodrug-activating enzyme. In some such embodiments, a prodrug-activating enzyme converts a prodrug (e.g., a peptidyl chemotherapeutic agent, see WO 81/01145) to an active drug, such as an anti-cancer drug. Such immunoconjugates are useful, in some embodiments, in antibody-dependent enzyme-mediated prodrug therapy ("ADEPT"). Enzymes that may be conjugated to an antibody include, but are not limited to, alkaline phosphatases, which are useful for converting phosphate-containing prodrugs into free drugs; arylsulfatases, which are useful for converting sulfate-containing prodrugs into free drugs; cytosine deaminase, which is useful for converting non-toxic 5-fluorocytosine into the anti-cancer drug, 5-fluorouracil; proteases, such as *serratia* protease, thermolysin, subtilisin, carboxypeptidases and cathepsins (such as cathepsins B and L), which are useful for converting peptide-containing prodrugs into free drugs; D-alanyl-carboxypeptidases, which are useful for converting prodrugs that contain D-amino acid substituents; carbohydrate-cleaving enzymes such as β-galactosidase and neuraminidase, which are useful for converting glycosylated prodrugs into free drugs; β-lactamase, which is useful for converting drugs derivatized with β-lactams into free drugs; and penicillin amidases, such as penicillin V amidase and penicillin G amidase, which are useful for converting drugs derivatized at their amine nitrogens with phenoxyacetyl or phenylacetyl groups, respectively, into free drugs. In some embodiments, enzymes may be covalently bound to antibodies by recombinant DNA techniques well known in the art. See, e.g., Neuberger et al., *Nature* 312:604-608 (1984).

c) Drug Loading

Drug loading is represented by p, the average number of drug moieties per antibody in a molecule of Formula I. Drug loading may range from 1 to 20 drug moieties (D) per antibody. ADCs of Formula I include collections of antibodies conjugated with a range of drug moieties, from 1 to 20. The average number of drug moieties per antibody in preparations of ADC from conjugation reactions may be characterized by conventional means such as mass spectroscopy, ELISA assay, and HPLC. The quantitative distribution of ADC in terms of p may also be determined In some instances, separation, purification, and characterization of homogeneous ADC where p is a certain value from ADC with other drug loadings may be achieved by means such as reverse phase HPLC or electrophoresis.

For some antibody-drug conjugates, p may be limited by the number of attachment sites on the antibody. For example, where the attachment is a cysteine thiol, as in certain exemplary embodiments above, an antibody may have only one or several cysteine thiol groups, or may have only one or several sufficiently reactive thiol groups through which a linker may be attached. In certain embodiments, higher drug loading, e.g. p>5, may cause aggregation, insolubility, toxicity, or loss of cellular permeability of certain antibody-drug conjugates. In certain embodiments, the average drug loading for an ADC ranges from 1 to about 8; from about 2 to about 6; or from about 3 to about 5. Indeed, it has been shown that for certain ADCs, the optimal ratio of drug moieties per antibody may be less than 8, and may be about 2 to about 5 (U.S. Pat. No. 7,498,298).

In certain embodiments, fewer than the theoretical maximum of drug moieties are conjugated to an antibody during a conjugation reaction. An antibody may contain, for example, lysine residues that do not react with the drug-linker intermediate or linker reagent, as discussed below. Generally, antibodies do not contain many free and reactive cysteine thiol groups which may be linked to a drug moiety; indeed most cysteine thiol residues in antibodies exist as disulfide bridges. In certain embodiments, an antibody may be reduced with a reducing agent such as dithiothreitol (DTT) or tricarbonylethylphosphine (TCEP), under partial or total reducing conditions, to generate reactive cysteine thiol groups. In certain embodiments, an antibody is subjected to denaturing conditions to reveal reactive nucleophilic groups such as lysine or cysteine.

The loading (drug/antibody ratio) of an ADC may be controlled in different ways, and for example, by: (i) limiting the molar excess of drug-linker intermediate or linker reagent relative to antibody, (ii) limiting the conjugation reaction time or temperature, and (iii) partial or limiting reductive conditions for cysteine thiol modification.

It is to be understood that where more than one nucleophilic group reacts with a drug-linker intermediate or linker reagent, then the resulting product is a mixture of ADC compounds with a distribution of one or more drug moieties attached to an antibody. The average number of drugs per antibody may be calculated from the mixture by a dual ELISA antibody assay, which is specific for antibody and specific for the drug. Individual ADC molecules may be identified in the mixture by mass spectroscopy and separated by HPLC, e.g. hydrophobic interaction chromatography (see, e.g., McDonagh et al (2006) Prot. Engr. Design & Selection 19(7):299-307; Hamblett et al (2004) Clin. Cancer Res. 10:7063-7070; Hamblett, K. J., et al. "Effect of drug loading on the pharmacology, pharmacokinetics, and toxicity of an anti-CD30 antibody-drug conjugate," Abstract No. 624, American Association for Cancer Research, 2004 Annual Meeting, Mar. 27-31, 2004, Proceedings of the AACR, Volume 45, March 2004; Alley, S. C., et al. "Controlling the location of drug attachment in antibody-drug conjugates," Abstract No. 627, American Association for Cancer Research, 2004 Annual Meeting, Mar. 27-31, 2004, Proceedings of the AACR, Volume 45, March 2004). In certain embodiments, a homogeneous ADC with a single loading value may be isolated from the conjugation mixture by electrophoresis or chromatography.

d) Certain Methods of Preparing Immunoconjugates

An ADC of Formula I may be prepared by several routes employing organic chemistry reactions, conditions, and reagents known to those skilled in the art, including: (1) reaction of a nucleophilic group of an antibody with a bivalent linker reagent to form Ab-L via a covalent bond, followed by reaction with a drug moiety D; and (2) reaction of a nucleophilic group of a drug moiety with a bivalent linker reagent, to form D-L, via a covalent bond, followed by reaction with a nucleophilic group of an antibody. Exemplary methods for preparing an ADC of Formula I via the latter route are described in U.S. Pat. No. 7,498,298, which is expressly incorporated herein by reference.

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; and (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol) or tricarbonylethylphosphine (TCEP), such that the antibody is fully or partially reduced. Each cysteine bridge will thus form, theoretically, two reactive thiol nucleophiles. Additional nucleophilic groups can be introduced into antibodies through modification of lysine residues, e.g., by reacting lysine residues with 2-iminothiolane (Traut's reagent), resulting in conversion of an amine into a thiol. Reactive thiol groups may also be introduced into an antibody by introducing one, two, three, four, or more cysteine residues (e.g., by preparing variant antibodies comprising one or more non-native cysteine amino acid residues).

Antibody-drug conjugates of the invention may also be produced by reaction between an electrophilic group on an antibody, such as an aldehyde or ketone carbonyl group, with a nucleophilic group on a linker reagent or drug. Useful nucleophilic groups on a linker reagent include, but are not limited to, hydrazide, oxime, amino, hydrazine, thiosemicarbazone, hydrazine carboxylate, and arylhydrazide. In one embodiment, an antibody is modified to introduce electrophilic moieties that are capable of reacting with nucleophilic substituents on the linker reagent or drug. In another embodiment, the sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either galactose oxidase or sodium meta-periodate may yield carbonyl (aldehyde and ketone) groups in the antibody that can react with appropriate groups on the drug (Hermanson, Bioconjugate Techniques). In another embodiment, antibodies containing N-terminal serine or threonine residues can react with sodium meta-periodate, resulting in production of an aldehyde in place of the first amino acid (Geoghegan & Stroh, (1992) *Bioconjugate Chem.* 3:138-146; U.S. Pat. No. 5,362,852). Such an aldehyde can be reacted with a drug moiety or linker nucleophile.

Exemplary nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Nonlimiting exemplary cross-linker reagents that may be used to prepare ADC are described herein in the section titled "Exemplary Linkers." Methods of using such cross-linker reagents to link two moieties, including a proteinaceous moiety and a chemical moiety, are known in the art. In some embodiments, a fusion protein comprising an antibody and a cytotoxic agent may be made, e.g., by recombinant techniques or peptide synthesis. A recombinant DNA molecule may comprise regions encoding the antibody and cytotoxic portions of the conjugate either adjacent to one another or separated by a region encoding a linker peptide which does not destroy the desired properties of the conjugate.

In yet another embodiment, an antibody may be conjugated to a "receptor" (such as streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a drug or radionucleotide).

E. Methods and Compositions for Diagnostics and Detection

In certain embodiments, any of the anti-PMEL17 antibodies provided herein is useful for detecting the presence of PMEL17 in a biological sample. The term "detecting" as used herein encompasses quantitative or qualitative detection. A "biological sample" comprises, e.g., a cell or tissue (e.g., biopsy material, including cancerous or potentially cancerous skin tissue, including possible or confirmed melanoma; biopsy material from lymphoma, such as cutaneous T-cell lymphoma; and biopsy material from kidney tumors).

In one embodiment, an anti-PMEL17 antibody for use in a method of diagnosis or detection is provided. In a further aspect, a method of detecting the presence of PMEL17 in a biological sample is provided. In certain embodiments, the method comprises contacting the biological sample with an anti-PMEL17 antibody as described herein under conditions permissive for binding of the anti-PMEL17 antibody to PMEL17, and detecting whether a complex is formed between the anti-PMEL17 antibody and PMEL17 in the biological sample. Such method may be an in vitro or in vivo method. In one embodiment, an anti-PMEL17 antibody is used to select subjects eligible for therapy with an anti-PMEL17 antibody, e.g. where PMEL17 is a biomarker for selection of patients. In a further embodiment, the biological sample is a cell or tissue (cancerous or potentially cancerous skin tissue, including possible or confirmed melanoma; biopsy material from lymphoma, such as cutaneous T-cell lymphoma; and biopsy material from kidney tumors).

In a further embodiment, an anti-PMEL17 antibody is used in vivo to detect, e.g., by in vivo imaging, a PMEL17-positive cancer in a subject, e.g., for the purposes of diagnosing, prognosing, or staging cancer, determining the appropriate course of therapy, or monitoring response of a cancer to therapy. One method known in the art for in vivo detection is immuno-positron emission tomography (immuno-PET), as described, e.g., in van Dongen et al., *The Oncologist* 12:1379-1389 (2007) and Verel et al., *J. Nucl. Med.* 44:1271-1281 (2003). In such embodiments, a method is provided for detecting a PMEL17-positive cancer in a subject, the method comprising administering a labeled anti-PMEL17 antibody to a subject having or suspected of having a PMEL17-positive cancer, and detecting the labeled anti-PMEL17 antibody in the subject, wherein detection of the labeled anti-PMEL17 antibody indicates a PMEL17-positive cancer in the subject. In certain of such embodiments, the labeled anti-PMEL17 antibody comprises an anti-PMEL17 antibody conjugated to a positron emitter, such as $^{68}$Ga, $^{18}$F, $^{64}$Cu, $^{86}$Y, $^{76}$Br, $^{89}$Zr, and $^{124}$I. In a particular embodiment, the positron emitter is $^{89}$Zr.

In further embodiments, a method of diagnosis or detection comprises contacting a first anti-PMEL17 antibody immobilized to a substrate with a biological sample to be tested for the presence of PMEL17, exposing the substrate to a second anti-PMEL17 antibody, and detecting whether the second anti-PMEL17 is bound to a complex between the first anti-PMEL17 antibody and PMEL17 in the biological sample. A substrate may be any supportive medium, e.g., glass, metal, ceramic, polymeric beads, slides, chips, and other substrates. In certain embodiments, a biological sample comprises a cell or tissue (cancerous or potentially cancerous skin tissue, including possible or confirmed melanoma; biopsy material from a lymphoma, such as cutaneous T-cell lymphoma; and biopsy material from a kidney tumor). In certain embodiments, the first or second anti-PMEL17 antibody is any of the antibodies described herein.

Exemplary disorders that may be diagnosed or detected according to any of the above embodiments include PMEL17-positive cancers, such as PMEL17-positive skin cancer (such as melanoma); PMEL17-positive lymphomas (such as cutaneous T-cell lymphoma); and PMEL17-positive kidney tumors. In some embodiments, a PMEL17-positive cancer is a cancer that receives an anti-PMEL17 immunohistochemistry (IHC) score greater than "0," which corresponds to very weak or no staining in >90% of tumor cells, under the conditions described herein in Example K. In some embodiments, a PMEL17-positive cancer expresses PMEL17 at a 1+, 2+ or 3+ level, as defined under the conditions described herein in Example K, using the 31D1 antibody (the 31D1-expressing hybridoma was deposited at the ATCC as 7509(31D1.6.7) on Apr. 24, 2012). In some embodiments, a PMEL17-positive cancer is a cancer that expresses PMEL17 according to an in situ hybridization (ISH) assay. In some such embodiments, a scoring system similar to that used for IHC is used. In some embodiments, a PMEL17-positive cancer is a cancer that expresses PMEL17 according to a reverse-transcriptase PCR (RT-PCR) assay that detects PMEL17 mRNA. In some embodiments, the RT-PCR is quantitative RT-PCR.

In certain embodiments, labeled anti-PMEL17 antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like. In another embodiment, a label is a positron emitter. Positron emitters include but are not limited to $^{68}$Ga, $^{18}$F, $^{64}$Cu, $^{86}$Y, $^{76}$Br, $^{89}$Zr, and $^{124}$I. In a particular embodiment, a positron emitter is $^{89}$Zr.

F. Pharmaceutical Formulations

Pharmaceutical formulations of an anti-PMEL17 antibody or immunoconjugate as described herein are prepared by mixing such antibody or immunoconjugate having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH2O, are described in US Patent Publication Nos. 2005/0260186 and 2006/0104968. In one aspect, a sHASEGP is combined with one or more additional glycosaminoglycanases such as chondroitinases.

Exemplary lyophilized antibody or immunoconjugate formulations are described in U.S. Pat. No. 6,267,958. Aqueous antibody or immunoconjugate formulations include those described in U.S. Pat. No. 6,171,586 and WO2006/044908, the latter formulations including a histidine-acetate buffer.

The formulation herein may also contain more than one active ingredient as necessary for the particular indication being treated, preferably those with complementary activities that do not adversely affect each other.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody or immunoconjugate, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Methods and Compositions

Any of the anti-PMEL17 antibodies or immunoconjugates provided herein may be used in methods, e.g., therapeutic methods.

In one aspect, an anti-PMEL17 antibody or immunoconjugate provided herein is used in a method of inhibiting proliferation of a PMEL17-positive cell, the method comprising exposing the cell to the anti-PMEL17 antibody or immunoconjugate under conditions permissive for binding of the anti-PMEL17 antibody or immunoconjugate to PMEL17 on the surface of the cell, thereby inhibiting the proliferation of the cell. In certain embodiments, the method is an in vitro or an in vivo method. In some embodiments, the cell is a melanoma cell. In some embodiments, the cell is a lymphoma cell, such as a cutaneous T cell lymphoma cell. In some embodiments, the cell is a kidney tumor cell.

Inhibition of cell proliferation in vitro may be assayed using the CellTiter-Glo™ Luminescent Cell Viability Assay, which is commercially available from Promega (Madison, Wis.). That assay determines the number of viable cells in culture based on quantitation of ATP present, which is an indication of metabolically active cells. See Crouch et al. (1993) *J. Immunol. Meth.* 160:81-88, U.S. Pat. No. 6,602,677. The assay may be conducted in 96- or 384-well format, making it amenable to automated high-throughput screening (HTS). See Cree et al. (1995) *AntiCancer Drugs* 6:398-404. The assay procedure involves adding a single reagent (CellTiter-Glo® Reagent) directly to cultured cells. This results in cell lysis and generation of a luminescent signal produced by a luciferase reaction. The luminescent signal is proportional to the amount of ATP present, which is directly proportional to the number of viable cells present in culture. Data can be recorded by luminometer or CCD camera imaging device. The luminescence output is expressed as relative light units (RLU).

In another aspect, an anti-PMEL17 antibody or immunoconjugate for use as a medicament is provided. In further aspects, an anti-PMEL17 antibody or immunoconjugate for use in a method of treatment is provided. In certain embodiments, an anti-PMEL17 antibody or immunoconjugate for use in treating PMEL17-positive cancer is provided. In certain embodiments, the invention provides an anti-PMEL17 antibody or immunoconjugate for use in a method of treating an individual having a PMEL17-positive cancer, the method comprising administering to the individual an effective amount of the anti-PMEL17 antibody or immunoconjugate. In one such embodiment, the method further comprises administering to the individual an effective amount of at least one additional therapeutic agent, e.g., as described below.

In a further aspect, the invention provides for the use of an anti-PMEL17 antibody or immunoconjugate in the manufacture or preparation of a medicament. In one embodiment, the medicament is for treatment of PMEL17-positive cancer. In a further embodiment, the medicament is for use in a method of treating PMEL17-positive cancer, the method comprising administering to an individual having PMEL17-positive cancer an effective amount of the medicament. In one such embodiment, the method further comprises administering to the individual an effective amount of at least one additional therapeutic agent, e.g., as described below.

In a further aspect, the invention provides a method for treating PMEL17-positive cancer. In one embodiment, the method comprises administering to an individual having such PMEL17-positive cancer an effective amount of an anti-PMEL17 antibody or immunoconjugate. In one such embodiment, the method further comprises administering to the individual an effective amount of at least one additional therapeutic agent, as described below.

A PMEL17-positive cancer according to any of the above embodiments may be, e.g., PMEL17-positive skin cancer (including melanoma); PMEL17-positive lymphoms (such as cutaneous T-cell lymphoma); and PMEL17-positive kidney tumors. In some embodiments, a PMEL17-positive cancer is a cancer that receives an anti-PMEL17 immunohistochemistry (IHC) or in situ hybridization (ISH) score greater than "0," which corresponds to very weak or no staining in >90% of tumor cells, under the conditions described herein in Example K. In another embodiment, a PMEL17-positive cancer expresses PMEL17 at a 1+, 2+ or 3+ level, as defined under the conditions described herein in Example K, using the 31D1 antibody (the 31D1-expressing hybridoma was deposited at the ATCC as 7509(31D1.6.7) on Apr. 24, 2012). In some embodiments, a PMEL17-positive cancer is a cancer that expresses PMEL17 according to a reverse-transcriptase PCR (RT-PCR) assay that detects PMEL17 mRNA. In some embodiments, the RT-PCR is quantitative RT-PCR.

In some embodiments, methods of treating an individual having a PMEL17-positive cancer are provided, wherein the PMEL17-positive cancer is resistant to a first therapeutic. In some embodiments, the method comprises administering to the individual an effective amount of an immunoconjugate comprising an antibody that binds to PMEL17. In some embodiments, the PMEL17-positive cancer is melanoma. In some embodiments, the first therapeutic comprises a first antibody that binds an antigen other than PMEL17. In some embodiments, the first therapeutic is a first immunoconjugate comprising a first antibody that binds an antigen other than PMEL17 and a first cytotoxic agent. In some embodiments, the first antibody binds an antigen selected from endothelin B receptor (ETBR), tyrosinase-related protein 1 (TYRP1), cytotoxic T lymphocyte antigen 4 (CTLA-4), and glycoprotein NMB (GPNMB). In some embodiments, the first antibody binds ETBR. In some such embodiments, the first immunoconjugate comprises anti-ETBR antibody hu5E9.v1, such as the immunoconjugate hu5E9.v1-MC-val-cit-PAB-MMAE. See U.S. Publication No. US 2011/0206702. The hypervariable regions (HVRs) of hu5E9.v1 are shown herein, e.g., in SEQ ID NOs: 33 to 38. The heavy and light chain variable regions of hu5E9.v1 are shown herein, e.g., in SEQ ID NOs: 40 and 39, respectively. In some embodiments, the first cytotoxic agent and the cytotoxic agent of the immunoconjugate comprising an antibody that binds to PMEL17 are different. In some such embodiments, the first cytotoxic agent is MMAE (such as, for example, when the first immunoconjugate is hu5E9.v1-MC-val-cit-PAB-MMAE) and the cytotoxic agent of the immunoconjugate comprising an antibody that binds to PMEL17 is selected from a calicheamicin, a pyrrolobenzodiazepine, and a nemorubicin derivative. In some embodiments, the cytotoxic agent of the immunoconjugate comprising an antibody that binds to PMEL17 is selected from a pyrrolobenzodiazepine and a nemorubicin derivative.

In some embodiments, methods of treating an individual with cancer are provided, wherein the cancer is resistant to a first therapeutic. In some embodiments, the first therapeutic is a first immunoconjugate comprising a first antibody linked to a first cytotoxic agent through a first linker. In some embodiments, a method of treating an individual with a cancer that is resistant to a first therapeutic (such as a first immunoconjugate) comprises administering a second immunoconjugate comprising a second antibody linked to a second cytotoxic agent through a second linker. In some embodiments, the first antibody and the second antibody bind to different antigens and the first cytotoxic agent and the second cytotoxic agents are the same or different. In some embodiments, the first antibody and the second antibody bind to different antigens that are present on at least some of the same cells. In some embodiments, the first antibody and the second antibody bind to different antigens and the first cytotoxic agent and the second cytotoxic agents are different. In some embodiments, the first antibody and the second antibody bind to the same antigens, and the first cytotoxic agent and the second cytotoxic agent are different. In any of the foregoing embodiments, the first linker and the second linker may be the same or different. In some embodiments, the first antibody and the second antibody bind to different antigens, the first and second linkers are different, and the first and second cytotoxic agents are different.

An "individual" according to any of the above embodiments may be a human.

In a further aspect, the invention provides pharmaceutical formulations comprising any of the anti-PMEL17 antibodies or immunoconjugate provided herein, e.g., for use in any of the above therapeutic methods. In one embodiment, a pharmaceutical formulation comprises any of the anti-PMEL17 antibodies or immunoconjugates provided herein and a pharmaceutically acceptable carrier. In another embodiment, a pharmaceutical formulation comprises any of the anti-PMEL17 antibodies or immunoconjugates provided herein and at least one additional therapeutic agent, e.g., as described below.

Antibodies or immunoconjugates of the invention can be used either alone or in combination with other agents in a therapy. For instance, an antibody or immunoconjugate of the invention may be co-administered with at least one additional therapeutic agent.

In some embodiments, methods of treating cancer comprise administering an immunoconjugate described herein in combination with a second immunoconjugate comprising an antibody that binds an antigen selected from endothelin B receptor (ETBR), tyrosinase-related protein 1 (TYRP1), cytotoxic T lymphocyte antigen 4 (CTLA-4), and glycoprotein NMB (GPNMB). In some such embodiments, the cytotoxic agent of the second immunoconjugate is selected from MMAE, a calicheamicin, a nemorubicin derivative, and a pyrrolobenzodiazepine. The cytotoxic agent of the immunoconjugae described herein and the cytotoxic agent of the second immunoconjugate may be the same or different. In some embodiments, the cytotoxic agents are different. In some embodiments, each cytotoxic agent is selected from MMAE, a nemorubicin derivative, and a pyrrolobenzodiazepine.

In some embodiments, methods of treating cancer comprise administering an immunoconjugate described herein in combination with a second immunoconjugate comprising an antibody that binds ETBR. In some such embodiments, the cancer is a PMEL17-positive cancer and also an ETBR-positive cancer. Determination of whether a cancer is also ETBR-positive may be carried out by any method, including, but not limited to, the methods described herein for determining whether a cancer is PMEL17-positive, and methods described in U.S. Publication No. US 2011/0206702. In some embodiments, the antibody that binds ETBR is hu5E9.v1, which is described, e.g., in U.S. Publication No. US 2011/0206702. In some embodiments, the antibody that binds ETBR comprises an HVR H1 comprising a sequence of SEQ ID NO: 33, an HVR H2 comprising a sequence of SEQ ID NO: 34, an HVR H3 comprising a sequence of SEQ ID NO: 35, an HVR L1 comprising a sequence of SEQ ID NO: 36, an HVR L2 comprising a sequence of SEQ ID NO: 37, and an HVR L3 comprising a sequence of SEQ ID NO: 38. In some embodiments, the antibody that binds ETBR comprises a heavy chain variable region that comprises the sequence of SEQ ID NO: 40 and a light chain variable region that comprises the sequence of SEQ ID NO: 39.

In some embodiments, methods of treating cancer comprise administering an anti-ETBR-MC-val-cit-PAB-MMAE immunoconjugate, such as hu5E9.v1-MC-val-cit-PAB-MMAE (see, e.g., U.S. Publication No. US 2011/0206702), in combination with an immunoconjugate comprising an anti-PMEL17 antibody, such as those described herein. The immunoconjugate comprising an anti-PMEL17 antibody may comprise the same or different cytotoxic agent as the immunoconjugate comprising an anti-ETBR antibody. In some embodiments, the immunoconjugate comprising an anti-PMEL17 antibody comprises a different cytotoxic agent, such as a nemorubicin derivative or a pyrrolobenzodiazepine, e.g., when the anti-ETBR immunoconjugate comprises MMAE.

Administration "in combination" encompasses combined administration (where two or more therapeutic agents are included in the same or separate formulations), and separate administration, in which case, administration of the antibody or immunoconjugate of the invention can occur prior to, simultaneously, and/or following, administration of the additional therapeutic agent (such as the anti-ETBR immunoconjugate) and/or adjuvant. In some embodiments, administration of the anti-PMEL17 immunoconjugate and administration of an anti-ETBR immunoconjugate occur within about one month, or within about one, two, or three weeks, or within about one, two, three, four, five, or six days of one another. Antibodies or immunoconjugates of the invention can also be used in combination with radiation therapy.

An antibody or immunoconjugate of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various timepoints, bolus administration, and pulse infusion are contemplated herein.

Antibodies or immunoconjugates of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody or immunoconjugate need not be, but is optionally formulated with one or more agents currently used to prevent or treat the disorder in question. The effective amount of such other agents depends on the amount of antibody or immunoconjugate present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody or immunoconjugate of the invention (when used alone or in combination with one or more other additional therapeutic agents) will depend on the type of disease to be treated, the type of antibody or immunoconjugate, the severity and course of the disease, whether the antibody or immunoconjugate is administered for preventive or therapeutic purposes, previous therapy, the patient's clinical history and response to the antibody or immunoconjugate, and the discretion of the attending physician. The antibody or immunoconjugate is suitably administered to the patient at one time or over a series of treatments. Depending on the type and severity of the disease, about 1 µg/kg to 15 mg/kg (e.g. 0.1 mg/kg-10 mg/kg) of antibody or immunoconjugate can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody or immunoconjugate would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using both an immunoconjugate of the invention and an anti-PMEL17 antibody.

H. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the disorder and may have a sterile access port (for example the container may be an intravenous solution bag or a vial having a stopper pierceable by a hypodermic injection needle). At least one active agent in the composition is an antibody or immunoconjugate of the invention. The label or package insert indicates that the composition is used for treating the condition of choice. Moreover, the article of manufacture may comprise (a) a first container with a composition contained therein, wherein the composition comprises an antibody or immunoconjugate of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution or dextrose solution. It may further include other materials desirable from a commercial and user standpoint, including other buffers, diluents, filters, needles, and syringes.

I. Deposit of Biological Material

The following biological material has been deposited with the American Type Culture Collection, 10801 University Boulevard, Manassas, Va. 20110-2209, USA (ATCC):

| Hybridoma Designation | ATCC No. | Deposit Date |
|---|---|---|
| 7509(31D1.6.7) | PTA-12862 | Apr. 24, 2012 |

The above-referenced deposited hybridoma produces the 31D1 antibody referred to herein.

This deposit was made under the provisions of the Budapest Treaty on the International Recognition of the Deposit of Microorganisms for the Purpose of Patent Procedure and the Regulations thereunder (Budapest Treaty). This assures the maintenance of a viable culture of the deposit for 30 years from the date of deposit and for at least five (5) years after the most recent request for furnishing of a sample of the deposit. The deposit will be made available by the ATCC under the terms of the Budapest Treaty, and subject to an agreement between Genentech, Inc., and the ATCC, which assures that all restrictions imposed by the depositor on the availability to the public of the deposited material will be irrevocably removed upon the granting of the pertinent U.S. patent, assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. §122 and the Commissioner's rules pursuant thereto (including 37 C.F.R. §1.14 with particular reference to 886 OG 638).

III. Examples

The following are examples of methods and compositions of the invention. It is understood that various other embodiments may be practiced, given the general description provided above.

A. Human PMEL17 Gene Expression

For the analysis of PMEL17 mRNA expression in multiple human tumor and normal biopsy samples was analyzed using Affymetrix data obtained from Gene Logic, Inc. (Gaithersburg, Md.). The analysis shown is for probe set ID 209848_s_at, performed using the HGU133 Plus v2 GeneChip on 3879 normal human tissue samples, 1605 human cancer tissue samples (1291 primary and 314 metastatic), and 3872 human non-cancer disease tissue samples. Microarray data were normalized using the Affymetrix MAS (Microarray Analysis Suite) version 5.0 software, with sample expression values scaled to a trimmed mean of 500. Analysis of cultured cell lines was performed in similar fashion.

Figure 1B:
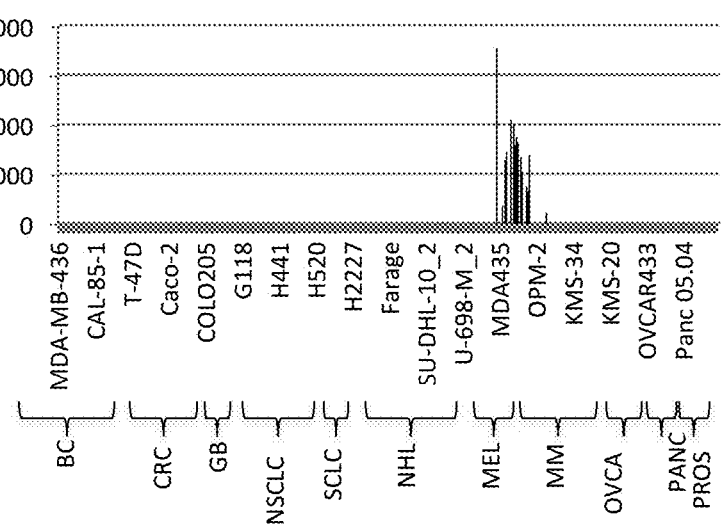

The results are shown in FIGS. 1A and B. The scale on the y-axis indicates gene expression levels based on hybridization signal intensity. In FIG. 1A, dots appear both above and below the line extending from the name of each listed tissue. The dots appearing above the line represent gene expression in normal tissue, and the dots appearing below the line represent gene expression in tumor and diseased tissue. As shown in FIG. 1A, high-level expression of PMEL17 mRNA was largely restricted to neoplasms derived from skin, and all of these were classified as melanoma. A small number of benign kidney tumors that were also positive were classified as epitheloid angiomyolipomas, and a handful of positive lymphomas were identified as cutaneous T-cell lymphomas. FIG. 1B shows that PMEL17 is overexpressed in many melanoma cell lines, whereas there was little or no expression in cell lines derived from other human cancers. BC, breast cancer; CRC, colorectal cancer; GB, glioblastoma; NSCLC, non-small cell lung cancer; SC, small cell lung cancer; NHL, Non-Hodgkin's lymphoma; MEL, melanoma; MM, multiple myeloma; OVCA, ovarian cancer; PANC, pancreatic cancer; PROS, prostate cancer. Only 5% of the 487 different cell lines analyzed are identified on the figure.

B. Mouse Monoclonal Antibody Generation

Monoclonal antibodies against human PMEL17 were generated using the following procedures. Two separate groups of Balb/C mice (Charles River Laboratories, Hollister, Calif.) were hyperimmunized with either purified human PMEL17 ECD (amino acids 25 to 591 with a C-terminal Fc expressed in CHO cells) in Ribi adjuvant (Group 1) or with plasmid DNA encoding full length PMEL17 (Group 2) via hydrodynamic tail vein (HTV) injection using a modified version of a previously described protocol (see, e.g., Herweijer, H., and Wolff, J. A. (2003) *Gene Ther* 10(6), 453-458; Liu, F., Song, Y., and Liu, D. (1999) *Gene Ther* 6(7), 1258-1266; and Zhang, et al. (1999) *Hum Gene Ther* 10(10), 1735-1737). Following a final boost with protein (Group 1) or PC3 cells over-expressing PMEL17 (Group 2) 3 days prior to fusion, B cells from mice demonstrating strong specific binding to PC3 cells by FACS from both groups were electro-fused (BTX ECM 2001, *Harvard Apparatus*) at a 1:1 ratio with X63-Ag8.653 mouse myeloma cells (American Type Culture Collection, Rockwille, Md.), plated at 100,000 cells/well in culture media containing 1× azaserine and hypoxanthine (HA, Sigma-Aldrich, St. Louis, Mo.) and incubated at 37° C., 7% CO2.

After 10-14 days, the supernatants were harvested and screened by ELISA and FACS. For FACS analysis, melanoma cell lines SK-MEL-23 (provided by Paul Robbins, Center for Cancer Research, Tumor Immunology Section), 1300mel (provided by Paul Robbins, Center for Cancer Research, Tumor Immunology Section), SKMEL5 (ATCC HTB-70), and UACC257 (National Cancer Institute), normal melanocytes (Invitrogen, Carlsbad, Calif.), and the prostate cancer cell line PC3 stably expressing human PMEL17 were contacted with antibody. One antibody from the PMEL17-immunized mice, designated 17A9, reacted strongly by fluorescent activated cell sorting (FACS) with live melanoma cells, normal human melanocytes and a PC3 cell line stably expressing PMEL17 cDNA, but not the parental PC3 cell line. Another antibody, 77E6, obtained from the DNA-immunized mice, was also positive by FACS, although 77E6 reacted with live cell lines expressing PMEL17 somewhat inconsistently and more weakly than 17A9.

Positive clones demonstrating strong PMEL17 specific binding by FACS were then expanded and subcloned by limiting dilution. Following two rounds of subcloning and screening, the final clones were cultured in bioreactors (Integra Biosciences, Chur, Switzerland) and supernatants purified by Protein A affinity chromatography as described previously (Hongo, et al. (2000) *Hybridoma* 19(4), 303-315). Three antibody clones, 8G3, 15F2, 17A9, and 31D1 from the PMEL17 ECD-immunized mice, and one antibody clone, 77E6, from the DNA-immunized mice, were selected for further analysis.

C. Mouse Monoclonal Antibody Cloning

Total RNA was extracted from hybridoma cells producing murine 8G3, 15F2, and 17A9 using standard methods. The variable light (VL) and variable heavy (VH) domains were amplified using RT-PCR with degenerate primers to the heavy and light chains. The forward primers were specific for the N-terminal amino acid sequence of the VL and VH regions. Respectively, the LC and HC reverse primers were designed to anneal to a region in the constant light (CL) and constant heavy domain 1 (CH$_1$), which are highly conserved across species. The polynucleotide sequence of the inserts was determined using routine sequencing methods. The 17A9 VH and VL amino acid sequences are shown in SEQ ID NOs: 50 and 2, respectively. The heavy chain hypervariable regions (HVRs) H1, H2, and H3 are shown in SEQ ID NOs: 3, 4, and 5, respectively. The light chain hypervariable regions (HVRs) L1, L2, and L3 are shown in SEQ ID NOs: 6, 7, and 8, respectively. The 8G3 VH and VL amino acid sequences are shown in SEQ ID NOs: 49 and 10, respectively. The heavy chain hypervariable regions (HVRs) H1, H2, and H3 are shown in SEQ ID NOs: 13, 14, and 15, respectively. The light chain hypervariable regions (HVRs) L1, L2, and L3 are shown in SEQ ID NOs: 16, 7, and 8, respectively. The 15F2 VH and VL amino acid sequences are shown in SEQ ID NOs: 51 and 12, respectively. The heavy chain hypervariable regions (HVRs) H1, H2, and H3 are shown in SEQ ID NOs: 20, 21, and 22, respectively. The light chain hypervariable regions (HVRs) L1, L2, and L3 are shown in SEQ ID NOs: 23, 24, and 25, respectively.

Figure 2A:
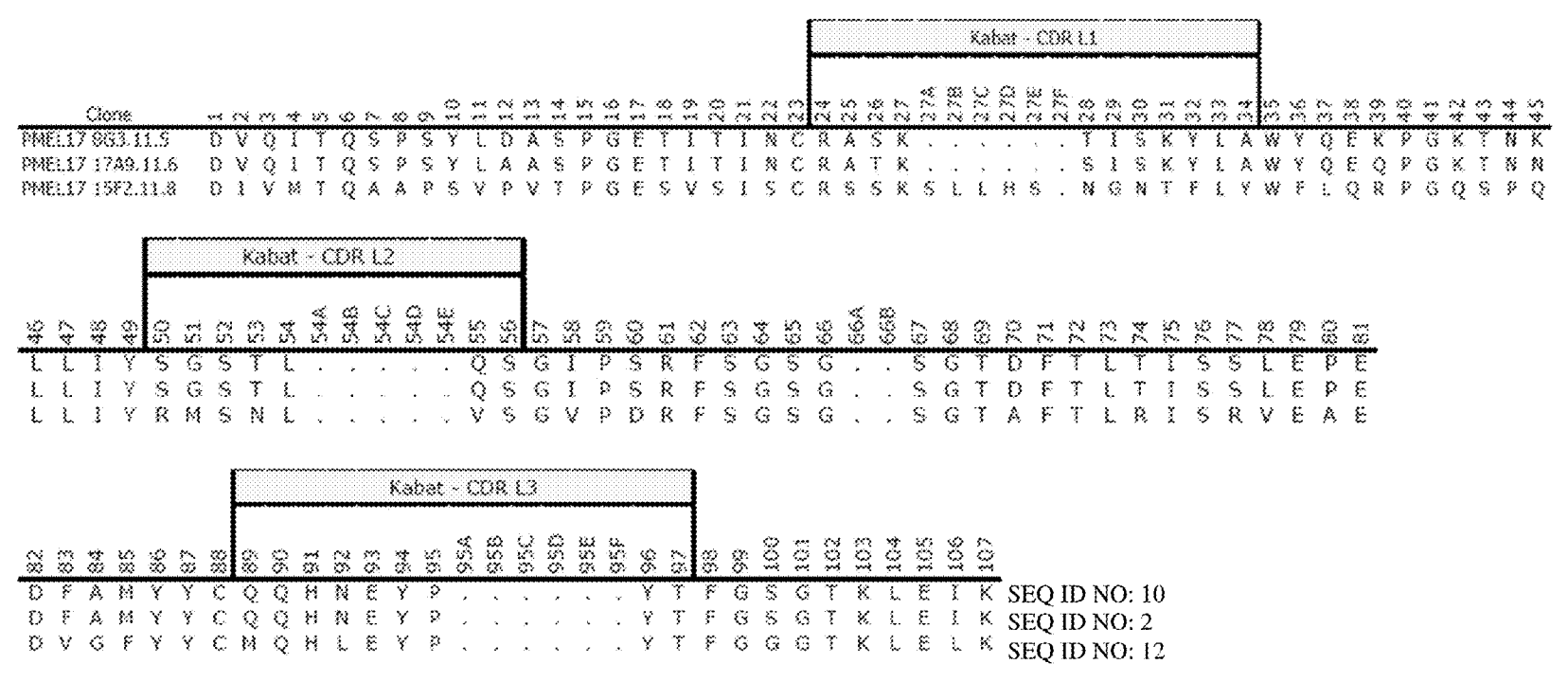
Figure 2B:
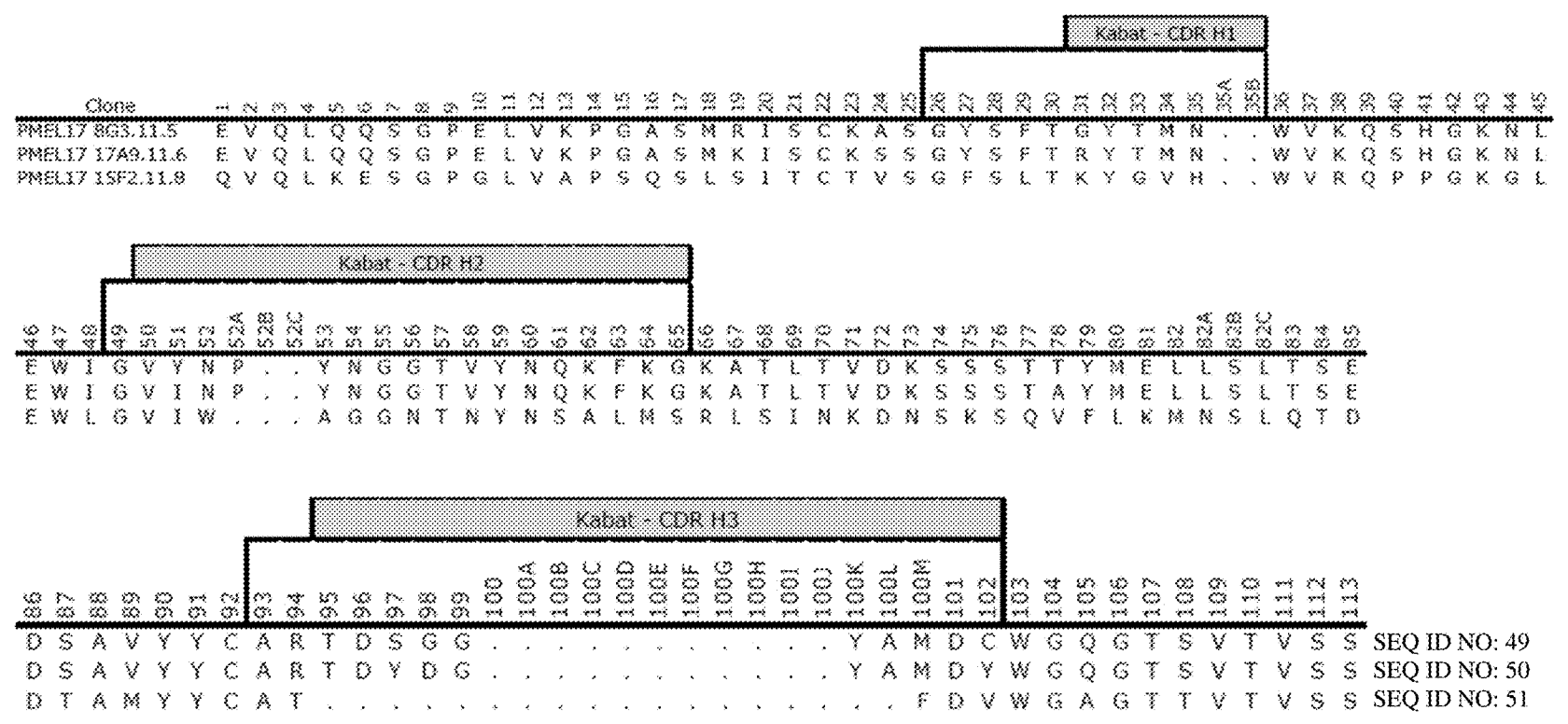

An alignment of the light chain and heavy chain variable regions of antibodies 8G3, 17A9, and 15F2 are shown in FIGS. 2A and 2B, respectively.

D. Monoclonal Antibody Epitope Mapping

All the constructs for epitope mapping were made by PCR amplification of each fragment and subcloning into either pRKtkneo vector with an N-terminal gD tag, or pRKtkneo vector with an N-terminal gD tag and a C-terminal GPI anchor. Transfections were performed using FuGene 6 (Roche *Applied Science*), and empty vector was used as control. Full-length human PMEL17 was subcloned into pRKtkneo vector with an N-terminal gD tag.

A signal sequence and a gD epitope tag were fused to the N-terminal sequence of a series of deletion mutants, which were then expressed in mammalian cells and the lysates analyzed by immuoblotting for reactivity with 17A9 or 77E6. The N-terminal deletions tested included Δ100, Δ255, Δ292, Δ315, Δ444, Δ515, and Δ567.

In addition, C-terminal deletions with an N-terminal gD tag and a C-terminal GPI anchor were transiently transfected into 293 cells and analyzed for antibody binding by FACS. The C-terminal deletions tested included PMEL17$_{25\text{-}125}$, PMEL17$_{25\text{-}105}$, PMEL17$_{25\text{-}85}$, PMEL17$_{25\text{-}65}$, and PMEL17$_{25\text{-}45}$. Finally, a PMEL17 fragment comprising the region from amino acid 515 through the transmembrane domain, but lacking the cytoplasmic region ("Δ515-C") and a PMEL17 fragment comprising just the cytoplasmic domain with an N-terminal gD tag and a C-terminal GPI anchor were analyzed by by immuoblotting for reactivity with 77E6.

The results of that experiment are shown in FIG. 3. FIG. 3A shows a diagram of the N-terminal PMEL17 deletion mutants, and immunoblots showing reactivity with an anti-gD antibody and 77E6. 77E6 reacted with all of the N-terminal deletions tested. FIG. 3B shows a diagram of the Δ515-C fragment and the cytoplasmid domain fragment, and immunoblots showing reactivity with an anti-gD antibody and 77E6. 77E6 bound to all deletion mutants that contained the cytoplasmic domain, but not to the Δ515-C mutant, which lacks the cytoplasmic domain. These results confirm that 77E6 binds to an epitope within the cytoplasmic domain of PMEL17.

FIG. 3C shows immunoblots showing reactivity with an anti-gD antibody and 17A6. 17A6 bound only to full-length PMEL17 and not to the 4225 or 4100 mutants. FIG. 3D shows a diagram of the C-terminal PMEL17 deletion mutants, and FACS analysis of anti-gD, 17A9, and 31D1 antibody binding to those mutants. 17A9 bound only to PMEL17$_{25\text{-}125}$, and not to any of the other mutants, including PMEL17$_{25\text{-}105}$, suggesting that 17A9 binds to an epitope within the region of amino acids 105 to 125 of PMEL17. 31D1 bound to all of the fragments tested, including PMEL17$_{25\text{-}45}$, suggesting that 31D1 binds to an epitope within the region of amino acids 25 to 45 of PMEL17.

E. Subcellular Localization of PMEL17 Epitopes

PMEL17 is known to undergo rather complex processing during its routing to the melanosome, some of which involves proteolytic cleavages ultimately resulting in deposition of limited RPT domain-containing fragments into fibrillar structures within the mature organelle. This processing involves cleavage at Arg-469 by a proprotein convertase, resulting in an N-terminal Mα and a C-terminal Mβ fragment that remain tethered by a disulfide bond. The Mβ fragment is cleaved further by a metallproteinase at Gln-583 and by γ-secretase in the transmembrane region. Thus, regions of PMEL17 containing the cytoplasmic and N-terminal epitopes are dissociated during this processing.

Because PMEL17 undergoes this complex processing, the subcellular distribution of PMEL17 antibody epitopes in fixed permeabilized 928mel cells (provided by Paul Robbins, Center for Cancer Research, Tumor Immunology Section) cells was determined using 77E6 labeled with Cy3 Fluorophor and 14C10 labeled with Alexa 488. Antibody 14C10 binds to the same deletion fragments as 17A9. A large pool of PMEL17 containing both cytoplasmic (detected by 77E6) and N-terminal epitopes (detected by 14C10) was present in the perinuclear structure, likely the endoplasmic reticulum. However, in extending toward the cell periphery, a downward gradient of staining intensity by 77E6 is evident, followed by an upward gradient of 14C10 staining, which includes reactivity at the cell membrane. These results suggest that the cytoplasmic epitope recognized by 77E6 is removed during trafficking of PMEL17 to the plasma membrane whereas that the N-terminal epitope progresses to the cell surface.

Consistent with the release of cytoplasmic structure during secretory processing, PMEL17 recovered from conditioned media also failed to react with 77E6. When excised from non-reducing SDS-gels, this secreted PMEL17 generated peptide sequences derived from both Mα and Mα, but not from the cytoplasmic region, as determined by mass spectrometry. Upon reduction with 2-mercaptoethanol, the secreted PMEL17 exhibited enhanced mobility on SDS-gels and Mα, but not Mβ, sequences were generated from this excised band. These results suggest that the secreted PMEL17 contains Mα and Mβ regions tethered by a disulfide, but lacks cytoplasmic sequence.

The predominance of the N-terminal epitope at the cell surface relative to the cytoplasmic epitope is consistent with stronger FACS signals observed with 17A9 over 77E6. Nevertheless, it appears that some portion of the cytoplasmic region is present at the cell surface to account for the FACS signals observed with 77E6. To address this, live cells were reacted with the 77E6 and 17A9 antibodies that were directly labeled with Alexa Fluors 555 and 488, respectively. To demonstrate that the antibodies did not compete with each other for binding to live cells, 928mel cells were incubated with either of the labeled antibodies alone or both together and FACS analysis was performed, gated for the individual fluorophors. The binding of the individual antibodies was unaffected by the presence of the other antibody. Visualization of live-labeled cells revealed uniform cell surface staining with 17A9, consistent with ample N-terminal epitopes accessible at the plasma membrane. By contrast, 77E6 staining was more isolated and patchy and largely non-overlapping with 17A9 reactivity. Further, although 17A9 stained all cells uniformly and consistently, 77E6 staining was variable from cell to cell and the overall degree of staining varied across preparations. Subsequent experiments demonstrated that suspension of cells greatly enhanced the presence of 77E6 staining at the cell surface, suggesting that culture conditions may account for this variability. Overall, the uniform and intense reactivity of 17A9 on melanoma cells makes this antibody a good candidate for drug conjugation.

F. Species Cross-Reactivity

Antibody 17A9 was tested to determine if it cross-reacts with PMEL17 from species other than human. FIG. 9 shows an alignment between human (SEQ ID NO: 26), cynomolgus monkey (SEQ ID NO: 28), rat (SEQ ID NO: 29) and mouse (SEQ ID NO: 31) PMEL17. All of the sequences include the signal sequence except for the cynomolgus monkey PMEL17. Residues that are identical among all four species are indicated by asterisks (*). In the region where the rat sequence has a deletion, residues that are identical among the remaining three species are indicated by a plus (+). Binding to each species of PMEL17 was determined by FACS analysis using 293S cells stably transfected with an N-terminal gD tagged PMEL17 (human, cynomolgus monkey, rat, or mouse PMEL17); stained with 10 µg/ml 17A9 antibody; and detected with R-Phycoerythrin conjugated goat anti-mouse antibody. Untransfected 293 cells do not normally express PMEL17. 17A9 was found to bind to all four species of PMEL17 tested: human, cynomolgus monkey, rat, and mouse.

G. Internalization of Anti-PMEL17 Antibody

One desirable attribute of an ADC target is the ability to internalize the antibody into a degradative compartment in the cell. 1300mel melanoma cells were seeded in Lab-Tek II cell culture treated 4-well chamber slides (Nalge Nunc International), and incubated with PMEL17 mAb, in the presence of lysosomal protease inhibitors leupeptin and pepstatin A (Sigma-Aldrich) at 50 nM and 5 nM respectively, at 2 µg/ml for either 2 hours or 20 hours in a 37° C. incubator with 5% $CO_2$. Cells were then washed with PBS, and fixed in 4% Para formaldehyde (Polysciences, Inc.) for 5 min. at room temperature and permeabilized with 0.05% saponin (Sigma-Aldrich) in PBS with 0.5% BSA for 5 minutes at 37° C.; cells were then incubated for one hour with 2 µg/ml rabbit polyclonal anti-LAMP 1 (Sigma-Aldrich), an antibody to a lysosomal marker, followed by one hour incubation of Cy3 labeled anti-mouse IgG (Jackson Immuno Research Laboratories, Inc.) and Alexa-488 labeled anti-rabbit IgG (Invitrogen Life Technology). PMEL17 antibodies were also directly labeled with either Alexa Fluro 555 or Alexa Fluro 488 (Invitrogen Life Technology), and stained cells after they were fixed and permeablized as above. Leica SP5 confocal microscope (Leica Microsystems) was used for imaging.

Figure 4:
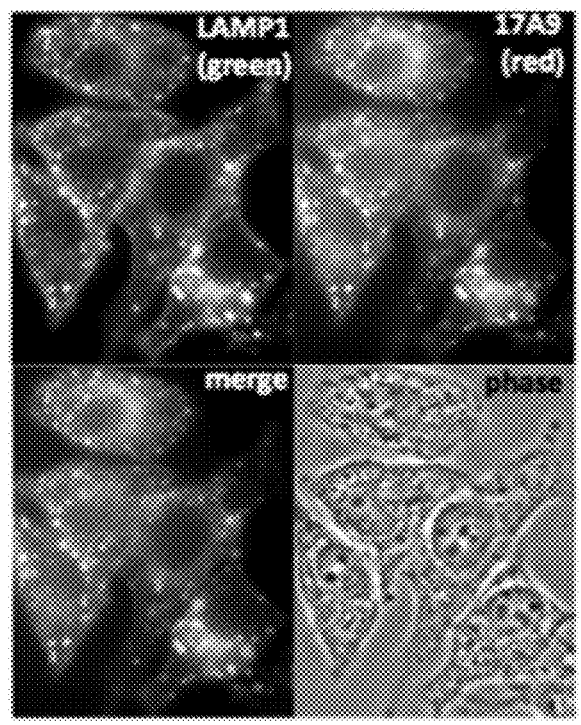
FIG. 4 shows internalization of 17A9 in melanoma cells, as described in Example G.

As shown in FIG. 4, considerable overlap of 17A9 and LAMP 1 staining was apparent within the cells. Rapid uptake of 17A9 into additional PMEL17+ melanoma cell lines, including 526mel, SK-MEL-5, and UACC257, was consistently observed. These results predict that a 17A9 ADC should effectively internalize, undergo degradation and release drug to kill melanoma cells.

H. Production of Anti-PMEL17 Antibody Drug Conjugates

For larger scale antibody production, antibodies were produced in CHO cells. Vectors coding for VL and VH were transfected into CHO cells and IgG was purified from cell culture media by protein A affinity chromatography.

Anti-PMEL17 antibody-drug conjugate (ADC) comprising a protease-cleavable val-cit linker and the drug MMAE was produced by conjugating 17A9 or ch17A9 (see, e.g., SEQ ID NOs: 47 and 48) to the drug-linker moiety MC-vc-PAB-MMAE, which is depicted herein. Anti-ETBR ADCs comprising a protease-cleavable val-cit linker and the drug MMAE were produced by conjugating ch5E9 (see, e.g., SEQ ID NOs: 43 and 44) or hu5E9.v1 (see, e.g., SEQ ID NOs: 45 and 46) to the drug-linker moiety MC-vc-PAB-MMAE. For convenience, the drug-linker moiety MC-vc-PAB-MMAE is sometimes referred to in these Examples and in the Figures as "vcMMAE" or "VCE."

Prior to conjugation, the antibody was partially reduced with TCEP using standard methods in accordance with the methodology described in WO 2004/010957 A2. The partially reduced antibody was conjugated to the drug-linker moiety using standard methods in accordance with the methodology described, e.g., in Doronina et al. (2003) *Nat. Biotechnol.* 21:778-784 and US 2005/0238649 A1. Briefly, the partially reduced antibody was combined with the drug-linker moiety to allow conjugation of the drug-linker moiety to reduced cysteine residues of the antibody. The conjugation reaction was quenched by adding excess N-acetylcysteine to react with any free linker-drug moiety, and the ADC was purified. The drug load (average number of drug moieties per antibody) for the ADC was determined to be 2.78. The structure of the ADCs comprising val-cit-MMAE linker-drug (also referred to as MC-val-cit-PAB-MMAE) is shown in FIG. 15A.

Anti-PMEL17 antibody-drug conjugate (ADC) comprising a protease-cleavable val-cit linker and the drug PNU-159682 was produced by conjugating ch17A9 to the drug-linker moiety MC-vc-PAB-PNU-159682, substantially as described above. Anti-ETBR ADC comprising a protease-cleavable val-cit linker and the drug PNU-159682 was produced by conjugating ch5E9 to the drug-linker moiety MC-vc-PAB-PNU-159682, substantially as described above. The structure of the ADCs comprising MC-val-cit-PAB-PNU-159682 is shown in FIG. 15C.

Anti-PMEL17 antibody-drug conjugate (ADC) comprising an acid-labile acetal linker and the drug PNU-159682 was produced by conjugating ch17A9 to the drug-linker moiety MC-acetal-PNU-159682, substantially as described above. Anti-ETBR ADC comprising an acid-labile acetal linker and the drug PNU-159682 was produced by conjugating ch5E9 to the drug-linker moiety MC-acetal-PNU-159682, substantially as described above. The structure of the ADCs comprising MC-acetal-PNU-159682 is shown in FIG. 15B.

Anti-PMEL17 antibody-drug conjugate (ADC) comprising non-cleavable linker and the drug PNU-159682 was produced by conjugating ch17A9 to the drug-linker moiety MC-PNU-159682, substantially as described above. Anti-ETBR ADC comprising non-cleavable linker and the drug PNU-159682 was produced by conjugating ch5E9 to the drug-linker moiety MC-PNU-159682, substantially as described above. The structure of the ADCs comprising PNU-159682 is shown in FIG. 15E.

Antibody drug conjugates (ADCs) comprising a protease-cleavable val-cit linker and a PBD dimer drug are produced by conjugating an antibody to the drug-linker moiety MCval-cit-PAB-PBD, substantially as described above. The structure of an antibody-MC-val-cit-PAB-PBD is shown in FIG. 15D.

I. Inhibition of In Vitro Cell Proliferation by an Anti-PMEL17 Antibody Drug Conjugate Proliferation in the presence of 17A9 ADC was assessed using PMEL17+ melanoma cells and PC3 cells stably expressing PMEL17 plated at 2,000 per well in 50 μL of normal growth medium in 96-well clear-bottom plates (PerkinElmer). Twenty-four hours later, an additional 50 μL of culture medium with serial dilutions of 17A9 ADC were added to triplicate wells. Three or five days later, cell numbers were determined using CellTiter-GloII (Promega Corp.) and with an EnVision 2101 Mutilabel Reader (PerkinElmer).

Figure 5:
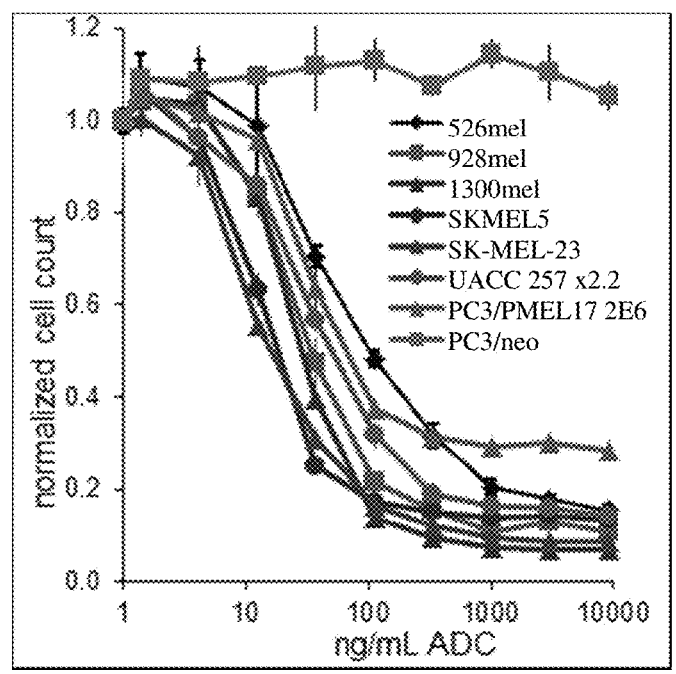
FIG. 5 shows killing of various PMEL17+ melanoma cell lines by increasing concentrations of 17A9 ADC, as described in Example I.

As shown in FIG. 5, titration of a panel of PMEL17+ melanoma cells with the 17A9 ADC resulted in effective cell killing with IC50's ranging from 10 to 100 ng/ml of ADC. The prostate cancer cell line, PC3, stably expressing PMEL17 was effectively killed, but no killing of the vector control PC3 parental cell line was noted out to 10 μg/ml of ADC.

While not intending to be bound by any particular theory, the variation in ADC IC50 values for the melanoma cell lines could reflect the variation in the levels of PMEL17 accessible to the ADC, although additional factors likely contribute. For example, the 1300mel cell line expresses significantly more cell surface PMEL17 than the SK-MEL-5 cell line, yet the ADC IC50 is slightly higher for 1300mel. In addition, variation in response of the cell lines to the released MMAE drug product could be another contributing factor. The IC50 values for free MMAE across eight melanoma cell lines ranged from approximately 0.1 to 0.5 nM. While there was not a strict correlation between the response to free drug and 17A9 ADC, a several-fold difference in free drug sensitivity could, in some instances, account for variation in sensitivity to ADC. Indeed, the SK-MEL-5 was more sensitive to free MMAE than 1300mel, which may compensate for having lower levels of cell surface PMEL17 than 1300mel. Other factors, including the relative rate of antibody internalization might also affect the response to the ADC. Accordingly, the ability of four different melanoma cell lines to accumulate and internalize antibody over time was compared. As expected, cells with higher levels of cell surface PMEL17 accumulated more antibody, but the percentage of that amount internalized appeared comparable, indicating little difference in the relative efficiency of uptake.

J. Toxicity of Anti-PMEL17 ADC in Normal Melanocytes

To assess the potential liability of targeting PMEL17 on normal melanocytes, the level of expression of this target in normal human skin was evaluated by immunohistochemistry Immunohistochemistry (IHC) was performed on 4 μm thick formalin-fixed paraffin embedded tissue sections mounted on glass slides. All IHC steps were carried out on the Ventana Discovery XT (Ventana Medical Systems; Tucson, Ariz.) autostainer. Pretreatment was done with Cell Conditioner 1, standard time. Primary antibody, PMEL17 clone 31D1 was used at a concentration of 10 μg/ml and was incubated on slides for 1 hour at 37° C. Ventana Mouse OmniMap (Ventana Medical Systems; AZ) was used as the detection system. Ventana DAB and Hematoxylin II were used for chromogenic detection and counterstain.

Figure 6A:
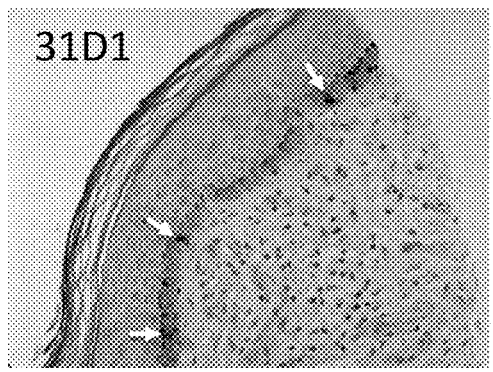
FIGS. 6A to 6C show (A) distribution of 31D1 staining in normal skin, (B) 17A9 staining of normal melanocytes and melanoma cell line SK-MEL-5 by FACS, and (C) the IC50 of 17A9 on normal melanocytes is nearly 100-fold higher than the IC50 of 17A9 on melanoma cell lines, as described in Example J.

The results of that experiment are shown in FIG. 6A. Staining with PMEL17 antibody 31D1 revealed intermittent reactivity along the basal layer of the dermis, consistent with the distribution of melanocytes in skin.

Figure 6B:
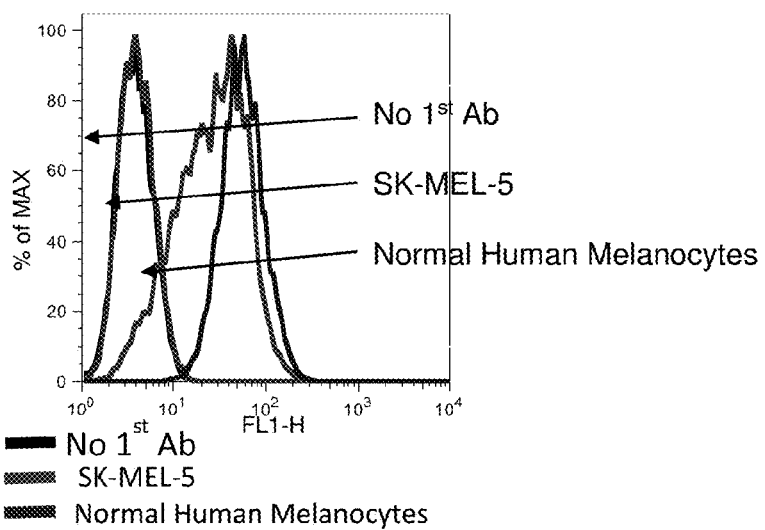

Normal human melanocytes and SK-MEL-5 melanoma cells were reacted with chimeric 17A9, or no primary antibody, followed by Alexa 488-labeled anti-human IgG and analyzed by flow cytometry. As shown in FIG. 6B, cultured normal human melanocytes were also FACS+ with antibody 17A9 and the intensity was comparable to that observed with melanoma cell line SK-MEL-5.

Figure 6C:
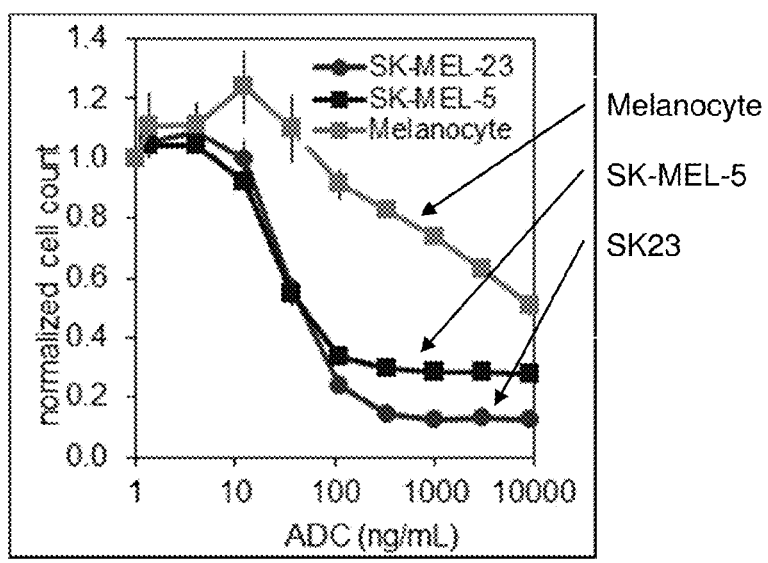

Finally, SK-MEL-5 and SK-MEL-23 melanoma cells, or normal human melanocytes, were incubated with serial dilutions of the 17A9 ADC and five days later cell numbers were determined using CellTiter-GloII. As shown in FIG. 6C, titration of the normal melanocytes with the 17A9 ADC resulted in cell killing with an IC50 nearly 100-fold higher than that observed with melanoma cell lines. These results are consistent with the mechanism of action of the antimitotic drug MMAE and the reduced proliferative capacity of normal melanocytes relative to melanoma cells.

K. Expression of PMEL17 on Human Melanoma Tissue Specimens

Figure 7A:
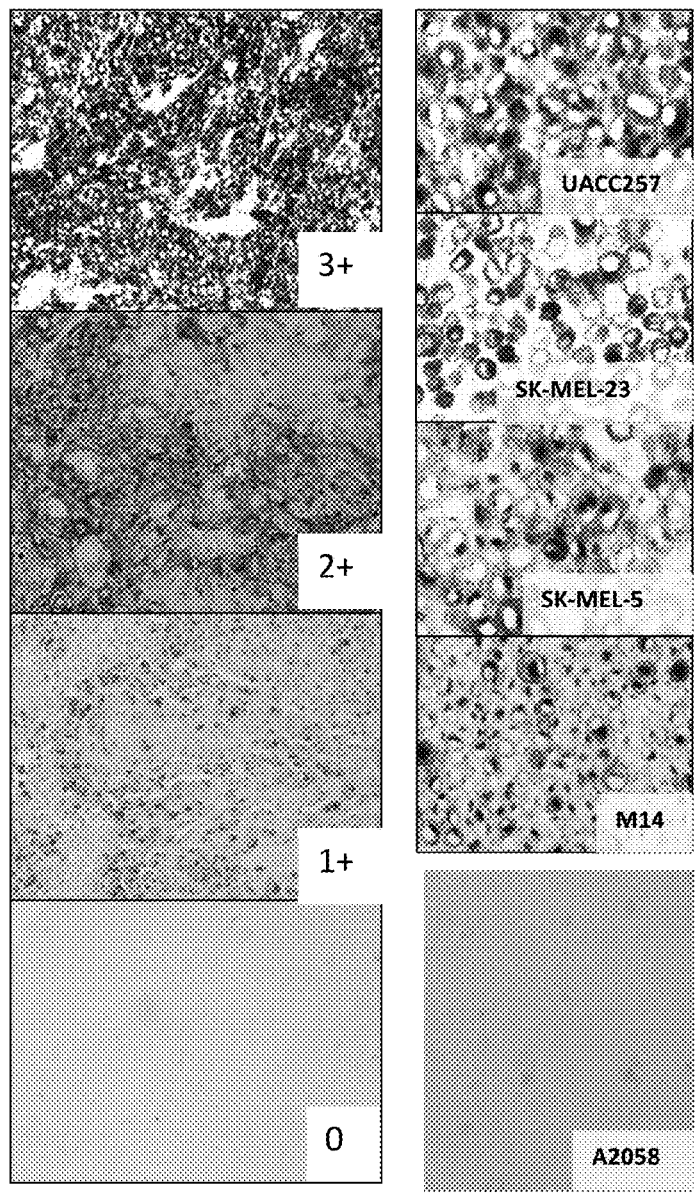

The expression of PMEL17 was evaluated across a panel of human melanoma tissue specimines by immunohistochemistry substantially as described above, using both 17A9 and 31D1. Staining was scored on an arbitrary scale ranging from zero, for absent, to 3+ for most intense:

0 (negative): very weak or no staining in >90% of melanoma cells
1+(mild): predominant staining pattern is weak
2+(moderate): predominant staining pattern is moderately strong in the majority (>50%) of melanoma cells
3+(strong): predominant staining pattern is strong in the majority (>50%) of melanoma cells Exemplary staining for each of the levels of the scale is shown in FIG. 7A, left panels.

Fifty-eight specimens were obtained from 30 primary and 28 metastatic melanomas. As shown in the table at FIG. 7B, the full spectrum of staining was observed across the 58 human melanoma specimens with the majority scoring positive with either antibody. 83% (48/58) of the human melanoma specimens were PMEL17+ when detected with 31D1, and 64% (37/58) were PMEL17+ when detected with 17A9. Relative to 17A9, the staining with 31D1 was more highly skewed toward the upper end of the scale. Fixed paraffin-embedded pellets of melanoma cell lines were also sectioned and stained them alongside the tissue specimens to gauge their staining intensity relative to actual melanoma. See FIG. 7A, right panels.

L. Efficacy of Anti-PMEL17 Antibody Drug Conjugates in SK-MEL-23 Melanoma Cell Line Xenograft All studies were conducted in accordance with the Guide for the Care and Use of Laboratory Animals (Ref-Institute of Laboratory Animal Resources, "Guide for the Care and Use of Laboratory Animals", (NIH Publication #85-23). Washington (DC): National Academy Press; 1996.

The efficacy of the anti-PMEL17 ADCs was investigated using an SK-MEL-23 melanoma cell line xenograft model. Female CRL Nu/Nu mice from Charles River Laboratories were inoculated subcutaneously in the dorsal right flank with five million SK-MEL-23 cells in HBSS with Matrigel. SK-MEL-23 cells exhibit a staining intensity of 2+ to 3+. When tumor volumes reached ~200 mm$^3$ (day 0), animals were randomized into groups of 10 each and administered a single IV injection of 2 or 6 mg/kg 17A9 ADC. MMAE conjugated to anti-GP120 antibody was used as a control. Tumor volumes were measured twice per week until study end. Tumor volumes were determined using digital calipers (Fred V. Fowler Company, Inc.) using the formula (L×w× W)/2. Tumor growth inhibition (% TGI) was calculated as the percentage of the area under the fitted curve (AUC) for the respective dose group per day in relation to the vehicle, such that % TGI=100×[1−(AUC$_{treatment/day}$)/(AUC$_{vehicle/day}$)]. Curve fitting was applied to Log$_2$ transformed individual tumor volume data using a linear mixed-effects model using the R package nlme, version 3.1-96 in R v2.10.1.

Figure 8:
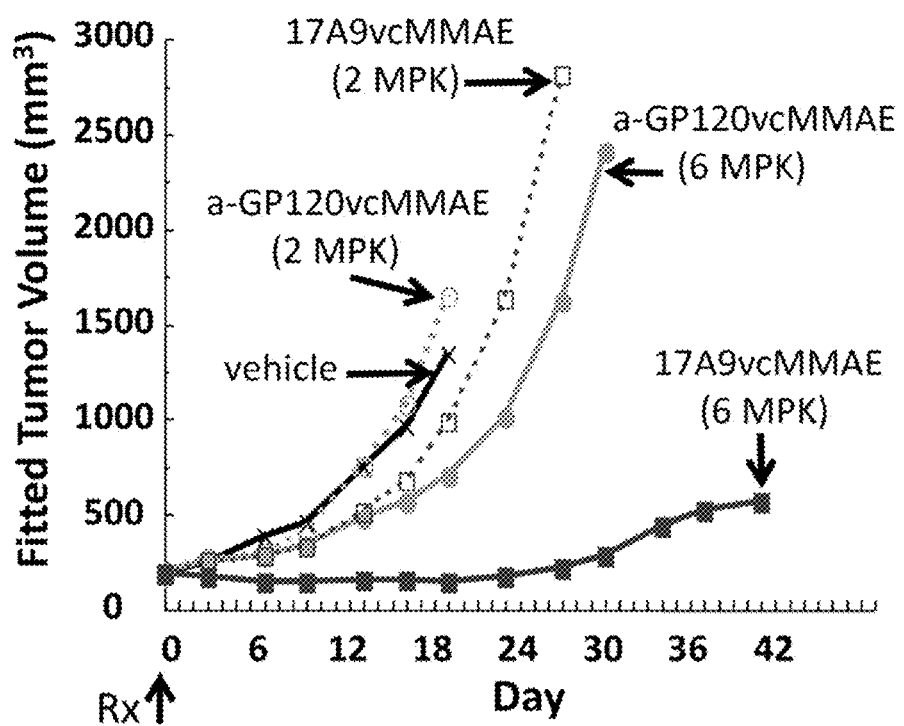
FIG. 8 shows efficacy of 17A9 ADC in an SK-MEL-23 cell line xenograft, as described in Example L.

As shown in FIG. 8, the 6 mg/kg dose of 17A9 ADC was found to retard tumor growth for several weeks, while neither dose of the control ADC had an appreciable effect on tumor growth. These results demonstrate robust and specific efficacy with an ADC targeting PMEL17 on a human melanoma tumor xenograft.

M. Efficacy of Anti-PMEL17 Antibody Drug Conjugates in UACC-257X2.2 Melanoma Cells Resistant to Anti-ETBR-Vc-MMAE To determine the efficacy of an anti-PMEL17 ADC in melanoma that had developed resistance to another therapeutic, UACC-257X2.2 melanoma cells that are resistant to an anti-endothelin B receptor (ETBR) immunoconjugate comprising a val-cit linker and MMAE drug (anti-ETBR-vc-MMAE, also referred to as anti-EDNRB-vc-MMAE, anti-ETBR-MC-val-cit-PAB-MMAE, etc.; see, e.g., U.S. Publication No. US 2011/0206702) were developed in vivo and in vitro.

For resistance developed in vivo, NCr nude mice (Taconic, Hudson, N.Y.) were inoculated subcutaneously in the dorsal right flank with 5 million UACC-257X2.2 cells in HBSS with Matrigel. UACC-257X2.2 cells are derived from UACC-257 cells (National Cancer Institute) and optimized for growth in vivo as follows. UACC-257 cells were injected subcutaneously in the right flank of female NCr nude mice to induce tumor growth. One tumor was harvested and grown in vitro (referred to as UACC-257X1.2 cell line). The UACC-257X1.2 line was injected again subcutaneously in the right flank of female NCr nude mice to improve the growth of the cell line in vivo. A tumor from the second injection round was collected and again adapted for in vitro growth to generate UACC-257X2.2. The UACC-257X2.2 cell line and tumors derived from this line express ETBR at levels comparable to the parental cell line UACC-257.

Ten mice inoculated with UACC-257X2.2 cells were dosed with 3 mg/kg hu5E9.v1-MC-vc-PAB-MMAE intravenously on day 0 (the heavy chain and light chain sequences for hu5E9.v1 are shown in SEQ ID NOs: 46 and 45, respectively). To determine when the mice would be dosed again, and at what doses, the following was taken into consideration: whether or not tumors re-grew after the initial treatment (i.e., tumors that grew back to initial tumor volume size at day 0), and the rate of re-growth. Frequency of doses administered varied over time but did not exceed 2 doses/week. Intravenous doses did not exceed 300 μL. The range of doses administered were 3 mg/kg, 6 mg/kg, 8 mg/kg, and 10 mg/kg. Dosing was discontinued once a tumor no longer responded (i.e., it showed resistance to) a series of increasing doses.

Figure 10A:
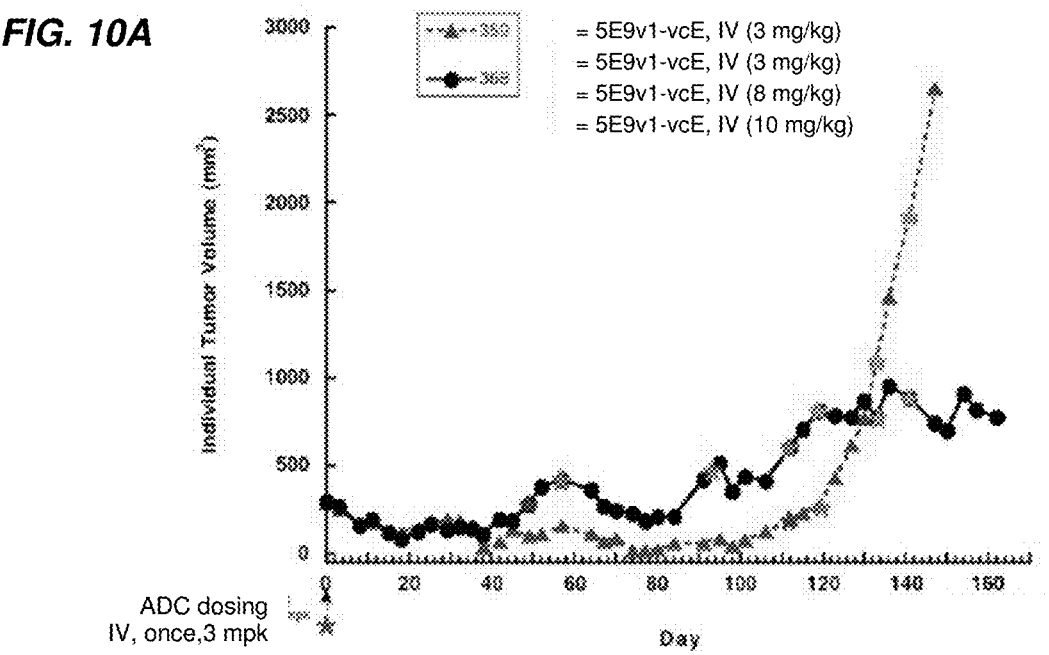
FIGS. 10A and 10B show (A) tumor volume over time in mice inoculated with UACC-257X2.2 melanoma cells and administered varying doses of anti-ETBR-vc-MMAE ("5E9v1-vcE"), and (B) parental and resistant UACC-257X2.2 cells grown in vitro in the presence of increasing concentrations of anti-ETBR-vc-MMAE ADC, as described in Example M.

As shown in FIG. 10A, the UACC-257X2.2 tumor #359 developed resistance to anti-ETBR-vc-MMAE after about 120 days, whereas tumor #368 developed resistance more slowly. Tumor #359 was harvested and the cells were dissociated for growth in vitro (referred to herein as in vivo-derived resistant UACC-257X2.2 cells).

Figure 10B:
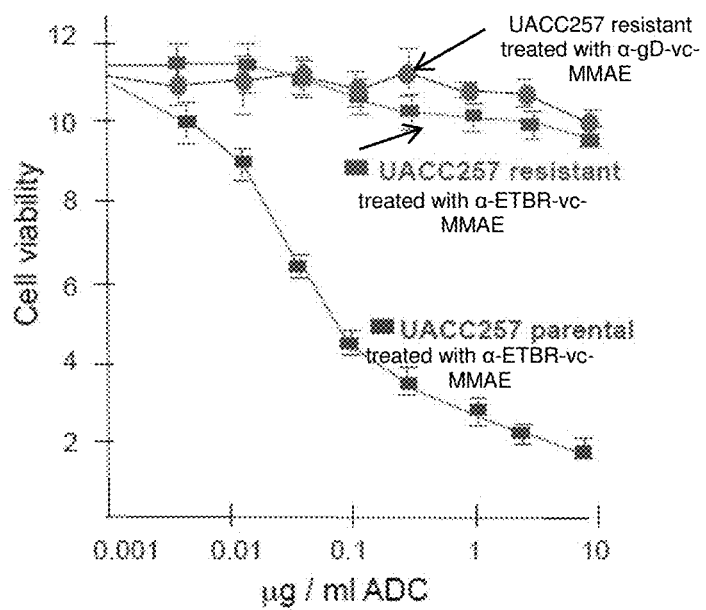

For resistance developed in vitro, UACC-257X2.2 cells were adapted to increasing concentrations of anti-ETBR-vc-MMAE in culture dishes over the course of two months. FIG. 10B shows the resistant UACC-257X2.2 cell line derived in vitro (referred to herein as in vitro-derived resistant UACC-257X2.2 cells), which was relatively unaffected by concentrations of anti-ETBR-vc-MMAE up to at least 10 μg/ml. FIG. 10B also shows the in vitro-derived resistant UACC-257X2.2 cells incubated with a control ADC, α-gD-vc-MMAE, and the parental UACC-257X2.2 cells incubated with α-ETBR-vc-MMAE.

Figure 11A:
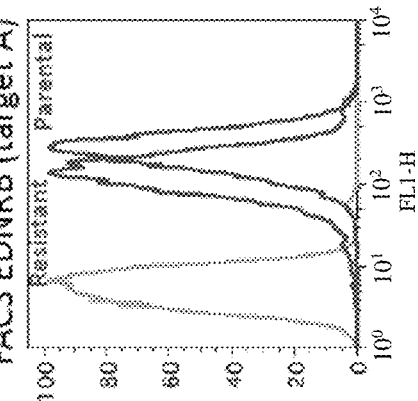
FIGS. 11A to 11D show expression of ETBR (A and B; also referred to as "EDNRB") and PMEL17 (C and D) in parental and resistant UACC-257X2.2 cells derived in vivo (A and C) and in vitro (B and D), as described in Example M.
Figure 11B:
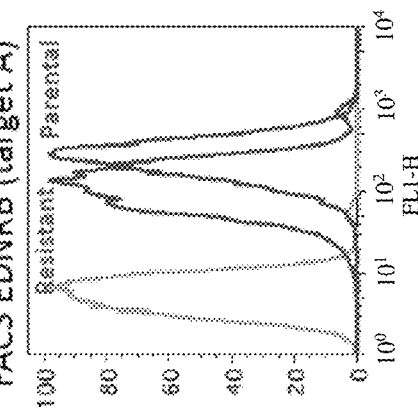
Figure 11C:
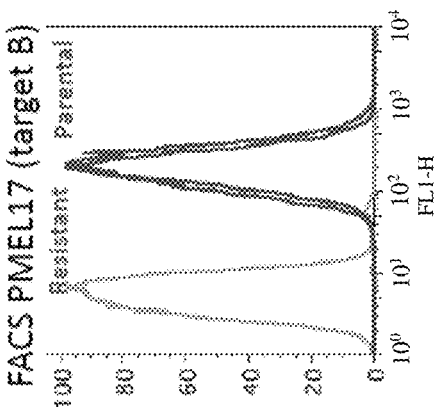
Figure 11D:
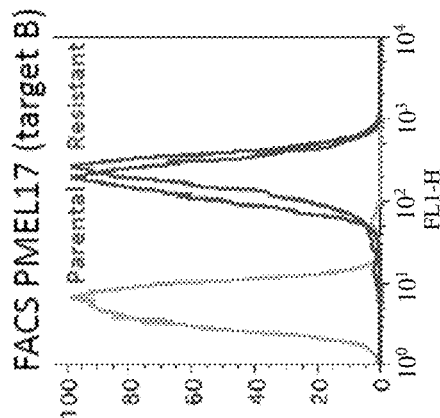

Expression of ETBR and PMEL17 on the surface of the in vivo- and in vitro-derived resistant UACC-257X2.2 cells and the parental UACC-257X2.2 cells was then determined by FACS. Cells were stained with anti-ETBR antibody (hu5E9.v1 or ch5E9) or with anti-PMEL17 antibody (ch17A9), followed by an anti-human Alexa 488 antibody conjugate. As shown in FIGS. 11A and B, both the in vivo-derived and in vitro-derived resistant UACC-257X2.2 cells had decreased expression of ETBR on the surface of the cells relative to the parental cell line. Surface expression of PMEL17 was unchanged in the resistant cells as compared to the parental cells. See FIGS. 11C and D. The control peak in each figure shows staining with secondary antibody only.

In vivo- and in vitro-derived resistant UACC-257X2.2 cells were then assayed for sensitivity to increasing concentrations of anti-ETBR-vc-MMAE, anti-PMEL17-vc-MMAE, and a control ADC, anti-gD-vc-MMAE. See Example H and FIG. 15A.

In vitro cell proliferation of the cell lines in the presence of the immunoconjugates was assessed. Cells were plated at 1,500 cells per well in 50 μL of normal growth medium in 96-well clear-bottom plates. Twenty-four hours later, an additional 50 μL of culture medium with serial dilutions of immunoconjugates were added to triplicate wells. Five days later, cell survival was determined using CellTiter-Glo Luminescent Cell Viability Reagent (G7572, Promega Corporation, Madison, Wis.) using an EnVision 2101 Mutilabel Reader (Perkin-Elmer, Waltham, Mass.).

The results of that experiment are shown in FIG. 12. The parental UACC-257X2.2 cell line was sensitive to both anti-ETBR-vc-MMAE and anti-PMEL17-vc-MMAE, with EC50s of 45 ng/mL and 33 ng/mL, respectively. See FIG. 12A. The parental line was also sensitive to linker-drug (without antibody; MC-vc-PAB-MMAE; referred to as "free drug" in FIG. 12), with an EC50 of 0.28 nM. The in vivo derived resistant UACC-257X2.2 cells were somewhat less sensitive to anti-PMEL17-vc-MMAE and significantly less sensitive to anti-ETBR-vc-MMAE, with EC50s of 119 ng/mL and 235 ng/mL, respectively. See FIG. 12B. The in vivo derived resistant UACC-257X2.2 cells were also less sensitive to linker-drug (without antibody), with an EC50 of 0.77 nM. The in vitro derived resistant UACC-257X2.2 cells were significantly less sensitive to anti-PMEL17-vc-MMAE, with an EC50 of 764 ng/mL, and insensitive to anti-ETBR-vc-MMAE. See FIG. 12C. The in vitro derived resistant UACC-257X2.2 cells were also less sensitive to linker-drug (without antibody), with an EC50 of 3.5 nM. These results suggest that resistance may be developed to both the antibody and drug portions of the ADC.

To determine the effect of the antibody portion of the ADC on resistance in UACC-257X2.2 cells, the in vivo- and in vitro-derived resistant UACC-257X2.2 cells were assayed for sensitivity to ADCs with different linkers and different drugs than were used to develop the resistant cells. The ADCs tested in this experiment were anti-ETBR linked to PNU-159682 through a non-cleavable linker (anti-ETBR-PNU) and anti-PMEL17 linked to PNU-159682 through a non-cleavable linker (anti-PMEL17-PNU). See Example H and FIG. 15E. An unrelated antibody, anti-gD, linked to PNU-159682 through a non-cleavable linker (anti-gD-PNU) was used as a control.

The results of that experiment are shown in FIG. 13. The parental UACC-257X2.2 cell line was sensitive to both anti-ETBR-PNU and anti-PMEL17-PNU, with EC50s of 4.2 ng/mL and 5.5 ng/mL, respectively. See FIG. 13A. The parental line was also sensitive to linker-drug (without antibody; MC-PNU-159682; referred to as "free drug" in FIG. 13), with an EC50 of 0.18 nM in this experiment. The in vivo derived resistant UACC-257X2.2 cells were as sensitive as the parental line to anti-PMEL17-PNU, but somewhat less sensitive to anti-ETBR-PNU, with EC50s of 4.7 ng/mL and 14.3 ng/mL, respectively. See FIG. 13B. The in vivo derived resistant UACC-257X2.2 cells were also as sensitive to linker-drug (without antibody) as the parental line, with an EC50 of 0.133 nM. Similar to the in vivo derived resistant UACC-257X2.2 cells, the in vitro derived resistant UACC-257X2.2 cells were as sensitive to anti-PMEL17-PNU, but somewhat less sensitive to anti-ETBR-PNU, with EC50s of 4.8 ng/mL and 14.6 ng/mL, respectively. See FIG. 13C. The in vitro derived resistant UACC-257X2.2 cells were also as sensitive to linker-drug (without antibody) as the parental line, with an EC50 of 0.15 nM. These results demonstrate the extent of resistance in the in vivo- and in vitro-derived resistant UACC-257X2.2 cells that is attributable to the antibody portion of the ADC (for example, because of a decrease in expression of ETBR), as opposed to resistance to the MMAE drug portion of the ADC. Similar results were obtained with anti-ETBR and anti-PMEL17 linked to PNU-159682 through an acid labile linker.

The in vivo- and in vitro-derived resistant UACC-257X2.2 cells were assayed for sensitivity to anti-ETBR linked to PNU-159682 through the vc linker used in the MMAE immunoconjugate (anti-ETBR-vc-PNU) and anti-PMEL17 linked to PNU-159682 through the vc linker (anti-PMEL17-vc-PNU). See Example H and FIG. 15C. An unrelated antibody, anti-gD, linked to PNU-159682 through the vc linker (anti-gD-vc-PNU) was used as a control.

The results of that experiment are shown in FIG. 14. The parental UACC-257X2.2 cell line was sensitive to both anti-ETBR-vc-PNU and anti-PMEL17-vc-PNU, with EC50s of 3 ng/mL and 2.5 ng/mL, respectively. See FIG. 14A. The parental line was also sensitive to linker-drug (without antibody; MC-vc-PAB-PNU-159682), with an EC50 of 2 nM in this experiment. The in vivo derived resistant UACC-257X2.2 cells were slightly less sensitive than the parental line to anti-PMEL17-vc-PNU, and less sensitive to anti-ETBR-vc-PNU, with EC50s of 6.4 ng/mL and 23 ng/mL, respectively. See FIG. 14B. The in vivo derived resistant UACC-257X2.2 cells were also slightly less sensitive to linker-drug (without antibody) than the parental line, with an EC50 of 4.2 nM. Similarly, the in vitro derived resistant UACC-257X2.2 cells were less sensitive to anti-PMEL17-PNU and anti-ETBR-PNU, with EC50s of 11.6 ng/mL and 41 ng/mL, respectively. See FIG. 14C. The in vitro derived resistant UACC-257X2.2 cells were also slightly less sensitive to linker-drug (without antibody) than the parental line, with an EC50 of 6.6 nM. These results suggest that the linker component of the ADC may contribute to the resistance in the in vivo- and in vitro-derived resistant UACC-257X2.2 cells. Compare, e.g., the sensitivity of the parental line and in vitro-derived resistant line to anti-PMEL17-vc-PNU (EC50s 2.5 ng/ml and 11.6 ng/ml, respectively), which has a different antibody and drug but the same linker as the ADC used to develop the resistant lines, versus the sensitivity of the parental line and in vitro-derived resistant line to anti-PMEL17-PNU (EC50s 5.5 ng/ml and 4.8 ng/ml, respectively), which has a different antibody, drug, and linker.

The in vivo- and in vitro-derived resistant UACC-257X2.2 cells were assayed for sensitivity to anti-ETBR linked to a PBD dimer through the vc linker used in the MMAE immunoconjugate (anti-ETBR-vc-PBD). The vc-PBD had the structure shown as "PBD dimer-val-cit-PAB-Ab" herein. See also Example H and FIG. 15D. In that experiment, similar to the results with anti-ETBR-vc-PNU, the resistant cell lines were less sensitive to anti-ETBR-vc-PBD than the parental line, although they were not completely resistant, suggesting that some of the resistance is due to the antibody and linker portions, but some sensitivity can be restored by changing the drug portion of the immunoconjugate.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

Table of Sequences

| SEQ ID NO | Description | Sequence |
|---|---|---|
| 1 | 17A9 heavy chain variable region | EVQLQQSGPE LVKPGASMKI SCKSSGYSFT RYTMNWVKQS HGKNLEWIGV INPYNGGTVY NQKFKGKATL TVDKSSSTAY MELLSLTSED SAVYYCARTD YDGYAMDYWG QGTSVTVSSA KT |
| 2 | 17A9 light chain variable region | DVQITQSPSY LAASPGETIT INCRATKSIS KYLAWYQEQP GKTNNLLIYS GSTLQSGIPS RFSGSGSGTD FTLTISSLEP EDFAMYYCQQ HNEYPYTFGS GTKLEIK |
| 3 | 17A9 HVR H1 | GYSFTRYTMN |
| 4 | 17A9 HVR H2 | VINPYNGGTVYNQKFKG |
| 5 | 17A9 HVR H3 | TDYDGYAMDY |
| 6 | 17A9 HVR L1 | RATKSISKYLA |
| 7 | 17A9 HVR L2; 8G3 HVR L2 | SGSTLQS |

-continued

| SEQ ID NO | Description | Sequence |
|---|---|---|
| 8 | 17A9 HVR L3; 8G3 HVR L3 | QQHNEYPYT |
| 9 | 8G3 heavy chain variable region | EVQLQQSGPE LVKPGASMRI SCKASGYSFT GYTMNWVKQS HGKNLEWIGV YNPYNGGTVY NQKFKGKATL TVDKSSSTTY MELLSLTSED SAVYYCARTD SGGYAMDCWG QGTSVTVSSA KT |
| 10 | 8G3 light chain variable region | DVQITQSPSY LDASPGETIT INCRASKTIS KYLAWYQEKP GKTNKLLIYS GSTLQSGIPS RFSGSGSGTD FTLTISSLEP EDFAMYYCQQ HNEYPYTFGS GTKLEIK |
| 11 | 15F2 heavy chain variable region | QVQLKESGPG LVAPSQSLSI TCTVSGFSLT KYGVHWVRQP PGKGLEWLGV IWAGGNTNYN SALMSRLSIN KDNSKSQVFL KMNSLQTDDT AMYYCATFDV WGAGTTVTVS SAKT |
| 12 | 15F2 light chain variable region | DIVMTQAAPS VPVTPGESVS ISCRSSKSLL HSNGNTFLYW FLQRPGQSPQ LLIYRMSNLV SGVPDRFSGS GSGTAFTLRI SRVEAEDVGF YYCMQHLEYP YTFGGGTKLE LK |
| 13 | 8G3 HVR H1 | GYSFTGYTMN |
| 14 | 8G3 HVR H2 | VYNPYNGGTVYNQKFKG |
| 15 | 8G3 HVR H3 | TDSGGYAMDC |
| 16 | 8G3 HVR L1 | RASKTISKYLA |
| 17 | 8G3/17A9 HVR H1 consensus | GYSFTX$_1$YTMN |
| 18 | 8G3/17A9 HVR H2 consensus | VX$_2$NPYNGGTVYNQKFKG |
| 19 | 8G3/17A9 HVR L1 consensus | RAX$_3$KX$_4$ISKYLA |
| 20 | 15F2 HVR H1 | GFSLTKYGVH |
| 21 | 15F2 HVR H2 | VIWAGGNTNYNSALMS |
| 22 | 15F2 HVR H3 | TFDV |
| 23 | 15F2 HVR L1 | RSSKSLLHSNGNTFLY |
| 24 | 15F2 HVR L2 | RMSNLVS |
| 25 | 15F2 HVR L3 | MQHLEYPYT |
| 26 | Human PMEL17 preproprotein; NP_008859; signal sequence = amino acids 1 to 24 | MDLVLKRCLL HLAVIGALLA VGATKVPRNQ DWLGVSRQLR TKAWNRQLYP EWTEAQRLDC WRGGQVSLKV SNDGPTLIGA NASFSIALNF PGSQKVLPDG QVIWVNNTII NGSQVWGGQP VYPQETDDAC IFPDGGPCPS GSWSQKRSFV YVWKTWGQYW QVLGGPVSGL SIGTGRAMLG THTMEVTVYH RRGSRSYVPL AHSSSAFTIT DQVPFSVSVS QLRALDGGNK HFLRNQPLTF ALQLHDPSGY LAEADLSYTW DFGDSSGTLI SRALVVTHTY LEPGPVTAQV VLQAAIPLTS CGSSPVPGTT DGHRPTAEAP NTTAGQVPTT EVVGTTPGQA PTAEPSGTTS VQVPTTEVIS TAPVQMPTAE STGMTPEKVP VSEVMGTTLA EMSTPEATGM TPAEVSIVVL SGTTAAQVTT TEWVETTARE LPIPEPEGPD ASSIMSTESI TGSLGPLLDG TATLRLVKRQ VPLDCVLYRY GSFSVTLDIV QGIESAEILQ AVPSGEGDAF ELTVSCQGGL PKEACMEISS PGCQPPAQRL CQPVLPSPAC QLVLHQILKG GSGTYCLNVS LADTNSLAVV STQLIMPGQE AGLGQVPLIV GILLVLMAVV LASLIYRRRL MKQDFSVPQL PHSSSHWLRL PRIFCSCPIG ENSPLLSGQQ V |
| 27 | Human PMEL17 proprotein, without signal sequence; amino acids 25 to 661 | KVPRNQ DWLGVSRQLR TKAWNRQLYP EWTEAQRLDC WRGGQVSLKV SNDGPTLIGA NASFSIALNF PGSQKVLPDG QVIWVNNTII NGSQVWGGQP VYPQETDDAC IFPDGGPCPS GSWSQKRSFV YVWKTWGQYW QVLGGPVSGL SIGTGRAMLG THTMEVTVYH RRGSRSYVPL AHSSSAFTIT DQVPFSVSVS QLRALDGGNK HFLRNQPLTF ALQLHDPSGY LAEADLSYTW DFGDSSGTLI SRALVVTHTY LEPGPVTAQV VLQAAIPLTS CGSSPVPGTT DGHRPTAEAP NTTAGQVPTT EVVGTTPGQA PTAEPSGTTS VQVPTTEVIS TAPVQMPTAE STGMTPEKVP VSEVMGTTLA EMSTPEATGM TPAEVSIVVL SGTTAAQVTT TEWVETTARE LPIPEPEGPD ASSIMSTESI TGSLGPLLDG TATLRLVKRQ VPLDCVLYRY GSFSVTLDIV QGIESAEILQ AVPSGEGDAF ELTVSCQGGL |

Table of Sequences

| SEQ ID NO | Description | Sequence |
|---|---|---|
| | | PKEACMEISS PGCQPPAQRL CQPVLPSPAC QLVLHQILKG GSGTYCLNVS LADTNSLAVV STQLIMPGQE AGLGQVPLIV GILLVLMAVV LASLIYRRRL MKQDFSVPQL PHSSSHWLRL PRIFCSCPIG ENSPLLSGQQ V |
| 28 | Cynomolgus monkey PMEL17, without signal sequence | KGPRNQDWLG VSRQLRTKAW NRQLYPEWTE AQRLDCWRGG QVSLKVSNDG PTLIGANASF SIALNFPGSQ KVLPDGQVIW VNNTIINGSQ VWGGQPVYPQ ETDDACIFPD GGPCPSGPWS QKRSFVYVWK TWGQYWQVLG GPVSGLSIGT GRAMLGTHTM EVTVYHRRGS RSYVPLAHSS SAFTITDQVP FSVSVSQLRA LDGGNKHFLR NQPLTFALQL HDPSGYLAEA DLSYTWDFGD SSGTLISRAL VVTHTYLEPG PVTAQVVLQA AIPLTSCGSS PVPGTTDGHR PTAEAPDTTA GRGPTTEVVG TTPGQVPTTQ PSGTTSVQVP TTEVISTTPV QMPTAESTGT TPEKVPVSEV MGTTLAEMST PEAIGMTPAE VSIVVPSGTT AAQVTTTEWV ETTAGELPTP EPEGPDTSSI MSTESITGSL GPLLDGTATL RLEKRQVPLD CVLYRYGSFS VTLDIVQGIE SAEILQVVPS SEGDAFELTV SCQGGLPTEA CMEISSPGCQ PPAQQLCQPV PPSPACQLVL YQILKGGLGT YCLNVSLADA NSLAVVSTQL IVPGQEAGLG QAPLFVGILL VLMAVVLASL IYRRRLMKQA FSIPQLPHGS SHWLRLPRIF RSCPIGENSP LLSGQEV |
| 29 | Rat PMEL17 precursor; NP_068682; signal sequence = amino acids 1 to 25 | MGVQRRCFLP VLVLGALLAL GSIEGSRNQN WHGVSRQLVT KVWNKQLYPE WTEVQGSNCW RGGQVSLKVR NDGPTLVGAN TSFSIALHFP GSQKVLPDGQ VIWVNNTIIN GSQVWGGQPV YPREPDDACI FPDGGPCPSG PKPPRRSFVY VWKTWGQYWQ VLGGPESKLS IPTGHARLGT HTMEVTVYHR RGSQSYVPLA HSSSTFTITG SVSRLLDDTD TIMLVKRQVP LDCVLYRYGS FSLTLDIVQG IESAEILQAV PSSEGDAFEL TVSCRGGLPK EACMDISSPG CQPPAQRLCQ PVPPSPDCQL VLHQILKGGL GTYCLNVSLA DANSLAVAST QLVVPGQEGS LGQAPLLVGV LLVLVAVVLA SLIYRHRLKK QDSVSQTPHG STHWLRLPPV FCARRLGESS PLLSGQQV |
| 30 | Rat PMEL17, without signal sequence, amino acids 26 to 418 | SRNQN WHGVSRQLVT KVWNKQLYPE WTEVQGSNCW RGGQVSLKVR NDGPTLVGAN TSFSIALHFP GSQKVLPDGQ VIWVNNTIIN GSQVWGGQPV YPREPDDACI FPDGGPCPSG PKPPRRSFVY VWKTWGQYWQ VLGGPESKLS IPTGHARLGT HTMEVTVYHR RGSQSYVPLA HSSSTFTITG SVSRLLDDTD TIMLVKRQVP LDCVLYRYGS FSLTLDIVQG IESAEILQAV PSSEGDAFEL TVSCRGGLPK EACMDISSPG CQPPAQRLCQ PVPPSPDCQL VLHQILKGGL GTYCLNVSLA DANSLAVAST QLVVPGQEGS LGQAPLLVGV LLVLVAVVLA SLIYRHRLKK QDSVSQTPHG STHWLRLPPV FCARRLGESS PLLSGQQV |
| 31 | Mouse PMEL17 precursor; NP_068682; signal sequence = amino acids 1 to 25 | MGVQRRSFLP VLVLSALLAV GALEGSRNQD WLGVPRQLVT KTWNRQLYPE WTEVQGSNCW RGGQVSLRVI NDGPTLVGAN ASFSIALHFP GSQKVLPDGQ VIWANNTIIN GSQVWGGQPV YPQEPDDACV FPDGGPCPSG PKPPKRSFVY VWKTWGKYWQ VLGGPVSRLS IATGHAKLGT HTMEVTVYHR RGSQSYVPLA HASSTFTITD QVPFSVSVSQ LQALDGETKH FLRNHPLIFA LQLHDPSGYL AEADLSYTWD FGDGTGTLIS RALDVTHTYL ESGSVTAQVV LQAAIPLVSC GSSPVPGTTD GYMPTAEAPG TTSRQGTTTK VVGTTPGQMP TTQPSGTTVV QMPTTEVTAT TSEQMLTSAV IDTTLAEVST TEGTGTTPTR PSGTTVAQAT TTEGPDASPL LPTQSSTGSI SPLLDDTDTI MLVKRQVPLD CVLYRYGSFS LALDIVQGIE SAEILQAVPF SEGDAFELTV SCQGGLPKEA CMDISSPGCQ PPAQRLCQSV PPSPDCQLVL HQVLKGGSGT YCLNVSLADA NSLAVASTQL VVPGQDGGLG QAPLLVGILL VLVAVVLASL IHRHRLKKQG SVSQMPHGST HWLRLPPVFR ARGLGENSPL LSGQQV |
| 32 | Mouse PMEL17, without signal sequence, amino acids 26 to 626 | SRNQD WLGVPRQLVT KTWNRQLYPE WTEVQGSNCW RGGQVSLRVI NDGPTLVGAN ASFSIALHFP GSQKVLPDGQ VIWANNTIIN GSQVWGGQPV YPQEPDDACV FPDGGPCPSG PKPPKRSFVY VWKTWGKYWQ VLGGPVSRLS IATGHAKLGT HTMEVTVYHR RGSQSYVPLA HASSTFTITD QVPFSVSVSQ LQALDGETKH FLRNHPLIFA LQLHDPSGYL AEADLSYTWD FGDGTGTLIS RALDVTHTYL ESGSVTAQVV LQAAIPLVSC GSSPVPGTTD GYMPTAEAPG TTSRQGTTTK VVGTTPGQMP TTQPSGTTVV QMPTTEVTAT TSEQMLTSAV IDTTLAEVST TEGTGTTPTR PSGTTVAQAT TTEGPDASPL LPTQSSTGSI SPLLDDTDTI MLVKRQVPLD CVLYRYGSFS LALDIVQGIE SAEILQAVPF SEGDAFELTV SCQGGLPKEA CMDISSPGCQ PPAQRLCQSV PPSPDCQLVL HQVLKGGSGT YCLNVSLADA NSLAVASTQL VVPGQDGGLG QAPLLVGILL VLVAVVLASL IHRHRLKKQG SVSQMPHGST HWLRLPPVFR ARGLGENSPL LSGQQV |
| 33 | 5E9 HVR H1 | GYTFTSYWMQ |
| 34 | 5E9 HVR H2 | TIYPGDGDTSYAQKFKG |
| 35 | 5E9 HVR H3 | WGYAYDIDN |
| 36 | 5E9 HVR L1 | KSSQSLLDSDGKTYLN |

| SEQ ID NO | Description | Sequence |
|---|---|---|
| 37 | 5E9 HVR L2 | LVSKLDS |
| 38 | 5E9 HVR L3 | WQGTHFPYT |
| 39 | hu5E9.v1 light chain variable region | DIQMTQSPSS LSASVGDRVT ITCKSSQSLL DSDGKTYLNW LQQKPGKAPK RLIYLVSKLD SGVPSRFSGS GSGTDFTLTI SSLQPEDFAT YYCWQGTHFP YTFGQGTKVE IK |
| 40 | hu5E9.v1 heavy chain variable region | EVQLVESGGG LVQPGGSLRL SCAASGYTFT SYWMQWVRQA PGKGLEWIGT IYPGDGDTSY AQKFKGRATL STDKSKNTAY LQMNSLRAED TAVYYCARWG YAYDIDNWG |
| 41 | mu5E9 light chain variable region | DVVMTQTPLT LSVTIGQPAS ISCKSSQSLL DSDGKTYLNW LLQRPGQSPK RLIYLVSKLD SGVPDRFTGS GSGTDFTLKI TRVEAEDLGV YYCWQGTHFP YTFGGGTKLE IK |
| 42 | mu5E9 heavy chain variable region | QVQLLQSGAE LARPGASVKL SCKASGYTFT SYWMQWVKQR PGQGLEWIGT IYPGDGDTSY AQKFKGKATL TTDKYSSTAY MQLSSLASED SAVYYCARWG YAYDIDNWG |
| 43 | ch5E9 ligh chain | DVVMTQTPLT LSVTIGQPAS ISCKSSQSLL DSDGKTYLNW LLQRPGQSPK RLIYLVSKLD SGVPDRFTGS GSGTDFTLKI TRVEAEDLGV YYCWQGTHFP YTFGGGTKLE IKRTVAAPSV FIFPPSDEQL KSGTASVVCL LNNFYPREAK VQWKVDNALQ SGNSQESVTE QDSKDSTYSL SSTLTLSKAD YEKHKVYACE VTHQGLSSPV TKSFNRGEC |
| 44 | ch5E9 heavy chain | QVQLLQSGAE LARPGASVKL SCKASGYTFT SYWMQWVKQR PGQGLEWIGT IYPGDGDTSY AQKFKGKATL TTDKYSSTAY MQLSSLASED SAVYYCARWG YAYDIDNWGQ GTLVTVSSAS TKGPSVFPLA PSSKSTSGGT AALGCLVKDY FPEPVTVSWN SGALTSGVHT FPAVLQSSGL YSLSSVVTVP SSSLGTQTYI CNVNHKPSNT KVDKKVEPKS CDKTHTCPPC PAPELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSREEMT KNQVSLTCLV KGFYPSDIAV EWESNGQPEN NYKTTPPVLD SDGSFFLYSK LTVDKSRWQQ GNVFSCSVMH EALHNHYTQK SLSLSPGK |
| 45 | hu5E9.v1 light chain | DIQMTQSPSS LSASVGDRVT ITCKSSQSLL DSDGKTYLNW LQQKPGKAPK RLIYLVSKLD SGVPSRFSGS GSGTDFTLTI SSLQPEDFAT YYCWQGTHFP YTFGQGTKVE IKRTVAAPSV FIFPPSDEQL KSGTASVVCL LNNFYPREAK VQWKVDNALQ SGNSQESVTE QDSKDSTYSL SSTLTLSKAD YEKHKVYACE VTHQGLSSPV TKSFNRGEC |
| 46 | hu5E9.v1 heavy chain | EVQLVESGGG LVQPGGSLRL SCAASGYTFT SYWMQWVRQA PGKGLEWIGT IYPGDGDTSY AQKFKGRATL STDKSKNTAY LQMNSLRAED TAVYYCARWG YAYDIDNWGQ GTLVTVSSAS TKGPSVFPLA PSSKSTSGGT AALGCLVKDY FPEPVTVSWN SGALTSGVHT FPAVLQSSGL YSLSSVVTVP SSSLGTQTYI CNVNHKPSNT KVDKKVEPKS CDKTHTCPPC PAPELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSREEMT KNQVSLTCLV KGFYPSDIAV EWESNGQPEN NYKTTPPVLD SDGSFFLYSK LTVDKSRWQQ GNVFSCSVMH EALHNHYTQK SLSLSPGK |
| 47 | ch17A9 light chain | DVQITQSPSY LAASPGETIT INCRATKSIS KYLAWYQEQP GKTNNLLIYS GSTLQSGIPS RFSGSGSGTD FTLTISSLEP EDFAMYCQQ HNEYPYTFGS GTKLEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 48 | ch17A9 heavy chain | EVQLQQSGPE LVKPGASMKI SCKSSGYSFT RYTMNWVKQS HGKNLEWIGV INPNYGGTVY NQKFKGKATL TVDKSSSTAY MELLSLTSED TAVYYCARTD YDGYAMDYWG QGTSVTVSSA KTKGPSVFPL APSSKSTSGG TAALGCLVKD YFPEPVTVSW NSGALTSGVH TFPAVLQSSG LYSLSSVVTV PSSSLGTQTY ICNVNHKPSN TKVDKKVEPK SCDKTHTCPP CPAPELLGGP SVFLFPPKPK DTLMISRTPE VTCVVVDVSH EDPEVKFNWY VDGVEVHNAK TKPREEQYNS TYRVVSVLTV LHQDWLNGKE YKCKVSNKAL PAPIEKTISK AKGQPREPQV YTLPPSREEM TKNQVSLTCL VKGFYPSDIA VEWESNGQPE NNYKTTPPVL DSDGSFFLYS KLTVDKSRWQ QGNVFSCSVM HEALHNHYTQ KSLSLSPGK |
| 49 | 8G3 heavy chain variable region | EVQLQQSGPE LVKPGASMRI SCKASGYSFT GYTMNWVKQS HGKNLEWIGV YNPNYGGTVY NQKFKGKATL TVDKSSSTTY MELLSLTSED SAVYYCARTD SGGYAMDCWG QGTSVTVSS |

-continued

Table of Sequences

| SEQ ID NO | Description | Sequence |
|---|---|---|
| 50 | 17A9 heavy chain variable region | EVQLQQSGPE LVKPGASMKI SCKSSGYSFT RYTMNWVKQS HGKNLEWIGV INPYNGGTVY NQKFKGKATL TVDKSSSTAY MELLSLTSED SAVYYCARTD YDGYAMDYWG QGTSVTVSS |
| 51 | 15F2 heavy chain variable region | QVQLKESGPG LVAPSQSLSI TCTVSGFSLT KYGVHWVRQP PGKGLEWLGV IWAGGNTNYN SALMSRLSIN KDNSKSQVFL KMNSLQTDDT AMYYCATFDV WGAGTTVTVS S |

What is claimed is:

1. An immunoconjugate comprising an antibody that binds PMEL17 and a cytotoxic agent, wherein the antibody comprises:
a) (i) HVR-H1 comprising the amino acid sequence of SEQ ID NO: 3, (ii) HVR-H2 comprising the amino acid sequence of SEQ ID NO: 4, (iii) HVR-H3 comprising the amino acid sequence of SEQ ID NO: 5, (iv) HVR-L1 comprising the amino acid sequence of SEQ ID NO: 6, (v) HVR-L2 comprising the amino acid sequence of SEQ ID NO: 7, and (vi) HVR-L3 comprising the amino acid sequence of SEQ ID NO: 8; or b) (i) HVR-H1 comprising the amino acid sequence of SEQ ID NO: 13, (ii) HVR-H2 comprising the amino acid sequence of SEQ ID NO: 14, and (iii) HVR-H3 comprising the amino acid sequence of SEQ ID NO: 15, (iv) HVR-L1 comprising the amino acid sequence of SEQ ID NO: 16, (v) HVR-L2 comprising the amino acid sequence of SEQ ID NO: 7, and (vi) HVR-L3 comprising the amino acid sequence of SEQ ID NO: 8; or c) HVR-H1, HVR-H2, HVR-H3, HVR-L1, HVR-L2, and HVR-L3 of the antibody produced by hybridoma 7509 (31D1.6.7) having ATCC Accession No. PTA-12862.

2. The immunoconjugate of claim 1, wherein the antibody comprises:
a) a VH sequence having at least 95% sequence identity to the amino acid sequence of SEQ ID NO: 1; or
b) a VL sequence having at least 95% sequence identity to the amino acid sequence of SEQ ID NO: 2; or
c) a VH sequence as in (a) and a VL sequence as in (b); or
d) a VH sequence having at least 95% sequence identity to the amino acid sequence of SEQ ID NO: 9; or
e) a VL sequence having at least 95% sequence identity to the amino acid sequence of SEQ ID NO: 10; or
f) a VH sequence as in (d) and a VL sequence as in (e); or
g) a VH sequence having at least 95% sequence identity to the VH sequence of the antibody produced by hybridoma 7509(31D1.6.7) having ATCC Accession No. PTA-12862; or
h) a VL sequence having at least 95% sequence identity to the VL sequence of the antibody produced by hybridoma 7509(31D1.6.7) having ATCC Accession No. PTA-12862; or
i) a VH sequence as in (g) and a VL sequence as in (h).

3. The immunoconjugate of claim 2, comprising a VH sequence having the amino acid sequence of SEQ ID NO: 1, a VH sequence having the amino acid sequence of SEQ ID NO: 9, or a VH sequence of the antibody produced by hybridoma 7509(31D1.6.7) having ATCC Accession No. PTA-12862.

4. The immunoconjugate of claim 2, comprising a VL sequence having the amino acid sequence of SEQ ID NO: 2, a VL sequence having the amino acid sequence of SEQ ID NO: 10, or a VL sequence of the antibody produced by hybridoma 7509(31D1.6.7) having ATCC Accession No. PTA-12862.

5. The immunoconjugate of claim 1, comprising (a) a VH sequence having the amino acid sequence of SEQ ID NO: 1 and a VL sequence having the amino acid sequence of SEQ ID NO: 2; or (b) a VH sequence having the amino acid sequence of SEQ ID NO: 9 and a VL sequence having the amino acid sequence of SEQ ID NO: 10; or (c) a VH sequence of the antibody produced by hybridoma 7509 (31D1.6.7) having ATCC Accession No. PTA-12862 and a VL sequence of the antibody produced by hybridoma 7509 (31D1.6.7) having ATCC Accession No. PTA-12862.

6. The immunoconjugate of claim 1, which is an IgG1, IgG2a or IgG2b antibody.

7. The immunoconjugate of claim 1 having the formula Ab-(L-D)p, wherein:
(a) Ab is the antibody;
(b) L is a linker;
(c) D is a cytotoxic agent; and
(d) p ranges from 1-8.

8. The immunoconjugate of claim 7, wherein D is an auristatin.

9. The immunoconjugate of claim 8, wherein D has formula $D_E$

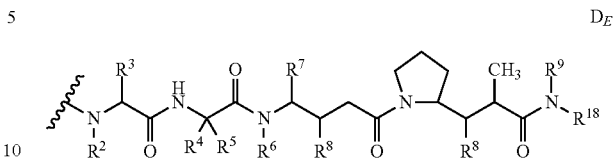

and wherein $R^2$ and $R^6$ are each methyl, $R^3$ and $R^4$ are each isopropyl, $R^5$ is H, $R^7$ is sec-butyl, each $R^8$ is independently selected from $CH_3$, $O-CH_3$, OH, and H; $R^9$ is H; and $R^{18}$ is $-C(R^8)_2-C(R^8)_2$-aryl.

10. The immunoconjugate of claim 7, wherein the drug is MMAE.

11. The immunoconjugate of claim 7, wherein D is a pyrrolobenzodiazepine of Formula A:

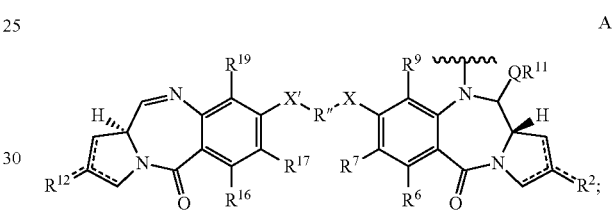

wherein the dotted lines indicate the optional presence of a double bond between C1 and C2 or C2 and C3;

$R^2$ is independently selected from H, OH, =O, =$CH_2$, CN, R, OR, =CH—$R^D$, =$C(R^D)_2$, O—$SO_2$—R, $CO_2R$ and COR, and optionally further selected from halo or dihalo, wherein $R^D$ is independently selected from R, $CO_2R$, COR, CHO, $CO_2H$, and halo;

$R^6$ and $R^9$ are independently selected from H, R, OH, OR, SH, SR, $NH_2$, NHR, NRR', $NO_2$, $Me_3Sn$ and halo;

$R^7$ is independently selected from H, R, OH, OR, SH, SR, $NH_2$, NHR, NRR', $NO_2$, $Me_3Sn$ and halo;

Q is independently selected from O, S and NH;

$R^{11}$ is either H, or R or, where Q is O, $SO_3M$, where M is a metal cation;

R and R' are each independently selected from optionally substituted $C_{1-8}$ alkyl, $C_{3-8}$ heterocyclyl and $C_{5-20}$ aryl groups, and optionally in relation to the group NRR', R and R' together with the nitrogen atom to which they are attached form an optionally substituted 4-, 5-, 6- or 7-membered heterocyclic ring;

$R^{12}$, $R^{16}$, $R^{19}$ and $R^{17}$ are as defined for $R^2$, $R^6$, $R^9$ and $R^7$ respectively;

R" is a $C_{3-12}$ alkylene group, which chain may be interrupted by one or more heteroatoms and/or aromatic rings that are optionally substituted; and X and X' are independently selected from O, S and N(H).

12. The immunoconjugate of claim 11, wherein D has a structure selected from:

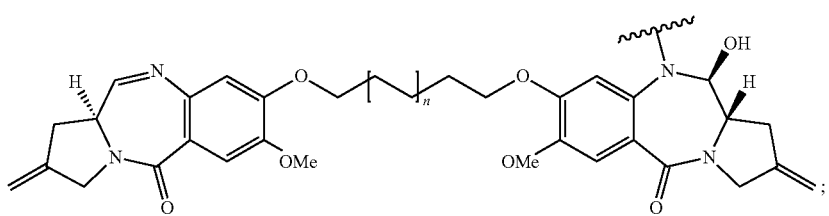

A(II)

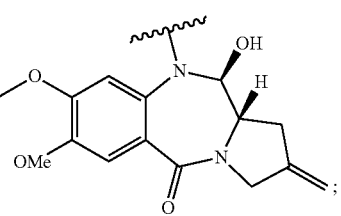

A(I)

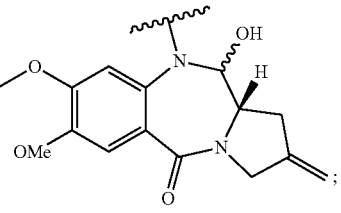

A(III)

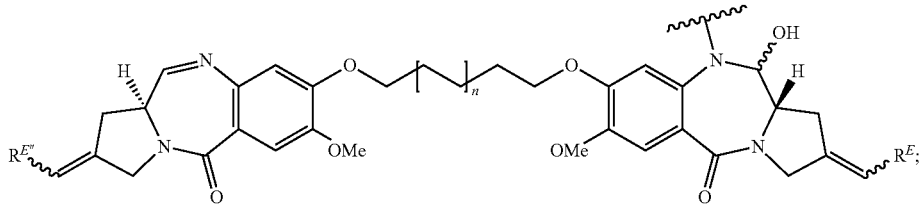

A(IV)

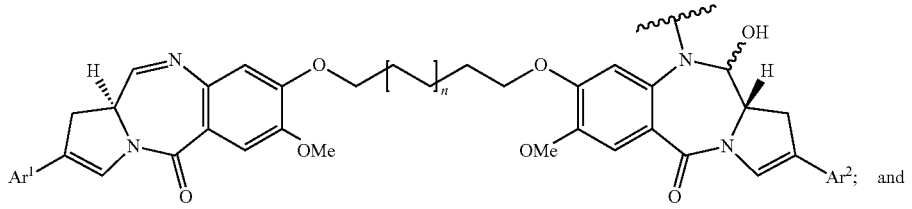

and

A(V)

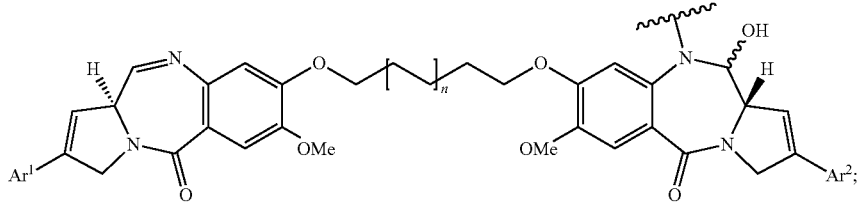

wherein $R^E$ and $R^{E''}$ are each independently selected from H or $R^D$, wherein $R^D$ is independently selected from R, $CO_2R$, COR, CHO, $CO_2H$, and halo;
wherein $Ar^1$ and $Ar^3$ are each independently optionally substituted $C_{5-20}$ aryl; and
wherein n is 0 or 1.

13. The immunoconjugate of claim 7, wherein D is a pyrrolobenzodiazepine of Formula B:

wherein the horizontal wavy line indicates the covalent attachment site to the linker;
$R^{V1}$ and $R^{V2}$ are independently selected from H, methyl, ethyl, phenyl, fluoro-substituted phenyl, and $C_{5-6}$ heterocyclyl; and
n is 0 or 1.

14. The immunoconjugate of claim 7, wherein D is a nemorubicin derivative.

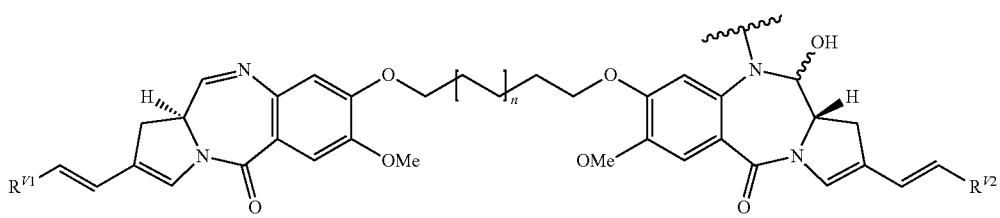

15. The immunoconjugate of claim 14, wherein D has a structure selected from:

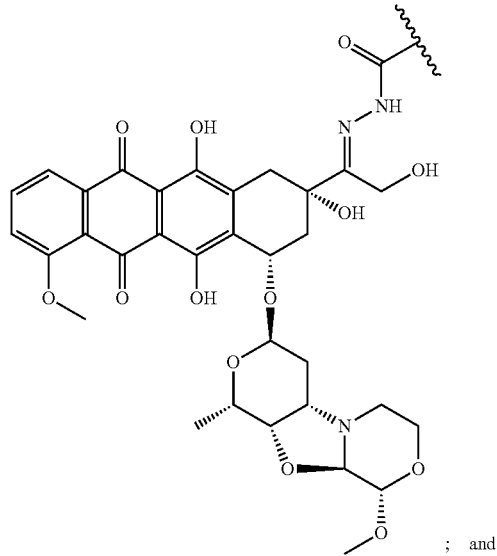 ; and

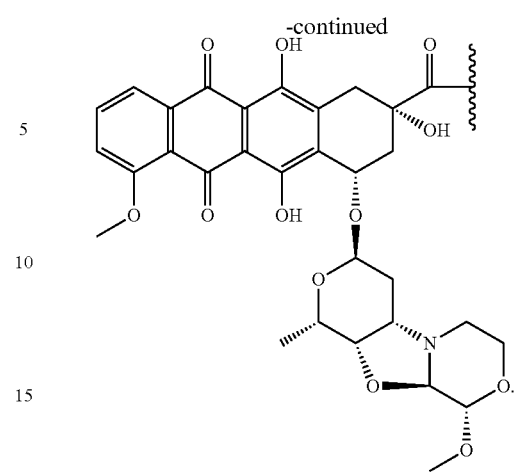

16. The immunoconjugate of claim 7, wherein the linker is cleavable by a protease.

17. The immunoconjugate of claim 16, wherein the linker comprises a val-cit dipeptide or a Phe-Lys dipeptide.

18. The immunoconjugate of claim 7, wherein the linker is acid-labile.

19. The immunoconjugate of claim 18, wherein the linker comprises hydrazone.

20. The immunoconjugate of claim 7 having the formula:

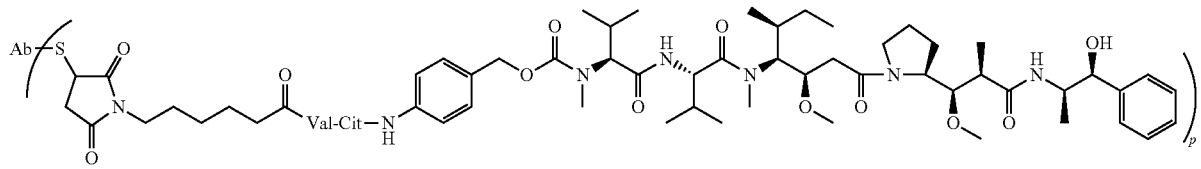

wherein S is a sulfur atom.

21. The immunoconjugate of claim 7 having the formula:

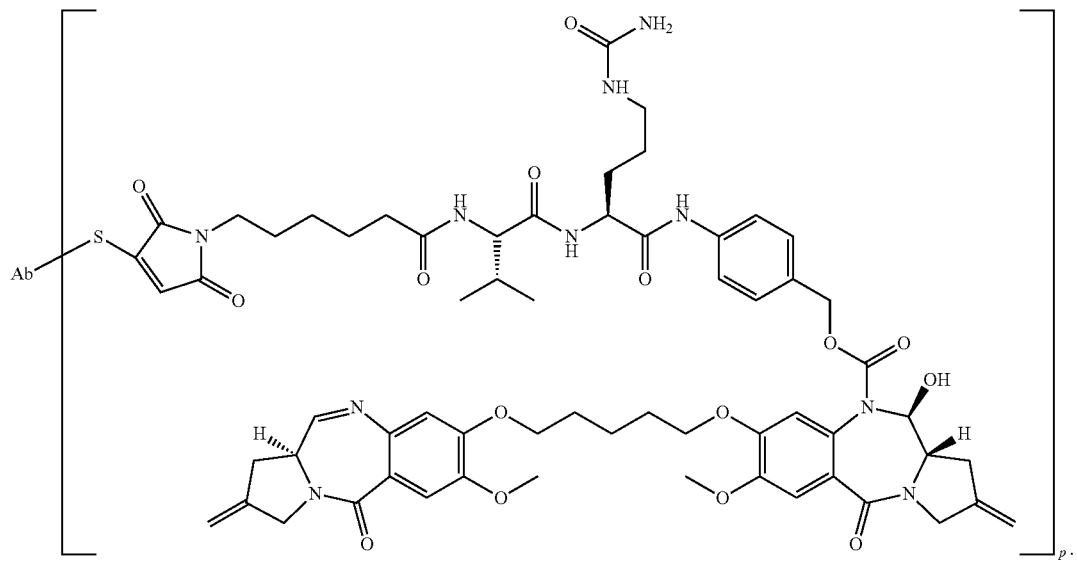

22. The immunoconjugate of claim 7 having a formula selected from:
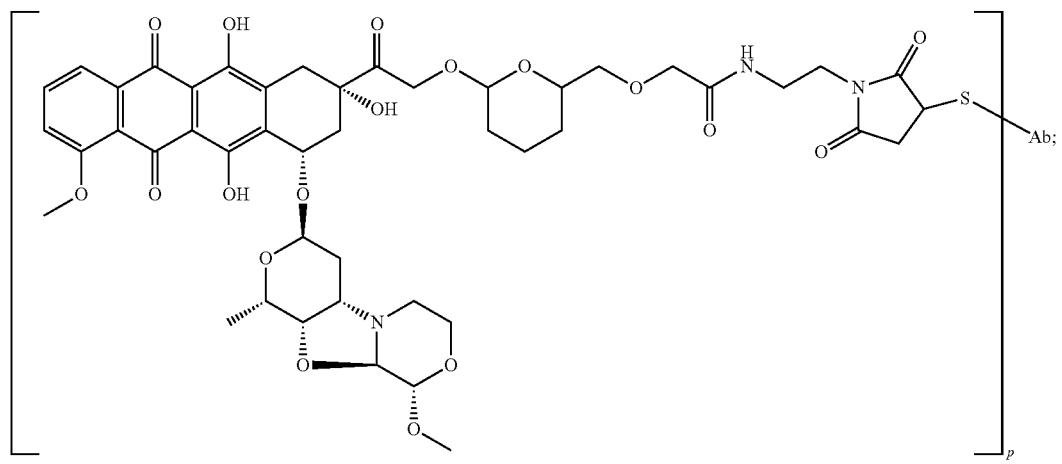
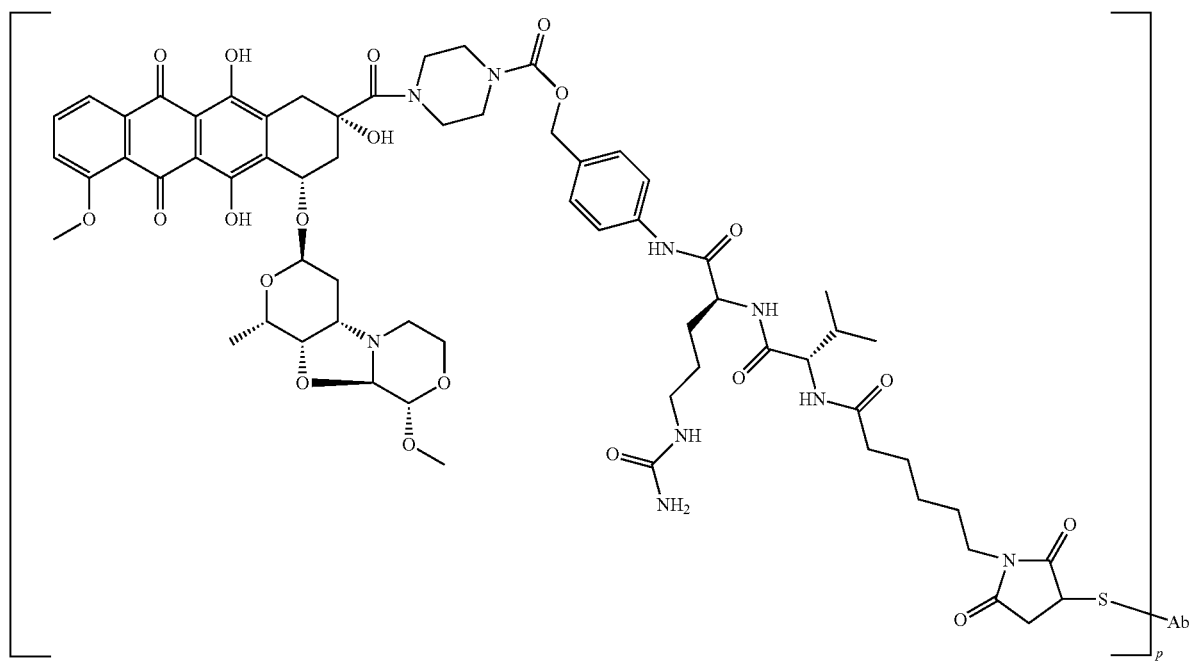
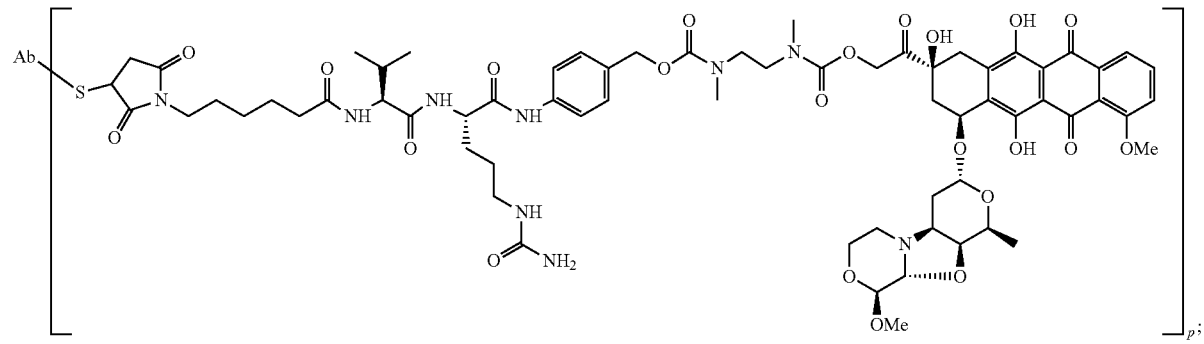

-continued

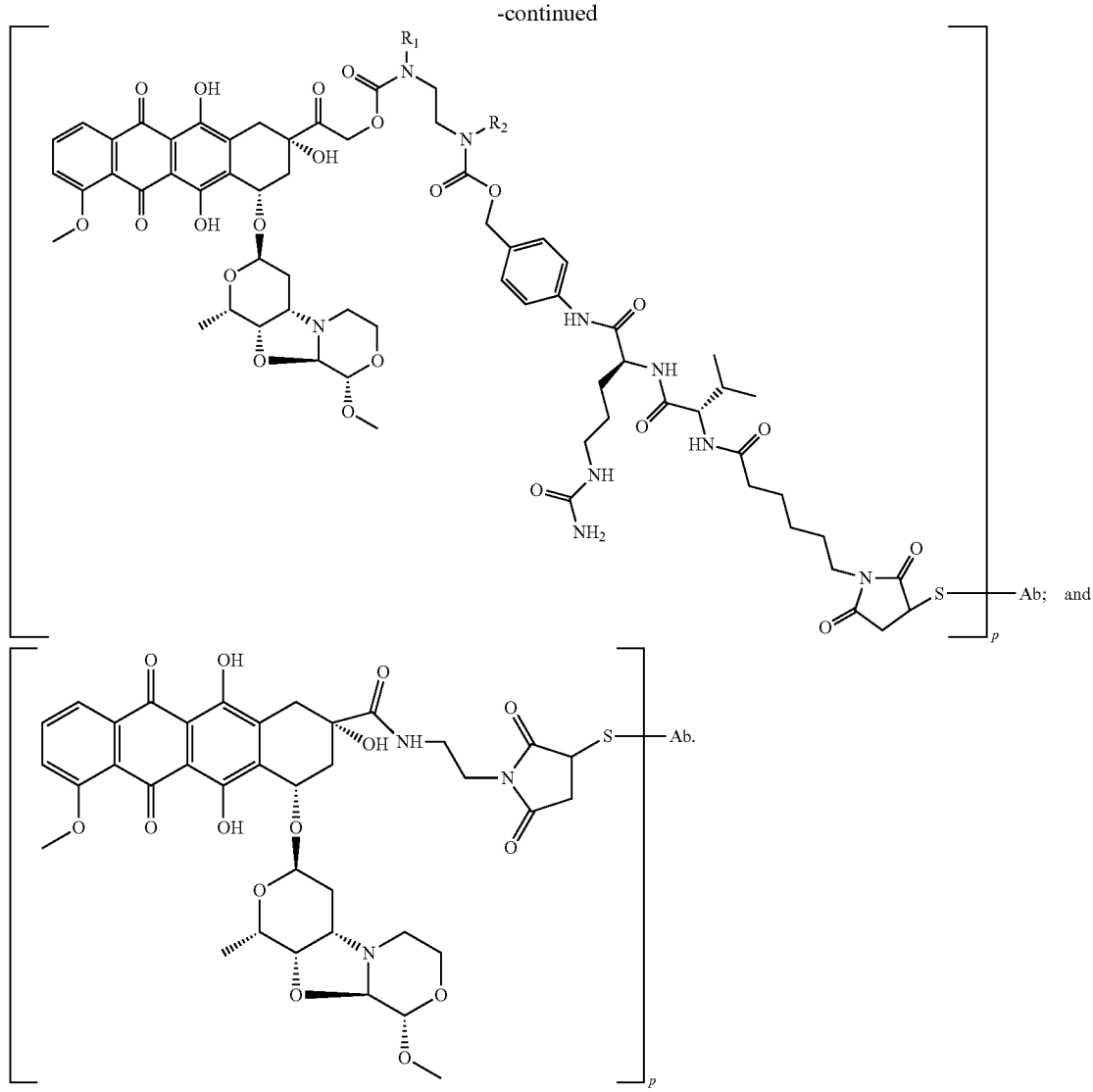

23. The immunoconjugate of claim 7, wherein p ranges from 2-5.

24. A pharmaceutical formulation comprising the immunoconjugate of claim 1 and a pharmaceutically acceptable carrier.

25. A method of treating an individual having a PMEL17-positive cancer, the method comprising administering to the individual an effective amount of the immunoconjugate of claim 1.

26. The method of claim 25, wherein the PMEL17-positive cancer is melanoma.

27. The method of claim 26, further comprising administering an additional therapeutic agent to the individual.

28. A method of inhibiting proliferation of a PMEL17-positive cell, the method comprising exposing the cell to the immunoconjugate of claim 1 under conditions permissive for binding of the immunoconjugate to PMEL17 on the surface of the cell, thereby inhibiting proliferation of the cell.

29. The method of claim 28, wherein the cell is a melanoma cell.

30. A method of treating an individual having a PMEL17-positive cancer, wherein the PMEL17-positive cancer is resistant to a first therapeutic, the method comprising administering to the individual an effective amount of the immunoconjugate of claim 1.

31. The method of claim 30, wherein the PMEL17-positive cancer is melanoma.

32. The method of claim 30, wherein the first therapeutic comprises a first antibody that binds an antigen other than PMEL17.

33. The method of claim 32, wherein the first therapeutic is a first immunoconjugate comprising a first antibody that binds an antigen other than PMEL17 and a first cytotoxic agent.

34. The method of claim 32, wherein the first antibody binds an antigen selected from endothelin B receptor (ETBR), tyrosinase-related protein 1 (TYRP1), cytotoxic T lymphocyte antigen 4 (CTLA-4), and glycoprotein NMB (GPNMB).

35. The method of claim 34, wherein the first antibody binds ETBR.

36. The method of claim 35, wherein the first antibody is hu5E9.v1.

37. The method of claim 33, wherein the first immunoconjugate is hu5E9.v1-MC-val-cit-PAB-MMAE.

38. The method of claim 33, wherein the first cytotoxic agent and the cytotoxic agent of the immunoconjugate comprising an antibody that binds PMEL17 are different.

39. The method of claim 38, wherein the first cytotoxic agent is MMAE and the cytotoxic agent of the immunoconjugate comprising an antibody that binds PMEL17 is selected from a calicheamicin, a pyrrolobenzodiazepine, and a nemorubicin derivative.

40. The method of claim 39, wherein the cytotoxic agent of the immunoconjugate comprising an antibody that binds PMEL17 is selected from a pyrrolobenzodiazepine and a nemorubicin derivative.

41. A method of treating an individual with PMEL17-positive cancer, comprising administering to the individual an effective amount of a first immunoconjugate of claim 1 in combination with a second immunoconjugate comprising an antibody that binds ETBR.

42. The method of claim 41, wherein the antibody that binds ETBR comprises:
   a) an HVR H1 comprising a sequence of SEQ ID NO: 33, an HVR H2 comprising a sequence of SEQ ID NO: 34, an HVR H3 comprising a sequence of SEQ ID NO: 35, an HVR L1 comprising a sequence of SEQ ID NO: 36, an HVR L2 comprising a sequence of SEQ ID NO: 37, and an HVR L3 comprising a sequence of SEQ ID NO: 38; or
   b) a heavy chain variable region comprising the sequence of SEQ ID NO: 40 and a light chain variable region comprising the sequence of SEQ ID NO: 39.

43. The method of claim 41, wherein the first immunoconjugate comprises a cytotoxic agent selected from an auristatin, a pyrrolobenzodiazepine, and a nemorubicin derivative, and the second immunoconjugate comprises a cytotoxic agent selected from an auristatin, a pyrrolobenzodiazepine, and a nemorubicin derivative.

44. The method of claim 41, wherein the first immunoconjugate comprises a cytotoxic agent selected from a pyrrolobenzodiazepine and a nemorubicin derivative, and the second immunoconjugate comprises an auristatin.

45. The method of claim 44, wherein the second immunoconjugate comprises MMAE.

46. The method of claim 41, wherein the second immunoconjugate comprises a linker-drug portion comprising MC-val-cit-PAB-MMAE.

47. The method of claim 41, wherein the second immunoconjugate is hu5E9.v1-MC-val-cit-PAB-MMAE.

48. The method of claim 41, wherein the PMEL17-positive cancer is melanoma.

49. The method of claim 41, wherein the PMEL17-positive cancer is also ETBR-positive.

* * * * *